(12) United States Patent
Chen et al.

(10) Patent No.: US 11,191,762 B2
(45) Date of Patent: Dec. 7, 2021

(54) ALKYL SUBSTITUTED TRIAZOLE COMPOUNDS AS AGONISTS OF THE APJ RECEPTOR

(71) Applicant: AMGEN INC., Thousand Oaks, CA (US)

(72) Inventors: Yinhong Chen, Hayward, CA (US); Mikkel V. Debenedetto, Waltham, MA (US); Paul John Dransfield, Arlington, MA (US); James S. Harvey, Arlington, MA (US); Jonathan Houze, Cambridge, MA (US); Aarif Yusuf Khakoo, Woodside, CA (US); Su-Jen Lai, Cambridge, MA (US); Zhihua Ma, Lexington, MA (US); Nobuko Nishimura, West Hills, CA (US); Vatee Pattaropong, Bedford, MA (US); Gayathri Swaminath, Brisbane, CA (US); Wen-Chen Yeh, Belmont, CA (US); Philip Dean Ramsden, Acton, MA (US); Ankit Sharma, Quincy, MA (US)

(73) Assignee: AMGEN INC., Thousand Oaks, CA (US)

( * ) Notice: Subject to any disclaimer, the term of this patent is extended or adjusted under 35 U.S.C. 154(b) by 274 days.

(21) Appl. No.: 16/347,924

(22) PCT Filed: Nov. 3, 2017

(86) PCT No.: PCT/US2017/059828
§ 371 (c)(1),
(2) Date: May 7, 2019

(87) PCT Pub. No.: WO2018/093576
PCT Pub. Date: May 24, 2018

(65) Prior Publication Data
US 2019/0290647 A1  Sep. 26, 2019

Related U.S. Application Data

(60) Provisional application No. 62/422,963, filed on Nov. 16, 2016.

(51) Int. Cl.
| | | |
|---|---|---|
| *C07D 401/12* | (2006.01) | |
| *C07D 401/14* | (2006.01) | |
| *C07D 403/12* | (2006.01) | |
| *C07D 403/14* | (2006.01) | |
| *C07D 405/14* | (2006.01) | |
| *A61K 31/506* | (2006.01) | |
| *A61P 9/04* | (2006.01) | |
| *A61K 31/4439* | (2006.01) | |

(Continued)

(52) U.S. Cl.
CPC ........ *A61K 31/506* (2013.01); *A61K 31/4196* (2013.01); *A61K 31/4439* (2013.01); *A61P 9/04* (2018.01); *C07D 401/04* (2013.01); *C07D 401/12* (2013.01); *C07D 401/14* (2013.01); *C07D 403/12* (2013.01); *C07D 403/14* (2013.01); *C07D 405/14* (2013.01); *C07D 413/04* (2013.01)

(58) Field of Classification Search
CPC .. C07D 401/12; C07D 401/14; C07D 403/12; C07D 403/14; C07D 405/14
See application file for complete search history.

(56) References Cited

U.S. PATENT DOCUMENTS

| | | |
|---|---|---|
| 4,844,730 A | 7/1989 | Moriya et al. |
| 4,941,912 A | 7/1990 | Kirsten et al. |

(Continued)

FOREIGN PATENT DOCUMENTS

| | | |
|---|---|---|
| AU | 199886243 B2 | 4/1999 |
| AU | 2012200157 A1 | 9/2012 |

(Continued)

OTHER PUBLICATIONS

SciFinder Structure Search with Substances Performed May 20, 2016.

(Continued)

*Primary Examiner* — Matthew P Coughlin
(74) *Attorney, Agent, or Firm* — Fenwick & West LLP

(57) ABSTRACT

Compounds of Formula I and Formula II, pharmaceutically acceptable salt thereof, stereoisomers of any of the foregoing, or mixtures thereof are agonists of the APJ Receptor and may have use in treating cardiovascular and other conditions. Compounds of Formula I and Formula II have the following structures: (I), (II) where the definitions of the variables are provided herein.

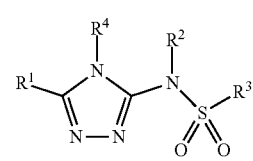

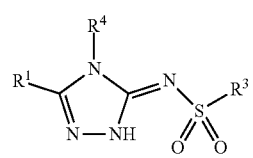

28 Claims, 3 Drawing Sheets

(51) Int. Cl.
  *A61K 31/4196*  (2006.01)
  *C07D 413/04*  (2006.01)
  *C07D 401/04*  (2006.01)

(56) References Cited

U.S. PATENT DOCUMENTS

| | | | |
|---|---|---|---|
| 5,302,718 | A | 4/1994 | Agback et al. |
| 5,328,803 | A | 7/1994 | Fukijura et al. |
| 5,411,839 | A | 5/1995 | Harder et al. |
| 5,451,588 | A | 9/1995 | Baker et al. |
| 5,510,362 | A | 4/1996 | Matassa et al. |
| 5,563,026 | A | 10/1996 | Singer |
| 5,910,504 | A | 6/1999 | Hutchinson |
| 6,069,141 | A | 5/2000 | Barbachyn et al. |
| 6,194,090 | B1 | 2/2001 | Okada |
| 6,555,693 | B2 | 4/2003 | Ge et al. |
| 6,586,423 | B2 | 7/2003 | Bilodeau et al. |
| 6,727,364 | B2 | 4/2004 | Tullis et al. |
| 6,787,555 | B2 | 9/2004 | Tullis et al. |
| 6,790,846 | B2 | 9/2004 | Clark et al. |
| 7,084,145 | B2 | 8/2006 | Armour et al. |
| 7,084,164 | B2 | 8/2006 | Tobe et al. |
| 7,169,797 | B2 | 1/2007 | Xin et al. |
| 7,297,168 | B2 | 11/2007 | Murphy et al. |
| 7,361,669 | B2 | 4/2008 | Scarborough et al. |
| 7,371,757 | B2 | 5/2008 | Morningstar et al. |
| 7,615,569 | B2 | 11/2009 | Fulp et al. |
| 7,635,751 | B2 | 12/2009 | Kitada et al. |
| 7,638,541 | B2 | 12/2009 | Chen et al. |
| 7,718,683 | B2 | 5/2010 | Charvat et al. |
| 7,776,897 | B2 | 8/2010 | Murakami et al. |
| 7,820,665 | B2 | 10/2010 | Booker et al. |
| 8,034,834 | B2 | 10/2011 | Du et al. |
| 8,053,456 | B2 | 11/2011 | Sun et al. |
| 8,063,083 | B2 | 11/2011 | Foley |
| 8,076,486 | B2 | 12/2011 | Goutopoulos et al. |
| 8,101,618 | B2 | 1/2012 | Kawamoto et al. |
| 8,252,822 | B2 | 8/2012 | An et al. |
| 8,299,107 | B2 | 10/2012 | Chimmanamada et al. |
| 8,318,790 | B2 | 11/2012 | Ying et al. |
| 8,399,464 | B2 | 3/2013 | Kuramochi et al. |
| 8,415,377 | B2 | 4/2013 | Sun et al. |
| 8,426,602 | B2 | 4/2013 | Meibom et al. |
| 8,431,604 | B2 | 4/2013 | Netz et al. |
| 8,445,518 | B2 | 5/2013 | Charvat et al. |
| 8,466,170 | B2 | 6/2013 | Klein |
| 8,492,427 | B2 | 7/2013 | Gancia et al. |
| 8,563,741 | B2 | 10/2013 | Qian et al. |
| 8,648,104 | B2 | 2/2014 | Du et al. |
| 8,673,848 | B2 | 3/2014 | Zecri et al. |
| 8,742,133 | B2 | 6/2014 | Ying et al. |
| 8,778,977 | B2 | 7/2014 | Lind et al. |
| 8,835,464 | B2 | 9/2014 | Sun et al. |
| 8,883,827 | B2 | 11/2014 | Holsworth et al. |
| 9,156,796 | B2 | 10/2015 | Hachtel et al. |
| 9,573,936 | B2 | 2/2017 | Chen et al. |
| 9,656,997 | B2 | 5/2017 | Chen et al. |
| 9,656,998 | B2 | 5/2017 | Chen et al. |
| 9,745,286 | B2 | 8/2017 | Chen et al. |
| 9,751,864 | B2 | 9/2017 | Chen et al. |
| 9,845,310 | B2 | 12/2017 | Chen et al. |
| 9,868,721 | B2 | 1/2018 | Chen et al. |
| 9,988,369 | B2 | 6/2018 | Chen et al. |
| 10,058,550 | B2 | 8/2018 | Chen et al. |
| 10,100,059 | B2 | 10/2018 | Runyon et al. |
| 10,150,760 | B2 | 12/2018 | Chen et al. |
| 10,221,162 | B2 | 3/2019 | Chen et al. |
| 2002/0107245 | A1 | 8/2002 | Wagle et al. |
| 2004/0167188 | A1 | 8/2004 | Xin et al. |
| 2005/0075275 | A1 | 4/2005 | Albrecht et al. |
| 2005/0165015 | A1 | 7/2005 | Ncube |
| 2005/0170431 | A1 | 8/2005 | Ibrahim et al. |
| 2005/0288347 | A1 | 12/2005 | Hodge et al. |
| 2006/0156480 | A1 | 7/2006 | Lim |
| 2006/0281749 | A1 | 12/2006 | Wagle et al. |
| 2008/0153869 | A1 | 6/2008 | Bressi et al. |
| 2008/0249131 | A1 | 10/2008 | Girardet et al. |
| 2009/0318438 | A1 | 12/2009 | Chen et al. |
| 2010/0130472 | A1 | 5/2010 | Young et al. |
| 2010/0249185 | A1 | 9/2010 | Du et al. |
| 2010/0280032 | A1 | 11/2010 | Zhou et al. |
| 2011/0046125 | A1 | 2/2011 | Ying |
| 2011/0158940 | A1 | 6/2011 | Byrd et al. |
| 2011/0190257 | A1 | 8/2011 | Heald et al. |
| 2011/0207788 | A1 | 8/2011 | Amberg et al. |
| 2011/0265691 | A1 | 11/2011 | Orth et al. |
| 2012/0094837 | A1 | 4/2012 | Muhlthau et al. |
| 2012/0208828 | A1 | 8/2012 | Holsworth et al. |
| 2012/0238576 | A1 | 9/2012 | Tao et al. |
| 2013/0034536 | A1 | 2/2013 | Gedulin |
| 2013/0040950 | A1 | 2/2013 | Short et al. |
| 2013/0059807 | A1 | 3/2013 | Gedulin et al. |
| 2013/0059845 | A1 | 3/2013 | Song et al. |
| 2013/0108573 | A1 | 5/2013 | Gedulin et al. |
| 2013/0109671 | A1 | 5/2013 | Gedulin et al. |
| 2013/0150385 | A1 | 6/2013 | Blackman et al. |
| 2013/0156755 | A1 | 6/2013 | Blackman et al. |
| 2013/0266636 | A1 | 10/2013 | Cheresh et al. |
| 2013/0303505 | A1 | 11/2013 | Bollu et al. |
| 2014/0005181 | A1 | 1/2014 | Smith et al. |
| 2016/0058705 | A1 | 3/2016 | Rajadas et al. |
| 2016/0060349 | A1 | 3/2016 | Van Schravendijk et al. |
| 2016/0340336 | A1 | 11/2016 | Chen et al. |
| 2016/0355507 | A1 | 12/2016 | Johnsen et al. |
| 2017/0035744 | A1 | 2/2017 | Chen et al. |
| 2017/0037026 | A1 | 2/2017 | Chen et al. |
| 2017/0042871 | A1 | 2/2017 | Chen et al. |
| 2017/0042872 | A1 | 2/2017 | Chen et al. |
| 2017/0042897 | A1 | 2/2017 | Chen et al. |
| 2017/0044131 | A1 | 2/2017 | Chen et al. |
| 2017/0281625 | A1 | 10/2017 | Chen et al. |
| 2017/0320860 | A1 | 11/2017 | Chen et al. |
| 2017/0355734 | A1 | 12/2017 | Llorens-Cortez et al. |
| 2018/0118698 | A1 | 5/2018 | Smith et al. |
| 2019/0100510 | A1 | 4/2019 | Dransfield et al. |

FOREIGN PATENT DOCUMENTS

| | | | | |
|---|---|---|---|---|
| DE | 3928605 | A1 | 3/1991 | |
| DE | 4035141 | A1 | 5/1992 | |
| EP | 0121082 | A1 * | 10/1984 | ........... C07D 239/47 |
| EP | 0121082 | B1 | 10/1984 | |
| EP | 0330959 | A2 | 2/1989 | |
| EP | 0409332 | A2 | 1/1991 | |
| EP | 0419831 | A2 * | 4/1991 | ........... C07D 403/14 |
| EP | 0484750 | A1 | 10/1991 | |
| JP | 2003-5356 | A | 8/2003 | |
| JP | 2003-321456 | A | 11/2003 | |
| JP | 2005-170939 | A | 6/2005 | |
| WO | 91/11909 | A1 | 8/1991 | |
| WO | 99/43671 | A1 | 9/1999 | |
| WO | 01/87855 | A1 | 11/2001 | |
| WO | 2005/039569 | A1 | 5/2005 | |
| WO | 2006/026488 | A1 | 3/2006 | |
| WO | 2006/055760 | A1 | 5/2006 | |
| WO | 2006/080533 | A1 | 8/2006 | |
| WO | 2006/095783 | A1 | 9/2006 | |
| WO | 2006/100588 | A1 | 9/2006 | |
| WO | 2006/109817 | A1 | 10/2006 | |
| WO | 2007/007688 | A1 | 1/2007 | |
| WO | 2007/139952 | A2 | 12/2007 | |
| WO | 2007/139967 | A2 | 12/2007 | |
| WO | 2008/008375 | A2 | 1/2008 | |
| WO | 2008/021364 | A2 | 2/2008 | |
| WO | 2008/103352 | A1 | 8/2008 | |
| WO | 2009/075890 | A2 | 6/2009 | |
| WO | 2009/115503 | A1 | 9/2009 | |
| WO | 2010/017545 | A2 | 2/2010 | |
| WO | 2011/146801 | A1 | 11/2011 | |
| WO | 2012/076898 | A1 | 6/2012 | |
| WO | 2012/116247 | A1 | 8/2012 | |
| WO | 2013/067162 | A1 | 5/2013 | |
| WO | 2013/067165 | A1 | 5/2013 | |
| WO | 2013/074594 | A1 | 5/2013 | |

(56) References Cited

FOREIGN PATENT DOCUMENTS

| | | | |
|---|---|---|---|
| WO | 2013/106437 A1 | 7/2013 | |
| WO | 2013/106614 A1 | 7/2013 | |
| WO | 2013/111110 A2 | 8/2013 | |
| WO | 2013/148857 A1 | 10/2013 | |
| WO | 2013/184755 A2 | 12/2013 | |
| WO | 2014/044738 A1 | 3/2014 | |
| WO | 2014/099984 A1 | 6/2014 | |
| WO | 2014/150326 A1 | 9/2014 | |
| WO | 2014/194270 A1 | 12/2014 | |
| WO | 2015/140296 A2 | 9/2015 | |
| WO | 2015/163818 A1 | 10/2015 | |
| WO | 2015/184011 A2 | 12/2015 | |
| WO | 2015/188073 A1 | 12/2015 | |
| WO | WO-2015184011 A2 * | 12/2015 | ........... C07D 409/14 |
| WO | 2016/151018 A1 | 9/2016 | |
| WO | 2016/196771 A1 | 12/2016 | |
| WO | 2017/066402 | 4/2017 | |
| WO | 2017/091513 A1 | 6/2017 | |
| WO | 2017/096130 A1 | 6/2017 | |
| WO | 2017/100558 A1 | 6/2017 | |
| WO | 2017/106396 A1 | 6/2017 | |
| WO | 2017/165640 A1 | 9/2017 | |
| WO | 2017/174758 A1 | 10/2017 | |
| WO | 2017/218617 A1 | 12/2017 | |
| WO | 2017/218633 A1 | 12/2017 | |
| WO | 2018/071526 A1 | 4/2018 | |
| WO | 2018/071622 A1 | 4/2018 | |
| WO | 2018/093577 A1 | 5/2018 | |
| WO | 2018/093579 A1 | 5/2018 | |
| WO | 2018/093580 A1 | 5/2018 | |
| WO | 2018/097944 A1 | 5/2018 | |
| WO | 2018/097945 A1 | 5/2018 | |

OTHER PUBLICATIONS

SciFinder Structute Search with References Performed May 20, 2016.
SciFinder Structure Search Sulfonamide Tail with Substance Performed May 12, 2016.
Berry, M. F. et al., "Apelin Has In Vivo Inotropic Effects on Normal and Failing Hearts," Circulation 110, pp. II187-II193, (2004).
Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett. 6b00038; lccn:2009200243; oclcnum:455500725; serissn:1948-5875; itc:84452717; itcp:10547084 (2016).
Chun, H. et al., "Apelin Signaling Antagonizes ANG II Effects in Mouse Models of Atherosclerosis," J. Clin. Invest. 118(10), pp. 3343-3354 (2008).
Japp, A. G. et al., "Acute Cardiovascular Effects of Apelin in Humans," Circulation 121, pp. 1818-1827 (2010).
Modzelewska-Banachiewicz et al., "Synthesis and Biological Action of 3-4-Disubstituted 5-Arylsulphonylamino-1,2,4-triazoles," Pharmazie 54, pp. 588-589 (1999).
Pauli, A. et al., "Toddler: An Embryonic Signal That Promotes Cell Movement via Apelin Receptors," Science 343, pp. 1248636-0-1248636-8 (2014).
Siddiquee, K. et al., "The Apelin receptor Inhibits the Angiotensin II Type 1 Receptor via Allosteric Trans-Inhibition," Br. J. Pharmacol. 168, pp. 1104-1117 (2013).
Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).
Tatemoto, K. et al., "Isolation and Characterization of a Novel Endogenous Peptide Ligand for the Human APJ Receptor," Bioch. Biophys. Res. Comm., 251, pp. 471-476 (1998).
Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).

Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).
Barnes, G. et al., "Translational Promise of the Apelin-APJ System," Heart 96(13), pp. 1011-1016 (2010).
Kawamata, Y. et al., "Molecular Properties of Apelin: Tissue Distribution and Receptor Binding," Biochemica et Biophysica Acta 1538(2-3), pp. 162-171 (2001).
Nishizawa, N. et al., "High Potency Analog of Apelin, A Ligand of Orphan GPCT APJ," T Shiori (ed.) Petptide Science 2000: Proceedings of the 37$^{th}$ Japanese Peptide Symposium, pp. 151-154 (2000).
Medhurst, A. D. et al., "Pharmacological and Immunohistochemical Characteization of the APJ Receptor and its Endogenous Ligand Apelin," J. Neurochem. 84(5), pp. 1162-1172 (2003).
Hamada, J. et al., "Evaluation of Novel Cyclic Analogoues of Apelin," Int. J. Mol. Med. 22, pp. 547-552 (2008).
Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).
Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).
Thomas, J.B. et al., "Identification of N-[5-{[(4-Methylphenyl)sulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).
Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett. 25, pp. 2060-2064 (2015).
Thompson, M. E. "α,N-Alkanesulfonamide Dianions: Formation and Chemoselective C-Alkylation," J. Org. Chem. 49, pp. 1700-1703 (1984).
Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).
Singh, O. M. et al., "A Facile One-Pot Synthetic Method for 1,2,4-Triazoles and 1,3-Disubstituted Thioureas," J. Chem. Res. pp. 483-485 (2006).
Carlsen, P.J.J. et al., "Synthesis of Unsymmetrically Substituted 4H-1,2,4-Triazoles," J. Heterocyclic Chem. 31, pp. 805-807 (1994).
Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).
Hassan, A. A. et al., "Thiosemicarbazides in Heterocyclization," J. Heterocyclic Chem. 48, pp. 495-516 (2011).
Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).
Ivanova, N. V. et al., "A Convenient Synthesis of 4,5-Disubstituted 1,2,4-Triazoles Functionalized in Position 3," Synthesis 1, pp. 156-160 (2005).
Modzelewska-Banaschiewicz, B et al., "Antiviral Activity of the Products of Cyclization of Dimethyl 2-[1-arylamino-1-arylmethylideine)hydrazono]succinate," Eur. J. Med. Chem. 36, pp. 93-99 (2001).
SciFinder Structure Search with Substances Performed Sep. 1, 2016.
SciFinder Structure Search with References Performed Sep. 1, 2016.
Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).
Johnson, M. G. et al., "Convenient Route to Secondary Sulfinates: Application to the Stereospecific Synthesis of α-C-Chiral Sulfonamides," Organic Letters 16(23), pp. 6248-6251 (2014).

(56) References Cited

OTHER PUBLICATIONS

Enders, D. et al., "Asymmetric Synthesis of α-Substituted N-Methylsulfonamides," Helvetica Chimica Acta, 85, pp. 3657-3677 (2002).
Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).
Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).
Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).
International Search Report and Written Opinion for analogous PCT Application No. PCT/US2017/059828, dated Mar. 26, 2018.
SciFinder Intermediate Structure Search with Substances Performed May 6, 2016.
SciFinder Intermediate Structure Search with References Performed May 6, 2016.
SciFinder Structure Search with Substances Performed May 3, 2016.
SciFinder Structure Search with References Performed May 3, 2016.

\* cited by examiner

ALKYL SUBSTITUTED TRIAZOLE COMPOUNDS AS AGONISTS OF THE APJ RECEPTOR

CROSS REFERENCES TO RELATED APPLICATIONS

This application is the National Stage of International Application No. PCT/US2017/059828, filed Nov. 3, 2017, which claims the benefit of U.S. Provisional Application No. 62/422,963, filed on Nov. 16, 2016, all of which are hereby incorporated by reference in their entireties and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77-also referred to as Apelin-36) and a smaller 13 residue polypeptide (Apelin 65-77-also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at subnanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin-13. Nishizawa et al., in: T. Shioiri (ed.), Peptide Science 2000: Proceedings of the $37^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule, but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMedChem 7:318-325, 2012. Additionally, PCT/US2013/075773 describes a group of modifications, including substitution of non-canonical amino acids and changes at the N- and C-terminal of the apelin molecule that can affect, inter alia, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336, WO 2016/187308, WO 2015/184011, and WO 2015/188073.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

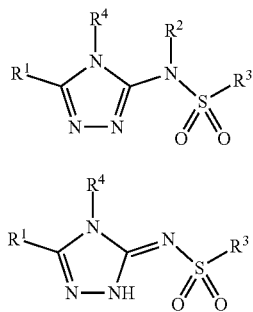

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted $C_1$-$C_8$ straight or branched chain alkyl or $R^1$ is a $C_1$-$C_8$ straight or branched chain alkyl substituted with 1, 2, or 3 $R^{1a}$ substituents;

$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O— (heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a}$ groups that include a $C_6$-$C_{10}$ aryl group, the heteroaryl of any of the $R^{1a}$ groups that include a heteroaryl group, the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group are unsubstituted or are substituted with 1, 2, or 3 $R^{1a'}$ substituents; and further wherein the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group may additionally be substituted with 1 or 2 oxo substituents, and the S atom of the heterocyclyl of any of the $R^{1a}$ groups that include a heterocyclyl group may contain one or two oxo substituents, and still further wherein, the heteroaryl of any of the $R^{1a}$ groups that include a heteroaryl group may include an N-oxide if the heteroaryl includes a N heteroatom;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q a group of formula —(CR$^{3d}$R$^{3e}$)—(CR$^{3f}$R$^{3g}$)—CH(OH)-Q, a group of formula —(CR$^{3a}$R$^{3e}$)—(CR$^{3f}$R$^{3g}$)—(CR$^{3f}$R$^{3g}$)-Q, a group of formula —($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl) heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, a monocyclic heteroaryl group with 5 or 6 ring members containing 1, 2, or 3 N atoms, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{4c}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

wherein if $R^4$ is a cyclopropyl group then $R^3$ is a group of formula —$(CR^{3d}R^{3e})$—$(CR^{3f}R^{3g})$-Q or $R^3$ is a group of formula -(heterocyclyl)-Q.

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy or chronic kidney disease.

Other objects, features and advantages of the invention will become apparent to those skilled in the art from the following description and claims.

DETAILED DESCRIPTION OF THE INVENTION

Figure 1:
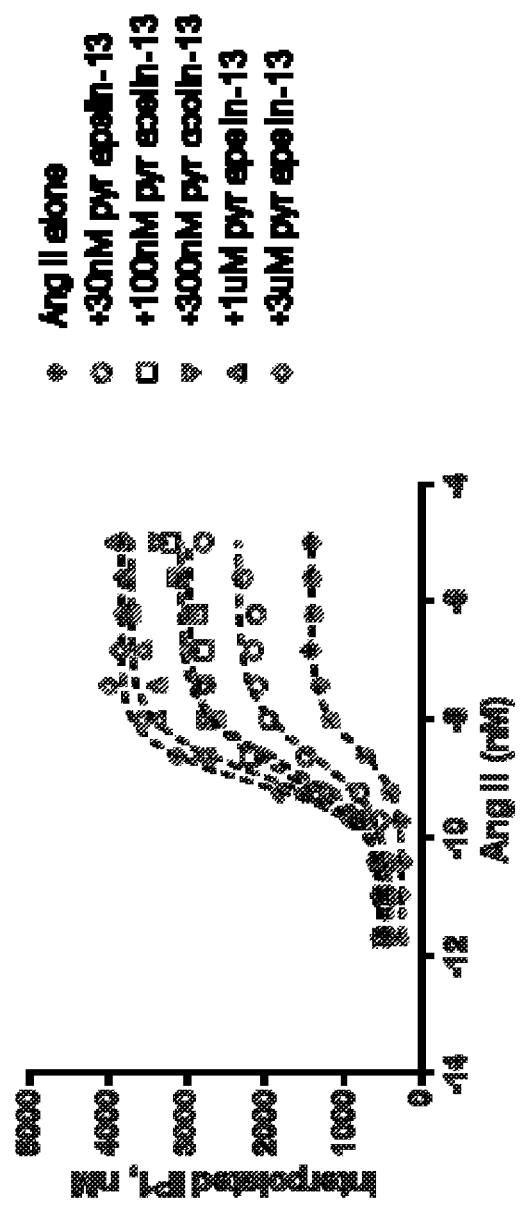
FIG. 1 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when R⁴ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where R² is H. These forms are illustrated below as Tautomer A and Tautomer B:

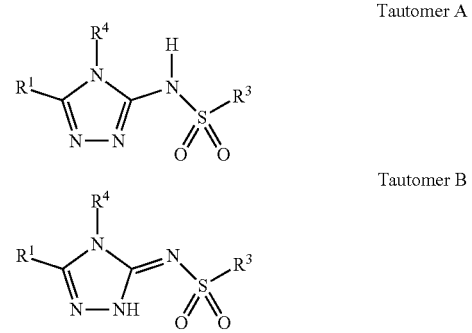

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

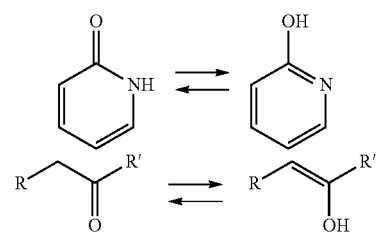

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 (4° C.). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—($C_1$-$C_6$ alkyl)-OH will be recognized as a group where an —O atom is bonded to a $C_1$-$C_6$ alkyl group and one of the H atoms bonded to a C atom of the $C_1$-$C_6$ alkyl group is replaced with a bond to the O atom of an —OH group. As another example, a group —O—($C_1$-$C_6$ alkyl)-O—($C_1$-$C_6$ alkyl) will be recognized as a group where an —O atom is bonded to a first $C_1$-$C_6$ alkyl group and one of the H atoms bonded to a C atom of the first $C_1$-$C_6$ alkyl group is replaced with a bond to a second O atom that is bonded to a second $C_1$-$C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a ($C_3$-$C_8$)cycloalkyl, a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_8$)cycloalkyl, a ($C_3$-$C_7$)cycloalkyl, a ($C_3$-$C_6$)cycloalkyl, or a ($C_4$-$C_7$)cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups using alternative language.

"Heterocyclyl" and "heterocyclic" refer to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

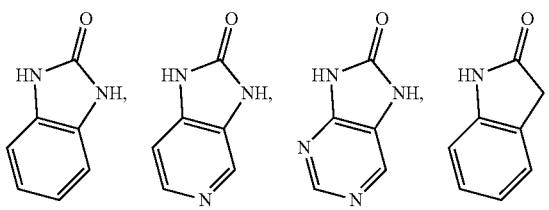 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O—) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like. In heterocyclyl group containing a sulfur atom, the sulfur atom may be bonded to 0, 1, or 2 O atoms in addition to the adjacent ring members such that the sulfur may in various oxidation states. For example, a saturated 5-membered hetereocycle containing one heteroatom which is a S may include the following heterocycles.

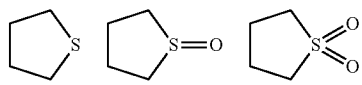

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

EMBODIMENTS

The embodiments listed below are presented in numbered form for convenience and in ease and clarity of reference in referring back to multiple embodiments.

In a first aspect the invention provides a first embodiment which is a compound of Formula I or Formula II:

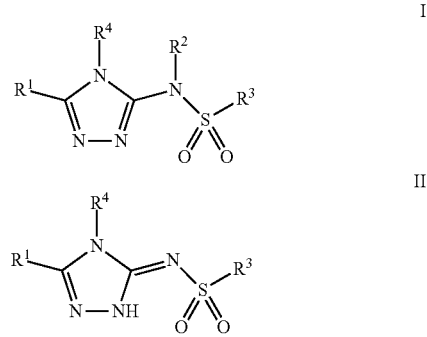

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted $C_1$-$C_8$ straight or branched chain alkyl or $R^1$ is a $C_1$-$C_8$ straight or branched chain alkyl substituted with 1, 2, or 3 $R^{1a}$ substituents;

$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a}$ groups that include a $C_6$-$C_{10}$ aryl group, the heteroaryl of any of the $R^{1a}$ groups that include a heteroaryl group, the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group are unsubstituted or are substituted with 1, 2, or 3 $R^{1a'}$ substituents; and further wherein the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group may additionally be substituted with 1 or 2 oxo substituents, and the S atom of the heterocyclyl of any of the $R^{1a}$ groups that include a heterocyclyl group may contain one or two oxo substituents, and still further wherein, the heteroaryl of any of the $R^{1a}$ groups that include a heteroaryl group may include an N-oxide if the heteroaryl includes a N heteroatom;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from a group of formula —(C$R^{3d}R^{3e}$)—(C$R^{3f}R^{3g}$)-Q, a group of formula —(C$R^{3d}R^{3e}$)—(C$R^{3f}R^{3g}$)—C(=O)-Q, a group of formula —(C$R^{3d}R^{3e}$)—(C$R^{3f}R^{3g}$)—CH(OH)-Q, a group of formula —(C$R^{3d}R^{3e}$)—(C$R^{3f}R^{3g}$)—(C$R^{3f}R^{3g}$)-Q, a group of formula —($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-NH$_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl) heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, phenyl, a monocyclic heteroaryl group with 5 or 6 ring members containing 1, 2, or 3 N atoms, —S(═O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{4c}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, or —S(═O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, or —S(═O)$_2$—($C_1$-$C_6$ alkyl);

wherein if $R^4$ is a cyclopropyl group then $R^3$ is a group of formula —($CR^{3d}R^{3e}$)—($CR^{3f}R^{3g}$)-Q or $R^3$ is a group of formula -(heterocyclyl)-Q.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —($CR^{3d}R^{3e}$)—($CR^{3f}R^{3g}$)-Q, or a group of formula -(heterocyclyl)-Q.

3. The compound of embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —($CR^{3d}R^{3e}$)—($CR^{3f}R^{3g}$)_Q.

4. The compound of embodiment 3 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —($CR^{3d}R^{3e}$)—($CR^{3f}R^{3g}$)-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

5. The compound of embodiment 3 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —($CR^{3d}R^{3e}$)—($CR^{3f}R^{3g}$)-Q and further wherein, $R^{3d}$ and $R^{3e}$ are independently selected from —H, or —$C_1$-$C_6$ alkyl; and $R^{3f}$ and $R^{3g}$ are independently selected from —H, —$C_1$-$C_6$ alkyl, —OH, or —O—($C_1$-$C_6$ alkyl).

6. The compound of any one of embodiments 3-5 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is not —H.

7. The compound of any one of embodiments 3-5 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is a —$C_1$-$C_6$ alkyl.

8. The compound of embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q.

9. The compound of embodiment 8 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent.

10. The compound of embodiment 8 or 9 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent independently selected from —OH, or —O—($C_1$-$C_6$ alkyl).

11. The compound of any one of embodiments 1, 2, or 8-10 or the pharmaceutically acceptable salt thereof, the tautomer thereof, the pharmaceutically acceptable salt of the tautomer, the stereoisomer of any of the foregoing, or the mixture thereof, wherein $R^3$ is selected from

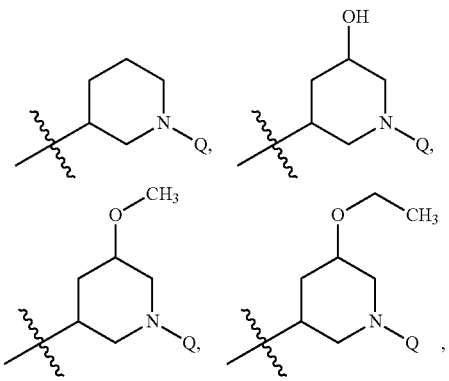

-continued

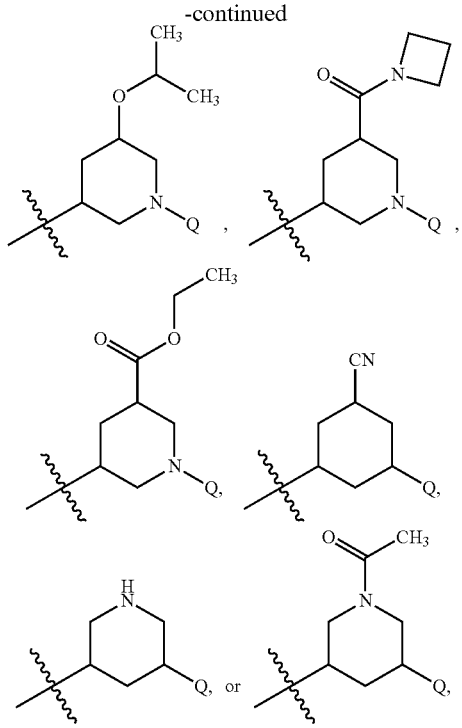

wherein the symbol ∿, when drawn across a bond, indicates the point of attachment to the rest of the molecule.

12. The compound of any one of embodiments 1, 2, or 8-10 or the pharmaceutically acceptable salt thereof, the tautomer thereof, the pharmaceutically acceptable salt of the tautomer, the stereoisomer of any of the foregoing, or the mixture thereof, wherein $R^3$ is selected from

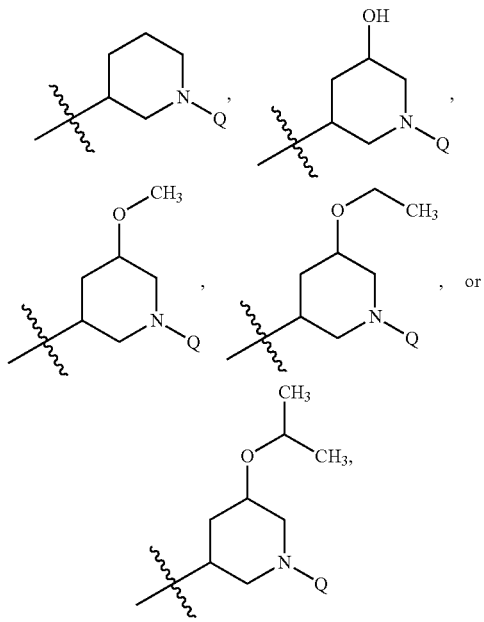

wherein the symbol ∿, when drawn across a bond, indicates the point of attachment to the rest of the molecule.

13. The compound of any one of embodiments 1, 2, or 8-10 or the pharmaceutically acceptable salt thereof, the tautomer thereof, the pharmaceutically acceptable salt of the tautomer, the stereoisomer of any of the foregoing, or the mixture thereof, wherein $R^3$ is selected from

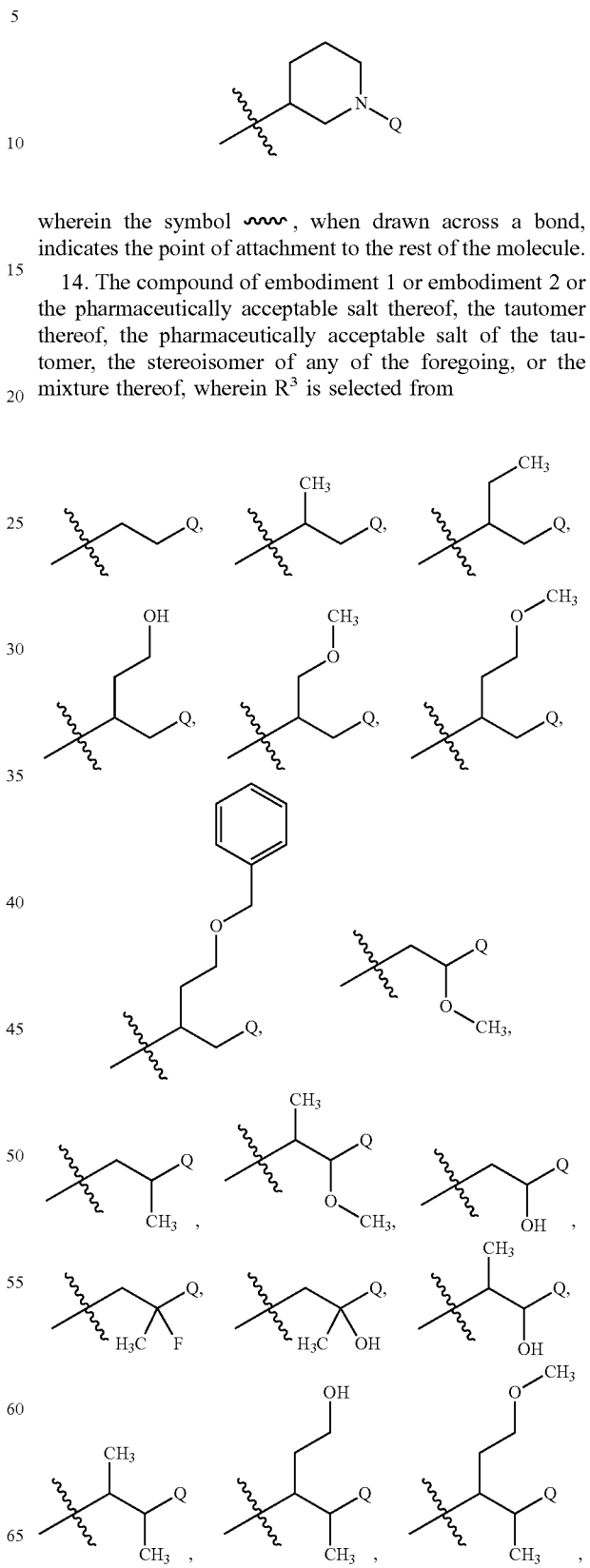

wherein the symbol ∿, when drawn across a bond, indicates the point of attachment to the rest of the molecule.

14. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is selected from -continued

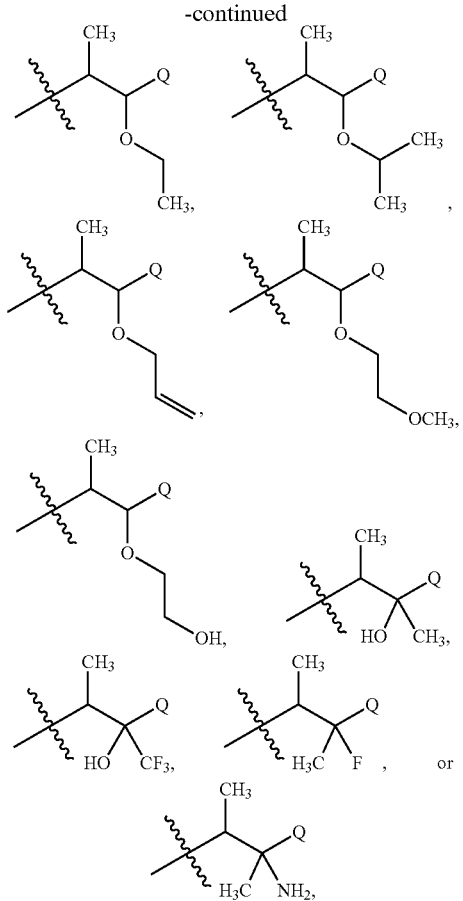

15. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is selected from

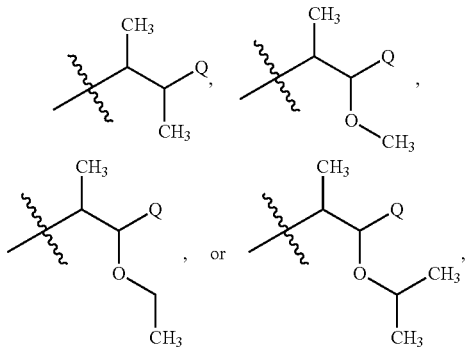

wherein the symbol ⌇, when drawn across a bond, indicates the point of attachment to the rest of the molecule.

16. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is

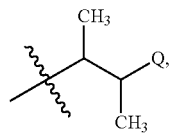

wherein the symbol ⌇, when drawn across a bond, indicates the point of attachment to the rest of the molecule.

17. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is

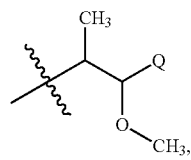

wherein the symbol ⌇, when drawn across a bond, indicates the point of attachment to the rest of the molecule.

18. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is

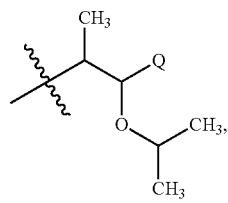

wherein the symbol ⌇, when drawn across a bond, indicates the point of attachment to the rest of the molecule.

19. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is selected from

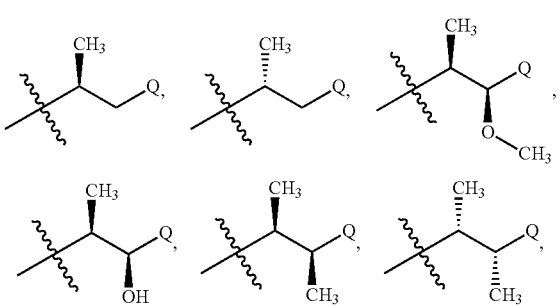

-continued

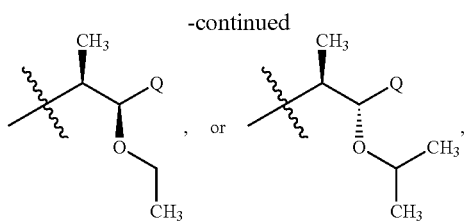

wherein the symbol ⌇, when drawn across a bond, indicates the point of attachment to the rest of the molecule.

20. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^3$ is

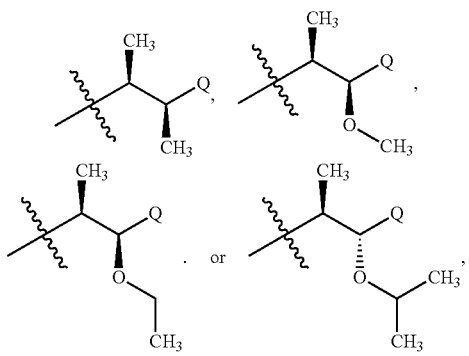

wherein the symbol ⌇, when drawn across a bond, indicates the point of attachment to the rest of the molecule.

21. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, or phenyl, any of which may be unsubstituted or substituted with 1, 2, or 3 $R^Q$ substituents.

22. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is an unsubstituted phenyl or is a phenyl substituted with 1, 2, or 3 $R^Q$ substituents.

23. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

24. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl, pyridinyl, or pyrazinyl group and Q is unsubstituted or is substituted with 1, 2, or 3 $R^Q$ substituents.

25. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl group and Q is unsubstituted or is substituted with 1, 2, or 3 $R^Q$ substituents.

26. The compound of any one of embodiments 1-25 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

27. The compound of any one of embodiments 1-25 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

28. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is selected from

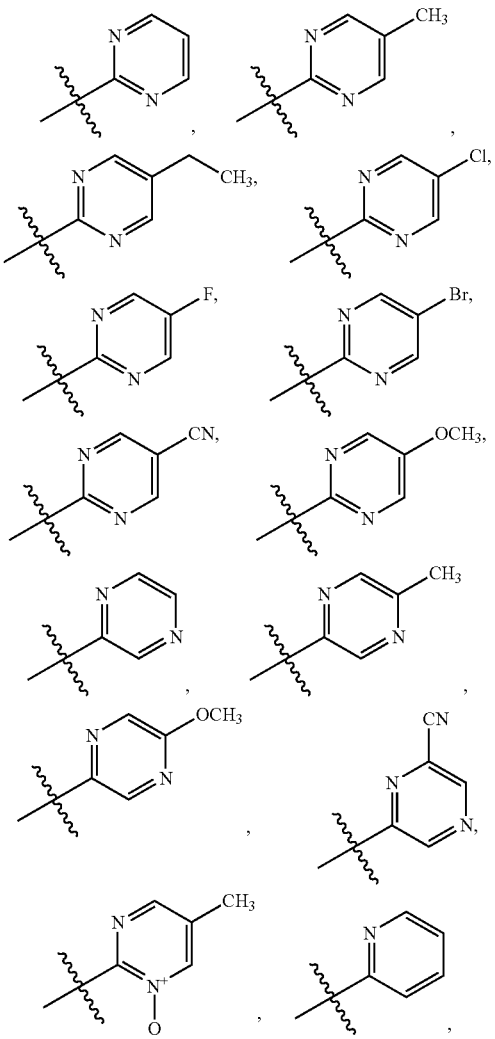

-continued

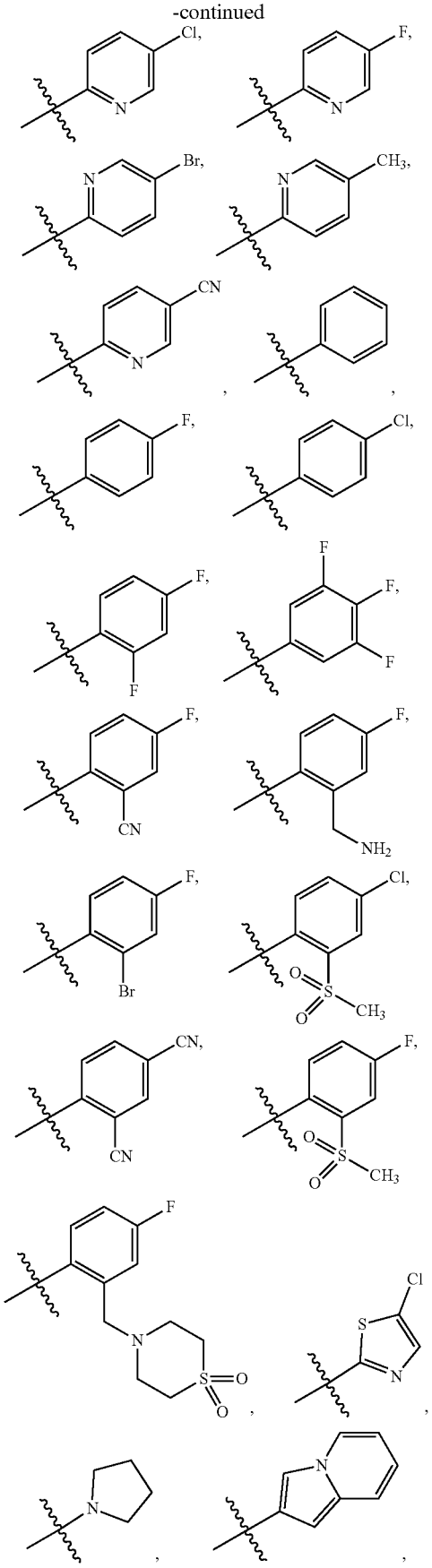

-continued

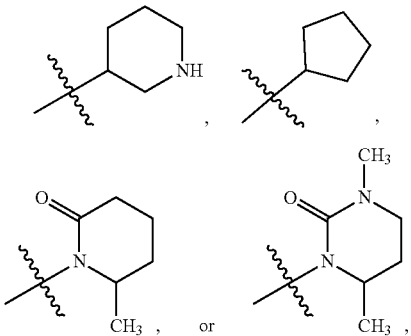

wherein the symbol ～, when drawn across a bond, indicates the point of attachment to the rest of the molecule.

29. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is selected from

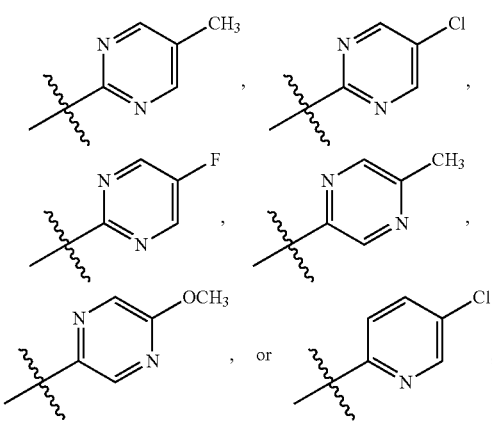

wherein the symbol ～, when drawn across a bond, indicates the point of attachment to the rest of the molecule.

30. The compound of embodiment 29 or the pharmaceutically acceptable salt thereof, the tautomer thereof, the pharmaceutically acceptable salt of the tautomer, the stereoisomer of any of the foregoing, or the mixture thereof, wherein Q is

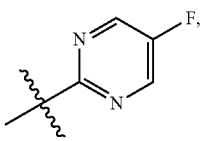

wherein the symbol ～, when drawn across a bond, indicates the point of attachment to the rest of the molecule.

31. The compound of embodiment 29 or the pharmaceutically acceptable salt thereof, the tautomer thereof, the pharmaceutically acceptable salt of the tautomer, the stereoisomer of any of the foregoing, or the mixture thereof, wherein Q is

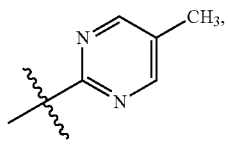 [SMILES: *c1ncc(C)cn1]

wherein the symbol ⌇, when drawn across a bond, indicates the point of attachment to the rest of the molecule. ⌇

32. The compound of embodiment 29 or the pharmaceutically acceptable salt thereof, the tautomer thereof, the pharmaceutically acceptable salt of the tautomer, the stereoisomer of any of the foregoing, or the mixture thereof, wherein Q is

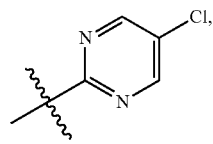 [SMILES: *c1ncc(Cl)cn1]

wherein the symbol ⌇, when drawn across a bond, indicates the point of attachment to the rest of the molecule. ⌇

33. The compound of embodiment 29 or the pharmaceutically acceptable salt thereof, the tautomer thereof, the pharmaceutically acceptable salt of the tautomer, the stereoisomer of any of the foregoing, or the mixture thereof, wherein Q is

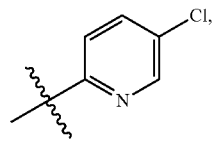

wherein the symbol ⌇, when drawn across a bond, indicates the point of attachment to the rest of the molecule.

34. The compound of embodiment 29 or the pharmaceutically acceptable salt thereof, the tautomer thereof, the pharmaceutically acceptable salt of the tautomer, the stereoisomer of any of the foregoing, or the mixture thereof, wherein Q is

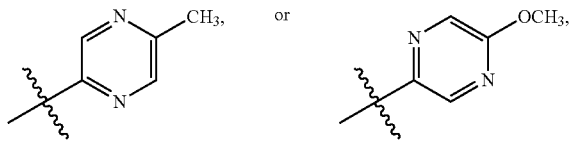 [SMILES: *c1cnc(C)cn1 ; "or" ; *c1cnc(OC)cn1]

wherein the symbol ⌇, when drawn across a bond, indicates the point of attachment to the rest of the molecule.

35. The compound of any one of embodiments 1-34 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

36. The compound of any one of embodiments 1-35 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

37. The compound of any one of embodiments 1-35 or the pharmaceutically acceptable salt thereof, the tautomer thereof, the pharmaceutically acceptable salt of the tautomer, the stereoisomer of any of the foregoing, or the mixture thereof, wherein $R^4$ is a cyclopropyl, cyclobutyl, cyclopentyl, cyclohexyl, or tetrahydropyranyl, any of which may be unsubstituted or substituted with 1, 2, or 3 $R^{4a}$ substituents.

38. The compound of any one of embodiments 1-37 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, NH($C_1$-$C_6$ alkyl-OH), —C(=O)$NH_2$, —C(=O)NH($C_1$-$C_6$ alkyl), or —C(=O)N($C_1$-$C_6$ alkyl)$_2$.

39. The compound of embodiment 38 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Cl, —Br, —CN, —$CF_3$, —$OCH_3$, or —$OCHF_2$.

40. The compound of embodiment 38 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F or, —$OCH_3$.

41. The compound of any one of embodiments 1-35 or the pharmaceutically acceptable salt thereof, the stereoisomer of any of the foregoing, or the mixture thereof, wherein $R^4$ is selected from

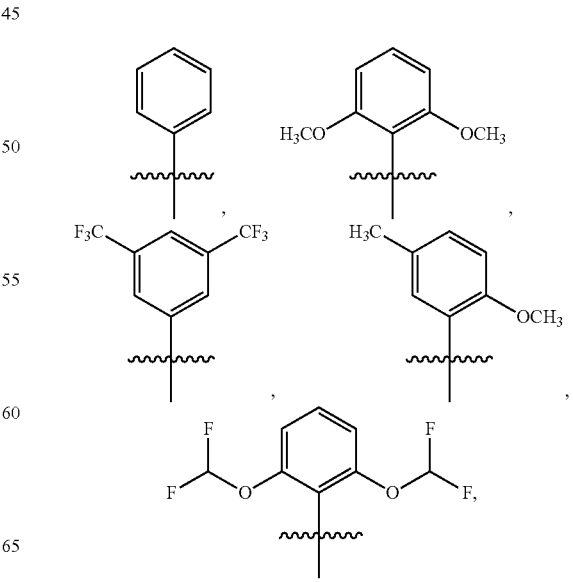

-continued
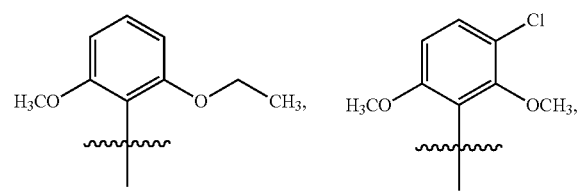
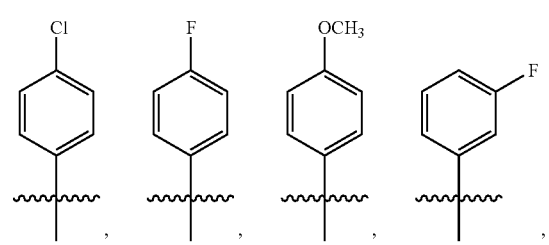
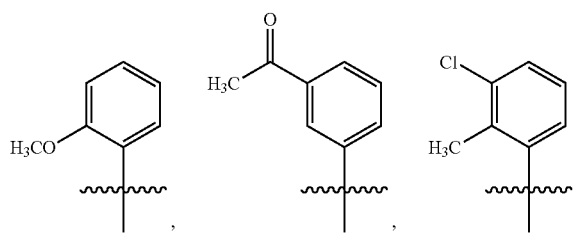
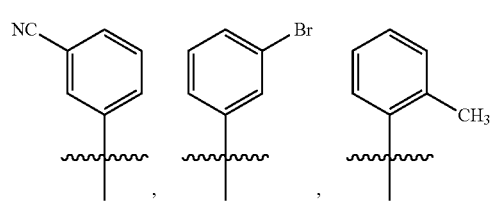
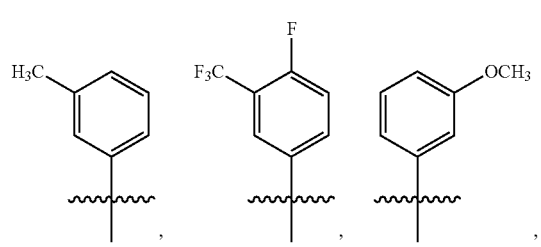
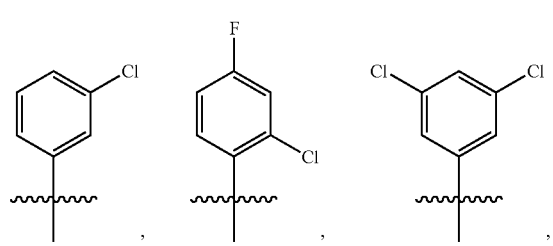
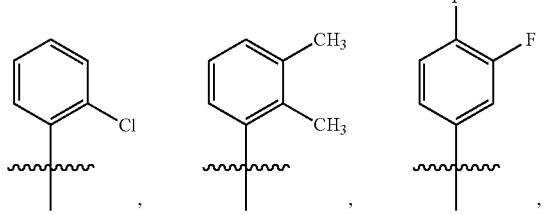
-continued
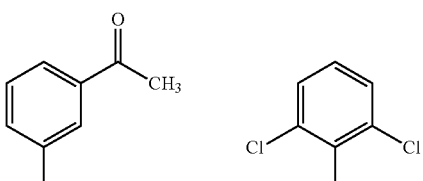
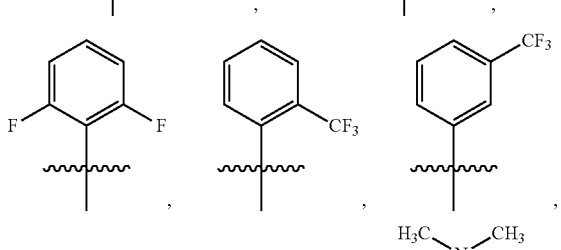
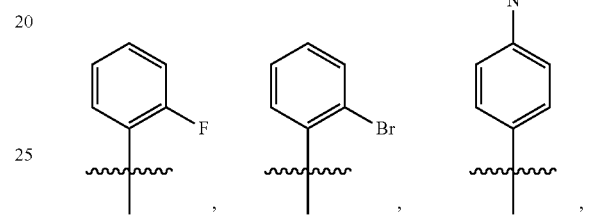
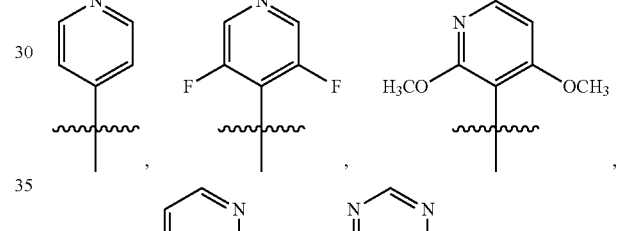
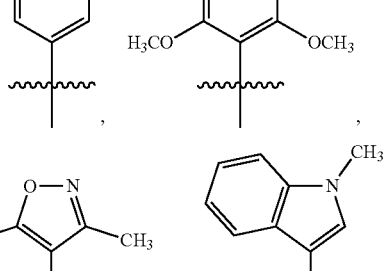
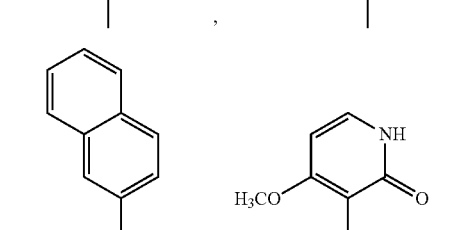
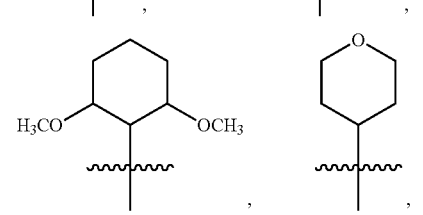

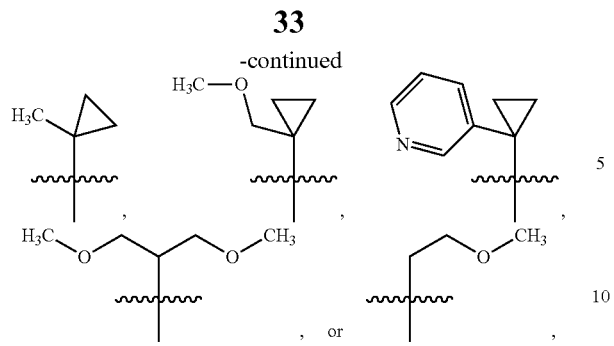

wherein the symbol ⌇, when drawn across a bond, indicates the point of attachment to the rest of the molecule.

42. The compound of any one of embodiments 1-35 or the pharmaceutically acceptable salt thereof, the stereoisomer of any of the foregoing, or the mixture thereof, wherein $R^4$ is selected from

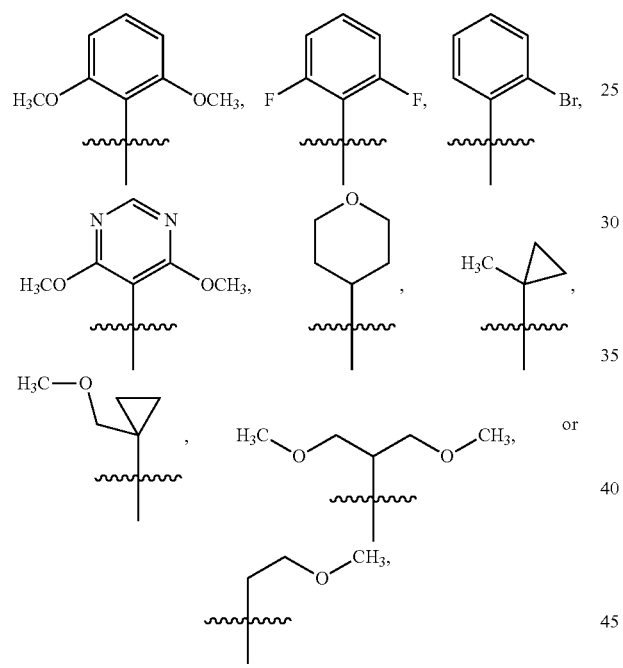

wherein the symbol ⌇, when drawn across a bond, indicates the point of attachment to the rest of the molecule.

43. The compound of any one of embodiments 1-35 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl or pyrimidinyl substituted with 1 or 2 $R^{4a}$ substituents.

44. The compound of embodiment 43 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

45. The compound of embodiment 43 or the pharmaceutically acceptable salt thereof, the tautomer thereof, the pharmaceutically acceptable salt of the tautomer, the stereoisomer of any of the foregoing, or the mixture thereof, wherein $R^4$ is

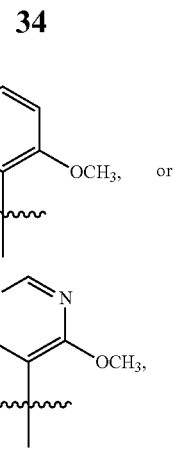

wherein the symbol ⌇, when drawn across a bond, indicates the point of attachment to the rest of the molecule.

46. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

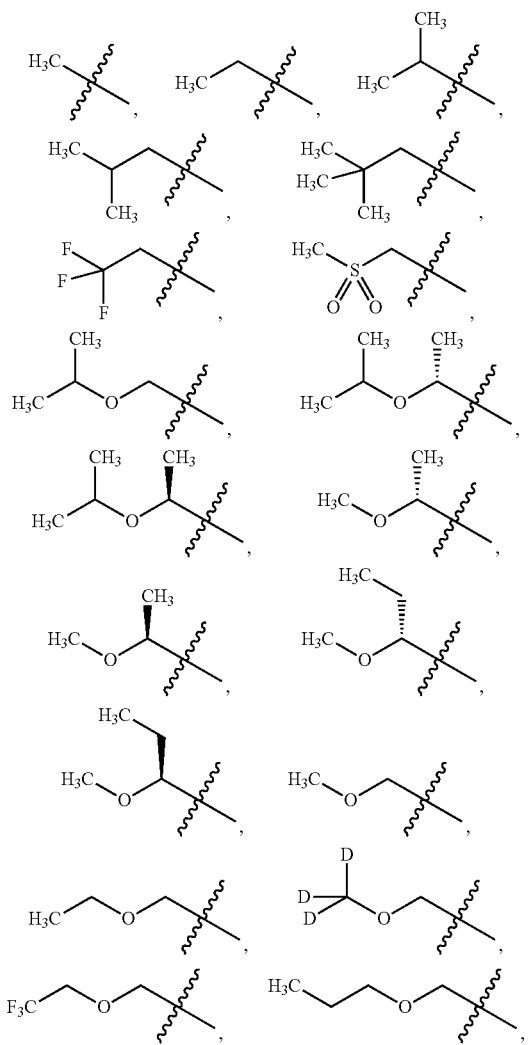

-continued
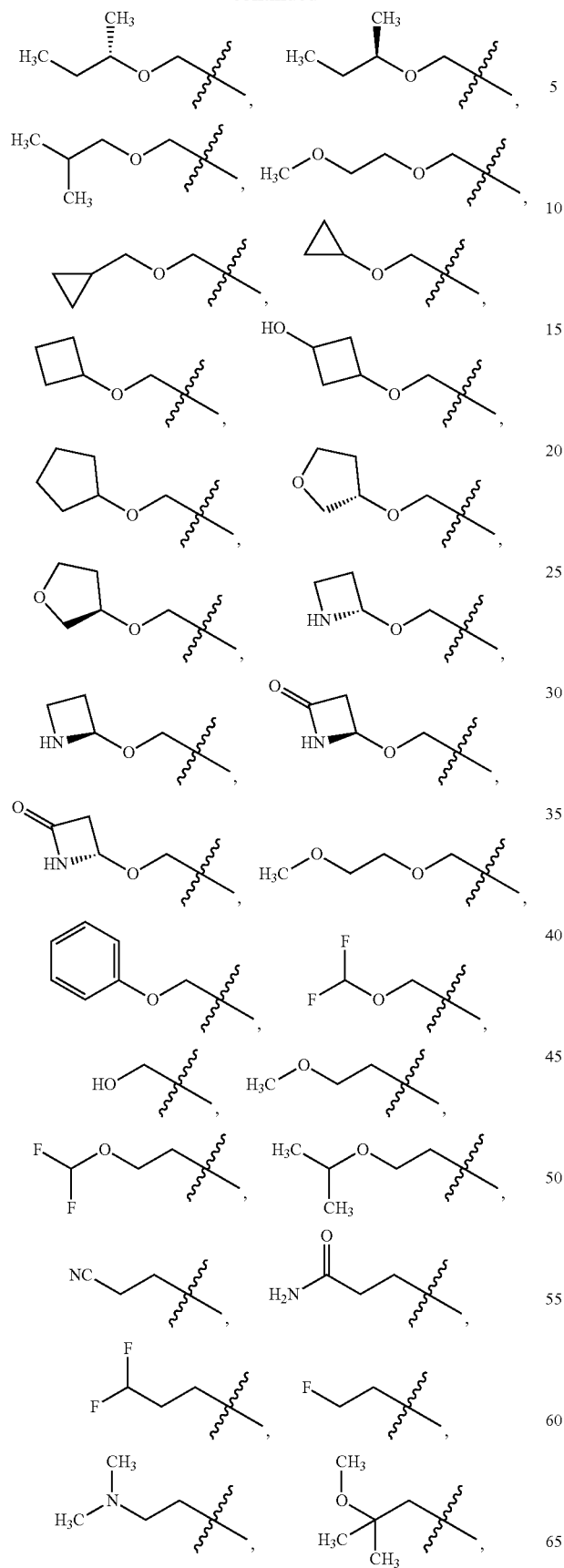
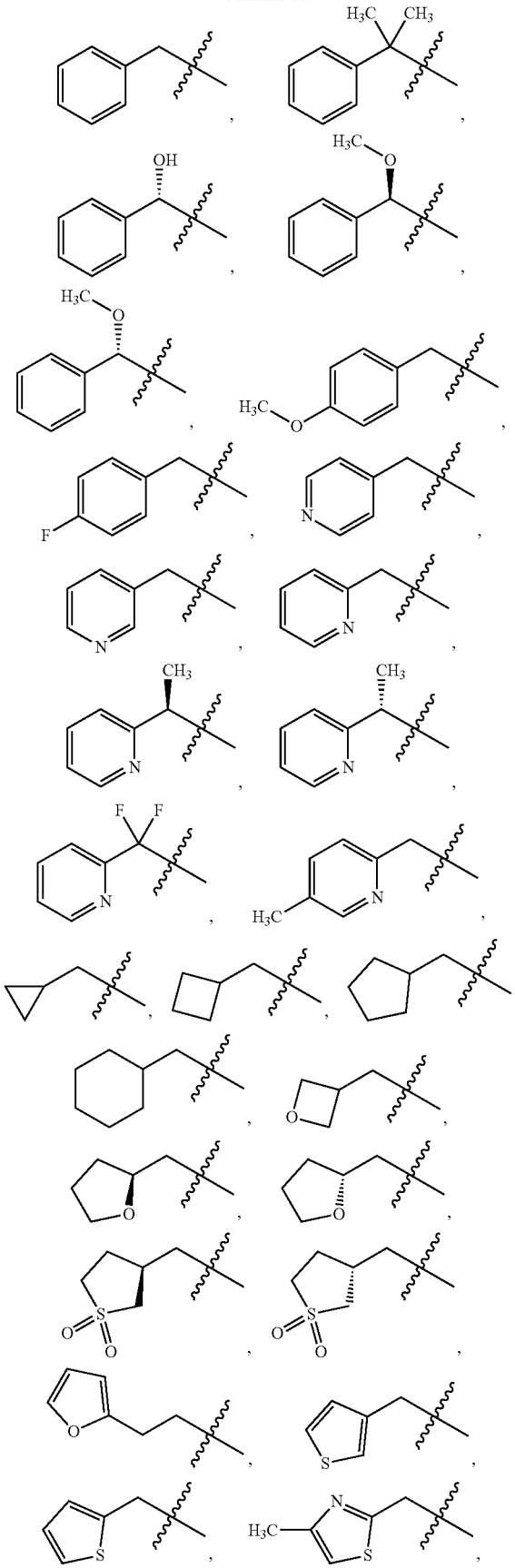

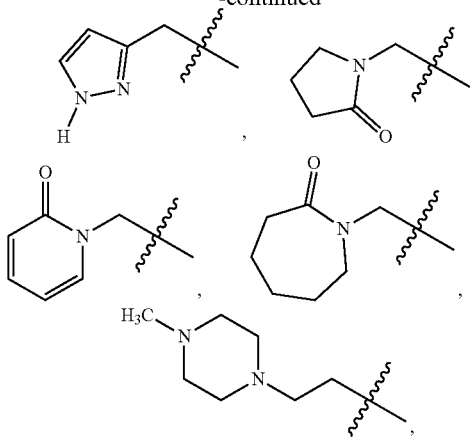

wherein the symbol ⌇, when drawn across a bond, indicates the point of attachment to the rest of the molecule.

47. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

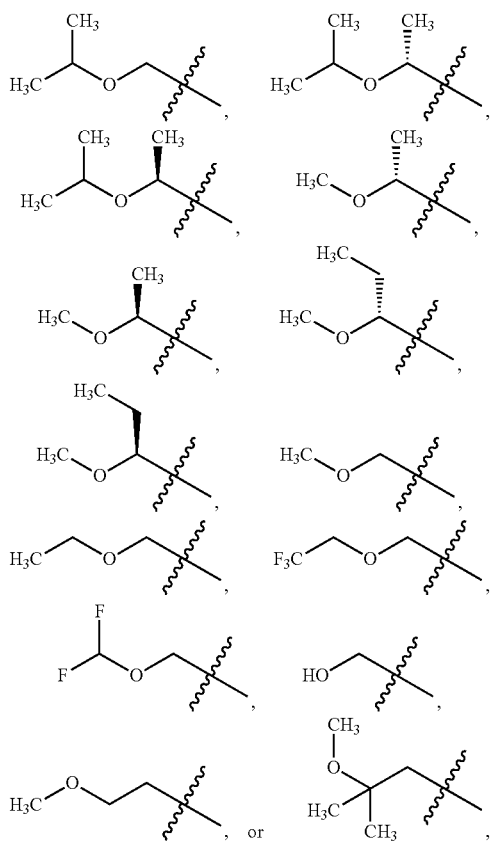

wherein the symbol ⌇, when drawn across a bond, indicates the point of attachment to the rest of the molecule.

48. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

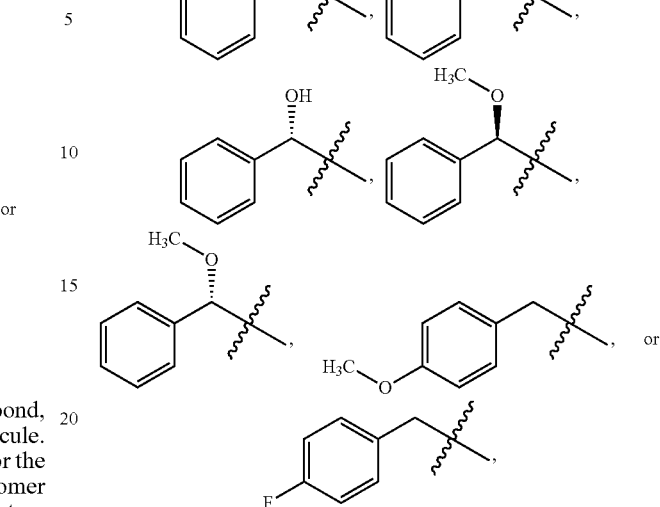

wherein the symbol ⌇, when drawn across a bond, indicates the point of attachment to the rest of the molecule.

49. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

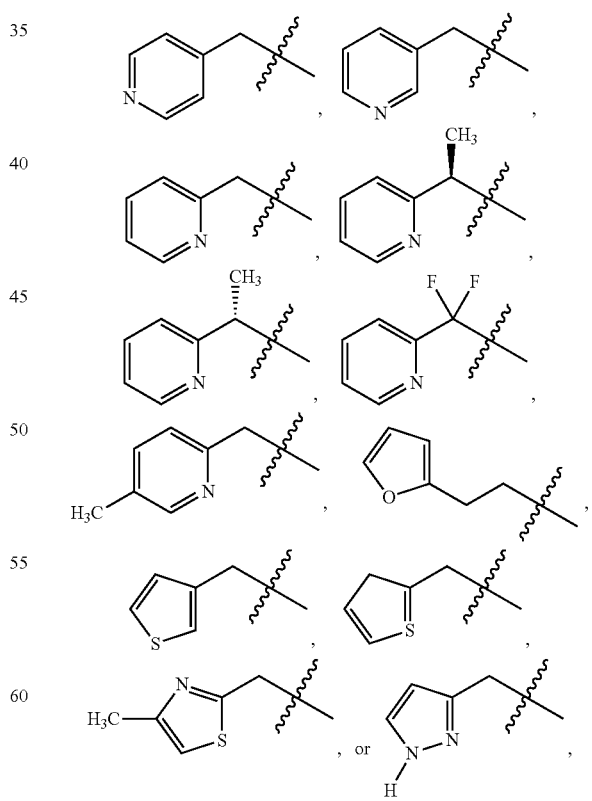

wherein the symbol ⌇, when drawn across a bond, indicates the point of attachment to the rest of the molecule.

50. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

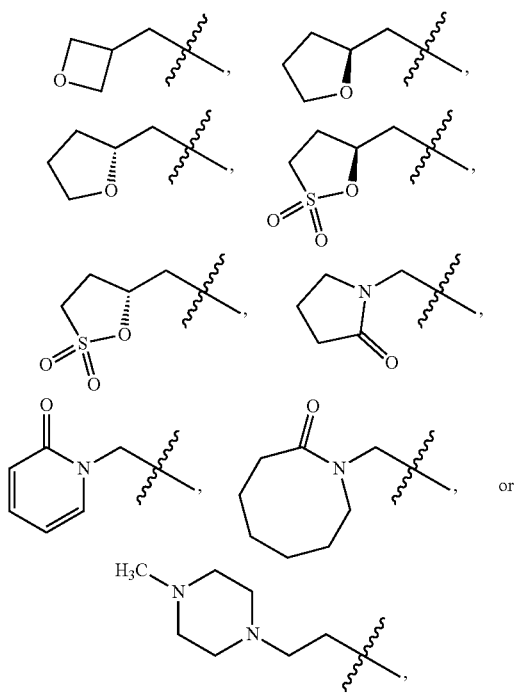

wherein the symbol ~~~, when drawn across a bond, indicates the point of attachment to the rest of the molecule.

51. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is selected from

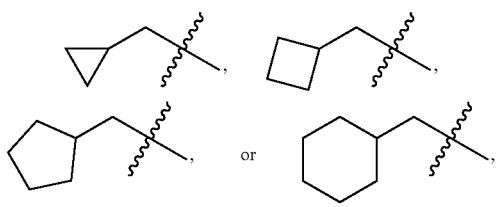

wherein the symbol ~~~, when drawn across a bond, indicates the point of attachment to the rest of the molecule.

52. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is a $C_1$-$C_8$ straight or branched chain alkyl substituted with 1, 2, or 3 $R^{1a}$ substituents, wherein at least one of the $R^{1a}$ substituents is selected from —O—($C_1$-$C_6$ alkyl), —O—($C_1$-$C_6$ haloalkyl), or —O—($C_1$-$C_6$ perhaloalkyl).

53. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is a $C_1$-$C_8$ straight or branched chain alkyl substituted with 1, 2, or 3 $R^{1a}$ substituents, wherein at least one of the $R^{1a}$ substituents is selected from a $C_3$-$C_8$ cycloalkyl group, a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a 3 to 10 membered heterocyclyl group containing 1, 2, or 3 heteroatoms independently selected from N, O, or S, wherein the $C_3$-$C_8$ cycloalkyl, the $C_6$-$C_{10}$ aryl, the heteroaryl, and the heterocyclyl $R^{1a}$ groups are unsubstituted or are substituted with 1, 2, or 3 $R^{1a'}$ substituents; and further wherein the $R^{1a}$ the $C_3$-$C_8$ cycloalkyl and heterocyclyl group may additionally be substituted with 1 or 2 oxo substituents, and the S atom of a heterocyclyl group may contain one or two oxo substituents, and still further wherein, the $R^{1a}$ heteroaryl group may include an N-oxide if the heteroaryl includes a N heteroatom.

54. The compound of any one of embodiments 1-45 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted $C_1$-$C_8$ straight or branched chain alkyl.

55. The compound of embodiment 1, wherein the compound has the Formula IA

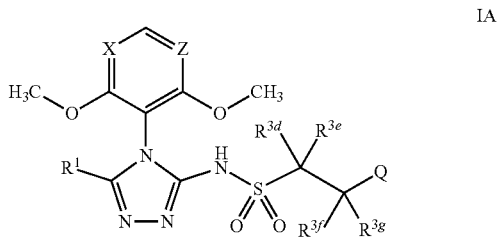

IA or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 1;
X is selected from CH or N;
Z is selected from CH or N;
$R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-NH$_2$ or —S(=O)$_2$—($C_1$-$C_6$ alkyl).

56. The compound of embodiment 55 or the pharmaceutically acceptable salt thereof, the tautomer thereof, the pharmaceutically acceptable salt of the tautomer, the stereoisomer of any of the foregoing, or the mixture thereof, wherein:

$R^{3d}$ and $R^{3e}$ are independently selected from —H, —$C_1$-$C_6$ alkyl, or —($C_1$-$C_6$ alkyl)-OH; and $R^{3f}$ and $R^{3g}$ are independently selected from —H, —$C_1$-$C_6$ alkyl, —OH, or —O—($C_1$-$C_6$ alkyl).

57. The compound of embodiment 55 or embodiment 56 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is not —H.

58. The compound of any one of embodiments 55-57 or the pharmaceutically acceptable salt thereof, the tautomer thereof, the pharmaceutically acceptable salt of the tautomer, the stereoisomer of any of the foregoing, or the mixture thereof, wherein at least one of $R^{3d}$, $R^{3e}$, $R^{3f}$, or $R^{3g}$ is —$CH_3$.

59. The compound of any one of embodiments 55-58 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, or —$CH_3$.

60. The compound of embodiment 1, wherein the compound has the Formula IB

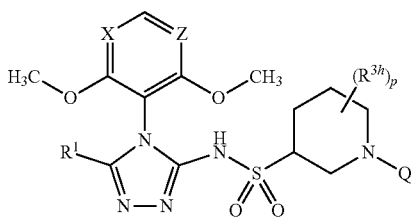

IB or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 1;

X is selected from CH or N;

Z is selected from CH or N;

$R^{3h}$ is independently selected from —OH, or —O—($C_1$-$C_6$ alkyl);

The subscript p is selected from 0, 1, 2, or 3;

Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and $R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —S(=O)$_2$—($C_1$-$C_6$ alkyl).

61. The compound of embodiment 60 or the pharmaceutically acceptable salt thereof, the tautomer thereof, the pharmaceutically acceptable salt of the tautomer, the stereoisomer of any of the foregoing, or the mixture thereof, wherein p is 0 or 1 and $R^{3h}$ is selected from —OH, —$OCH_3$, —$OCH_2CH_3$, or —$OCH(CH_3)_2$.

62. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein:

X is CH;

Z is CH; and

Q is a phenyl, a pyrimidinyl, a pyridinyl, or a pyrazinyl any of which are unsubstituted or are substituted with 1, 2, or 3 $R^Q$ substituent.

63. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein:

X is N;

Z is N; and

Q is a phenyl, a pyrimidinyl, a pyridinyl, or a pyrazinyl any of which are unsubstituted or are substituted with 1, 2, or 3 $R^Q$ substituent.

64. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein $R^1$ is a $C_1$-$C_8$ straight or branched chain alkyl substituted with 1, 2, or 3 $R^{1a}$ substituents, wherein at least one of the $R^{1a}$ substituents is selected from —O—($C_1$-$C_6$ alkyl), —O—($C_1$-$C_6$ haloalkyl), or —O—($C_1$-$C_6$ perhaloalkyl).

65. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein $R^1$ is a $C_1$-$C_8$ straight or branched chain alkyl substituted with 1, 2, or 3 $R^{1a}$ substituents, wherein at least one of the $R^{1a}$ substituents is selected from a $C_3$-$C_5$ cycloalkyl group, a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a 3 to 10 membered heterocyclyl group containing 1, 2, or 3 heteroatoms independently selected from N, O, or S, wherein the $C_3$-$C_8$ cycloalkyl, the $C_6$-$C_{10}$ aryl, the heteroaryl, and the heterocyclyl $R^{1a}$ groups are unsubstituted or are substituted with 1, 2, or 3 $R^{1a'}$ substituents; and further wherein the $R^{1a}$ $C_3$-$C_8$ cycloalkyl and heterocyclyl group may additionally be substituted with 1 or 2 oxo substituents, and the S atom of a heterocyclyl group may contain one or two oxo substituents, and still further wherein, the $R^{1a}$ heteroaryl group may include an N-oxide if the heteroaryl includes a N heteroatom.

66. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted $C_1$-$C_8$ straight or branched chain alkyl.

67. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein $R^1$ is selected from

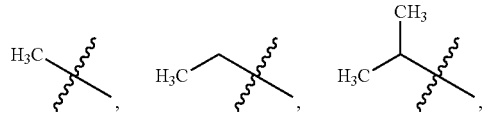

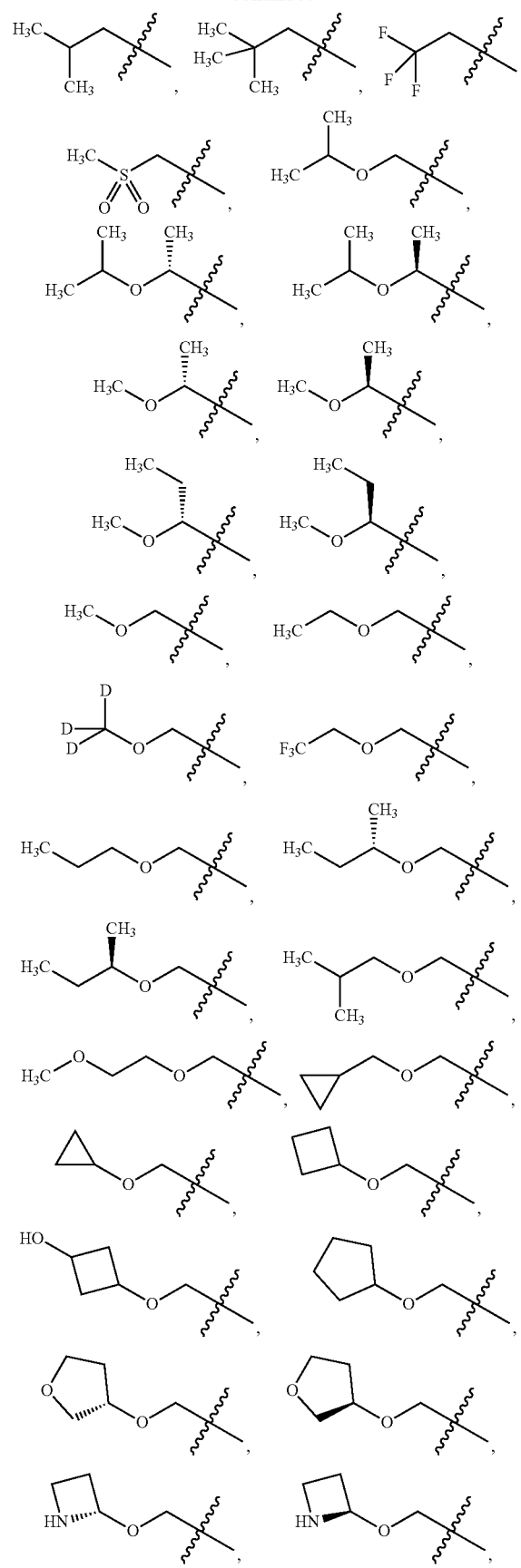
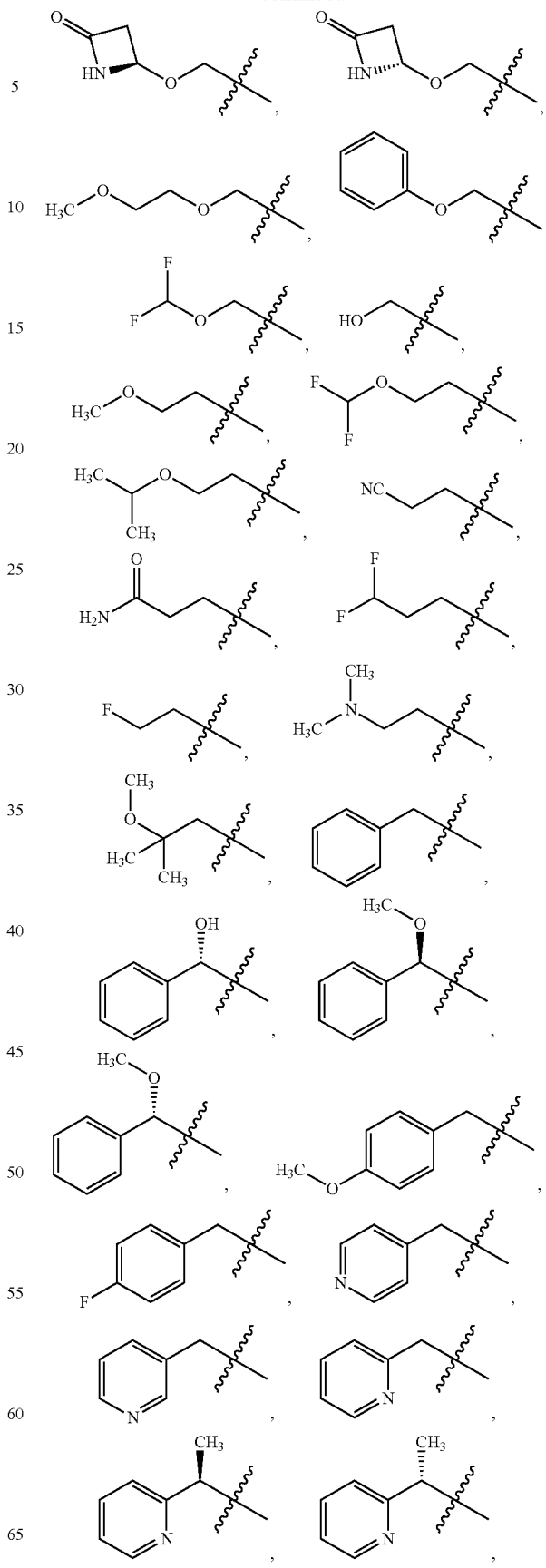

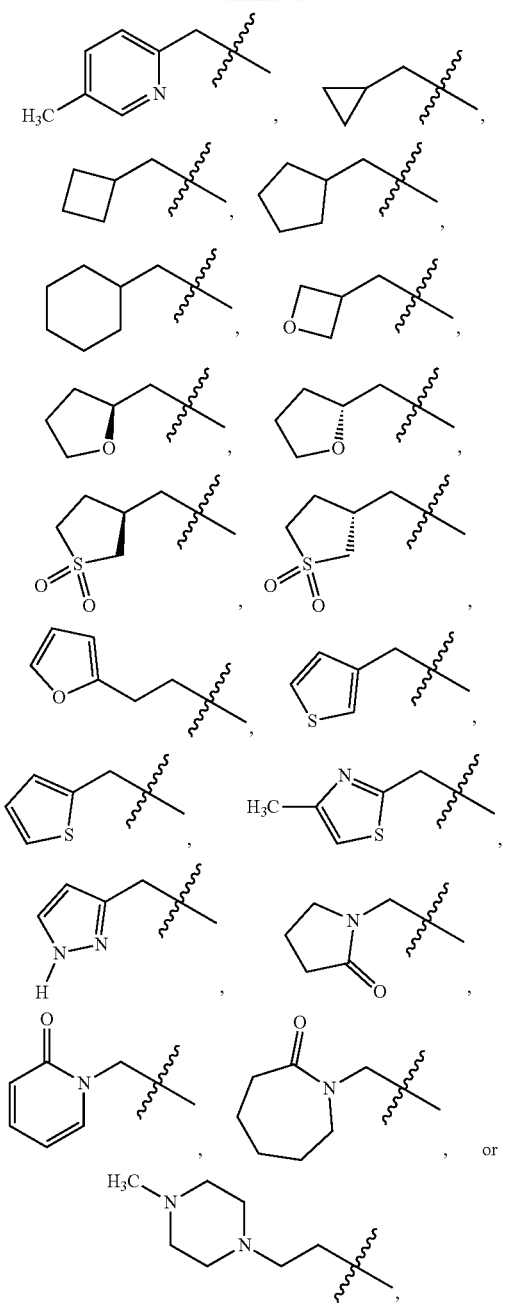

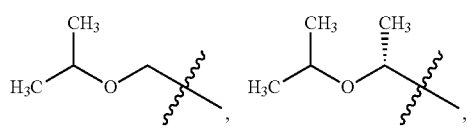

wherein the symbol ⌇, when drawn across a bond, indicates the point of attachment to the rest of the molecule.

68. The compound of any one of embodiments 55-61 or the pharmaceutically acceptable salt thereof, the tautomer thereof, the pharmaceutically acceptable salt of the tautomer, the stereoisomer of any of the foregoing, or the mixture thereof, wherein $R^1$ is selected from

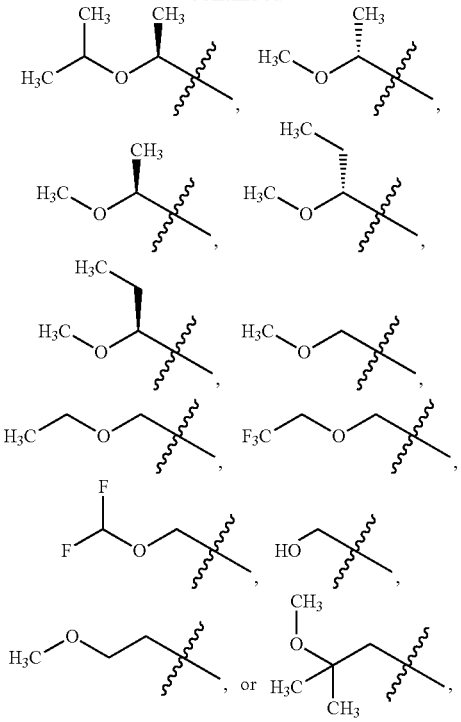

wherein the symbol ⌇, when drawn across a bond, indicates the point of attachment to the rest of the molecule.

69. The compound of embodiment 1, wherein the compound is selected from (2S,3R)-3-(5-chloro-2-pyrimidinyl)-N-(4-(4,6-dimethoxy-5-pyrimidinyl)-5-(2,2-dimethylpropyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1R)-1-(1-methylethoxy)ethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1S)-1-(1-methylethoxy)ethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1R)-1-methoxyethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1S)-1-methoxyethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1R)-1-methoxypropyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-((1S)-1-methoxypropyl)-4H-1,2,4-triazol-3-yl)-2-butanesulfonamide;

(2S,3R)—N-(4-(2,6-dimethoxyphenyl)-5-(methoxymethyl)-4H-1,2,4-triazol-3-yl)-3-(5-methyl-2-pyrazinyl)-2-butanesulfonamide;

(2S,3R)—N-(4-(4,6-dimethoxy-5-pyrimidinyl)-5-(methoxymethyl)-4H-1,2,4-triazol-3-yl)-3-(5-methyl-2-pyrazinyl)-2-butanesulfonamide;

(2S,3R)-3-(5-chloro-2-pyrimidinyl)-N-(4-(2,6-dimethoxyphenyl)-5-(methoxymethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-(methoxymethyl)-4H-1,2,4-triazol-3-yl)-2-butanesulfonamide;

(1R,2S)-1-(5-chloro-2-pyrimidinyl)-N-(4-(2,6-dimethoxyphenyl)-5-(methoxymethyl)-4H-1,2,4-triazol-3-yl)-1-methoxy-2-propanesulfonamide;

(2S,3R)-3-(5-chloro-2-pyrimidinyl)-N-(4-(2,6-dimethoxyphenyl)-5-((S)-hydroxy(phenyl)methyl)-4H-1,2,4-triazol-3-yl)-2-butanesulfonamide;

(2S,3R)—N-(5-benzyl-4-(2,6-dimethoxyphenyl)-4H-1,2,4-triazol-3-yl)-3-(5-chloro-2-pyrimidinyl)-2-butanesulfonamide;

(2S,3R)—N-(4-(2,6-dimethoxyphenyl)-5-(3-pyridinylmethyl)-4H-1,2,4-triazol-3-yl)-3-(5-methyl-2-pyrimidinyl)-2-butanesulfonamide;

(2S,3R)-3-(5-chloro-2-pyrimidinyl)-N-(4-(2,6-dimethoxyphenyl)-5-((1R)-1-(2-pyridinyl)ethyl)-4H-1,2,4-triazol-3-yl)-2-butanesulfonamide;

(2S,3R)-3-(5-chloro-2-pyrimidinyl)-N-(4-(2,6-dimethoxyphenyl)-5-((1S)-1-(2-pyridinyl)ethyl)-4H-1,2,4-triazol-3-yl)-2-butanesulfonamide;

(2S,3R)—N-(4-(2,6-dimethoxyphenyl)-5-((R)-methoxy(phenyl)methyl)-4H-1,2,4-triazol-3-yl)-3-(5-methyl-2-pyrimidinyl)-2-butanesulfonamide;

(2S,3R)—N-(4-(2,6-dimethoxyphenyl)-5-((S)-methoxy(phenyl)methyl)-4H-1,2,4-triazol-3-yl)-3-(5-methyl-2-pyrimidinyl)-2-butanesulfonamide;

(2S,3R)—N-(4-(2,6-dimethoxyphenyl)-5-((5-methyl-2-pyridinyl)methyl)-4H-1,2,4-triazol-3-yl)-3-(5-methyl-2-pyrimidinyl)-2-butanesulfonamide;

(2S,3R)—N-(5-benzyl-4-(4,6-dimethoxy-5-pyrimidinyl)-4H-1,2,4-triazol-3-yl)-3-(5-chloro-2-pyrimidinyl)-2-butanesulfonamide;

(1R,2S)—N-(5-benzyl-4-(4,6-dimethoxy-5-pyrimidinyl)-4H-1,2,4-triazol-3-yl)-1-(5-chloro-2-pyrimidinyl)-1-methoxy-2-propanesulfonamide;

(2S,3R)—N-(5-benzyl-4-(4,6-dimethoxy-5-pyrimidinyl)-4H-1,2,4-triazol-3-yl)-3-(5-methyl-2-pyrimidinyl)-2-butanesulfonamide;

(1R,2S)-1-(5-chloro-2-pyrimidinyl)-N-(5-(cyclobutylmethyl)-4-(4,6-dimethoxy-5-pyrimidinyl)-4H-1,2,4-triazol-3-yl)-1-methoxy-2-propanesulfonamide;

(1R,2S)-1-(5-chloro-2-pyrimidinyl)-N-(5-(cyclobutylmethyl)-4-(tetrahydro-2H-pyran-4-yl)-4H-1,2,4-triazol-3-yl)-1-methoxy-2-propanesulfonamide;

(1R,2S)—N-(4-(2,6-dimethoxyphenyl)-5-methyl-4H-1,2,4-triazol-3-yl)-1-methoxy-1-(5-methyl-2-pyrimidinyl)-2-propanesulfonamide;

(1R,2S)-1-(5-chloro-2-pyrimidinyl)-N-(5-(cyclopropylmethyl)-4-(4,6-dimethoxy-5-pyrimidinyl)-4H-1,2,4-triazol-3-yl)-1-methoxy-2-propanesulfonamide;

(1R,2S)-1-(5-chloro-2-pyrimidinyl)-N-(5-(cyclopentylmethyl)-4-(4,6-dimethoxy-5-pyrimidinyl)-4H-1,2,4-triazol-3-yl)-1-methoxy-2-propanesulfonamide;

(1R,2S)-1-(5-chloro-2-pyrimidinyl)-N-(5-(cyclohexylmethyl)-4-(4,6-dimethoxy-5-pyrimidinyl)-4H-1,2,4-triazol-3-yl)-1-methoxy-2-propanesulfonamide;

(1S,2S)—N-(4-(2,6-difluorophenyl)-5-(methoxymethyl)-4H-1,2,4-triazol-3-yl)-1-(1-methylethoxy)-1-(5-methyl-2-pyrimidinyl)-2-propanesulfonamide;

(1R,2S)-1-(5-chloro-2-pyrimidinyl)-N-(4-(4,6-dimethoxy-5-pyrimidinyl)-5-(2-methylpropyl)-4H-1,2,4-triazol-3-yl)-1-methoxy-2-propanesulfonamide;

(2S,3R)-3-(5-chloro-2-pyrimidinyl)-N-(4-(2,6-dimethoxyphenyl)-5-(2-methoxyethyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-(3-oxetanylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(3-oxetanylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(2-pyridinylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(2-(2-furanyl)ethyl)-4H-1,2,4-triazol-3-yl)-2-butanesulfonamide;

(2S,3R)-3-(5-chloro-2-pyrimidinyl)-N-(4-(2,6-dimethoxyphenyl)-5-((methylsulfonyl)methyl)-4H-1,2,4-triazol-3-yl)-2-butanesulfonamide;

(2S,3R)-3-(5-chloro-2-pyrimidinyl)-N-(4-(2,6-dimethoxyphenyl)-5-(3-thiophenylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(1H-pyrazol-3-ylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(2-methoxy-2-methylpropyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2-oxo-1-pyrrolidinyl)methyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2-oxo-1(2H)-pyridinyl)methyl)-4H-1,2,4-triazol-3-yl)-2-butanesulfonamide;

(2S,3R)-3-(5-chloro-2-pyrimidinyl)-N-(4-(2,6-dimethoxyphenyl)-5-(2-thiophenylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-((4-methyl-1,3-thiazol-2-yl)methyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2R)-tetrahydro-2-furanylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-tetrahydro-2-furanylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-(((3R)-1,1-dioxidotetrahydro-3-thiophenyl)methyl)-4H-1,2,4-triazol-3-yl)-2-butanesulfonamide;

(2S,3R)-3-(5-chloro-2-pyrimidinyl)-N-(4-(2,6-dimethoxyphenyl)-5-(((3S)-1,1-dioxidotetrahydro-3-thiophenyl)methyl)-4H-1,2,4-triazol-3-yl)-2-butanesulfonamide;

(1R,2S)—N-(4-(2,6-dimethoxyphenyl)-5-(phenoxymethyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(4-methoxybenzyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(4-fluorobenzyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(2-(dimethylamino)ethyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-((2-oxo-1-azepanyl)methyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(2-(4-methyl-1-piperazinyl)ethyl)-4H-1,2,4-triazol-3-yl)-1-methoxy-1-(5-methyl-2-pyrimidinyl)-2-propanesulfonamide;

(1R,2S)—N-(5-benzyl-4-(2,6-dimethoxyphenyl)-4H-1,2,4-triazol-3-yl)-1-methoxy-1-(5-methyl-2-pyrimidinyl)-2-propanesulfonamide;

(1R,2S)-1-(5-chloro-2-pyrimidinyl)-1-methoxy-N-(5-methyl-4-(1-methylcyclopropyl)-4H-1,2,4-triazol-3-yl)-2-propanesulfonamide;

(1R,2S)-1-(5-chloro-2-pyrimidinyl)-1-methoxy-N-(4-(1-methylcyclopropyl)-5-((2R)-tetrahydro-2-furanylmethyl)-4H-1,2,4-triazol-3-yl)-2-propanesulfonamide;

(1R,2S)-1-(5-chloro-2-pyrimidinyl)-1-methoxy-N-(4-(1-methylcyclopropyl)-5-((2S)-tetrahydro-2-furanylmethyl)-4H-1,2,4-triazol-3-yl)-2-propanesulfonamide;

(1R,2S)-1-(5-chloro-2-pyrimidinyl)-N-(4-(4,6-dimethoxy-5-pyrimidinyl)-5-(methoxymethyl)-4H-1,2,4-triazol-3-yl)-1-methoxy-2-propanesulfonamide;

(1R,2S)-1-(5-chloro-2-pyrimidinyl)-1-methoxy-N-(5-(methoxymethyl)-4-(1-methylcyclopropyl)-4H-1,2,4-triazol-3-yl)-2-propanesulfonamide;

(1R,2S)—N-(4-(2,6-dimethoxyphenyl)-5-(methoxymethyl)-4H-1,2,4-triazol-3-yl)-1-methoxy-1-(5-methyl-2-pyrimidinyl)-2-propanesulfonamide;

(2S,3R)—N-(4-(2,6-dimethoxyphenyl)-5-(methoxymethyl)-4H-1,2,4-triazol-3-yl)-3-(5-methyl-2-pyrimidinyl)-2-butanesulfonamide;

(1S,2S)—N-(4-(2,6-dimethoxyphenyl)-5-(methoxymethyl)-4H-1,2,4-triazol-3-yl)-1-(1-methylethoxy)-1-(5-methyl-2-pyrimidinyl)-2-propanesulfonamide;

(1R,2S)-1-(5-chloro-2-pyrimidinyl)-1-methoxy-N-(5-(methoxymethyl)-4-(tetrahydro-2H-pyran-4-yl)-4H-1,2,4-triazol-3-yl)-2-propanesulfonamide;

(1R,2S)-1-(5-chloro-2-pyrimidinyl)-N-(4-(2,6-dimethoxyphenyl)-5-(hydroxymethyl)-4H-1,2,4-triazol-3-yl)-1-methoxy-2-propanesulfonamide;

(1R,2S)-1-(5-chloro-2-pyrimidinyl)-N-(5-(((difluoromethoxy)methyl)-4-(2,6-dimethoxyphenyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-ethyl-4H-1,2,4-triazol-3-yl)-1-methoxy-2-propanesulfonamide;

(1R,2S)-1-(5-chloro-2-pyrimidinyl)-N-(4-(4,6-dimethoxy-5-pyrimidinyl)-5-(2,2,2-trifluoroethyl)-4H-1,2,4-triazol-3-yl)-1-methoxy-2-propanesulfonamide;

(2S,3R)—N-(4-(2,6-dimethoxyphenyl)-5-(methoxymethyl)-4H-1,2,4-triazol-3-yl)-3-(5-fluoro-2-pyrimidinyl)-2-butanesulfonamide;

(1R,2S)-1-(5-chloro-2-pyrimidinyl)-N-(4-(2,6-dimethoxyphenyl)-5-(((1-methylethoxy)methyl)-4H-1,2,4-triazol-3-yl)-1-methoxy-2-propanesulfonamide;

(1S,2S)-1-(5-chloro-2-pyrimidinyl)-N-(4-(2,6-dimethoxyphenyl)-5-(methoxymethyl)-4H-1,2,4-triazol-3-yl)-1-(1-methylethoxy)-2-propanesulfonamide;

(1R,2S)-1-(5-chloro-2-pyrimidinyl)-N-(4-(2,6-dimethoxyphenyl)-5-(ethoxymethyl)-4H-1,2,4-triazol-3-yl)-1-methoxy-2-propanesulfonamide;

(1R,2S)—N-(4-(2,6-dimethoxyphenyl)-5-(methoxymethyl)-4H-1,2,4-triazol-3-yl)-1-ethoxy-1-(5-methyl-2-pyrimidinyl)-2-propanesulfonamide;

(2S,3R)—N-(4-(2,6-dimethoxyphenyl)-5-(methoxymethyl)-4H-1,2,4-triazol-3-yl)-3-(5-methoxy-2-pyrazinyl)-2-butanesulfonamide;

(2S,3R)-3-(5-chloro-2-pyridinyl)-N-(4-(2,6-dimethoxyphenyl)-5-(methoxymethyl)-4H-1,2,4-triazol-3-yl)-2-butanesulfonamide;

(1R,2S)-1-(5-chloro-2-pyrimidinyl)-N-(4-(2,6-dimethoxyphenyl)-5-(methoxymethyl)-4H-1,2,4-triazol-3-yl)-1-methoxy-2-propanesulfonamide;

(3S)—N-(4-(2,6-dimethoxyphenyl)-5-(methoxymethyl)-4H-1,2,4-triazol-3-yl)-1-(5-fluoro-2-pyrimidinyl)-3-piperidinesulfonamide;

(3R)—N-(4-(2,6-dimethoxyphenyl)-5-(methoxymethyl)-4H-1,2,4-triazol-3-yl)-1-(5-fluoro-2-pyrimidinyl)-3-piperidinesulfonamide;

(1R,2S)-1-(5-chloro-2-pyrimidinyl)-N-(4-(4,6-dimethoxy-5-pyrimidinyl)-5-((2-propanyloxy)methyl)-4H-1,2,4-triazol-3-yl)-1-methoxy-2-propanesulfonamide;

(2S,3R)-3-(5-chloro-2-pyrimidinyl)-N-(4-(4,6-dimethoxy-5-pyrimidinyl)-5-((2-propanyloxy)methyl)-4H-1,2,4-triazol-3-yl)-2-butanesulfonamide;

(2S,3R)-3-(5-chloro-2-pyrimidinyl)-N-(5-((difluoromethoxy)methyl)-4-(4,6-dimethoxy-5-pyrimidinyl)-4H-1,2,4-triazol-3-yl)-2-butanesulfonamide;

(1R,2S)-1-(5-chloro-2-pyrimidinyl)-N-(5-((difluoromethoxy)methyl)-4-(4,6-dimethoxy-5-pyrimidinyl)-4H-1,2,4-triazol-3-yl)-1-methoxy-2-propanesulfonamide;

(2S,3R)—N-(4-(2,6-dimethoxyphenyl)-5-(methoxymethyl)-4H-1,2,4-triazol-3-yl)-3-(5-methoxy-2-pyrimidinyl)-2-butanesulfonamide;

(1R,2S)-1-(5-chloro-2-pyrimidinyl)-N-(4-(2,6-difluorophenyl)-5-(methoxymethyl)-4H-1,2,4-triazol-3-yl)-1-methoxy-2-propanesulfonamide;

(1R,2S)-1-(5-chloro-2-pyrimidinyl)-1-methoxy-N-(5-(methoxymethyl)-4-(2-methoxyphenyl)-4H-1,2,4-triazol-3-yl)-2-propanesulfonamide;

(1R,2S)-1-(5-chloro-2-pyrimidinyl)-N-(4-(4,6-dimethoxy-5-pyrimidinyl)-5-(2-propanyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(((trideutero)methyloxy)methyl)-4H-1,2,4-triazol-3-yl)-1-methoxy-2-propanesulfonamide;

(1R,2S)-1-(5-chloropyrimidin-2-yl)-N-(4-(1,3-dimethoxypropan-2-yl)-5-(methoxymethyl)-4H-1,2,4-triazol-3-yl)-1-methoxypropane-2-sulfonamide;

(1S,2S)-1-(5-chloro-2-pyrimidinyl)-N-(4-(4,6-dimethoxy-5-pyrimidinyl)-5-(methoxymethyl)-4H-1,2,4-triazol-3-yl)-1-(2-propanyloxy)-2-propanesulfonamide;

(1R,2S)-1-(5-chloro-2-pyrimidinyl)-N-(4-(4,6-dimethoxy-5-pyrimidinyl)-5-((2,2,2-trifluoroethoxy)methyl)-4H-1,2,4-triazol-3-yl)-1-methoxy-2-propanesulfonamide;

(1S,2S)-1-(5-chloro-2-pyrimidinyl)-N-(4-(4,6-dimethoxy-5-pyrimidinyl)-5-(methoxymethyl)-4H-1,2,4-triazol-3-yl)-1-(2-propanyloxy)-2-propanesulfonamide;

(1R,2S)-1-(5-chloro-2-pyrimidinyl)-N-(4-(4,6-dimethoxy-5-pyrimidinyl)-5-((2,2,2-trifluoroethoxy)methyl)-4H-1,2,4-triazol-3-yl)-1-methoxy-2-propanesulfonamide;

(2S,3R)-3-(5-chloro-2-pyrimidinyl)-N-(5-(difluoro(2-pyridinyl)methyl)-4-(2,6-dimethoxyphenyl)-4H-1,2,4-triazol-3-yl)-2-butanesulfonamide;

(2S,3R)—N-(5-(difluoro(2-pyridinyl)methyl)-4-(2,6-dimethoxyphenyl)-4H-1,2,4-triazol-3-yl)-3-(5-methyl-2-pyrimidinyl)-2-butanesulfonamide;

(2S,3R)—N-(4-(2,6-dimethoxyphenyl)-5-(1-methyl-1-phenylethyl)-4H-1,2,4-triazol-3-yl)-3-(5-methyl-2-pyrimidinyl)-2-butanesulfonamide;

(1R,2S)-1-(5-chloro-2-pyrimidinyl)-1-methoxy-N-(4-(tetrahydro-2H-pyran-4-yl)-5-(2,2,2-trifluoroethyl)-4H-1,2,4-triazol-3-yl)-2-propanesulfonamide;

(1R,2S)-1-(5-chloro-2-pyrimidinyl)-1-methoxy-N-(5-(methoxymethyl)-4-(1-(3-pyridinyl)cyclopropyl)-4H-1,2,4-triazol-3-yl)-2-propanesulfonamide; or (2S,3R)-3-(5-chloro-2-pyrimidinyl)-N-(4-(2,6-dimethoxyphenyl)-5-(4-pyridinylmethyl)-4H-1,2,4-triazol-3-yl)-2-butanesulfonamide; or the pharmaceutically acceptable salt thereof, the tautomer thereof, the pharmaceutically acceptable salt of the tautomer, the stereoisomer of any of the foregoing, or the mixture thereof.

70. The compound of embodiment 1, wherein the compound is selected from (1R,2S)—N-(4-(2-chlorophenyl)-5-(methoxymethyl)-4H-1,2,4-triazol-3-yl)-1-(5-chloropyrimidin-2-yl)-1-methoxypropane-2-sulfonamide;

(1R,2S)-1-(5-chloropyrimidin-2-yl)-N-(4-(4,6-dimethoxypyrimidin-5-yl)-5-(ethoxymethyl)-4H-1,2,4-triazol-3-yl)-1-methoxypropane-2-sulfonamide;

(2S,3R)-3-(5-chloropyrimidin-2-yl)-N-(4-(4,6-dimethoxypyrimidin-5-yl)-5-(ethoxymethyl)-4H-1,2,4-triazol-3-yl)butane-2-sulfonamide;

(1S,2S)—N-(4-(2,6-dimethoxyphenyl)-5-(ethoxymethyl)-4H-1,2,4-triazol-3-yl)-1-isopropoxy-1-(5-methylpyrimidin-2-yl)propane-2-sulfonamide;

(1S,2S)-1-(5-chloropyrimidin-2-yl)-N-(4-(4,6-dimethoxypyrimidin-5-yl)-5-(ethoxymethyl)-4H-1,2,4-triazol-3-yl)-1-isopropoxypropane-2-sulfonamide;

(1R,2S)-1-(5-chloropyrimidin-2-yl)-N-(4-(2,6-dimethoxyphenyl)-5-(propoxymethyl)-4H-1,2,4-triazol-3-yl)-1-methoxypropane-2-sulfonamide;

(2S,3R)-3-(5-chloropyrimidin-2-yl)-N-(4-(2,6-dimethoxyphenyl)-5-(propoxymethyl)-4H-1,2,4-triazol-3-yl)butane-2-sulfonamide;

(2S,3R)-3-(5-chloropyrimidin-2-yl)-N-(4-(4,6-dimethoxypyrimidin-5-yl)-5-(propoxymethyl)-4H-1,2,4-triazol-3-yl)butane-2-sulfonamide;

(1R,2S)—N-(5-((S)-sec-butoxymethyl)-4-(2,6-dimethoxyphenyl)-4H-1,2,4-triazol-3-yl)-1-(5-chloropyrimidin-2-yl)-1-methoxypropane-2-sulfonamide;

(1R,2S)—N-(5-((R)-sec-butoxymethyl)-4-(2,6-dimethoxyphenyl)-4H-1,2,4-triazol-3-yl)-1-(5-chloropyrimidin-2-yl)-1-methoxypropane-2-sulfonamide;

(1R,2S)-1-(5-chloropyrimidin-2-yl)-N-(4-(2,6-dimethoxyphenyl)-5-(isobutoxymethyl)-4H-1,2,4-triazol-3-yl)-1-methoxypropane-2-sulfonamide;

(1R,2S)-1-(5-chloropyrimidin-2-yl)-N-(5-((cyclopropylmethoxy)methyl)-4-(2,6-dimethoxyphenyl)-4H-1,2,4-triazol-3-yl)-1-methoxypropane-2-sulfonamide;

(1R,2S)-1-(5-chloropyrimidin-2-yl)-N-(5-(cyclopropoxymethyl)-4-(2,6-dimethoxyphenyl)-4H-1,2,4-triazol-3-yl)-1-methoxypropane-2-sulfonamide;

(1R,2S)-1-(5-chloropyrimidin-2-yl)-N-(5-(cyclobutoxymethyl)-4-(2,6-dimethoxyphenyl)-4H-1,2,4-triazol-3-yl)-1-methoxypropane-2-sulfonamide;

(1R,2S)—N-(5-((azetidin-2-yloxy)methyl)-4-(2,6-dimethoxyphenyl)-4H-1,2,4-triazol-3-yl)-1-(5-chloropyrimidin-2-yl)-1-methoxypropane-2-sulfonamide;

(1R,2S)-1-(5-chloropyrimidin-2-yl)-N-(4-(2,6-dimethoxyphenyl)-5-(((4-oxoazetidin-2-yl)oxy)methyl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-((3-hydroxycyclobutoxy)methyl)-4H-1,2,4-triazol-3-yl)-1-methoxypropane-2-sulfonamide;

(1R,2S)-1-(5-chloropyrimidin-2-yl)-N-(5-((cyclopentyloxy)methyl)-4-(2,6-dimethoxyphenyl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-(((tetrahydrofuran-3-yl)oxy)methyl)-4H-1,2,4-triazol-3-yl)-1-methoxypropane-2-sulfonamide;

(2S,3R)-3-(5-chloropyrimidin-2-yl)-N-(4-(2,6-dimethoxyphenyl)-5-((2-methoxyethoxy)methyl)-4H-1,2,4-triazol-3-yl)butane-2-sulfonamide;

(1R,2S)-1-(5-chloropyrimidin-2-yl)-N-(5-(2-(difluoromethoxy)ethyl)-4-(2,6-dimethoxyphenyl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-(2-isopropoxyethyl)-4H-1,2,4-triazol-3-yl)-1-methoxypropane-2-sulfonamide;

(1R,2S)-1-(5-chloropyrimidin-2-yl)-N-(5-(2-cyanoethyl)-4-(2,6-dimethoxyphenyl)-4H-1,2,4-triazol-3-yl)-1-methoxypropane-2-sulfonamide;

3-(5-((1S,2R)-2-(5-chloropyrimidin-2-yl)-2-methoxy-1-methylethylsulfonamido)-4-(2,6-dimethoxyphenyl)-4H-1,2,4-triazol-3-yl)propanamide;

(1R,2S)-1-(5-chloropyrimidin-2-yl)-N-(4-(2,6-dimethoxyphenyl)-5-isobutyl-4H-1,2,4-triazol-3-yl)-1-methoxypropane-2-sulfonamide;

(1R,2S)-1-(5-chloropyrimidin-2-yl)-N-(5-(3,3-difluoropropyl)-4-(2,6-dimethoxyphenyl)-4H-1,2,4-triazol-3-yl)-1-methoxypropane-2-sulfonamide;

(1R,2S)-1-(5-chloropyrimidin-2-yl)-N-(4-(2,6-dimethoxyphenyl)-5-(2-fluoroethyl)-4H-1,2,4-triazol-3-yl)-1-methoxypropane-2-sulfonamide;

(1R,2S)-1-(5-chloropyrimidin-2-yl)-1-methoxy-N-(4-(2-methoxyethyl)-5-(methoxymethyl)-4H-1,2,4-triazol-3-yl)propane-2-sulfonamide; or (1R,2S)-1-(5-chloropyrimidin-2-yl)-1-methoxy-N-(5-(methoxymethyl)-4-(1-(methoxymethyl)cyclopropyl)-4H-1,2,4-triazol-3-yl)propane-2-sulfonamide; or the pharmaceutically acceptable salt thereof, the tautomer thereof, the pharmaceutically acceptable salt of the tautomer, the stereoisomer of any of the foregoing, or the mixture thereof.

71. The compound of embodiment 1, wherein the compound is selected from (1S,2S)—N-(4-(2,6-dimethoxyphenyl)-5-(methoxymethyl)-4H-1,2,4-triazol-3-yl)-1-(1-methylethoxy)-1-(5-methyl-2-pyrimidinyl)-2-propanesulfonamide;

(1R,2S)-1-(5-chloro-2-pyrimidinyl)-N-(5-((difluoromethoxy)methyl)-4-(2,6-dimethoxyphenyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(methoxymethyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(ethoxymethyl)-4H-1,2,4-triazol-3-yl)-1-methoxy-2-propanesulfonamide;

(2S,3R)—N-(5-benzyl-4-(2,6-dimethoxyphenyl)-4H-1,2,4-triazol-3-yl)-3-(5-chloro-2-pyrimidinyl)-2-butanesulfonamide;

(1R,2S)-1-(5-chloro-2-pyrimidinyl)-N-(5-(cyclopentylmethyl)-4-(4,6-dimethoxy-5-pyrimidinyl)-4H-1,2,4-triazol-3-yl)-1-methoxy-2-propanesulfonamide;

(1R,2S)-1-(5-chloro-2-pyrimidinyl)-N-(4-(4,6-dimethoxy-5-pyrimidinyl)-5-((2-propanyloxy)methyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-ethyl-4H-1,2,4-triazol-3-yl)-1-methoxy-2-propanesulfonamide;

(1S,2S)-1-(5-chloro-2-pyrimidinyl)-N-(4-(2,6-dimethoxyphenyl)-5-(methoxymethyl)-4H-1,2,4-triazol-3-yl)-1-(1-methylethoxy)-2-propanesulfonamide;

(2S,3R)-3-(5-chloro-2-pyrimidinyl)-N-(4-(2,6-dimethoxyphenyl)-5-((2R)-tetrahydro-2-furanylmethyl)-4H-1,2,4-triazol-3-yl)-2-butanesulfonamide;

(2S,3R)-3-(5-chloro-2-pyrimidinyl)-N-(4-(2,6-dimethoxyphenyl)-5-((2S)-tetrahydro-2-furanylmethyl)-4H-1,2,4-triazol-3-yl)-2-butanesulfonamide;

(1R,2S)-1-(5-chloro-2-pyrimidinyl)-N-(5-(cyclobutylmethyl)-4-(4,6-dimethoxy-5-pyrimidinyl)-4H-1,2,4-triazol-3-yl)-1-methoxy-2-propanesulfonamide; or (1R,2S)-1-(5-chloro-2-pyrimidinyl)-N-(4-(2,6-dimethoxyphenyl)-5-((1-methylethoxy)methyl)-4H-1,2,4-triazol-3-yl)-1-methoxy-2-propanesulfonamide; or the pharmaceutically acceptable salt thereof, the tautomer thereof, the pharmaceutically acceptable salt of the tautomer, the stereoisomer of any of the foregoing, or the mixture thereof.

72. The compound of embodiment 1, wherein the compound is selected from (1R,2S)-1-(5-chloropyrimidin-2-yl)-N-(4-isopropyl-5-(methoxymethyl)-4H-1,2,4-triazol-3-yl)-1-methoxypropane-2-sulfonamide;

(1R,2S)-1-(5-chloropyrimidin-2-yl)-1-methoxy-N-(5-(methoxymethyl)-4-(1-(methoxymethyl)cyclopropyl)-4H-1,2,4-triazol-3-yl)propane-2-sulfonamide;

(1R,2S)-1-(5-chloro-2-pyrimidinyl)-N-(4-(1,3-dimethoxy-2-propanyl)-5-(2-methoxyethyl)-4H-1,2,4-triazol-3-yl)-1-methoxy-2-propanesulfonamide;

(1R,2S)-1-(5-chloro-2-pyrimidinyl)-1-methoxy-N-(5-(methoxymethyl)-4-(3-pentanyl)-4H-1,2,4-triazol-3-yl)-2-propanesulfonamide;

(2S,3R)-3-(5-chloro-2-pyrimidinyl)-N-(4-(2,6-dimethoxyphenyl)-5-((2-methoxyethoxy)methyl)-4H-1,2,4-triazol-3-yl)-2-butanesulfonamide;

(1S,2S)—N-(4-(2,6-dimethoxyphenyl)-5-((trideuteromethyloxy)methyl)-4H-1,2,4-triazol-3-yl)-1-(5-methyl-2-pyrimidinyl)-1-(2-propanyloxy)-2-propanesulfonamide;

(1S,2S)-1-(5-chloro-2-pyrimidinyl)-N-(4-(2,6-dimethoxyphenyl)-5-((trideuteromethyloxy)methyl)-4H-1,2,4-triazol-3-yl)-1-(2-propanyloxy)-2-propanesulfonamide;

(1S,2S)—N-(4-(2,6-dimethoxyphenyl)-5-(methoxymethyl)-4H-1,2,4-triazol-3-yl)-1-(5-fluoro-2-pyrimidinyl)-1-(2-propanyloxy)-2-propanesulfonamide;

(1S,2S)—N-(4-(2,6-dimethoxyphenyl)-5-(methoxymethyl)-4H-1,2,4-triazol-3-yl)-1-(5-methyl-2-pyridinyl)-1-(2-propanyloxy)-2-propanesulfonamide;

(1R,2S)-1-(5-chloro-2-pyrimidinyl)-1-methoxy-N-(4-(2-methoxyethyl)-5-(methoxymethyl)-4H-1,2,4-triazol-3-yl)-2-propanesulfonamide;

(1R,2S)-1-(5-chloro-2-pyrimidinyl)-N-(4-(2,6-dichlorophenyl)-5-(methoxymethyl)-4H-1,2,4-triazol-3-yl)-1-methoxy-2-propanesulfonamide;

(1R,2S)—N-(4-(2-chloro-5-methoxyphenyl)-5-(methoxymethyl)-4H-1,2,4-triazol-3-yl)-1-(5-chloro-2-pyrimidinyl)-1-methoxy-2-propanesulfonamide;

(1R,2S)—N-(4-(2-chloro-5-methoxyphenyl)-5-((trideuteromethyloxy)methyl)-4H-1,2,4-triazol-3-yl)-1-(5-chloro-2-pyrimidinyl)-1-methoxy-2-propanesulfonamide;

(1R,2S)—N-(4-(2-chloro-5-methoxyphenyl)-5-((difluoromethoxy)methyl)-4H-1,2,4-triazol-3-yl)-1-(5-chloro-2-pyrimidinyl)-1-methoxy-2-propanesulfonamide;

(2S,3R)-3-(5-chloro-2-pyrimidinyl)-N-(4-(2,6-dimethoxyphenyl)-5-((2-propanyloxy)methyl)-4H-1,2,4-triazol-3-yl)-2-butanesulfonamide;

(2S,3R)—N-(4-(2-chloro-5-methoxyphenyl)-5-(methoxymethyl)-4H-1,2,4-triazol-3-yl)-3-(5-chloro-2-pyrimidinyl)-2-butanesulfonamide;

(1S,2S)—N-(4-(2-chloro-5-methoxyphenyl)-5-(methoxymethyl)-4H-1,2,4-triazol-3-yl)-1-(5-methyl-2-pyrimidinyl)-1-(2-propanyloxy)-2-propanesulfonamide;

(2S,3R)—N-(5-butyl-4-(2,6-dimethoxyphenyl)-4H-1,2,4-triazol-3-yl)-3-(5-chloro-2-pyrimidinyl)-2-butanesulfonamide;

(1R,2S)—N-(5-butyl-4-(2,6-dimethoxyphenyl)-4H-1,2,4-triazol-3-yl)-1-(5-chloropyrimidin-2-yl)-1-methoxypropane-2-sulfonamide;

(1R,2S)—N-(5-butyl-4-(2,6-dimethoxyphenyl)-4H-1,2,4-triazol-3-yl)-1-methoxy-1-(5-methylpyrimidin-2-yl)propane-2-sulfonamide;

(2S,3R)—N-(5-butyl-4-(2,6-dimethoxyphenyl)-4H-1,2,4-triazol-3-yl)-3-(5-methylpyrimidin-2-yl)butane-2-sulfonamide;

(1R,2S)-1-(5-chloro-2-pyrimidinyl)-N-(5-((1R)-1-cyclopropylethyl)-4-(4,6-dimethoxy-5-pyrimidinyl)-4H-1,2,4-triazol-3-yl)-1-methoxy-2-propanesulfonamide;

(1R,2S)-1-(5-chloro-2-pyrimidinyl)-N-(5-((1S)-1-cyclopropylethyl)-4-(4,6-dimethoxy-5-pyrimidinyl)-4H-1,2,4-triazol-3-yl)-1-methoxy-2-propanesulfonamide; or (1S,2S)—N-(4-(2-bromo-6-methoxyphenyl)-5-(but-3-en-1-yl)-4H-1,2,4-triazol-3-yl)-1-isopropoxy-1-(5-methylpyrimidin-2-yl)propane-2-sulfonamide; or the pharmaceutically acceptable salt thereof, the tautomer thereof, the pharmaceutically acceptable salt of the tautomer, the stereoisomer of any of the foregoing, or the mixture thereof.

73. A pharmaceutical composition, comprising the compound of any one of embodiments 1-72 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

74. A pharmaceutical composition, comprising the compound of any one of embodiments 1-72 or the pharmaceutically acceptable salt thereof and at least one pharmaceutically acceptable excipient.

75. A pharmaceutical composition, comprising the compound of any one of embodiments 1-72 and at least one pharmaceutically acceptable excipient.

76. A pharmaceutical composition, comprising the pharmaceutically acceptable salt of the compound of any one of embodiments 1-72 and at least one pharmaceutically acceptable excipient.

77. The pharmaceutical composition of any one of embodiments 73-76, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

78. The pharmaceutical composition of any one of embodiments 73-76, further comprising a therapeutic agent selected from an angiotensin converting enzyme (ACE) inhibitor or an angiotensin-receptor blocker (ARB).

79. A method of treating a cardiovascular condition, the method comprising: administering to a subject an effective amount of the compound of any one of embodiments 1-72 or the pharmaceutically acceptable salt thereof, the stereoisomer of any of the foregoing, or the mixture thereof, or the pharmaceutical composition of any one of embodiments 73-76.

80. The method of embodiment 79, wherein the cardiovascular condition is heart failure.

81. The method of embodiment 79, wherein the cardiovascular condition is heart failure with reduced ejection fraction.

82. The method of embodiment 79, wherein the cardiovascular condition is heart failure with preserved ejection fraction.

83. The method of embodiment 79, wherein the cardiovascular condition is chronic systolic heart failure or chronic diastolic heart failure.

84. The method of embodiment 79, wherein the cardiovascular condition is acute heart failure.

85. The method of embodiment 79, wherein the cardiovascular condition is hypertension.

86. A method of improving cardiac contractility in a subject suffering from a cardiovascular condition, the method comprising: administering to the subject an effective amount of the compound of any one of embodiments 1-72 or the pharmaceutically acceptable salt thereof, the stereoisomer of any of the foregoing, or the mixture thereof, or the pharmaceutical composition of any one of embodiments 73-76, wherein cardiac contractility is improved in the subject after administration.

87. A method of increasing ejection fraction in a subject suffering from a cardiovascular condition, the method comprising: administering to the subject an effective amount of the compound of any one of embodiments 1-72 or the pharmaceutically acceptable salt thereof, the stereoisomer of any of the foregoing, or the mixture thereof, or the pharmaceutical composition of any one of embodiments 73-76, wherein the ejection fraction is increased in the subject after administration.

88. A method of treating a condition in a subject where it is desired to activate the APJ Receptor, the method comprising: administering to the subject an effective amount of the compound of any one of embodiments 1-72 or the pharmaceutically acceptable salt thereof, the stereoisomer of any of the foregoing, or the mixture thereof or the pharmaceutical composition of any one of embodiments 73-76.

89. The method of embodiment 88, wherein the condition is obesity or diabetes.

90. The method of embodiment 88, wherein the condition is diabetic nephropathy or chronic kidney disease.

91. The method of any one of embodiments 79-90, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

92. The method of any one of embodiments 79-90, wherein the method includes administering at least one additional therapeutic agent to the subject, wherein the additional therapeutic agent is selected from an angiotensin converting enzyme (ACE) inhibitor or an angiotensin-receptor blocker (ARB).

93. A compound of any one of embodiments 1-72 or the pharmaceutically acceptable salt thereof, the stereoisomer of any of the foregoing, or the mixture thereof, or the pharmaceutical composition of any one of embodiments 73-76 for use in treating a cardiovascular condition.

94. The compound of embodiments 93, wherein the cardiovascular condition is heart failure.

95. The compound of embodiment 93, wherein the cardiovascular condition is heart failure with reduced ejection fraction.

96. The compound of embodiment 93, wherein the cardiovascular condition is heart failure with preserved ejection fraction.

97. The compound of embodiment 93, wherein the cardiovascular condition is chronic systolic heart failure or chronic diastolic heart failure.

98. The compound of embodiment 93, wherein the cardiovascular condition is acute heart failure.

99. The compound of embodiment 93, wherein the cardiovascular condition is hypertension.

100. A compound of any one of embodiments 1-72 or the pharmaceutically acceptable salt thereof, the stereoisomer of any of the foregoing, or the mixture thereof, or the pharmaceutical composition of any one of embodiments 73-76 for use in activating the APJ Receptor or for treating a condition where it is desirable to activate the APJ Receptor.

101. The compound of embodiment 100, wherein the condition is obesity or diabetes.

102. The compound of embodiment 100, wherein the condition is diabetic nephropathy or chronic kidney disease.

103. A use of the compound of any one of embodiments 1-72 or the pharmaceutically acceptable salt thereof, the stereoisomer of any of the foregoing, or the mixture thereof in the preparation of a medicament for treating a cardiovascular condition.

104. The use of embodiment 103, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

105. The use of embodiment 103, further comprising a therapeutic agent selected from an angiotensin converting enzyme (ACE) inhibitor or an angiotensin-receptor blocker (ARB).

106. The use of the compound of any one of embodiments 103-105, wherein the cardiovascular condition is heart failure.

107. The use of the compound of any one of embodiments 103-105, wherein the cardiovascular condition is heart failure with reduced ejection fraction.

108. The use of the compound of any one of embodiments 103-105, wherein the cardiovascular condition is heart failure with preserved ejection fraction.

109. The use of the compound of any one of embodiments 103-105, wherein the cardiovascular condition is chronic systolic heart failure or chronic diastolic heart failure.

110. The use of the compound of any one of embodiments 103-105, wherein the cardiovascular condition is acute heart failure.

111. The use of the compound of any one of embodiments 103-105, wherein the cardiovascular condition is hypertension.

112. A use of the compound of any one of embodiments 1-72 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

113. The use of embodiment 112, wherein the condition is obesity or diabetes.

114. The use of embodiment 112, wherein the condition is diabetic nephropathy or chronic kidney disease.

115. A treatment regimen for a cardiovascular disease, the regimen comprising: the compound of any one of embodiments 1-72 or the pharmaceutically acceptable salt thereof, the stereoisomer of any of the foregoing, or the mixture thereof.

116. The treatment regimen of embodiment 115, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

117. The treatment regimen of embodiment 115, wherein the regimen further comprises a therapeutic agent selected from an angiotensin converting enzyme (ACE) inhibitor or an angiotensin-receptor blocker (ARB).

118. A kit, the kit comprising: the compound of any one of embodiments 1-72 or the pharmaceutically acceptable salt thereof, the stereoisomer of any of the foregoing, or the mixture thereof.

119. The kit of embodiment 118, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

120. The kit of embodiment 118, wherein the kit further comprises a therapeutic agent selected from an angiotensin converting enzyme (ACE) inhibitor or an angiotensin-receptor blocker (ARB).

121. In another aspect, the invention provides an embodiment which is a compound of Formula V, a salt thereof, a tautomer thereof, or a salt of the tautomer:

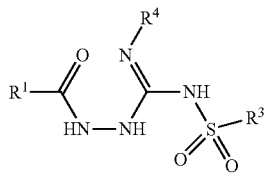

V wherein:

$R^1$ is an unsubstituted $C_1$-$C_8$ straight or branched chain alkyl or $R^1$ is a $C_1$-$C_8$ straight or branched chain alkyl substituted with 1, 2, or 3 $R^{1a}$ substituents;

$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a}$ groups that include a $C_6$-$C_{10}$ aryl group, the heteroaryl of any of the $R^{1a}$ groups that include a heteroaryl group, the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group are unsubstituted or are substituted with 1, 2, or 3 $R^{1a'}$ substituents; and further wherein the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group may additionally be substituted with 1 or 2 oxo substituents, and the S atom of the heterocyclyl of any of the $R^{1a}$ groups that include a heterocyclyl group may contain one or two oxo substituents, and still further wherein, the heteroaryl of any of the $R^{1a}$ groups that include a heteroaryl group may include an N-oxide if the heteroaryl includes a N heteroatom;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^3$ is selected from a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q a group of formula —(CR$^{3d}$R$^{3e}$)—(CR$^{3f}$R$^{3g}$)—CH(OH)-Q, a group of formula —(CR$^{3a}$R$^{3e}$)—(CR$^{3f}$R$^{3g}$)—(CR$^{3f}$R$^{3g}$)-Q a group of formula —($C_3$-$C_5$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 R$^{3h}$ substituents, and further wherein the $C_3$-$C_8$ cycloalkyl of the —($C_3$-$C_8$ cycloalkyl)-Q group is unsubstituted or is substituted with 1 or 2 R$^{3h}$ substituents;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_{58}$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —$NH(C_1$-$C_6$ alkyl), —$N(C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-$NH_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl) heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_1$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —$NH(C_1$-$C_6$ alkyl), —$N(C_1$-$C_6$ alkyl)$_2$, $NH(C_1$-$C_6$ alkyl-OH), —$N(C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N ($C_1$-$C_6$ alkyl)$_2$, phenyl, a monocyclic heteroaryl group with 5 or 6 ring members containing 1, 2, or 3 N atoms, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{4c}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —$NH(C_1$-$C_6$ alkyl), —$N(C_1$-$C_6$ alkyl)$_2$, $NH(C_1$-$C_6$ alkyl-OH), —$N(C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O) NH($C_1$-$C_6$ alkyl), —C(=O)N($C_1$-$C_6$ alkyl)$_2$, or —S(=O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —$NH(C_1$-$C_6$ alkyl), —$N(C_1$-$C_6$ alkyl)$_2$, $NH(C_1$-$C_6$ alkyl-OH), —$N(C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O) NH($C_1$-$C_6$ alkyl), —C(=O)N($C_1$-$C_6$ alkyl)$_2$, or —S(=O)$_2$—($C_1$-$C_6$ alkyl).

122. The compound of embodiment 121, the salt thereof, the tautomer thereof, or the salt of the tautomer, wherein the compound has any of the $R^1$, $R^{1a}$, $R^3$, $R^{3d}$, $R^{3e}$, $R^{3f}$, $R^{3g}$, $R^{3h}$, $R^4$, $R^{4a}$, Q, or $R^Q$, values or combinations of values of any one of embodiments 2-68.

123. In another aspect, the invention provides an embodiment which is a method for preparing a compound of Formula VI, a salt thereof, a tautomer thereof, or a salt of the tautomer:

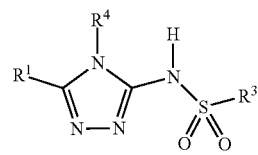

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

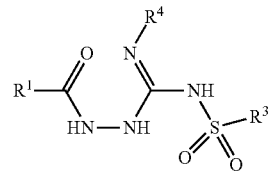

V wherein:
$R^1$ is an unsubstituted $C_1$-$C_8$ straight or branched chain alkyl or $R^1$ is a $C_1$-$C_8$ straight or branched chain alkyl substituted with 1, 2, or 3 $R^a$ substituents;

$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(═O)—($C_1$-$C_6$ alkyl), —C(═O)OH, —C(═O)—O—($C_1$-$C_6$ alkyl), —C(═O)NH$_2$, —C(═O)NH($C_1$-$C_6$ alkyl), —C(═O)N($C_1$-$C_6$ alkyl)$_2$, —NHS(═O)$_2$—($C_1$-$C_6$ alkyl), —S(═O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a}$ groups that include a $C_6$-$C_{10}$ aryl group, the heteroaryl of any of the $R^{1a}$ groups that include a heteroaryl group, the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group are unsubstituted or are substituted with 1, 2, or 3 $R^{1a'}$ substituents; and further wherein the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group may additionally be substituted with 1 or 2 oxo substituents, and the S atom of the heterocyclyl of any of the $R^{1a}$ groups that include a heterocyclyl group may contain one or two oxo substituents, and still further wherein, the heteroaryl of any of the $R^{1a}$ groups that include a heteroaryl group may include an N-oxide if the heteroaryl includes a N heteroatom;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(═O)—($C_1$-$C_6$ alkyl), —C(═O)OH, —C(═O)—O—($C_1$-$C_6$ alkyl), —C(═O)NH$_2$, —C(═O)NH($C_1$-$C_6$ alkyl), —C(═O)N($C_1$-$C_6$ alkyl)$_2$, or —S(═O)$_2$—($C_1$-$C_6$ alkyl);

$R^3$ is selected from a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(═O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, a group of formula —($C_3$-$C_5$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(═O)—($C_1$-$C_6$ alkyl), —C(═O)—($C_3$-$C_6$ cycloalkyl), —C(═O)—O—($C_1$-$C_6$ alkyl), oxo, or —C(═O)-(heterocyclyl), wherein the heterocyclyl group of the $R^h$—C(═O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(═O)($C_1$-$C_6$ alkyl), —C(═O)—($C_1$-$C_6$ alkyl), —C(═O)OH, —C(═O)—O—($C_1$-$C_6$ alkyl), —C(═O)NH$_2$, —C(═O)NH($C_1$-$C_6$ alkyl), —C(═O)N($C_1$-$C_6$ alkyl)$_2$, —S(═O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-NH$_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl) heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(═O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_1$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, phenyl, a monocyclic heteroaryl group with 5 or 6 ring members containing 1, 2, or 3 N atoms, —S(═O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{4c}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, or —S(═O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(═O)—($C_1$-$C_6$ alkyl), —C(═O)OH, —C(═O)—O—($C_1$-$C_6$ alkyl), —C(═O)$NH_2$, —C(═O)NH($C_1$-$C_6$ alkyl), —C(═O)N($C_1$-$C_6$ alkyl)$_2$, or —S(═O)$_2$—($C_1$-$C_6$ alkyl).

124. The method of embodiment 123, wherein $R^1$, $R^{1a}$, $R^3$, $R^{3d}$, $R^{3e}$, $R^{3f}$, $R^{3g}$, $R^{3h}$, $R^4$, $R^{4a}$, Q, or $R^Q$, have any of the values or combination of values of any one of embodiments 2-68.

125. The method of embodiment 123 or embodiment 124, wherein cyclizing further comprises heating the compound of Formula V, the salt thereof, the tautomer thereof, or the salt of the tautomer in the presence of the acid or the base.

126. The method of embodiment 125, wherein heating the compound of Formula V, the salt thereof, the tautomer thereof, or the salt of the tautomer comprises heating the compound to a temperature of from 50° C. to 100° C.

127. The method of embodiment 125, wherein heating the compound of Formula V, the salt thereof, the tautomer thereof, or the salt of the tautomer comprises heating the compound to a temperature of from 60° C. to 85° C.

128. The method of any one of embodiments 123-127, wherein the cyclizing of the compound of Formula V, the salt thereof, the tautomer thereof, or the salt of the tautomer is performed in the presence of the base.

129. The method of any one of embodiments 123-128, wherein the base is a metal hydroxide.

130. The method of embodiment 129, wherein the metal hydroxide is selected from NaOH or LiOH.

131. The method of any one of embodiments 128-130, wherein the cyclizing is carried out in an alcohol solvent.

132. The method of embodiment 131, wherein the alcohol is isopropanol.

133. The method of any one of embodiments 123-127, wherein cyclizing further comprises heating the compound of Formula V, the salt thereof, the tautomer thereof, or the salt of the tautomer in the presence of the acid.

134. The method of embodiment 133, wherein the acid is selected from a sulfonic acid, a carboxylic acid, polyphosphoric acid, phosphoric acid, sulfuric acid, or hydrochloric acid.

135. The method of embodiment 134, wherein the sulfonic acid is methanesulfonic acid.

136. The method of embodiment 134, wherein the acid is trifluoroacetic acid, acetic acid, or trichloroacetic acid.

137. The method of any one of embodiments 133-136, wherein the cyclizing is carried out in a cyclic ether, an acyclic ether, N,N-dimethylformamide, or acetonitrile.

138. The method of embodiment 137, wherein the cyclizing is carried out in a cyclic ether.

139. The method of embodiment 138, wherein the cyclic ether is selected from tetrahydrofuran, tetrahydropyran, or 1,4-dioxane.

140. The method of embodiment 138, wherein the cyclic ether is 1,4-dioxane.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, edema, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, 3-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 µL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^3$, $R^4$, and Q groups taught in WO 2016/187308 and U.S. Pat. Appl. Pub. No. US 2016/0340336.

The following Abbreviations are used to refer to various reagents and solvents:
ACN Acetonitrile
AcOH Acetic Acid
d day or days
CV Column volume
DCM Dichloromethane
DEA Diethylamine
DMF N,N-Dimethylformamide
DMSO Dimethylsulfoxide
EtOAc Ethyl Acetate
EtOH Ethanol
EtOTf Ethyl trifluoromethanesulfonate
h hour or hours
IPA Isopropanol
LAH Lithium aluminum hydride
MeOH Methanol
MeOTf Methyl trifluoromethanesulfonate
min minute or minutes
MS Mass spectrum
MSA Methanesulfonic acid
RT Room temperature
SFC Supercritical fluid chromatography
TBS t-Butyldimethylsilane
TBSOTf t-Butyldimethylsilyl trifluoromethanesulfonate
t-BuOH t-Butyl alcohol
TEA Triethylamine
TFA Trifluoroacetic acid
THF Tetrahydrofuran
TLC Thin Layer Chromatography The compounds set forth in the following table were synthesized following the procedure in Example 14.0 using the known starting material as described.

TABLE 1.0

| Example | Reagents | Structure, Name and Data |
|---|---|---|
| 1.0 | (2S,3R)-3-(5-chloropyrimidin-2-yl)butane-2-sulfonamide (Example 81.4), 3,3-dimethylbutanehydrazide (commercially available from Enamine), and 5-isothiocyanato-4,6-dimethoxypyrimidine (Example 82.1). | 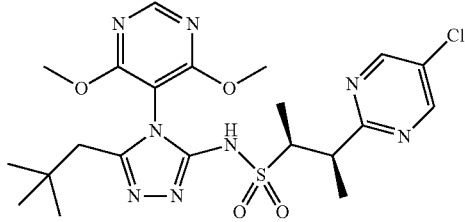 [SMILES: COc1ncnc(OC)c1-n1c(CC(C)(C)C)nnc1NS(=O)(=O)[C@@H](C)[C@H](C)c1ncc(Cl)cn1]<br>(2S,3R)-3-(5-chloro-2-pyrimidinyl)-N-(4-(4,6-dimethoxy-5-pyrimidinyl)-5-(2,2-dimethylpropyl)-4H-1,2,4-triazol-3-yl)-2-butanesulfonamide.<br>$^1$H NMR (400 MHz, DMSO-$d_6$) δ 12.94 (1H, s) 8.80 (2 H, s) 8.65 (1H, s) 3.85-3.90 (6H, m) 3.58 (1H, qd, J = 6.99, 4.48 Hz) 3.44-3.52 (1H, m) 2.20 (2H, s) 1.18 (3H, d, J = 7.10 Hz) 1.05 (3H, d, J = 6.95 Hz) 0.84 (9H, s). LCMS-ESI (pos.) m/z: 525.2 (M + H)$^+$. |
| 2.0 | (2S,3R)-3-(5-chloropyrimidin-2-yl)butane-2-sulfonamide (Example 81.4), 2-isopropoxypropanohydrazide (commercially available from ChemBridge Corporation), and 5-isothiocyanato-4,6-dimethoxypyrimidine (Example 82.1). | 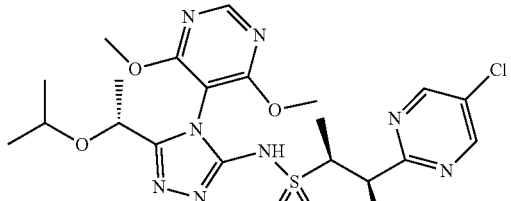<br>or |
|  | The racemic mixture was separated by preparative SFC method: Column: Chiralpak AS-H 2 × 25 cm + Chiralpak AS-H 2 × 15 cm, Mobile Phase: 70:30 (A:B) A: Liquid CO$_2$; B: IPA, Flowrate: 70 mL/min, 217 nm, Inlet Pressure: 150 bar to deliver Peak 1. | 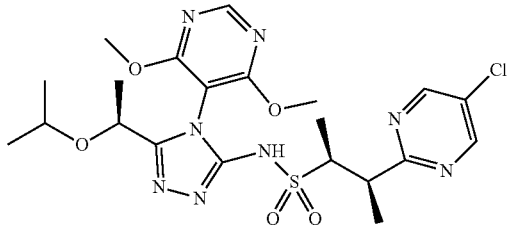 [SMILES: COc1ncnc(OC)c1-n1c(NS(=O)(=O)[C@@H](C)[C@H](C)c2ncc(Cl)cn2)nnc1[C@H](C)OC(C)C]<br>(2S,3R)-3-(5-chloro-2-pyrimidinyl)-N-(4-(4,6-dimethoxy-5-pyrimidinyl)-5-((1R)-1-(1-methylethoxy)ethyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-(1-methylethoxy)ethyl)-4H-1,2,4-triazol-3-yl)-2-butanesulfonamide. |

TABLE 1.0-continued

| Example | Reagents | Structure, Name and Data |
|---|---|---|
| | | $^1$H NMR (400 MHz, DMSO-d$_6$) δ 13.10 (1H, s) 8.86 (2 H, s) 8.68 (1H, s) 4.42 (1H, q, J = 6.41 Hz) 3.94 (3H, s) 3.92 (3H, s) 3.46-3.64 (3H, m) 1.32 (3H, d, J = 6.43 Hz) 1.23 (3H, d, J = 7.05 Hz) 1.10 (3H, d, J = 6.95 Hz) 0.92 (3H, d, J = 6.06 Hz) 0.65 (3H, d, J = 6.06 Hz). LCMS-ESI (pos.) m/z: 542.2 (M + H)$^+$. |
| 3.0 | (2S,3R)-3-(5-chloropyrimidin-2-yl)butane-2-sulfonamide (Example 81.4), 2-isopropoxypropanohydrazide (commercially available from ChemBridge Corporation), and 5-isothiocyanato-4,6-dimethoxypyrimidine (Example 82.1). | 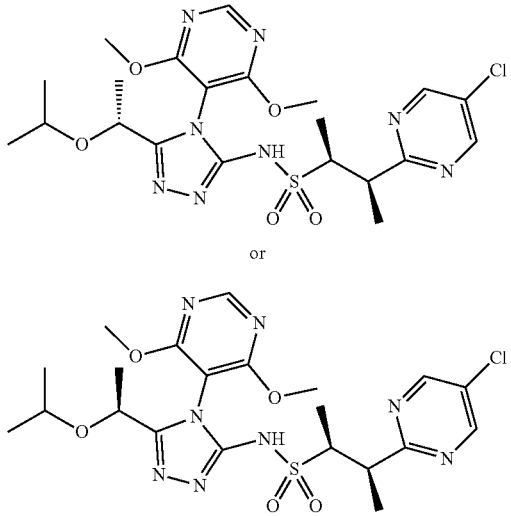 |
| | | or |
| | The racemic mixture was separated by preparative SFC method: Column: Chiralpak AS-H 2 × 25 cm + Chiralpak AS-H 2 × 15 cm, Mobile Phase: 70:30 (A:B) A: Liquid CO$_2$; B: IPA, Flowrate: 70 mL/min, 217 nm, Inlet Pressure: 150 bar to deliver Peak 2. | |
| | | (2S,3R)-3-(5-chloro-2-pyrimidinyl)-N-(4-(4,6-dimethoxy-5-pyrimidinyl)-5-((1R)-1-(1-methylethoxy)ethyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-(1-methylethoxy)ethyl)-4H-1,2,4-triazol-3-yl)-2-butane sulfonamide. $^1$H NMR (400 MHz, DMSO-d$_6$) δ 13.11 (1H, s) 8.86 (2 H, s) 8.68 (1H, s) 4.42 (1H, q, J = 6.41 Hz) 3.94 (3H, s) 3.92 (3H, s) 3.46-3.64 (3H, m) 1.32 (3H, d, J = 6.43 Hz) 1.23 (3H, d, J = 7.05 Hz) 1.10 (3H, d, J = 6.95 Hz) 0.92 (3H, d, J = 6.06 Hz) 0.65 (3H, d, J = 6.06 Hz). LCMS-ESI (pos.) m/z: 542.2 (M + H)$^+$. |
| 4.0 | (2S,3R)-3-(5-chloropyrimidin-2-yl)butane-2-sulfonamide (Example 81.4), 2-methoxypropanohydrazide (commercially available from ChemBridge Corporation), and 5-isothiocyanato-4,6-dimethoxypyrimidine (Example 82.1). | 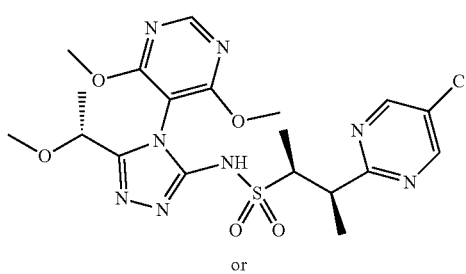 |
| | | or |
| | The racemic mixture was separated by preparative SFC method: Column: Chiralpak AD-H 2 × 25 cm, Mobile Phase: 70:30 (A:B) A: Liquid CO$_2$; B: IPA, Flowrate: 60 mL/min, 254 nm, Inlet Pressure: 100 bar to deliver Peak 1. | |
| | | (2S,3R)-3-(5-chloro-2-pyrimidinyl)-N-(4-(4,6-dimethoxy-5-pyrimidinyl)-5-((1R)-1-methoxyethyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-methoxyethyl)-4H-1,2,4-triazol-3-yl)-2-butanesulfonamide. |

| Example | Reagents | Structure, Name and Data |
|---|---|---|
| | | $^1$H NMR (400 MHz, DMSO-$d_6$) δ 13.18 (1H, s) 8.86 (2 H, s) 8.67 (1H, s) 4.28 (1H, q, J = 6.57 Hz) 3.94 (3H, s) 3.93 (3H, s) 3.59-3.68 (1H, m) 3.49-3.58 (1H, m) 3.05 (3H, s) 1.25 (6H, dd, J = 11.74, 6.87 Hz) 1.11 (3H, d, J = 6.95 Hz). LCMS-ESI (pos.) m/z: 513.0 (M + H)$^+$. |
| 5.0 | (2S,3R)-3-(5-chloropyrimidin-2-yl)butane-2-sulfonamide (Example 81.4), 2-methoxypropanohydrazide (commercially available from ChemBridge Corporation), and 5-isothiocyanato-4,6-dimethoxypyrimidine (Example 82.1). | 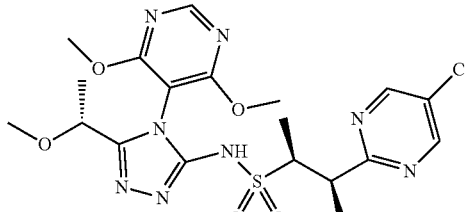<br>or |
| | The racemic mixture was separated by preparative SFC method: Column: Chiralpak AD-H 2 × 25 cm, Mobile Phase: 70:30 (A:B) A: Liquid CO$_2$; B: IPA, Flowrate: 60 mL/min, 254 nm, Inlet Pressure: 100 bar to deliver Peak 2. | 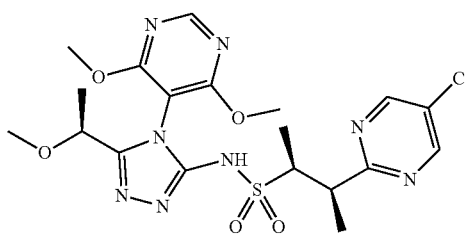<br>(2S,3R)-3-(5-chloro-2-pyrimidinyl)-N-(4-(4,6-dimethoxy-5-pyrimidinyl)-5-((1R)-1-methoxyethyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-methoxyethyl)-4H-1,2,4-triazol-3-yl)-2-butanesulfonamide.<br>$^1$H NMR (400 MHz, DMSO-$d_6$) δ 13.17 (1H, s) 8.86 (2 H, s) 8.67 (1H, s) 4.25-4.31 (1H, m) 3.94 (3H, s) 3.93 (3H, s) 3.58-3.65 (1H, m) 3.50-3.58 (1H, m) 3.05 (3 H, s) 1.25 (6H, dd, J = 13.86, 6.87 Hz) 1.10 (3H, d, J = 6.89 Hz). LCMS-ESI (pos.) m/z: 513.0 (M + H)$^+$. |
| 6.0 | (2S,3R)-3-(5-chloropyrimidin-2-yl)butane-2-sulfonamide (Example 81.4), 2-methoxybutanehydrazide hydrochloride (commercially available from ChemBridge Corporation), and 5-isothiocyanato-4,6-dimethoxypyrimidine (Example 82.1). | 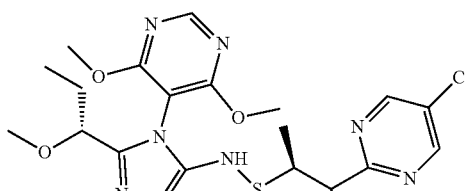<br>or |
| | The racemic mixture was separated by preparative SFC method: Column: Chiralpak AD-H 2 × 25 cm, Mobile Phase: 85:15 (A:B) A: Liquid CO$_2$; B: 1:1 ACN:MeOH, Flowrate: 60 mL/min, 220 nm, Inlet Pressure: 100 bar to deliver Peak 1. | 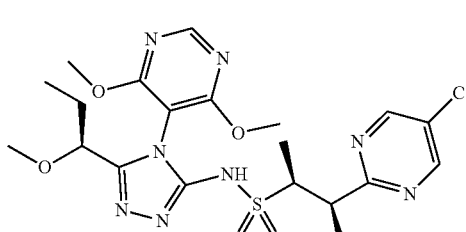<br>(2S,3R)-3-(5-chloro-2-pyrimidinyl)-N-(4-(4,6-dimethoxy-5-pyrimidinyl)-5-((1R)-1-methoxypropyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-methoxypropyl)-4H-1,2,4-triazol-3-yl)-2-butanesulfonamide.<br>$^1$H NMR (400 MHz, DMSO-$d_6$) δ 13.19 (1H, s) 8.85 (2 H, s) 8.66 (1H, s) 4.05 (1H, br s) 3.92 (6H, s) 3.63 (1 H, br s) 3.54 (1H, br s) 3.10 (3H, s) 1.60 (1H, br dd, |

TABLE 1.0-continued

| Example | Reagents | Structure, Name and Data |
|---|---|---|
| | | J = 14.15, 6.95 Hz) 1.43-1.51 (1H, m) 1.23 (3H, d, J = 7.05 Hz) 1.10 (3H, br d, J = 6.79 Hz) 0.80 (3H, t, J = 7.36 Hz). LCMS-ESI (pos.) m/z: 527.1 (M + H)⁺. |
| 7.0 | (2S,3R)-3-(5-chloropyrimidin-2-yl)butane-2-sulfonamide (Example 81.4), 2-methoxybutanehydrazide hydrochloride (commercially available from ChemBridge Corporation), and 5-isothiocyanato-4,6-dimethoxypyrimidine (Example 82.1). | <br>or<br> |
| | The racemic mixture was separated by preparative SFC method: Column: Chiralpak AD-H 2 × 25 cm, Mobile Phase: 85:15 (A:B) A: Liquid CO₂; B: 1:1 ACN:MeOH, Flowrate: 60 mL/min, 220 nm, Inlet Pressure: 100 bar to deliver Peak 2. | <br>(2S,3R)-3-(5-chloro-2-pyrimidinyl)-N-(4-(4,6-dimethoxy-5-pyrimidinyl)-5-((1R)-1-methoxypropyl)-4H-1,2,4-triazol-3-yl)-2-butanesulfonamide or (2S,3R)-3-(5-chloro-2-pyrimidinyl)-N-(4-(4,6-dimethoxy-5-pyrimidinyl)-5-((1S)-1-methoxypropyl)-4H-1,2,4-triazol-3-yl)-2-butanesulfonamide.<br>¹H NMR (400 MHz, DMSO-d₆) δ 13.19 (1H, br s) 8.86 (2H, s) 8.66 (1H, s) 4.04 (1H, br s) 3.91-3.94 (6H, m) 3.63 (1H, br s) 3.55 (1H, br s) 3.10 (3H, s) 1.55-1.64 (1H, m) 1.43-1.52 (1H, m) 1.23 (3H, d, J = 7.05 Hz) 1.10 (3H, br d, J = 6.84 Hz) 0.80 (3H, t, J = 7.41 Hz). LCMS-ESI (pos.) ink: 527.1 (M + H)⁺. |
| 8.0 | (2S,3R)-3-(5-methylpyrazin-2-yl)butane-2-sulfonamide (Example 81.2), methoxyacetic acid hydrazide (commercially available from Combi-Blocks, Inc.), and 2-isothiocyanato-1,3-dimethoxybenzene (Example 82.0). | <br>(2S,3R)-N-(4-(2,6-dimethoxyphenyl)-5-(methoxymethyl)-4H-1,2,4-triazol-3-yl)-3-(5-methyl-2-pyrazinyl)-2-butanesulfonamide.<br>¹H NMR (400 MHz, DMSO-d₆) δ 13.01 (1H, s) 8.44 (1 H, s) 8.31 (1H, s) 7.49 (1H, t, J = 8.58 Hz) 6.85 (1H, d, J = 1.61 Hz) 6.82-6.83 (1H, m) 4.12 (2H, s) 3.73 (6H, s) 3.56 (1H, s) 3.09 (3H, s) 2.45 (4H, s) 1.22 (3H, d, J = 7.10 Hz) 1.11 (3H, d, J = 7.05 Hz). LCMS-ESI (pos.) m/z: 477.2 (M + H)⁺. |
| 9.0 | (2S,3R)-3-(5-methylpyrazin-2-yl)butane-2-sulfonamide (Example 81.2), methoxyacetic acid hydrazide (commercially available from Combi-Blocks, Inc.), and 5-isothiocyanato-4,6-dimethoxypyrimidine (Example 82.1). |  |

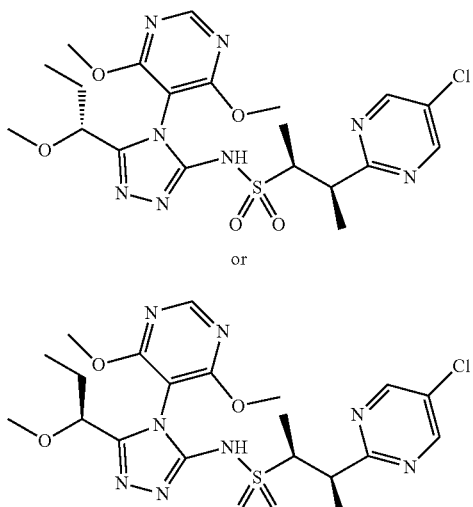
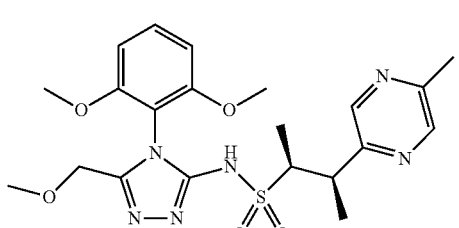
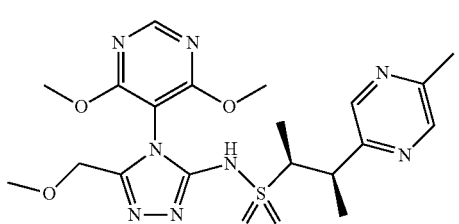

TABLE 1.0-continued

| Example | Reagents | Structure, Name and Data |
|---|---|---|
| | | (2S,3R)-N-(4-(4,6-dimethoxy-5-pyrimidinyl)-5-(methoxymethyl)-4H-1,2,4-triazol-3-yl)-3-(5-methyl-2-pyrazinyl)-2-butanesulfonamide.<br>$^1$H NMR (400 MHz, DMSO-d$_6$) δ 13.22 (1H, s) 8.67 (1 H, s) 8.44 (1H, s) 8.35 (1H, d, J = 1.30 Hz) 4.25 (2H, s) 3.93 (6H, s) 3.56 (1H, dd, J = 6.89, 3.58 Hz) 3.36 (1H, br d, J = 7.00 Hz) 3.12 (3H, s) 2.45 (3H, s) 1.23 (3H, d, J = 7.10 Hz) 1.12 (3H, d, J = 7.05 Hz). LCMS-ESI (pos.) m/z: 479.2 (M + H)$^+$. |
| 10.0 | (2S,3R)-3-(5-chloropyrimidin-2-yl)butane-2-sulfonamide (Example 81.4), methoxyacetic acid hydrazide (commercially available from Combi-Blocks, Inc.), and 2-isothiocyanato-1,3-dimethoxybenzene (Example 82.0). | 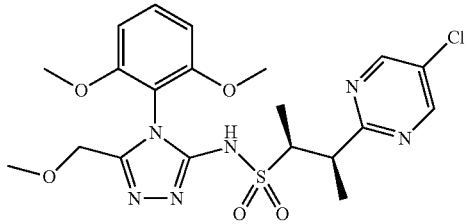 [SMILES: COCc1nnc(NS(=O)(=O)[C@@H](C)[C@H](C)c2ncc(Cl)cn2)n1-c1c(OC)cccc1OC]<br>(2S,3R)-3-(5-chloro-2-pyrimidinyl)-N-(4-(2,6-dimethoxyphenyl)-5-(methoxymethyl)-4H-1,2,4-triazol-3-yl)-2-butanesulfonamide.<br>$^1$H NMR (400 MHz, DMSO-d$_6$) δ 12.97 (1H, s) 8.85 (2 H, s) 7.47 (1H, br t, J = 8.53 Hz) 6.82 (2H, d, J = 8.71 Hz) 4.11 (2H, s) 3.73 (6H, s) 3.63-3.69 (1H, m) 3.52-3.61 (1H, m) 3.06-3.09 (3H, m) 1.24 (3H, d, J = 7.10 Hz) 1.10 (3H, d, J = 6.95 Hz). LCMS-ESI (pos.) m/z: 498.2 (M + H)$^+$. |
| 11.0 | (2S,3R)-3-(5-chloropyrimidin-2-yl)butane-2-sulfonamide (Example 81.4), methoxyacetic acid hydrazide (commercially available from Combi-Blocks, Inc.), and 5-isothiocyanato-4,6-dimethoxypyrimidine (Example 82.1). | 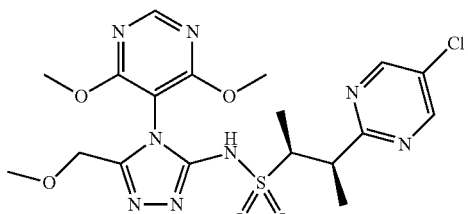<br>(2S,3R)-3-(5-chloro-2-pyrimidinyl)-N-(4-(4,6-dimethoxy-5-pyrimidinyl)-5-(methoxymethyl)-4H-1,2,4-triazol-3-yl)-2-butanesulfonamide.<br>$^1$H NMR (400 MHz, DMSO-d$_6$) δ 13.19 (1H, s) 8.86 (2 H, s) 8.66 (1H, br s) 4.25 (2H, br s) 3.93 (6H, s) 3.64 (1 H, br s) 3.57 (1H, br s) 3.11 (3H, s) 1.24 (3H, br d, J = 7.20 Hz) 1.12 (3H, br d, J = 6.17 Hz). LCMS-ESI (pos.) m/z: 499.2 (M + H)$^+$. |
| 12.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 2-isothiocyanato-1,3-dimethoxybenzene (Example 82.0). | 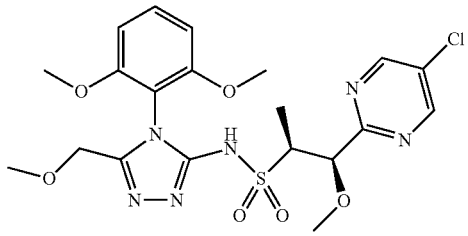 [SMILES: COCc1nnc(NS(=O)(=O)[C@@H](C)[C@H](OC)c2ncc(Cl)cn2)n1-c1c(OC)cccc1OC]<br>(1R,2S)-1-(5-chloro-2-pyrimidinyl)-N-(4-(2,6-dimethoxyphenyl)-5-(methoxymethyl)-4H-1,2,4-triazol-3-yl)-1-methoxy-2-propanesulfonamide.<br>$^1$H NMR (500 MHz, DMSO-d$_6$) δ 12.98 (1H, s) 8.93 (2 H, s) 7.48 (1H, t, J = 8.50 Hz) 6.84 (2H, br d, J = 9.34 Hz) 4.79 (1H, d, J = 4.15 Hz) 4.12 (2H, s) 3.75 (3H, s) 3.74 (3H, s) 3.40 (1H, br dd, J = 6.81, 4.61 Hz) 3.14 (3H, s) 3.08 (3H, s) 1.14 (3H, d, J = 6.88 Hz). LCMS-ESI (pos.) m/z: 513.2 (M + H)$^+$. |

Example 13.01: Preparation of (S)-2-hydroxy-2-phenylacetohydrazide

(S)-2-Hydroxy-2-phenylacetohydrazide, Example 13.01

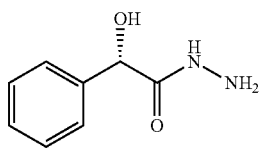

13.01

To a solution of (+)-methyl mandelate (1 g, 6.02 mmol) in MeOH (9.12 ml) was added hydrazine, monohydrate (0.90 ml, 12.04 mmol). The reaction mixture was then heated to reflux. After 12 h, the reaction showed complete conversion to product by LCMS. The reaction was cooled to RT, EtOAc added, and the mixture was stirred for 30 min. The mixture was then concentrated in vacuo to yield (S)-2-hydroxy-2-phenylacetohydrazide (0.9 g, 5.42 mmol, 90% yield). The material thus obtained was carried forward without further purification.

The compounds set forth in the following table were synthesized following the procedure in Example 13.01 using the known starting material as described.

TABLE 2.0

| Example | Reagents | Structure, Name and Data |
|---|---|---|
| 13.02 | (+)-methyl mandelate (commercially available from Sigma-Aldrich Chemical Company, Inc.). | (S)-2-hydroxy-2-phenylacetohydrazide. LCMS-ESI (pos.) m/z: 189.2 $(M + Na)^+$. |
| 13.03 | methyl 2-(pyridin-2-yl)propanoate (commercially available from Enamine). | (R)-2-(pyridin-2-yl)propanehydrazide and (S)-2-(pyridin-2-yl)propanehydrazide. LCMS-ESI (pos.) m/z: 166.2 $(M + H)^+$. |
| 13.04 | 2-methoxy-2-phenylacetic acid methyl ester (commercially available from Enamine). | (R)-2-methoxy-2-phenylacetohydrazide and (S)-2-methoxy-2-phenylacetohydrazide. LCMS-ESI (pos.) m/z: 203.2 $(M + Na)^+$. |
| 13.05 | 2-(5-methylpyridin-2-yl)acetic acid (commercially available from AstaTech, Inc.). | 2-(5-methylpyridin-2-yl)acetohydrazide. LCMS-ESI (pos.) m/z: 166.2 $(M + H)^+$. |
| 13.06 | cyclobutyl-acetic acid methyl ester (commercially available from Synchem, Inc.). | 2-cyclobutylacetohydrazide. LCMS-ESI (pos.) m/z: 129.2 $(M + H)^+$. |

Example 14.0. Preparation of: (Z)—N-(((2S,3R)-3-(5-chloropyrimidin-2-yl)butan-2-yl)sulfonyl)-N'-(2,6-dimethoxyphenyl)-2-(2-phenylacetyl)hydrazinecarboximidamide

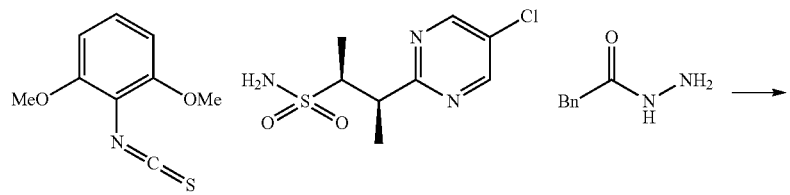

(Z)—N-(((2S,3R)-3-(5-Chloropyrimidin-2-yl)butan-2-yl)sulfonyl)-N'-(2,6-dimethoxyphenyl)-2-(2-phenylacetyl)hydrazinecarboximidamide, Example 14.01

To a solution of (2S,3R)-3-(5-chloropyrimidin-2-yl)butane-2-sulfonamide (Example 81.4, 0.3 g, 1.201 mmol) in ACN (12.01 ml) was added 2-isothiocyanato-1,3-dimethoxybenzene (Example 82.0, 0.235 g, 1.201 mmol) and cesium carbonate (0.509 g, 1.562 mmol). The mixture was stirred at RT for 15 hrs after which LCMS indicated complete consumption of starting materials. To the white slurry was added 2-phenylacetohydrazide (0.180 g, 1.201 mmol) followed by silver(I) nitrate (0.408 g, 2.403 mmol). The resulting mixture was stirred at RT. After 15 min, the mixture was loaded directly onto silica gel and purified (30-100% EtOAc:EtOH 3:1) to yield the desired product as a white solid (Z)—N-(((2S,3R)-3-(5-chloropyrimidin-2-yl)butan-2-yl)sulfonyl)-N'-(2,6-dimethoxyphenyl)-2-(2-phenylacetyl)hydrazinecarboximidamide (0.55 g, 0.980 mmol, 82% yield). LCMS-ESI (POS.) m/z: 561.2 (M+H)$^+$.

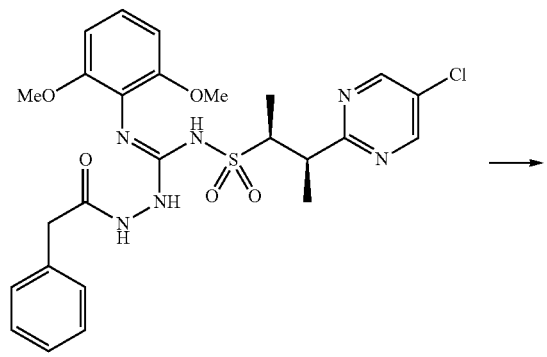

14.01

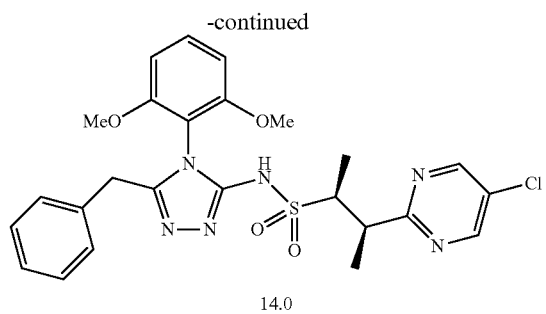

14.0

(Z)—N-(((2S,3R)-3-(5-Chloropyrimidin-2-yl)butan-2-yl)sulfonyl)-N'-(2,6-dimethoxyphenyl)-2-(2-phenylacetyl)hydrazinecarboximidamide, Example 14.0

To a solution of (Z)—N-(((2S,3R)-3-(5-chloropyrimidin-2-yl)butan-2-yl)sulfonyl)-N'-(2,6-dimethoxyphenyl)-2-(2-phenylacetyl)hydrazinecarboximidamide (Exampe 14.01, 0.55 g, 0.980 mmol) in IPA (3.27 ml)/water (1.634 ml) was added 1N NaOH (0.980 ml, 0.980 mmol). The resulting mixture was then heated to 80° C. After 4 h, the reaction was complete by LCMS. The mixture was neutralized to pH 7 using 1M HCl, diluted with water and extracted with DCM. The combined organic layers were washed with water, brine, dried over sodium sulfate and concentrated in vacuo. The reaction mixture was purified by flash chromatography (0-100% EtOAc:EtOH (3:1)/heptanes) to yield (2S,3R)—N-(5-benzyl-4-(2,6-dimethoxyphenyl)-4H-1,2,4-triazol-3-yl)-3-(5-chloropyrimidin-2-yl)butane-2-sulfonamide (0.21 g, 0.387 mmol, 39.4% yield). $^1$H NMR (400 MHz, DMSO-d$_6$) δ ppm 12.84-12.92 (m, 1H) 8.53-8.59 (m, 2H) 8.37-8.43 (m, 1H) 8.01-8.07 (m, 1H) 7.45 (t, J=8.5 Hz, 1H) 7.38 (br d, J=7.7 Hz, 1H) 7.28 (dd, J=7.8, 4.9 Hz, 1H) 6.68-6.77 (m, 2H) 3.73 (d, J=2.1 Hz, 2H) 3.60-3.67 (m, 1H) 3.51-3.58 (m, 7H) 2.22 (s, 3H) 1.20 (d, J=7.2 Hz, 3H) 1.02-1.07 (m, 3H) LCMS-ESI (POS.) M/Z: 543.2 (M+H)$^+$.

The compounds set forth in the following table were synthesized following the procedure in Example 14.0 using the known starting material as described.

TABLE 3.0

| | | |
|---|---|---|
| 13.0 | (2S,3R)-3-(5-chloropyrimidin-2-yl)butane-2-sulfonamide (Example 81.4), (S)-2-hydroxy-2-phenylacetohydrazide (Example 13.01), and isothiocyanato-1,3-dimethoxybenzene (Example 82.0). | 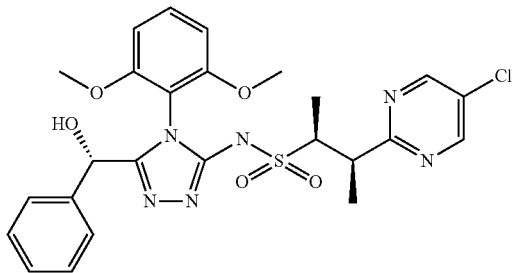 [SMILES: COc1cccc(OC)c1-n1c(NS(=O)(=O)[C@@H](C)[C@H](C)c2ncc(Cl)cn2)nnc1[C@@H](O)c1ccccc1]<br>(2S,3R)-3-(5-chloro-2-pyrimidinyl)-N-(4-(2,6-dimethoxyphenyl)-5-((S)-hydroxy(phenyl)methyl)-4H-1,2,4-triazol-3-yl)-2-butanesulfonamide.<br>$^1$H NMR (500 MHz, CDCl$_3$) δ 8.71-8.78 (m, 2H) 7.39-7.44 (m, 1H) 7.28-7.29 (m, 1H) 7.13-7.18 (m, 3H) 6.84-6.90 (m, 2H) 6.46-6.52 (m, 1H) 3.87-3.99 (m, 2H) 3.76-3.87 (m, 1H) 3.72-3.75 (m, 3H) 3.59-3.64 (m, 1H) 3.42-3.46 (m, 3H) 1.41-1.46 (m, 3H) 1.35-1.39 (m, 3H). LCMS-ESI (pos.) m/z: 560.0 (M + H)$^+$. |
| 14.0 | (2S,3R)-3-(5-chloropyrimidin-2-yl)butane-2-sulfonamide (Example 81.4), 2-phenylacetohydrazide (Commercially available from Acros Organics), and isothiocyanato-1,3-dimethoxybenzene (Example 82.0). | 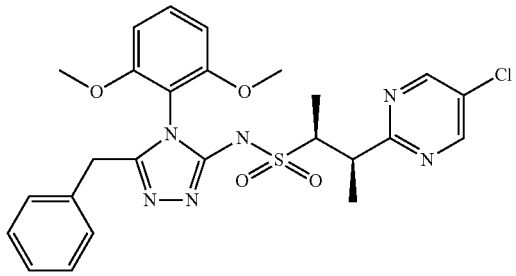 [SMILES: COc1cccc(OC)c1-n1c(Cc2ccccc2)nnc1NS(=O)(=O)[C@@H](C)[C@H](C)c1ncc(Cl)cn1]<br>(2S,3R)-N-(5-benzyl-4-(2,6-dimethoxyphenyl)-4H-1,2,4-triazol-3-yl)-3-(5-chloro-2-pyrimidinyl)-2-butanesulfonamide.<br>$^1$H NMR (500 MHz, CDCl$_3$) δ 8.62-8.70 (m, 2H) 7.31-7.37 (m, 1H) 7.17 (br s, 3H) 6.85-6.92 (m, 2H) 6.45-6.55 (m, 2H) 3.71-3.89 (m, 4H) 3.51-3.64 (m, 6H) 1.32-1.41 (m, 6H). LCMS-ESI (pos.) m/z: 543.2 (M + H)$^+$. |
| 15.0 | (2S,3R)-3-(5-methylpyrimidin-2-yl)butane-2-sulfonamide (Example 81.0), 2-(pyridin-2-yl)acetohydrazide (commercially available from Enamine), and isothiocyanato-1,3-dimethoxybenzene (Example 82.0). | 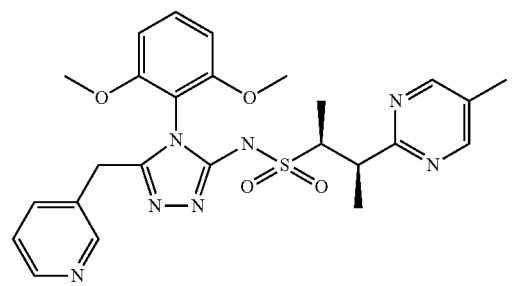 [SMILES: COc1cccc(OC)c1-n1c(Cc2cccnc2)nnc1NS(=O)(=O)[C@@H](C)[C@H](C)c1ncc(C)cn1]<br>(2S,3R)-N-(4-(2,6-dimethoxyphenyl)-5-(3-pyridinylmethyl)-4H-1,2,4-triazol-3-yl)-3-(5-methyl-2-pyrimidinyl)-2-butanesulfonamide.<br>$^1$H NMR (400 MHz, DMSO-d$_6$) δ 12.84-12.92 (m, 1H) 8.53-8.59 (m, 2H) 8.37-8.43 (m, 1H) 8.01-8.07 (m, 1H) 7.45 (t, J = 8.5 Hz, 1H) 7.38 (br d, J = 7.7 Hz, 1H) 7.28 (dd, J = 7.8, 4.9 Hz, 1H) 6.68-6.77 (m, 2H) 3.73 (d, J = 2.1 Hz, 2H) 3.60-3.67 (m, 1H) 3.51-3.58 (m, 7H) 2.22 (s, 3H) 1.20 (d, J = 7.2 Hz, 3H) 1.02-1.07 (m, 3H). LCMS-ESI (pos.) m/z: 524.2 (M + H)$^+$. |

TABLE 3.0-continued

| | | |
|---|---|---|
| 16.0 | (2S,3R)-3-(5-chloropyrimidin-2-yl)butane-2-sulfonamide (Example 81.4), 2-(pyridin-2-yl)propanehydrazide (Example 13.03), and isothiocyanato-1,3-dimethoxybenzene (Example 82.0). Racemic compound was separated by SFC: Chiralpak AD-H 2 × 25 cm, Mobile Phase: 45% IPA, Flowrate: 80 mL/min, Wavelength: 215 nm, Injection Volume: 1.0 mL, Cycle Time: 7 min.<br>Example 16.0 was the first isomer to elute under these conditions. | 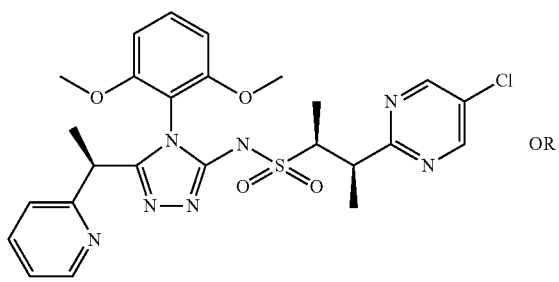 [SMILES: COc1cccc(OC)c1-n1c(NS(=O)(=O)[C@@H](C)[C@H](C)c2ncc(Cl)cn2)nnc1[C@H](C)c1ccccn1] OR<br>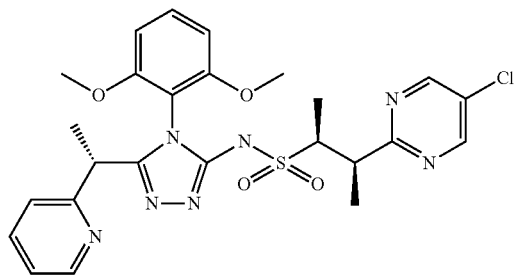 [SMILES: COc1cccc(OC)c1-n1c(NS(=O)(=O)[C@@H](C)[C@H](C)c2ncc(Cl)cn2)nnc1[C@@H](C)c1ccccn1]<br>(2S,3R)-N-(4-(2,6-dimethoxyphenyl)-5-(2-oxoindolin-4-yl)-4H-1,2,4-triazol-3-yl)-3-(5-methylpyrimidin-2-yl)butane-2-sulfonamide.<br>$^1$H NMR (400 MHz, CDCl$_3$) δ 8.62-8.63 (m, 2H) 8.59-8.64 (m, 1H) 7.36 (br dd, J = 9.0, 7.4 Hz, 1H) 7.28-7.33 (m, 3H) 6.63-6.70 (m, 1H) 6.27 (d, J = 8.2 Hz, 1H) 3.88-3.91 (m, 3H) 3.72-3.86 (m, 3H) 3.35 (s, 3H) 1.71 (d, J = 7.0 Hz, 3H) 1.30-1.36 (m, 6H)). LCMS-ESI (pos.) m/z: 559.0 (M + H)$^+$. |
| 17.0 | (2S,3R)-3-(5-chloropyrimidin-2-yl)butane-2-sulfonamide (Example 81.4), 2-(pyridin-2-yl)propanehydrazide (Example 13.03), and isothiocyanato-1,3-dimethoxybenzene (Example 82.0). Racemic compound was separated by SFC: Chiralpak AD-H 2 × 25 cm, Mobile Phase: 45% IPA Flowrate: 80 mL/min, Wavelength: 215 nm, Injection Volume: 1.0 mL, Cycle Time: 7 min.<br>Example 17.0 was the second isomer to elute under these conditions. | 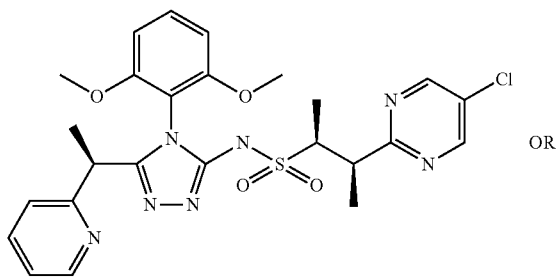 [SMILES: COc1cccc(OC)c1-n1c(NS(=O)(=O)[C@@H](C)[C@H](C)c2ncc(Cl)cn2)nnc1[C@H](C)c1ccccn1] OR<br>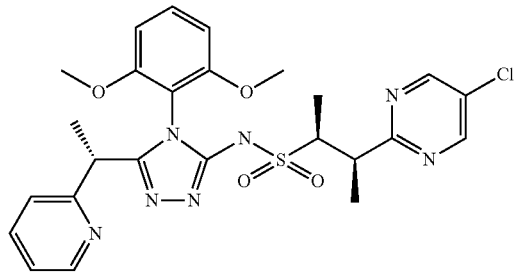 [SMILES: COc1cccc(OC)c1-n1c(NS(=O)(=O)[C@@H](C)[C@H](C)c2ncc(Cl)cn2)nnc1[C@@H](C)c1ccccn1]<br>(2S,3R)-N-(4-(2,6-dimethoxyphenyl)-5-(2-oxoindolin-4-yl)-4H-1,2,4-triazol-3-yl)-3-(5-methylpyrimidin-2-yl)butane-2-sulfonamide.<br>$^1$H NMR (400 MHz, CDCl$_3$) δ 8.59-8.65 (m, 3H) 8.38 (d, J = 5.0 Hz, 1H) 7.29-7.38 (m, 2H) 7.28-7.29 (m, 1 H) 6.66-6.73 (m, 1H) 6.22-6.28 (m, 1H) 3.91-3.95 (m, 3H) 3.73-3.85 (m, 3H) 3.35-3.38 (m, 3H) 1.34-1.36 (m, 3H) 1.31 (d, J = 6.7 Hz, 3H). LCMS-ESI (pos.) m/z: 559.0 (M + H)$^+$. |

TABLE 3.0-continued

| | | |
|---|---|---|
| 18.0 | (2S,3R)-3-(5-methylpyrimidin-2-yl)butane-2-sulfonamide (Example 81.0), 2-methoxy-2-phenylacetohydrazide (Example 13.04), and isothiocyanato-1,3-dimethoxybenzene (Example 82.0). Racemic compound separated by SFC: Chiralpak AD-H 2 × 25 cm Mobile Phase: 35% IPA, Flowrate: 80 mL/min, Wavelength: 215 mn, Injection Volume: 0.5 mL, Cycle Time: 8 min+.<br>Example 18.0 was the first isomer to elute under these conditions. | 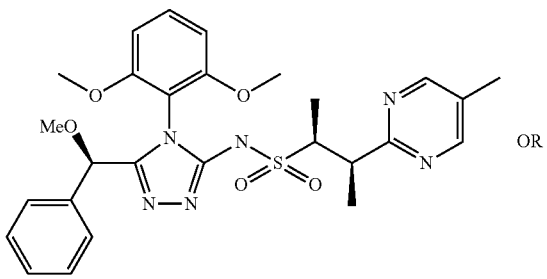 [SMILES: COc1cccc(OC)c1-n1c(NS(=O)(=O)[C@@H](C)[C@H](C)c2ncc(C)cn2)nnc1[C@H](OC)c1ccccc1] OR<br><br>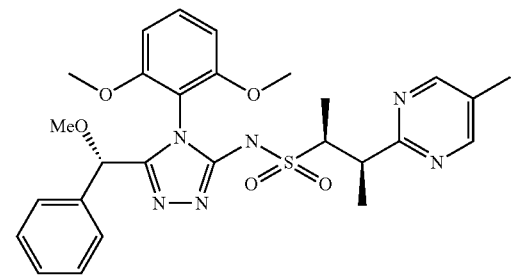 [SMILES: COc1cccc(OC)c1-n1c(NS(=O)(=O)[C@@H](C)[C@H](C)c2ncc(C)cn2)nnc1[C@@H](OC)c1ccccc1]<br><br>(2S,3R)-N-(4-(2,6-dimethoxyphenyl)-5-((R)-methoxy(phenyl)methyl)-4H-1,2,4-triazol-3-yl)-3-(5-methyl-2-pyrimidinyl)-2-butanesulfonamide.<br>$^1$H NMR (500 MHz, CDCl$_3$) δ 8.46-8.51 (m, 2H) 7.26-7.32 (m, 1H) 7.15-7.24 (m, 3H) 6.98-7.02 (m, 2H) 6.38-6.48 (m, 2H) 4.94-4.97 (m, 1H) 3.76-3.82 (m, 1H) 3.70-3.74 (m, 1H) 3.54 (s, 3H) 3.44 (s, 3H) 3.30 (s, 3H) 2.23-2.27 (m, 3H) 1.32 (d, J = 7.0 Hz, 3H) 1.24-1.26 (m, 3H). LCMS-ESI (pos.) m/z: 553.2 (M + H)$^+$. |
| 19.0 | (2S,3R)-3-(5-methylpyrimidin-2-yl)butane-2-sulfonamide (Example 81.0), 2-methoxy-2-phenylacetohydrazide (Example 13.04), and isothiocyanato-1,3-dimethoxybenzene (Example 82.0). Racemic compound separated by SFC: Chiralpak AD-H 2 × 25 cm, Mobile Phase: 35% IPA Flowrate: 80 mL/min, Wavelength: 215 mn, Injection Volume: 0.5 mL, Cycle Time: 8 min+.<br>Example 19.0 was the second isomer to elute under these conditions. | 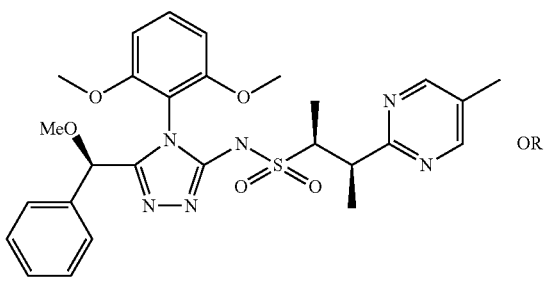 [SMILES: COc1cccc(OC)c1-n1c(NS(=O)(=O)[C@@H](C)[C@H](C)c2ncc(C)cn2)nnc1[C@H](OC)c1ccccc1] OR<br><br>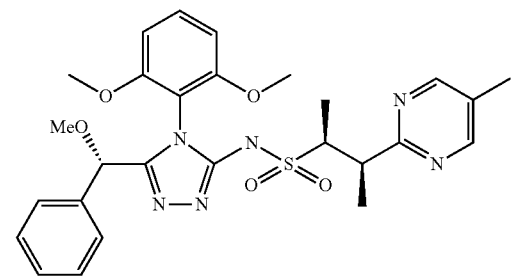 [SMILES: COc1cccc(OC)c1-n1c(NS(=O)(=O)[C@@H](C)[C@H](C)c2ncc(C)cn2)nnc1[C@@H](OC)c1ccccc1]<br><br>(2S,3R)-N-(4-(2,6-dimethoxyphenyl)-5-((S)-methoxy(phenyl)methyl)-4H-1,2,4-triazol-3-yl)-3-(5-methyl-2-pyrimidinyl)-2-butanesulfonamide.<br>$^1$H NMR (400 MHz, CDCl$_3$) δ 8.47-8.54 (m, 2H) 7.17-7.34 (m, 4H) 6.99-7.05 (m, 2H) 6.41-6.47 (m, 2H) 4.95-5.05 (m, 1H) 3.78-3.87 (m, 1H) 3.69-3.77 (m, 1H) 3.52-3.54 (m, 3H) 3.48-3.51 (m, 3H) 3.31-3.33 (m, 3H) 2.22-2.31 (m, 3H) 1.26-1.41 (m, 6H). LCMS-ESI (pos.) m/z: 553.2 (M + H)$^+$. |

TABLE 3.0-continued

| | | |
|---|---|---|
| 20.0 | (2S,3R)-3-(5-methylpyrimidin-2-yl)butane-2-sulfonamide (Example 81.0), 2-(5-methylpyridin-2-yl)acetohydrazide (Example 13.05), isothiocyanato-1,3-dimethoxybenzene (Example 82.0. | 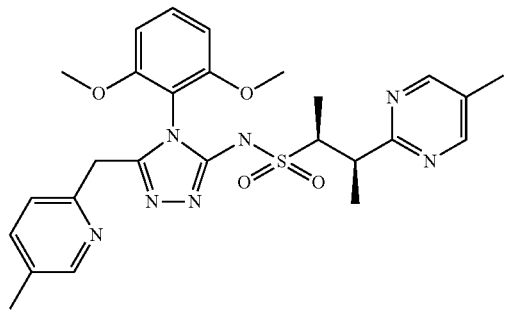 [SMILES: COc1cccc(OC)c1-n1c(Cc2ccc(C)cn2)nnc1NS(=O)(=O)[C@@H](C)[C@H](C)c1ncc(C)cn1]<br><br>(2S,3R)-N-(4-(2,6-dimethoxyphenyl)-5-((5-methyl-2-pyridinyl)methyl)-4H-1,2,4-triazol-3-yl)-3-(5-methyl-2-pyrimidinyl)-2-butanesulfonamide.<br>¹H NMR (400 MHz, CDCl₃) δ 8.51 (s, 2H) 8.27-8.29 (m, 1H) 7.50-7.58 (m, 1H) 7.31-7.37 (m, 1H) 7.08-7.17 (m, 1H) 6.49-6.57 (m, 2H) 3.70-3.90 (m, 4H) 3.66 (d, J = 12.1 Hz, 6H) 2.33-2.39 (m, 3H) 2.27-2.29 (m, 3H) 1.34-1.38 (m, 3H) 1.29-1.33 (m, 3H). LCMS-ESI (pos.) m/z: 538.2 (M + H)⁺. |
| 21.0 | (2S,3R)-3-(5-chloropyrimidin-2-yl)butane-2-sulfonamide (Example 81.4), 2-phenylacetohydrazide (commercially available from Acros Organics), and 5-isothiocyanato-4,6-dimethoxypyrimidine (Example 82.1). | 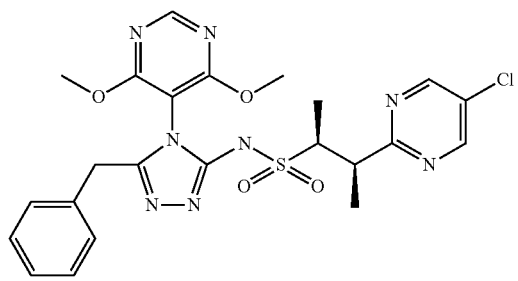<br><br>(2S,3R)-N-(5-benzyl-4-(4,6-dimethoxy-5-pyrimidinyl)-4H-1,2,4-triazol-3-yl)-3-(5-chloro-2-pyrimidinyl)-2-butanesulfonamide.<br>¹H NMR (500 MHz, CDCl₃) δ 8.61-8.66 (m, 2H) 8.38-8.41 (m, 1H) 7.18-7.22 (m, 3H) 6.89-6.92 (m, 2H) 3.74-3.85 (m, 10H) 1.35-1.38 (m, 3H) 1.30-1.34 (m, 3H). LCMS-ESI (pos.) m/z: 542.2 (M + H)⁺. |
| 22.0 | (1R,2S)-1-methoxy-1-(5-chloropyrimidin-2-yl)propane-2-sulfonamide (Example 83.3), 2-phenylacetohydrazide (commercially available from Acros Organics), and 5-isothiocyanato-4,6-dimethoxypyrimidine (Example 82.1). | 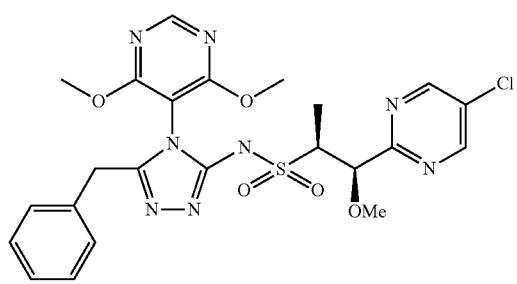 [SMILES: COc1ncnc(OC)c1-n1c(Cc2ccccc2)nnc1NS(=O)(=O)[C@@H](C)[C@H](OC)c1ncc(Cl)cn1]<br><br>(1R,2S)-N-(5-benzyl-4-(4,6-dimethoxy-5-pyrimidinyl)-4H-1,2,4-triazol-3-yl)-1-(5-chloro-2-pyrimidinyl)-1-methoxy-2-propanesulfonamide.<br>¹H NMR (500 MHz, CDCl₃) δ 8.71-8.72 (m, 2H) 8.39-8.41 (m, 1H) 7.18-7.22 (m, 3H) 6.88-6.91 (m, 2H) 4.92-4.95 (m, 1H) 3.79 (d, J = 9.1 Hz, 8H) 3.74-3.84 (m, 1H) 3.66-3.71 (m, 1H) 3.32-3.34 (m, 3H) 1.31-1.35 (m, 3H). LCMS-ESI (pos.) m/z: 561.2 (M + H)⁺. |

TABLE 3.0-continued

| | | |
|---|---|---|
| 23.0 | (2S,3R)-3-(5-methylpyrimidin-2-yl)butane-2-sulfonamide (Example 81.0), 2-phenylacetohydrazide (commercially available from Acros Organics), and 5-isothiocyanato-4,6-dimethoxypyrimidine (Example 82.1). | 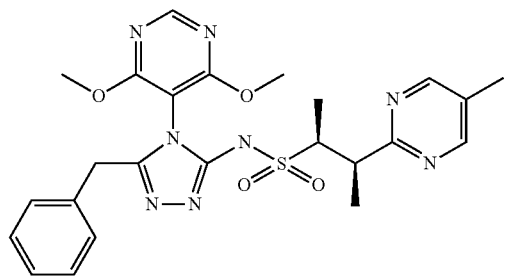 [SMILES: COc1ncnc(OC)c1-n1c(Cc2ccccc2)nnc1NS(=O)(=O)[C@@H](C)[C@H](C)c1ncc(C)cn1] |

(2S,3R)-N-(5-benzyl-4-(4,6-dimethoxy-5-pyrimidinyl)-4H-1,2,4-triazol-3-yl)-3-(5-methyl-2-pyrimidinyl)-2-butanesulfonamide.
$^1$H NMR (500 MHz, CDCl$_3$) δ 8.48-8.53 (m, 2H) 8.35-8.38 (m, 1H) 7.14-7.19 (m, 3H) 6.86-6.91 (m, 2H) 3.82-3.88 (m, 1H) 3.75-3.79 (m, 5H) 3.74-3.79 (m, 4H) 2.26 (s, 3H) 1.33-1.38 (m, 3H) 1.29 (d, J = 7.0 Hz, 3H). LCMS-ESI (pos.) m/z: 525.2 (M + H)$^+$.

| | | |
|---|---|---|
| 24.0 | (1R,2S)-1-methoxy-1-(5-chloropyrimidin-2-yl)propane-2-sulfonamide (Example 83.3), 2-2-cyclobutylacetohydrazide (Example 13.06), and 5-isothiocyanato-4,6-dimethoxypyrimidine (Example 82.1). | 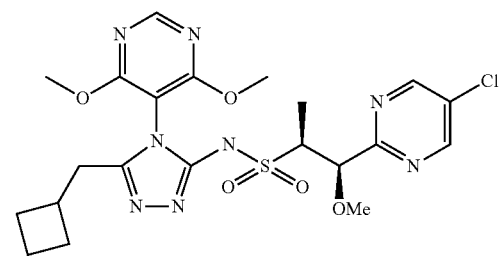 [SMILES: COc1ncnc(OC)c1-n1c(CC2CCC2)nnc1NS(=O)(=O)[C@@H](C)[C@H](OC)c1ncc(Cl)cn1] |

(1R,2S)-1-(5-chloro-2-pyrimidinyl)-N-(5-(cyclobutylmethyl)-4-(4,6-dimethoxy-5-pyrimidinyl)-4H-1,2,4-triazol-3-yl)-1-methoxy-2-propanesulfonamide.
$^1$H NMR (500 MHz, CDCl$_3$) δ 8.66-8.68 (m, 2H) 8.46-8.48 (m, 1H) 4.89-4.94 (m, 1H) 3.96-3.99 (m, 6H) 3.62-3.69 (m, 1H) 3.26-3.30 (m, 3H) 2.47-2.55 (m, 1H) 2.37-2.41 (m, 2H) 2.00-2.06 (m, 2H) 1.71-1.87 (m, 2H) 1.55-1.64 (m, 2H) 1.28-1.32 (m, 3H) 1.20-1.22 (m, 3H). LCMS-ESI (pos.) m/z: 539.2 (M + H)$^+$.

| | | |
|---|---|---|
| 25.0 | (1R,2S)-1-methoxy-1-(5-chloropyrimidin-2-yl)propane-2-sulfonamide (Example 83.3), 2-2-cyclobutylacetohydrazide (Example 13.06), and 4-isothiocyanatotetrahydro-2H-pyran (commercially available from Oakwood Products Inc.). | 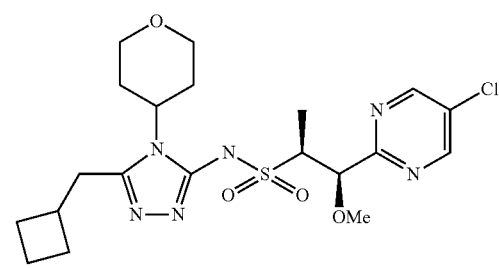 [SMILES: CO[C@H](c1ncc(Cl)cn1)[C@H](C)S(=O)(=O)Nc1nnc(CC2CCC2)n1C1CCOCC1] |

(1R,2S)-1-(5-chloro-2-pyrimidinyl)-N-(5-(cyclobutylmethyl)-4-(tetrahydro-2H-pyran-4-yl)-4H-1,2,4-triazol-3-yl)-1-methoxy-2-propanesulfonamide. $^1$H NMR (500 MHz, CDCl$_3$) δ 8.66-8.67 (m, 2H) 5.03-5.08 (m, 1H) 4.14-4.24 (m, 1H) 4.02-4.08 (m, 3H) 3.58 (qd, J = 7.0, 3.4 Hz, 1H) 3.37-3.46 (m, 2H) 3.23-3.27 (m, 3H) 2.72-2.76 (m, 1H) 2.65-2.71 (m, 1H) 2.54-2.64 (m, 2H) 2.06-2.16 (m, 2H) 1.79-1.93 (m, 2H) 1.63-1.75 (m, 4H) 1.29-1.33 (m, 3H). LCMS-ESI (pos.) m/z: 485.2 (M + H)$^+$.

| | | |
|---|---|---|
| 26.0 | (1R,2S)-1-methoxy-1-(5-chloropyrimidin-2-yl)propane-2-sulfonamide (Example 83.0), acetohydrazide (commercially available from Frontier Scientific Services Inc.), and isothiocyanato-1,3-dimethoxybenzene (Example 82.0). | 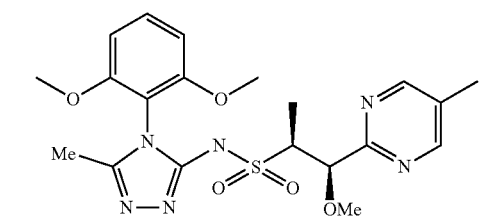 |

TABLE 3.0-continued (1R,2S)-N-(4-(2,6-dimethoxyphenyl)-5-methyl-4H-1,2,4-triazol-3-yl)-1-methoxy-1-(5-methylpyrimidin-2-yl)propane-2-sulfonamide.
$^1$H NMR (500 MHz, DMSO-d6) δ 12.62-12.77 (m, 1H) 8.49-8.54 (m, 1H) 8.39-8.44 (m, 1H) 7.46-7.53 (m, 1H) 6.80-6.89 (m, 2H) 4.79-4.85 (m, 1H) 3.71-3.77 (m, 6H) 3.21-3.27 (m, 1H) 3.14-3.19 (m, 3H) 2.49 (s, 3H) 1.92-1.97 (m, 3H) 0.96-1.07 (m, 3H). LCMS-ESI (POS.) m/z: 463.0 (M + H)$^+$.

The compounds set forth in the following table were synthesized following the procedure Example 14.0 using the known starting material as described.

TABLE 4.0

| Example | Reagents | Structure, Name and Data |
|---|---|---|
| 27.0 | (1R,2S)-1-(5-chloropyrimidin-2-yl)-1-methoxypropane-2-sulfonamide (Example 83.3), 5-isothiocyanato-4,6-dimethoxypyrimidine (Example 82.1), and 2-cyclopropylacetohydrazide (commercially available from Enamine). | 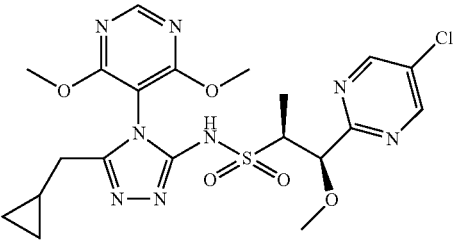 [SMILES: COc1ncnc(OC)c1-n1c(CC2CC2)nnc1NS(=O)(=O)[C@@H](C)[C@H](OC)c1ncc(Cl)cn1]<br>(1R,2S)-1-(5-chloro-2-pyrimidinyl)-N-(5-(cyclopropylmethyl)-4-(4,6-dimethoxy-5-pyrimidinyl)-4H-1,2,4-triazol-3-yl)-1-methoxy-2-propanesulfonamide.<br>$^1$H NMR (500 MHz, CDCl$_3$) δ 10.70 (br s, 1H), 8.72 (s, 2H), 8.52 (s, 1H), 4.95 (d, J = 4.67 Hz, 1H), 4.01 (s, 3H), 4.00 (s, 3H), 3.65-3.77 (m, 1H), 3.35 (s, 3H), 2.30 (d, J = 6.88 Hz, 2H), 1.37 (d, J = 7.01 Hz, 3H), 0.79-0.94 (m, 1H), 0.45-0.57 (m, 2H), 0.07 (q, J = 5.06 Hz, 2H). LCMS-ESI (pos.) m/z: 525.2 (M + H)$^+$. |
| 28.0 | (1R,2S)-1-(5-chloropyrimidin-2-yl)-1-methoxypropane-2-sulfonamide (Example 83.3), 5-isothiocyanato-4,6-dimethoxypyrimidine (Example 82.1), and 2-cyclopentylacetohydrazide (commercially available from Frontier Scientific Services). | 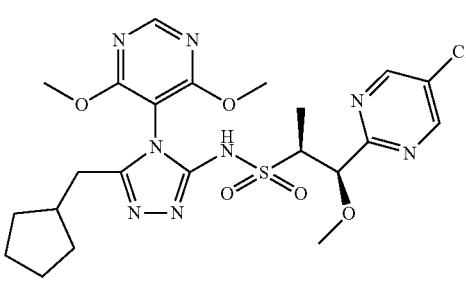<br>(1R,2S)-1-(5-chloro-2-pyrimidinyl)-N-(5-(cyclopentylmethyl)-4-(4,6-dimethoxy-5-pyrimidinyl)-4H-1,2,4-triazol-3-yl)-1-methoxy-2-propanesulfonamide.<br>$^1$H NMR (500 MHz, DMSO-d$_6$) δ 12.89 (s, 1H), 8.93 (s, 1H), 8.69 (s, 1H), 4.78 (d, J = 3.96 Hz, 1H), 3.96 (s, 3H), 3.95 (s, 3H), 3.34-3.54 (m, 2H), 3.13 (s, 3H), 2.31-2.38 (m, 2H), 1.99 (td, J = 7.64, 15.21 Hz, 1H), 1.60-1.75 (m, 2H), 1.41-1.59 (m, 4H), 1.05-1.19 (m, 5H). LCMS-ESI (pos.) m/z: 553.2 (M + H)$^+$. |

TABLE 4.0-continued

| Example | Reagents | Structure, Name and Data |
|---|---|---|
| 29.0 | (1R,2S)-1-(5-chloropyrimidin-2-yl)-1-methoxypropane-2-sulfonamide (Example 83.3), 5-isothiocyanato-4,6-dimethoxypyrimidine (Example 82.1), and 2-cyclohexylacetohydrazide (commercially available from Frontier Scientific Services). | 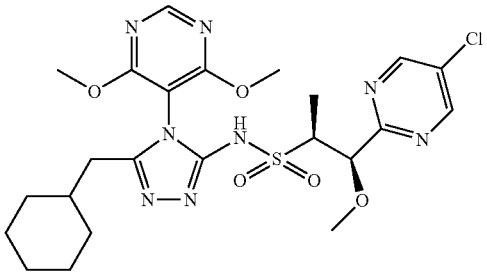 [SMILES: COc1ncnc(OC)c1-n1c(CC2CCCCC2)nnc1NS(=O)(=O)[C@@H](C)[C@H](OC)c1ncc(Cl)cn1]<br>(1R,2S)-1-(5-chloro-2-pyrimidinyl)-N-(5-(cyclohexylmethyl)-4-(4,6-dimethoxy-5-pyrimidinyl)-4H-1,2,4-triazol-3-yl)-1-methoxy-2-propanesulfonamide.<br>$^1$H NMR (500 MHz, DMSO-d$_6$) δ 8.92 (s, 2H), 8.69 (s, 1H), 4.78 (d, J = 3.96 Hz, 1H), 3.95 (m, 6H), 3.35-3.48 (m, 1H), 3.13 (s, 3H), 2.24 (m, J = 7.14 Hz, 2H), 1.50-1.67 (m, 5H), 1.42 (dt, J = 3.67, 7.09 Hz, 1H), 1.02-1.21 (m, 6H), 0.81-0.95 (m, 2H). LCMS-ESI (pos.) m/z: 567.2 (M + H)$^+$. |
| 30.0 | (1S,2S)-1-isopropoxy-1-(5-methylpyrimidin-2-yl)propane-2-sulfonamide (Example 85.0), 1,3-difluoro-2-isothiocyanatobenzene (Sigma Aldrich), and methoxyacetic acid hydrazide (commercially available from Combi-Blocks, Inc.). | 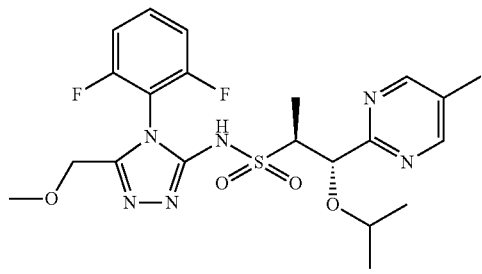<br>(1S,2S)-N-(4-(2,6-difluorophenyl)-5-(methoxymethyl)-4H-1,2,4-triazol-3-yl)-1-(1-methylethoxy)-1-(5-methyl-2-pyrimidinyl)-2-propanesulfonamide.<br>$^1$H NMR (500 MHz, CDCl$_3$) δ 8.64 (s, 2H), 7.38-7.60 (m, 1H), 7.09 (q, J = 9.21 Hz, 2H), 4.86 (d, J = 3.11 Hz, 1H), 4.35 (s, 2H), 3.74 (dq, J = 3.37, 6.92 Hz, 1H), 3.56 (td, J = 6.03, 12.07 Hz, 1H), 3.49 (s, 1H), 3.25 (s, 3H), 2.35 (s, 3H), 1.55 (d, J = 7.01 Hz, 3H), 1.11 (d, J = 5.97 Hz, 3H), 0.99 (d, J = 6.10 Hz, 3H). LCMS-ESI (pos.) m/z: 497.2 (M + H)$^+$. |
| 31.0 | (1R,2S)-1-(5-chloropyrimidin-2-yl)-1-methoxypropane-2-sulfonamide (Example 83.3), 5-isothiocyanato-4,6-dimethoxypyrimidine (Example 82.1), and 3-methylbutanehydrazide (commercially available from Frontier Scientific Services). | 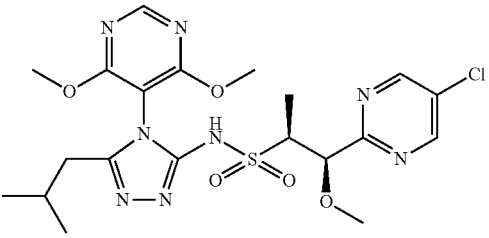 [SMILES: COc1ncnc(OC)c1-n1c(CC(C)C)nnc1NS(=O)(=O)[C@@H](C)[C@H](OC)c1ncc(Cl)cn1]<br>(1R,2S)-1-(5-chloro-2-pyrimidinyl)-N-(4-(4,6-dimethoxy-5-pyrimidinyl)-5-(2-methylpropyl)-4H-1,2,4-triazol-3-yl)-1-methoxy-2-propanesulfonamide.<br>$^1$H NMR (500 MHz, CDCl$_3$) δ 10.71 (br s, 1H), 8.72 (s, 2H), 8.52 (s, 1H), 4.95 (d, J = 4.80 Hz, 1H), 4.01 (s, 3H), 4.01 (s, 3H), 3.67-3.74 (m, 1H), 3.34 (s, 3H), 2.22 (d, J = 7.27 Hz, 2H), 1.90 (quind, J = 6.77, 13.65 Hz, 1H), 1.36 (d, J = 7.01 Hz, 3H), 0.92 (d, J = 6.62 Hz, 6H). LCMS-ESI (pos.) m/z: 527.2 (M + H)$^+$. |

TABLE 4.0-continued

| Example | Reagents | Structure, Name and Data |
|---|---|---|
| 133.0 | (1R,2S)-1-(5-chloropyrimidin-2-yl)-1-methoxypropane-2-sulfonamide (Example 83.3), 5-isothiocyanato-4,6-dimethoxypyrimidine (Example 82.1), and isobutyrohydrazide (commercially available from Frontier Scientific Services). | 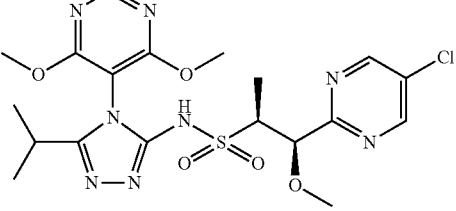<br>(1R,2S)-1-(5-chloro-2-pyrimidinyl)-N-(4-(4,6-dimethoxy-5-pyrimidinyl)-5-(2-propanyl)-4H-1,2,4-triazol-3-yl)-1-methoxy-2-propanesulfonamide.<br>$^1$H NMR (500 MHz, CDCl$_3$) δ 10.68 (br s, 1H), 8.72 (s, 2H), 8.52 (s, 1H), 4.95 (d, J = 4.80 Hz, 1H), 4.02 (s, 3H), 4.01 (s, 3H), 3.64-3.74 (m, 1H), 3.34 (s, 3H), 2.54 (app t, J = 6.86 Hz, 1H), 1.35 (d, J = 7.01 Hz, 3H), 1.20 (dd, J = 3.11, 6.88 Hz, 6H). LCMS-ESI (pos.) m/z: 513.2 (M + H)$^+$ |

Example 33.01. Preparation of 2-(oxetan-3-yl)acetohydrazide

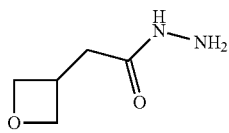

33.01

2-(Oxetan-3-yl)acetohydrazide, Example 33.01

To a solution of methyl 2-(oxetan-3-yl)acetate (commercially available from PharmaBlock Sciences (Nanjing), Inc., 1.2 g, 9.22 mmol) in MeOH (18.44 ml) was added hydrazine hydrate (3 ml, 92 mmol). The reaction was stirred at RT for 3 d. The resulting solution was concentrated in vacuo (with ice water in trap to absorb excess of NH$_2$NH$_2$) to afford the title compound (1.2 g, 100% yield) as a white solid. LCMS-ESI (pos.), m/z: 131.1 (M+H)$^+$.

The compounds set forth in the following table were synthesized following the procedure in Example 14.0 using the known starting material as described.

TABLE 5

| Example | Reagents | Structure, Name and Data |
|---|---|---|
| 32.0 | (2S,3R)-3-(5-chloropyrimidin-2-yl)butane-2-sulfonamide (Example 81.4), 2-isothiocyanato-1,3-dimethoxybenzene (Example 82.0), and 3-methoxypropanehydrazide (commercially available from FSSI). | 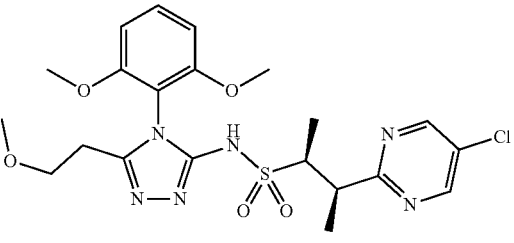 [SMILES: COCCc1nnc(NS(=O)(=O)[C@@H](C)[C@H](C)c2ncc(Cl)cn2)n1-c1c(OC)cccc1OC]<br>(2S,3R)-3-(5-chloro-2-pyrimidinyl)-N-(4-(2,6-dimethoxyphenyl)-5-(2-methoxyethyl)-4H-1,2,4-triazol-3-yl)-2-butanesulfonamide.<br>$^1$H NMR (400 MHz, CDCl$_3$) δ 10.76 (br s, 1H) 8.62 (s, 2H) 7.41 (t, J = 8.50 Hz, 1H) 6.61-6.69 (m, 2H) 3.73-3.86 (m, 1 H) 3.79 (s, 3H) 3.79 (s, 3H) 3.58 (t, J = 6.79 Hz, 2H) 3.30 (s, 3 H) 2.61 (t, J = 6.79 Hz, 2H) 1.36 (d, J = 6.95 Hz, 3H) 1.32 (d, J = 6.84 Hz, 3H). LCMS-ESI (pos.) m/z: 511.2 (M + H)$^+$. |
| 33.0 | (2S,3R)-3-(5-chloropyrimidin-2-yl)butane-2-sulfonamide (Example 81.4), 3,3-dimethylbutanehydrazide (commercially available from Enamine), 5-isothiocyanato-4,6-dimethoxypyrimidine (Example 82.1), and 2-(oxetan-3-yl)acetohydrazide (Example 33.01). | 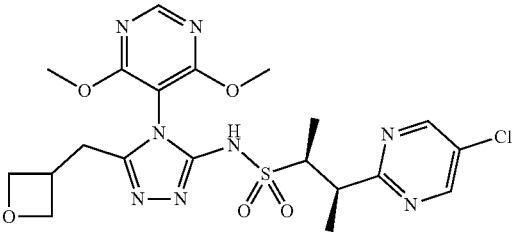 [SMILES: COc1ncnc(OC)c1-n1c(CC2COC2)nnc1NS(=O)(=O)[C@@H](C)[C@H](C)c1ncc(Cl)cn1]<br>(2S,3R)-3-(5-chloro-2-pyrimidinyl)-N-(4-(4,6-dimethoxy-5-pyrimidinyl)-5-(3-oxetanylmethyl)-4H-1,2,4-triazol-3-yl)-2-butanesulfonamide. |

TABLE 5-continued

| Example | Reagents | Structure, Name and Data |
|---|---|---|
| | | ¹H NMR (400 MHz, CDCl₃) δ 10.86 (br s, 1H) 8.62 (s, 2H) 8.52 (s, 1H) 4.86 (t, J = 7.05 Hz, 2H) 4.37 (td, J = 6.22, 1.76 Hz, 2H) 4.01 (s, 3H) 4.00 (s, 3H) 3.70-3.88 (m, 2H) 3.34-3.47 (m, 1H) 2.72 (d, J = 7.77 Hz, 2H) 1.37 (d, J = 7.05 Hz, 3H) 1.33 (d, J = 6.95 Hz, 3H). LCMS-ESI (pos.) m/z: 525.2 (M + H)⁺. |
| 34.0 | (2S,3R)-3-(5-chloropyrimidin-2-yl)butane-2-sulfonamide (Example 81.4), 2-isothiocyanato-1,3-dimethoxybenzene (Example 82.0), and 2-(oxetan-3-yl)acetohydrazide (Example 33.01). | 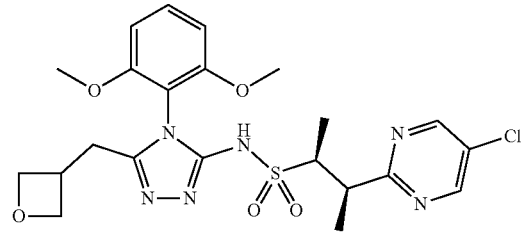 [SMILES: COc1cccc(OC)c1-n1c(CC2COC2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(3-oxetanylmethyl)-4H-1,2,4-triazol-3-yl)-2-butanesulfonamide.<br>¹H NMR (400 MHz, CD₃OD) δ 8.72 (s, 2H) 7.53 (t, J = 8.55 Hz, 1H) 6.85 (dq, J = 8.55, 1.05 Hz, 2H) 4.78 (dd, J = 7.77, 6.32 Hz, 2H) 4.35 (td, J = 6.27, 2.07 Hz, 2H) 3.84 (d, J = 1.45 Hz, 6H) 3.65-3.78 (m, 2H) 2.72 (d, J = 7.88 Hz, 2H) 1.33 (d, J = 6.95 Hz, 3H) 1.27 (d, J = 6.84 Hz, 3H). LCMS-ESI (pos.) m/z: 522.2 (M + H)⁺. |
| 35.0 | (2S,3R)-3-(5-chloropyrimidin-2-yl)butane-2-sulfonamide (Example 81.4), 2-isothiocyanato-1,3-dimethoxybenzene (Example 82.0), and 2-(pyridin-2-yl)acetohydrazide (commercially available from FSSI). | 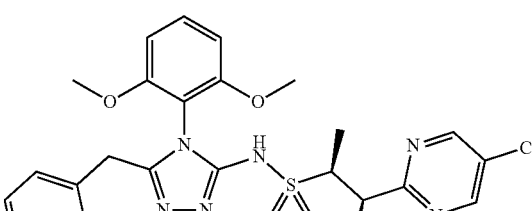<br>(2S,3R)-3-(5-chloro-2-pyrimidinyl)-N-(4-(2,6-dimethoxyphenyl)-5-(2-pyridinylmethyl)-4H-1,2,4-triazol-3-yl)-2-butanesulfonamide.<br>¹H NMR (500 MHz, CD₃OD) δ 8.72 (s, 2H) 8.29-8.34 (m, 1H) 7.64 (td, J = 7.72, 1.87 Hz, 1H) 7.40 (t, J = 8.55 Hz, 1H) 7.23 (ddd, J = 7.62, 4.98, 1.09 Hz, 1H) 7.00 (dt, J = 7.85, 1.00 Hz, 1H) 6.59-6.68 (m, 2H) 3.97 (d, J = 0.93 Hz, 2H) 3.66-3.78 (m, 2H) 3.65 (s, 3H) 3.62 (s, 3H) 1.32 (d, J = 6.95 Hz, 3H) 1.26 (d, J = 6.84 Hz, 3H). LCMS-ESI (pos.) m/z: 544.1 (M + H)⁺. |
| 36.0 | (2S,3R)-3-(5-chloropyrimidin-2-yl)butane-2-sulfonamide (Example 81.4), 2-isothiocyanato-1,3-dimethoxybenzene (Example 82.0), and 3-(furan-2-yl)propanehydrazide (commercially available from FSSI). | 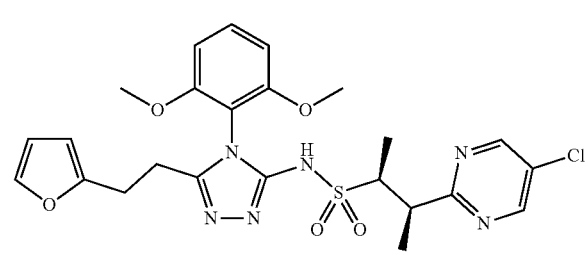 [SMILES: COc1cccc(OC)c1-n1c(CCc2ccco2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(2-(2-furanyl)ethyl)-4H-1,2,4-triazol-3-yl)-2-butanesulfonamide<br>¹H NMR (400 MHz, CD₃OD) δ 8.72 (s, 2H) 7.52 (t, J = 8.55 Hz, 1H) 7.32 (dd, J = 1.87, 0.83 Hz, 1H) 6.84 (dq, J = 8.63, 1.03 Hz, 2H) 6.26 (dd, J = 3.16, 1.92 Hz, 1H) 5.99 (dd, J = 3.21, 0.83 Hz, 1H) 3.82 (s, 3H) 3.82 (s, 3H) 3.66-3.79 (m, 2H) 2.85-2.91 (m, 2H) 2.61-2.68 (m, 2H) 1.33 (d, J = 6.95 Hz, 3H) 1.28 (d, J = 6.84 Hz, 3H). LCMS-ESI (pos.) m/z: 547.2 (M + H)⁺. |

TABLE 5-continued

| Example | Reagents | Structure, Name and Data |
|---|---|---|
| 37.0 | (2S,3R)-3-(5-chloropyrimidin-2-yl)butane-2-sulfonamide (Example 81.4), 2-isothiocyanato-1,3-dimethoxybenzene (Example 82.0), and 2-(methylsulfonyl)acetohydrazide (commercially available from FSSI). | 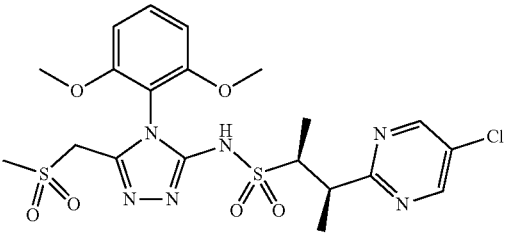 [SMILES: COc1cccc(OC)c1-n1c(CS(C)(=O)=O)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-((methylsulfonyl)methyl)-4H-1,2,4-triazol-3-yl)-2-butanesulfonamide.<br>$^1$H NMR (500 MHz, DMSO-$d_6$) δ 12.91-13.52 (m, 1H) 8.86 (s, 2H) 7.50 (t, J = 8.50 Hz, 1H) 6.83 (dd, J = 8.43, 1.95 Hz, 2H) 4.29-4.52 (m, 2H) 3.73 (s, 3H) 3.72 (s, 3H) 3.62-3.70 (m, 1 H) 3.56 (br dd, J = 6.81, 4.48 Hz, 1H) 3.02 (s, 3H) 2.50 (br s, 3 H) 1.24 (br d, J = 7.01 Hz, 3H) 1.05-1.17 (m, 3H). LCMS-ESI (pos.) m/z: 545.2 (M + H)$^+$. |
| 38.0 | (2S,3R)-3-(5-chloropyrimidin-2-yl)butane-2-sulfonamide (Example 81.4), 2-isothiocyanato-1,3-dimethoxybenzene (Example 82.0), and 2-(thiophen-3-yl)acetohydrazide (commercially available from FSSI). | 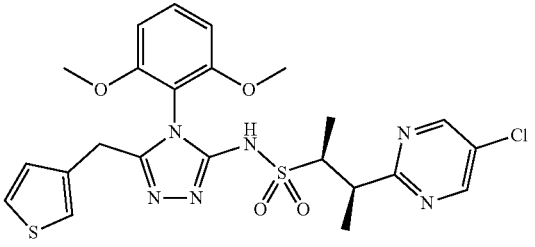 [SMILES: COc1cccc(OC)c1-n1c(Cc2ccsc2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(3-thiophenylmethyl)-4H-1,2,4-triazol-3-yl)-2-butanesulfonamide.<br>$^1$H NMR (500 MHz, DMSO-$d_6$) δ 12.79 (s, 1H) 8.85 (s, 2H) 7.46 (t, J = 8.50 Hz, 1H) 7.39 (dd, J = 4.74, 3.05 Hz, 1H) 6.89 (br s, 1H) 6.76 (t, J = 8.11 Hz, 2H) 6.69 (br d, J = 4.28 Hz, 1H) 3.56-3.74 (m, 9H) 3.42-3.56 (m, 1H) 1.22 (br d, J = 7.01 Hz, 3H) 1.08 (br d, J = 7.01 Hz, 3H). LCMS-ESI (pos.) m/z: 549.0 (M + H)$^+$. |
| 39.0 | (2S,3R)-3-(5-chloropyrimidin-2-yl)butane-2-sulfonamide (Example 81.4), 2-isothiocyanato-1,3-dimethoxybenzene (Example 82.0), and 2-(1H-pyrazol-3-yl)acetohydrazide (commercially available from FSSI). | 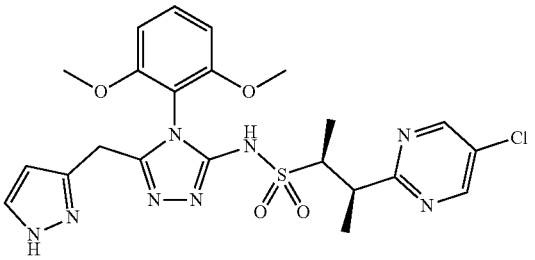 [SMILES: COc1cccc(OC)c1-n1c(Cc2cc[nH]n2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(1H-pyrazol-3-ylmethyl)-4H-1,2,4-triazol-3-yl)-2-butanesulfonamide.<br>$^1$H NMR (500 MHz, CDCl$_3$) δ 12.74 (br s, 1H) 12.52 (br s, 1H) 8.85 (s, 2H) 7.53 (br s, 1H) 7.46 (br t, J = 8.37 Hz, 1H) 6.77 (br t, J = 7.46 Hz, 2H) 5.75 (br d, J = 2.98 Hz, 1H) 4.10 (br d, J = 5.06 Hz, 1H) 3.59-3.69 (m, 8H) 3.48-3.56 (m, 1H) 1.22 (br d, J = 7.14 Hz, 3H) 1.08 (br d, J = 6.88 Hz, 3H). LCMS-ESI (pos.) m/z: 533.1 (M + H)$^+$. |

TABLE 5-continued

| Example | Reagents | Structure, Name and Data |
|---|---|---|
| 40.0 | (2S,3R)-3-(5-chloropyrimidin-2-yl)butane-2-sulfonamide (Example 81.4), 2-isothiocyanato-1,3-dimethoxybenzene (Example 82.0), and 3-methoxy-3-methylbutanehydrazide (commercially available from ChemShuttle). | 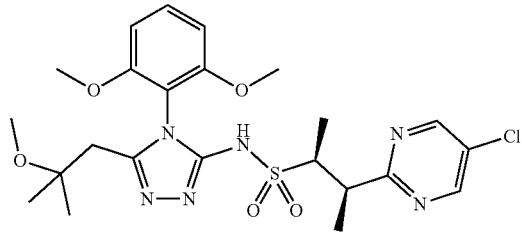 [SMILES: COc1cccc(OC)c1-n1c(CC(C)(C)OC)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(2-methoxy-2-methylpropyl)-4H-1,2,4-triazol-3-yl)-2-butanesulfonamide.<br>$^1$H NMR (500 MHz, DMSO-$d_6$) δ 12.78 (s, 1H) 8.85 (s, 2H) 7.49 (t, J = 8.56 Hz, 1H) 6.83 (dd, J = 8.43, 2.34 Hz, 2H) 3.72 (app s, 6H) 3.59-3.69 (m, 1H) 3.52 (br dd, J = 6.88, 4.28 Hz, 1 H) 2.91 (s, 3H) 2.39-2.47 (m, 2H) 1.23 (br d, J = 7.01 Hz, 3H) 1.09 (br d, J = 7.01 Hz, 3H) 1.05 (s, 6H). LCMS-ESI (pos.) m/z: 539.2 (M + H)$^+$. |
| 41.0 | (2S,3R)-3-(5-chloropyrimidin-2-yl)butane-2-sulfonamide (Example 81.4), 2-isothiocyanato-1,3-dimethoxybenzene (Example 82.0), and 2-(2-oxopyrrolidin-1-yl)acetohydrazide (commercially available from FSSI). | 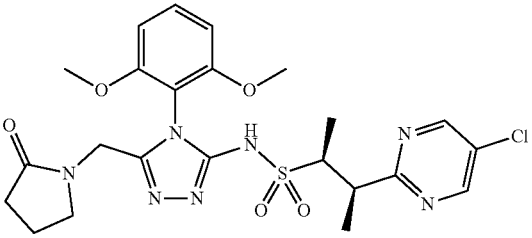 [SMILES: COc1cccc(OC)c1-n1c(CN2CCCC2=O)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-((2-oxo-1-pyrrolidinyl)methyl)-4H-1,2,4-triazol-3-yl)-2-butanesulfonamide.<br>$^1$H NMR (500 MHz, DMSO-$d_6$) δ 12.41-13.36 (m, 1H) 8.85 (s, 2H) 7.44 (t, J = 8.50 Hz, 1H) 6.71-6.85 (m, 2H) 4.16 (s, 2 H) 3.74 (app s, 6H) 3.59-3.70 (m, 1H) 3.53 (br dd, J = 7.01, 4.28 Hz, 1H) 1.94-2.05 (m, 2H) 1.75-1.86 (m, 2H) 1.23 (br d, J = 7.01 Hz, 3H) 1.04-1.16 (m, 3H). LCMS-ESI (pos.) m/z: 550.1 (M + H)$^+$. |
| 42.0 | (2S,3R)-3-(5-chloropyrimidin-2-yl)butane-2-sulfonamide (Example 81.4), 2-isothiocyanato-1,3-dimethoxybenzene (Example 82.0), and 2-(2-oxopyridin-1(2H)-yl)acetohydrazide (commercially available from FSSI). | 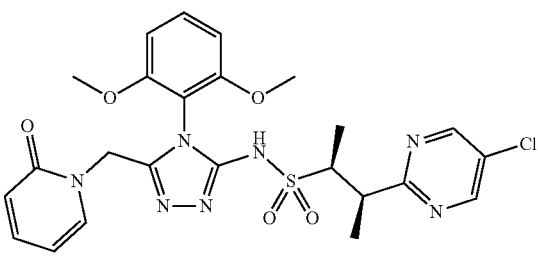 [SMILES: COc1cccc(OC)c1-n1c(Cn2ccccc2=O)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-((2-oxo-1(2H)-pyridinyl)methyl)-4H-1,2,4-triazol-3-yl)-2-butanesulfonamide<br>$^1$H NMR (500 MHz, DMSO-$d_6$) δ 12.94 (s, 1H) 8.85 (s, 1H) 7.45 (t, J = 8.50 Hz, 1H) 7.35 (ddd, J = 8.92, 6.78, 1.82 Hz, 1H) 7.23-7.31 (m, 1H) 6.76 (t, J = 7.53 Hz, 2H) 6.27 (d, J = 9.08 Hz, 1H) 6.01-6.15 (m, 1H) 4.86 (s, 2H) 3.69 (s, 3H) 3.67 (s, 3H) 3.59-3.65 (m, 1H) 3.53 (br dd, J = 6.94, 4.35 Hz, 1H) 1.22 (br d, J = 7.14 Hz, 3H) 1.09 (br d, J = 7.01 Hz, 3H). LCMS-ESI (pos.) m/z: 560.2 (M + H)$^+$. |

TABLE 5-continued

| Example | Reagents | Structure, Name and Data |
|---|---|---|
| 43.0 | (2S,3R)-3-(5-chloropyrimidin-2-yl)butane-2-sulfonamide (Example 81.4), 2-isothiocyanato-1,3-dimethoxybenzene (Example 82.0), and 2-(thiophen-2-yl)acetohydrazide (commercially available from FSSI). | 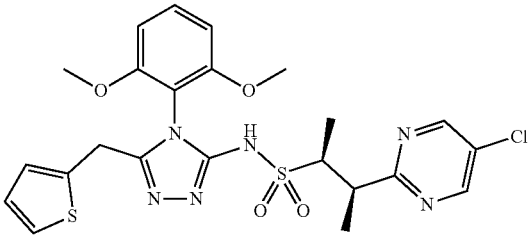 [SMILES: COc1cccc(OC)c1-n1c(Cc2cccs2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-(2-thiophenylmethyl)-4H-1,2,4-triazol-3-yl)-2-butanesulfonamide.<br>$^1$H NMR (500 MHz, CDCl$_3$) δ 12.82 (s, 1H) 8.84 (s, 2H) 7.47 (t, J = 8.50 Hz, 1H) 7.29-7.40 (m, 1H) 6.84 (dd, J = 4.93, 3.63 Hz, 1H) 6.74-6.81 (m, 2H) 6.47-6.54 (m, 1H) 3.81-3.98 (m, 2H) 3.58-3.75 (m, 7H) 3.41-3.58 (m, 1H) 1.22 (br d, J = 7.14 Hz, 3H) 1.09 (br d, J = 6.88 Hz, 3H). LCMS-ESI (pos.) m/z: 550.2 (M + H)$^+$. |
| 44.0 | (2S,3R)-3-(5-chloropyrimidin-2-yl)butane-2-sulfonamide (Example 81.4), 2-isothiocyanato-1,3-dimethoxybenzene (Example 82.0), and 2-(4-methylthiazol-2-yl)acetohydrazide (commercially available from FSSI). | 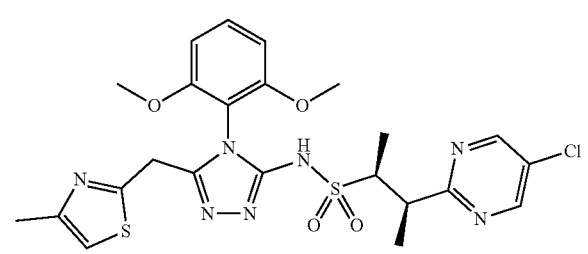 [SMILES: COc1cccc(OC)c1-n1c(Cc2nc(C)cs2)nnc1NS(=O)(=O)[C@@H](C)[C@H](C)c1ncc(Cl)cn1]<br>(2S,3R)-3-(5-chloro-2-pyrimidinyl)-N-(4-(2,6-dimethoxyphenyl)-5-((4-methyl-1,3-thiazol-2-yl)methyl)-4H-1,2,4-triazol-3-yl)-2-butanesulfonamide.<br>$^1$H NMR (500 MHz, CDCl$_3$) δ 12.88 (br s, 1H) 8.85 (s, 2H) 7.45 (t, J = 8.43 Hz, 1H) 7.11 (s, 1H) 6.75 (br t, J = 8.50 Hz, 3H) 3.96-4.20 (m, 2H) 3.47-3.84 (m, 8H) 2.24 (s, 3H) 1.22 (br d, J = 7.01 Hz, 3H) 1.09 (br d, J = 6.88 Hz, 3H). LCMS-ESI (pos.) m/z: 565.3 (M + H)$^+$. |
| 45.0 | (2S,3R)-3-(5-chloropyrimidin-2-yl)butane-2-sulfonamide (Example 81.4), 2-isothiocyanato-1,3-dimethoxybenzene (Example 82.0), and 2-(pyridin-4-yl)acetohydrazide (commercially available from FSSI). | 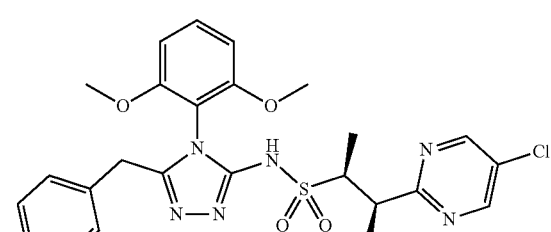<br>(2S,3R)-3-(5-chloro-2-pyrimidinyl)-N-(4-(2,6-dimethoxyphenyl)-5-(4-pyridinylmethyl)-4H-1,2,4-triazol-3-yl)-2-butanesulfonamide.<br>$^1$H NMR (500 MHz, CDCl$_3$) δ 8.72 (s, 2H) 8.62-8.66 (m, 2H) 7.58 (d, J = 6.53 Hz, 2H) 7.48 (t, J = 8.55 Hz, 1H) 6.69-6.76 (m, 2H) 4.08 (s, 2H) 3.62-3.81 (m, 8H) 1.32 (d, J = 7.05 Hz, 3H) 1.27 (d, J = 6.84 Hz, 3H). LCMS-ESI (pos.) m/z: 544.2 (M + H)$^+$. |
| 46.0 | (2S,3R)-3-(5-chloropyrimidin-2-yl)butane-2-sulfonamide (Example 81.4), 2-isothiocyanato-1,3-dimethoxybenzene (Example 82.0), and (R)-2-(tetrahydrofuran-2-yl)acetohydrazide and (S)-2-(tetrahydrofuran-2-yl)acetohydrazide (commercially available from ChemShuttle). | 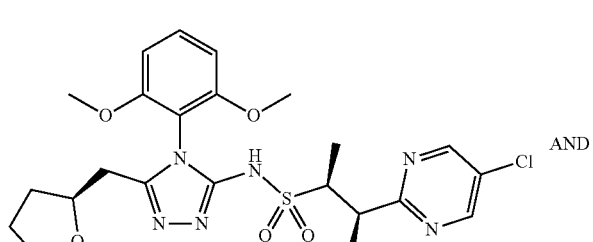 AND |

| Example | Reagents | Structure, Name and Data |
| --- | --- | --- |
| | | 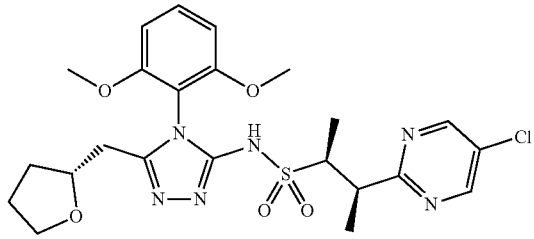 [SMILES: COc1cccc(OC)c1-n1c(C[C@H]2CCCO2)nnc1NS(=O)(=O)[C@@H](C)[C@H](C)c1ncc(Cl)cn1]
(2S,3R)-3-(5-chloro-2-pyrimidinyl)-N-(4-(2,6-dimethoxyphenyl)-5-((2R)-tetrahydro-2-furanylmethyl)-4H-1,2,4-triazol-3-yl)-2-butanesulfonamide and (2S,3R)-3-(5-chloro-2-pyrimidinyl)-N-(4-(2,6-dimethoxyphenyl)-5-((2S)-tetrahydro-2-furanylmethyl)-4H-1,2,4-triazol-3-yl)-2-butanesulfonamide.
$^1$H NMR (500 MHz, CDCl$_3$) δ 10.74 (br s, 1H) 8.63 (s, 2H) 7.41 (t, J = 8.50 Hz, 1H) 7.28 (s, 3H) 6.60-6.67 (m, 2H) 4.05-4.19 (m, 1H) 3.68-3.87 (m, 10H) 2.56-2.68 (m, 1H) 2.38-2.49 (m, 1H) 2.00-2.13 (m, 1H) 1.81-1.93 (m, 2H) 1.50-1.64 (m, 1H) 1.36 (d, J = 6.74 Hz, 3H) 1.33 (d, J = 6.63 Hz, 3H). LCMS-ESI (pos.) m/z: 537.2 (M + H)$^+$. |
| 47.0 | (2S,3R)-3-(5-chloropyrimidin-2-yl)butane-2-sulfonamide (Example 81.4), 2-isothiocyanato-1,3-dimethoxybenzene (Example 82.0), and (R)-2-(1,1-dioxidotetrahydrothiophen-3-yl)acetohydrazide and (S)-2-(1,1-dioxidotetrahydrothiophen-3-yl)acetohydrazide (commercially available from FSSI). | 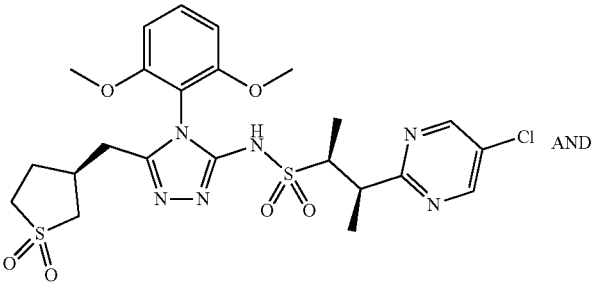 [SMILES: COc1cccc(OC)c1-n1c(C[C@@H]2CCS(=O)(=O)C2)nnc1NS(=O)(=O)[C@@H](C)[C@H](C)c1ncc(Cl)cn1]
(2S,3R)-3-(5-chloro-2-pyrimidinyl)-N-(4-(2,6-dimethoxyphenyl)-5-(((3R)-1,1-dioxidotetrahydro-3-thiophenyl)methyl)-4H-1,2,4-triazol-3-yl)-2-butanesulfonamide and (2S,3R)-3-(5-chloro-2-pyrimidinyl)-N-(4-(2,6-dimethoxyphenyl)-5-(((3S)-1,1-dioxidotetrahydro-3-thiophenyl)methyl)-4H-1,2,4-triazol-3-yl)-2-butanesulfonamide.
$^1$H NMR (500 MHz, CDCl$_3$) δ 10.55-11.07 (br s, 1H) 8.64 (s, 2H) 7.45 (t, J = 8.50 Hz, 1H) 6.68 (ddt, J = 8.59, 3.74, 0.98, 0.98 Hz, 2H) 3.72-3.88 (m, 8H) 3.26-3.35 (m, 1H) 3.13-3.22 (m, 1H) 3.03 (ddd, J = 13.27, 10.78, 7.88 Hz, 1H) 2.75-2.88 (m, 1H) 2.66-2.75 (m, 1H) 2.46-2.60 (m, 2H) 1.80-1.96 (m, 2H) 1.36 (d, J = 7.05 Hz, 3H) 1.33 (d, J = 6.74 Hz, 3H). LCMS-ESI (pos.) m/z: 585.2 (M + H)$^+$. |

Example 48.0: Preparation of (1R,2S)—N-(4-(2,6-dimethoxyphenyl)-5-(phenoxymethyl)-4H-1,2,4-triazol-3-yl)-1-methoxy-1-(5-methyl-2-pyrimidinyl)-2-propanesulfonamide

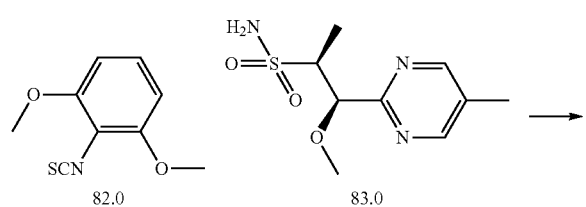

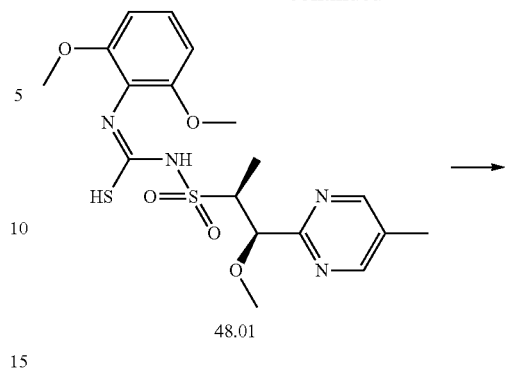

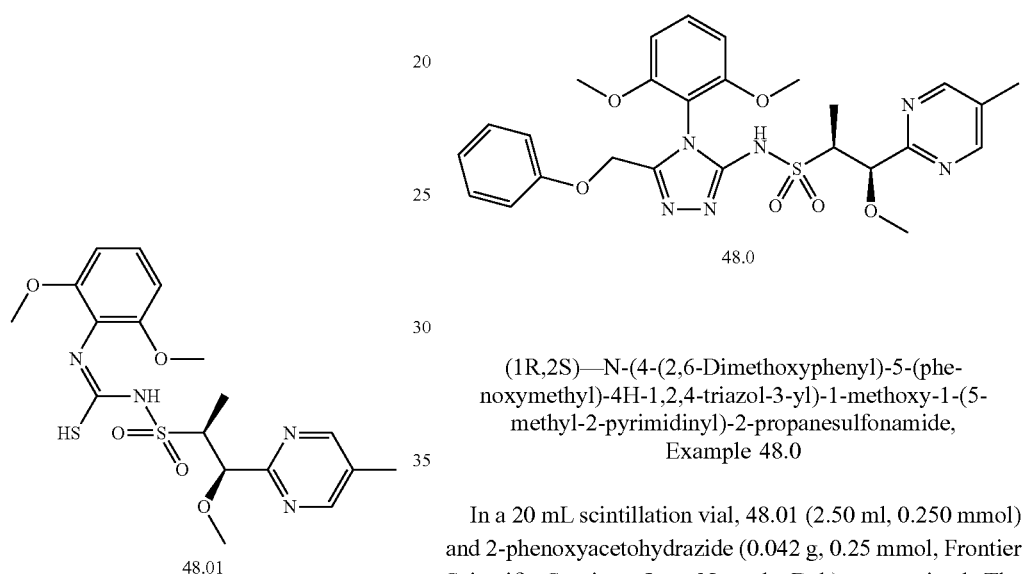

(1R,2S)—N-(4-(2,6-Dimethoxyphenyl)-5-(phenoxymethyl)-4H-1,2,4-triazol-3-yl)-1-methoxy-1-(5-methyl-2-pyrimidinyl)-2-propanesulfonamide, Example 48.0

In a 20 mL scintillation vial, 48.01 (2.50 ml, 0.250 mmol) and 2-phenoxyacetohydrazide (0.042 g, 0.25 mmol, Frontier Scientific Services, Inc., Newark, Del.) were mixed. The mixture was cooled in an ice-water bath and silver (I) nitrate (0.085 g, 0.50 mmol) was added. The cold bath was removed, and the brown mixture was stirred at RT. After 15 min, the mixture was filtered through a pad of Celite® brand filter agent and washed with ACN. The filtrate was concentrated in GeneVac into a 20 mL scintillation vial. Dioxane (2 mL) was added to the yellow residue followed by MSA (0.073 g, 0.76 mmol). The mixture was stirred at 80° C. for 16 h. The reaction mixture was allowed to cool to RT and concentrated in vacuo. The residue was dissolved in MeOH (2 mL), and the mixture was passed through a PS-carbonate column, eluting with MeOH. The filtrate was concentrated and purified by mass-triggered HPLC to afford 48.0, (0.061 g, 0.11 mmol, 42% yield). $^1$H NMR (500 MHz, DMSO-d$_6$) δ 13.03 (br. s., 1H), 8.63 (s, 2H), 7.44 (t, J=8.5 Hz, 1H), 7.22 (t, J=7.9 Hz, 2H), 6.91 (t, J=7.3 Hz, 1H), 6.84-6.75 (m, 4H), 4.83 (s, 2H), 4.80 (d, J=3.4 Hz, 1H), 3.71 (s, 3H), 3.70 (s, 3H), 3.39 (dd, J=3.5, 7.0 Hz, 1H), 3.10 (s, 3H), 2.26 (s, 3H), 1.11 (d, J=7.0 Hz, 3H). LCMS (pos.) m/z: 555.1 (M+H)$^+$.

(E)-N'-(2,6-Dimethoxyphenyl)-N-(((1R,2S)-1-methoxy-1-(5-methylpyrimidin-2-yl)propan-2-yl)sulfonyl)carbamimidothioic acid, Example 48.01

In a 20 mL scintillation vial, 83.0 (0.203 g, 0.829 mmol) was suspended in ACN (8 mL). To the solution at RT, 82.0 (0.168 g, 0.86 mmol) was added followed by portion-wise addition of cesium carbonate (0.367 g, 1.13 mmol). The slightly cloudy mixture was stirred at RT for 15 h to obtain a suspension. LCMS (pos.) m/z: 440.9 (M+H)$^+$. A suspension of 48.01 was used as 0.1 M stock solution for the next step.

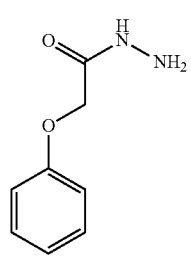

The compounds set forth in the following table were synthesized following the procedure in Example 48.0 using the known starting material as described.

TABLE 6

| Example | Reagents | Structure, Name and Data |
|---|---|---|
| 49.0 | Example 48.01<br><br>2-(4-methoxyphenyl)acetohydrazide (commercially available from Frontier Scientific Services, Inc., Newark, DE). | (1R,2S)-N-(4-(2,6-dimethoxyphenyl)-5-(4-methoxybenzyl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 12.72 (br. s., 1H), 8.75-8.50 (m, 2H), 7.44 (t, J = 8.5 Hz, 1H), 6.81-6.66 (m, 6H), 4.79 (d, J = 3.5 Hz, 1H), 3.68 (s, 3H), 3.58-3.54 (m, 8H), 3.35 (dd, J = 3.5, 7.0 Hz, 1H), 3.12 (s, 3H), 2.25 (s, 3H), 1.08 (d, J = 7.0 Hz, 3H). LCMS (pos.) m/z: 569.1 (M + H)$^+$. |
| 50.0 | Example 48.01<br><br>2-(4-fluorophenyl)acetohydrazide (commercially available from Frontier Scientific Services, Inc., Newark, DE). | (1R,2S)-N-(4-(2,6-dimethoxyphenyl)-5-(4-fluorobenzyl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 12.78 (s, 1H), 8.63 (s, 2H), 7.44 (t, J = 8.5 Hz, 1H), 7.00 (t, J = 8.8 Hz, 2H), 6.92-6.84 (m, 2H), 6.72 (d, J = 8.2 Hz, 2H), 4.79 (d, J = 3.4 Hz, 1H), 3.66 (s, 2H), 3.58 (s, 3H), 3.57 (s, 3H), 3.36 (dd, J = 3.5, 7.1 Hz, 1H), 3.13 (s, 3H), 2.26 (s, 3H), 1.09 (d, J = 6.9 Hz, 3H). LCMS (pos.) m/z: 557.1 (M + H)$^+$. |

TABLE 6-continued

| Example | Reagents | Structure, Name and Data |
|---|---|---|
| 51.0 | Example 48.01 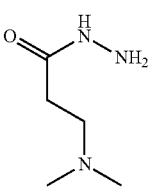 3-(dimethylamino)propanehydrazide (commercially available from Frontier Scientific Services, Inc., Newark, DE). | 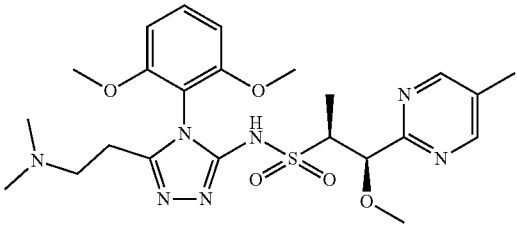 (1R,2S)-N-(4-(2,6-dimethoxyphenyl)-5-(2-(dimethylamino)ethyl)-4H-1,2,4-triazol-3-yl)-1-methoxy-1-(5-methyl-2-pyrimidinyl)-2-propanesulfonamide. $^1$H NMR (500 MHz, DMSO-$d_6$) δ 12.95 (br. s., 1H), 9.66 (br. s., 1H), 8.64 (s, 2H), 7.53 (t, J = 8.5 Hz, 1H), 6.88 (dd, J = 2.7, 8.5 Hz, 2H), 4.79 (d, J = 3.6 Hz, 1H), 3.77 (s, 3H), 3.77 (br. s., 3H), 3.45-3.34 (m, 3H), 3.14 (s, 3H), 2.76 (app s, 6H), 2.69 (t, J = 7.8 Hz, 2H), 2.26 (s, 3H), 1.12 (d, J = 7.0 Hz, 3H). LCMS (pos.) m/z: 520.1 (M + H)$^+$. |
| 52.0 | Example 48.01 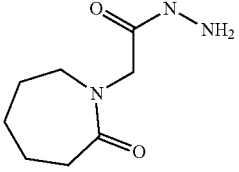 2-(2-oxoazepan-1-yl)acetohydrazide (commercially available from Frontier Scientific Services, Inc., Newark, DE). | 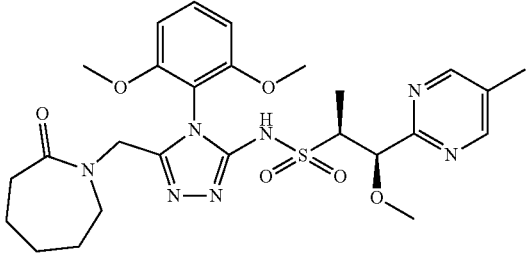 (1R,2S)-N-(4-(2,6-dimethoxyphenyl)-5-((2-oxo-1-azepanyl)methyl)-4H-1,2,4-triazol-3-yl)-1-methoxy-1-(5-methyl-2-pyrimidinyl)-2-propanesulfonamide. $^1$H NMR (500 MHz, DMSO-$d_6$) δ 12.84 (br. s., 1H), 8.64 (s, 2H), 7.44 (t, J = 8.5 Hz, 1H), 6.79 (dd, J = 2.8, 8.5 Hz, 2H), 4.81 (d, J = 3.5 Hz, 1H), 4.34-4.24 (m, 2H), 3.75 (s, 3H), 3.74 (s, 3H), 3.38 (dd, J = 3.5, 7.0 Hz, 1H), 3.18-3.13 (m, 5H), 2.26 (s, 3H), 2.21 (d, J = 10.9 Hz, 2H), 1.57 (d, J = 5.1 Hz, 2H), 1.49 (br. s., 2H), 1.40 (br. s., 2H), 1.11 (d, J = 7.0 Hz, 3H). LCMS (pos.) m/z: 574.1 (M + H)$^+$. |
| 53.0 | Example 48.01 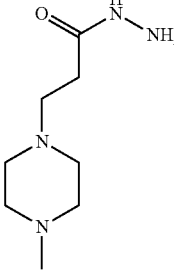 3-(4-methylpiperazin-1-yl)propanehydrazide (commercially available from Frontier Scientific Services, Inc., Newark, DE). | 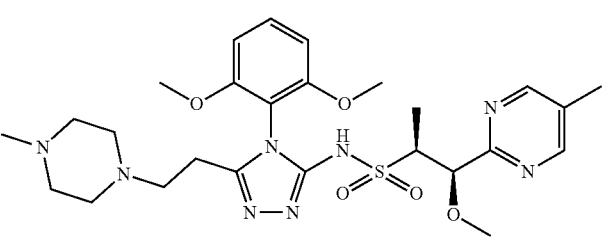 (1R,2S)-N-(4-(2,6-dimethoxyphenyl)-5-(2-(4-methyl-1-piperazinyl)ethyl)-4H-1,2,4-triazol-3-yl)-1-methoxy-1-(5-methyl-2-pyrimidinyl)-2-propanesulfonamide. (Very broad peak across the aliphatic region makes $^1$H NMR integration difficult). LCMS (pos.) m/z: 575.2 (M + H)$^+$. |

TABLE 6-continued

| Example | Reagents | Structure, Name and Data |
|---|---|---|
| 54.0 | Example 48.01<br>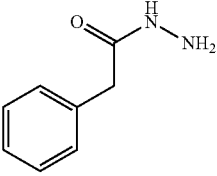<br>2-phenylacetohydrazide (commercially available from Frontier Scientific Services, Inc., Newark, DE). | 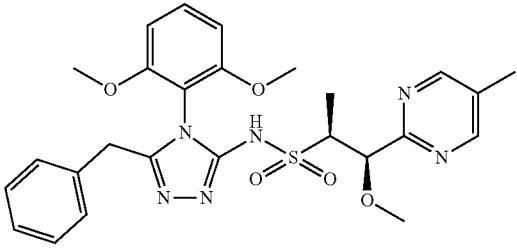<br>(1R,2S)-N-(5-benzyl-4-(2,6-dimethoxyphenyl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 12.76 (br. s., 1H), 8.63 (s, 2H), 7.44 (t, J = 8.5 Hz, 1H), 7.22-7.12 (m, 3H), 6.89-6.81 (m, 2H), 6.71 (d, J = 8.6 Hz, 2H), 4.79 (d, J = 3.4 Hz, 1H), 3.65 (s, 2H), 3.55 (s, 3H), 3.53 (s, 3H), 3.36 (dd, J = 3.5, 7.0 Hz, 1H), 3.13 (s, 3H), 2.26 (s, 3H), 1.09 (d, J = 7.0 Hz, 3H). LCMS (pos.) m/z: 539.1 (M + H)$^+$. |

The compounds set forth in the following table were synthesized following the procedure in Example 14.0 using the known starting material as described.

TABLE 7

| | | |
|---|---|---|
| 55.0 | (1R,2S)-1-(5-chloropyrimidin-2-yl)-1-methoxypropane-2-sulfonamide (Example 83.3. (R)-2-(tetrahydrofuran-2-yl)acetohydrazideoxolane-2-carbohydrazide and (S)-2-(tetrahydrofuran-2-yl)acetohydrazide (commercially available from Ukrorgsyntez), and 1-isothiocyanato-1-methylcyclopropane (commercially available from Enamine). The mixture was purified by preparative SFC method: Column: AD-H (2 x 25 cm) + AD-H (2x 15 cm) Mobile Phase: 65:35 (A:B) A: Liquid CO$_2$, B: MeOH, Flow Rate: 60 mL/min. 219 nm, 100 bar inlet pressure to deliver Peak 1. | 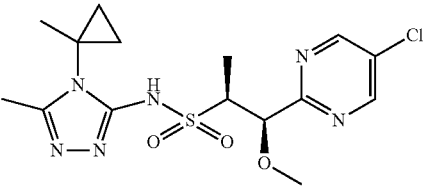 [SMILES: CO[C@H](c1ncc(Cl)cn1)[C@H](C)S(=O)(=O)Nc1nnc(C)n1C1(C)CC1]<br>(1R,2S)-1-(5-chloropyrimidin-2-yl)-1-methoxy-N-(5-methyl-4-(1-methylcyclopropyl)-4H-1,2,4-triazol-3-yl)propane-2-sulfonamide.<br>$^1$H NMR (400 MHz, DMSO-d$_6$) δ 12.42 (br. s., 1H). 8.98-8.87 (m, 2H), 4.91 (d, J = 3.9 Hz, 1H), 3.47-3.39 (m, 1H), 3.08 (s, 3H), 2.34 (s, 3H), 1.38 (s, 3H). 1.26 (d, J = 7.0 Hz, 3H), 1.21- 1.07 (m, 2H), 0.97- 0.88 (m, 2H). LCMS (pos.) m/z: 401.0 (M + H)$^+$. |
| 56.0 | (1R,2S)-1-(5-chloropyrimidin-2-yl)-1-methoxypropane-2-sulfonamide (Example 83.3). (R)-2-(tetrahydrofuran-2-yl)acetohydrazideoxolane-2-carbohydrazide and (S)-2-(tetrahydrofuran-2-yl)acetohydrazide (commercially available from Ukrorgsyntez), and 1-isothiocyanato-1-methylcyclopropane (commercially available from Enamine). The mixture was purified by preparative SFC method: Column: AD-H (2 x 25 cm) + AD-H (2x 15 cm) Mobile Phase: 65:35 (A:B) A: Liquid CO$_2$. B: MeOH, Flow Rate: 60 mL/min, 219 nm, 100 bar inlet pressure to deliver Peak 2. | 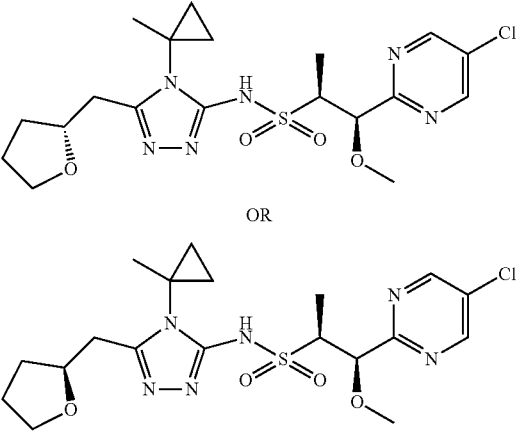 [SMILES: CO[C@H](c1ncc(Cl)cn1)[C@H](C)S(=O)(=O)Nc1nnc(C[C@H]2CCCO2)n1C1(C)CC1 ; CO[C@H](c1ncc(Cl)cn1)[C@H](C)S(=O)(=O)Nc1nnc(C[C@@H]2CCCO2)n1C1(C)CC1]<br>OR<br>(1R,2S)-1-(5-chloropyrimidin-2-yl)-1-methoxy-N-(4-(1-methylaclopropyl)-5-(((R)-tetrahydrofurcan-2-yl)methyl)-4H-1,2,4-triazol-3-yl)propane-2-sulfonainide or (1R,2S)-1-(5-chloroprimidin-2-yl)-1- |

TABLE 7-continued

| | | |
|---|---|---|
| | | methoxy-N-(4-(1-methylcyclopropyl)-5-(((S)-tetrahydrofuran-2-yl)methyl)-4H-1,2,4-triazol-3-yl)propane-2-sulfonamide.<br>$^1$H NMR (400MHz, CD$_2$Cl$_2$) δ 10.73 (br, s., 1H), 8.74 - 8.68 (m, 2H), 4.99 (d, J = 3.5 Hz, 1H), 4.36-4.27 (m, 1H), 3.90-3.82 (m, 1H), 3.71 (dt, J = 6.5, 7.8 Hz, 1H), 3.55 (dq, J = 3.7, 7.0 Hz, 1H), 3.22-3.15 (m, 3H), 3.05-2.97 (m, 1H), 2.85 (dd, J = 5.7. 15.7 Hz, 1H). 2.22 - 2.12 (m, 1H), 2.01-1.87 (m, 2H), 1.70-1.61 (m, 1H). 1.48 (s, 3H), 1.34 (d, J = 7.0 Hz, 3H), 1.28-1.20 (m, 2H), 1.07-0.97 (m, 2H). LCMS (pos.) m/z: 471.0 (M + H)$^+$. |
| 57.0 | (1R.2S)-1-(5-chloropyrimidin-2-yl)-1-methoxypropane-2-sulfonamide (Example 83.3). (R)-2-(tetrahydrofuran-2-yl)acetohydrazideoxolane-2-carbohydrazide and (S)-2-(tetrahydrofuran-2-yl)acetohydrazide (commercially available from Ukrorgsyntez), and 1-isothiocyanato-1-methylcyclopropane (commercially available from Enamine)<br>The mixture was purified by preparative SFC method: Column: AD-H (2 x 25 cm) + AD-H (2x 15 cm) Mobile Phase: 65:35 (A:B) A: Liquid CO$_2$. B: MeOH. Flow Rate: 60 mL/min, 219 nm, 100 bar inlet pressure to deliver Peak 3. | 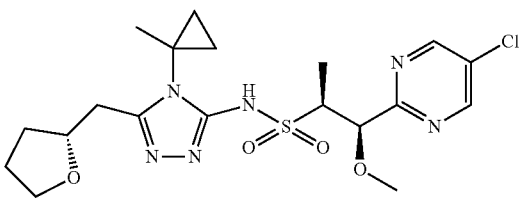<br>OR<br>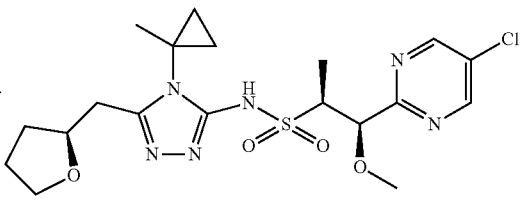<br>(1R.2S)-1-(5-chloropyrimidin-2-yl)-1-methoxy-N-(4-(1-methylcyclopropyl)-5-(((R)-tetrahydrofuran-2-yl)methyl)-4H-1,2,4-triazol-3-yl)propane-2-sulfonamide<br>or (1R,2S)-1-(5-chloropyrimidin-2-yl)-1-methoxy-N-(4-(1-methylcyclopropyl)-5-(((S)-tetrahydrofuran-2-yl)methyl)-4H-1,2,4-triazol-3-yl)propane-2-sulfonamide.<br>$^1$H NMR (400MHz, CD$_2$Cl$_2$) δ 11.03-10.36 (m. 1H), 8.72 (s, 2H), 4.99 (d, J = 3.7 Hz, 1H), 4.32 (quin, J = 6.7 Hz, 1H), 3.91-3.82 (m, 1H). 3.77-3.68 (m, 1H), 3.57 (dq, J = 3.8. 7.0 Hz, 1H), 3.21 (s, 3H), 3.06-2.96 (m, 1H), 2.91-2.82 (m, 1H), 2.21-2.12 (m, 1H), 2.00-1.87 (m. 2H), 1.69-1.60 (m, 1H), 1.48 (s, 3H), 1.35 (d, J = 7.0 Hz, 3H), 1.30-1.15 (m, 2H), 1.06-0.97 (m, 2H). LCMS (pos.) m/z: 471.2 (M + H)$^+$. |
| 58.0 | (1R,2S)-1-(5-chloropy rimidin-2-yl)-1-methoxypropane-2-sulfonamide (Example 83.3), methoxyacetic acid hydrazide (commercially available from CombiBlocks Inc.), and 5-isothiocyanato-4.6-dimethoxypyrimidine (Example 82.1). | 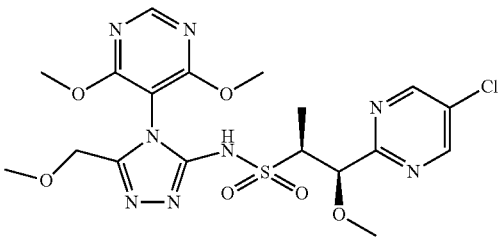 [SMILES: COCc1nnc(NS(=O)(=O)[C@@H](C)[C@H](OC)c2ncc(Cl)cn2)n1-c1c(OC)ncnc1OC]<br>(1R,2S)-1-(5-chloropyrimidin-2yl)-N-(4-(4.6-dimethoxypyrimidin-5-yl)-5-(methoxymethyl)-4H-1,2,4-triazol-3-yl)-1-methoxypropane-2-sulfonamide.<br>$^1$H NMR (500MHz, DMSO-d$_6$) δ 13.21 (br. s., 1H), 8.94 (s, 2H), 8.67 (s, 1H), 4.80 (d, J = 3.9 Hz, 1H), 4.26 (s, 2H), 3.95 (br. s., 3H), 3.94-3.82 (m, 3H), 3.41 (dd, J = 4.2, 6.7 Hz, 1H). 3.13 (s, 3H), 3.12 (s, 3H), 1.14 (d, J = 6.7 Hz, 3H). LCMS (pos.) m/z: 515.0 (M + H)$^+$. |
| 59.0 | (1R,2S)-1-(5-chloropyrimidin-2-yl)-1-methoxypropane-2-sulfonamide (Example 83.3), methoxyacetic acid hydrazide (commercially available fromCombiBlocks Inc.), and 1-isothiocyanato-1-methylcyclopropane (commercially available from Enamine). | 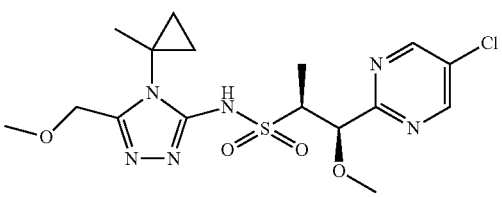 [SMILES: COCc1nnc(NS(=O)(=O)[C@@H](C)[C@H](OC)c2ncc(Cl)cn2)n1C1(C)CC1] |

TABLE 7-continued

| | | |
|---|---|---|
| | | (1R,2S)-1-(5-chloropyrimidin-2-yl)-1-methoxy-N-(5-(methoxymethyl)-4-(1-methylcyclopropyl)-4H-1,2,4-triazol-3-yl)propane-2-sulfonamide. $^1$H NMR (500MHz. DMSO-d$_6$) δ 12.78 (s, 1H), 9.00-8.85 (m, 2H), 4.93 (d, J = 3.9 Hz. 1H), 4.55-4.43 (m, 2H), 3.48-3.40 (m, 1H), 3.31 (s, 3H), 3.06 (s, 3H), 1.39 (s, 3H), 1.27 (d, J = 7.0 Hz, 3H), 1.24-1.13 (m, 2H), 0.99-0.83 (m, 2H). LCMS (pos.) m/z: 431.0 (M + H)$^+$. |
| 60.0 | (1R, 2S)-1-methoxy-1-(5-methylpyrimidin-2-yl)propane-2-sulfonamide (Example 83.0), methoxyacetic acid hydrazide (commercially available from CombiBlocks Inc.), and 2-isothiocyanato-1,3-dimethoxybenzene, Example 82.0. | 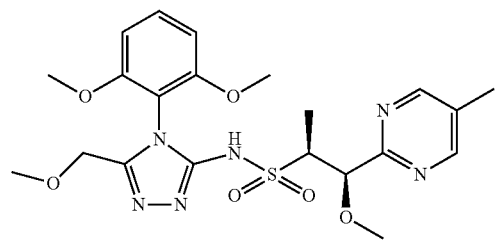<br>(1R,2S)-N-(4-(2.6-dimethoxyphenyl)-5-(methoxymethyl)-4H-1.2,4-triazol-3-yl)-1-methoxy-1-(5-methylpyrimidin-2-yl)propane-2-sulfonamide. $^1$H NMR (500MHz, DMSO-d$_6$) δ 13.00 (s, 1H). 8.64 (s, 2H), 7.47 (t, J = 8.4 Hz, 1H), 6.83 (dd, J = 1.7, 8.4 Hz, 2H), 4.82 (d, J = 3.4 Hz, 1H), 4.12 (s, 2H), 3.74 (s, 3H). 3.73 (s, 3H), 3.43-3.37 (m, 1H), 3.14 (s, 3H), 3.08 (s, 3H), 2.26 (s, 3H), 1.12 (d, J = 7.0 Hz, 3H). LCMS (pos.) m/z: 493.2 (M + H)$^+$. |
| 61.0 | (2S,3R)-3-(5-methylpyrimidin-2-yl)butane-2-sulfonamide (Example 81.0), methoxyacetic acid hydrazide (commercially available from CoinbiBlocks Inc.), and 2-isothiocyanato-1,3-dimethoxybenzene (Example 82.0). | 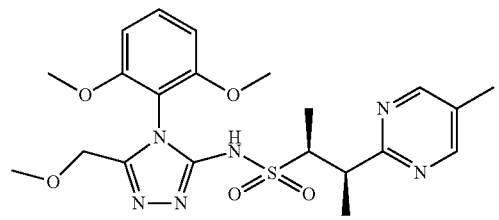<br>(2S,3R)-N-(4-(2,6-dimethoxyphenyl)-5-(methoxymethyl)-4H-1.2.4-triazol-3-yl)-3-(5-methylpyrimidin-2-yl)butane-2-sulfonamide. $^1$H NMR (500MHz, DMSO-d$_6$) δ 13.02 (s, 1H), 8.58 (s, 2H), 7.47 (t, J = 8.6 Hz, 1H), 6.82 (dd, J = 1.3. 8.6 Hz. 2H), 4.11 (s, 2H), 3.72 (s, 3H), 3.71 (s, 3H), 3.66 (dq, J = 3.4, 7.0 Hz, 1H), 3.57 (dq, J = 3.4, 6.9 Hz. 1H). 3.08 (s, 3H), 2.22 (s, 3H), 1.23 (d, J = 7.3 Hz, 3H), 1.08 (d, J = 7.0 Hz. 3H). LCMS (pos.) m/z: 477.2 (M + H)$^+$. |
| 62.0 | (1S,2S)-1-isopropoxy-1-(5-methylpyrimidin-2-yl)propane-2-sulfonamide (Example 85.0), methoxyacetic acid hydrazide (commercially available from CombiBlocks Inc.), and 2-isothiocyanato-1,3-dimethoxybenzene (Example 82.0). | 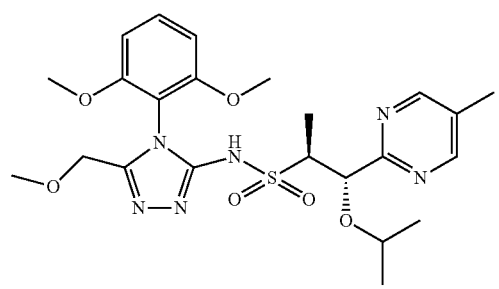<br>(1S,2S)-N-(4-(2,6-dimethoxyphenyl)-5-(methoxymethyl)-4H-1,2,4-triazol-3-yl)-1-isopropoxy-1-(5-methylpyrimidin-2-yl)propane-2-sulfonamide. $^1$H NMR (500MHz, DMSO-d$_6$) δ 13.00 (s, 1H), 8.65 (s, 2H), 7.47 (t, J = 8.4 Hz. 1H), 6.84 (d, J = 8.6 Hz. 2H), 4.70 (d, J = 7.5 Hz, IH), 4.13 (s, 2H), 3.78 (s, 3H), 3.77 (s, 3H), 3.44-3.36 (m, 2H), 3.08 (s, 3H), 2.26 (s, 3H), 0.98 (d, J = 6.0 Hz. 3H), 0.91 (d, J = 7.0 Hz, 3H), 0.79 (d, J = 6.2 Hz. 3H), LCMS (pos.) m/z: 521.2 (M + H)$^+$. |

TABLE 7-continued

| | | |
|---|---|---|
| 63.0 | (1R,2S)-1-(5-chloropyrimidin-2-yl)-1-methoxypropane-2-sulfonamide (Example 83.3), methoxyacetic acid hydrazide (commercially available from CombiBlocks Inc.), and 4-isothiocyanatooxane (commercially available from Oakwood Products Inc.). | 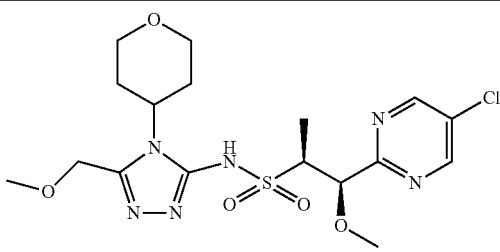 (1R, 2S)-1-(5-chloropyrimidin-2-yl)-1-methoxy-N-(5-(methoxymethyl)-4-(tetrahydro-2H-pyran-4-yl)-4H-1,2,4-triazol-3-yl)propane-2-sulfonamide. <br> $^1$H NMR (500MHz, DMSO-d$_6$) δ 12.88 (s, 1H), 8.98-8.86 (m, 2H), 4.92 (d, J = 3.9 Hz, 1H), 4.59-4.45 (m, 2H), 4.23 (tt, J = 3.9, 12.0 Hz, 1H), 3.96 (br dd, J = 3.9, 11.2 Hz, 2H), 3.52-3.44 (m, 1H), 3.41-3.34 (m, 2H), 3.28 (s, 3H), 3.11 (s, 3H), 2.56-2.45 (m, 2H), 1.63 (br t, J = 7.1 Hz, 2H), 1.26 (d, J = 7.0 Hz, 3H). LCMS (pos.) m/z: 461.2 (M + H)$^+$. |
| 64.0 | (1R.2S)-1-(5-chloropyrimidin-2-yl)-1-methoxypropane-2-sulfonamide (Example 83.3), 2-hydroxy-acetic acid hydrazide (commercially available from Matrix Scientific.), and 2-isothiocyanato-1.3-dimethoxy benzene (Example 82.0). | 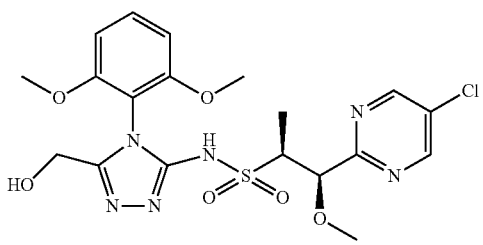 [SMILES: COc1cccc(OC)c1-n1c(CO)nnc1NS(=O)(=O)[C@@H](C)[C@H](OC)c1ncc(Cl)cn1] (1R,2S)-1-(5-chloropyrimidin-2-yl)-N-(4-(2,6-dimethoxyphenyl)-5-(hydroxymethyl)-4H-1.2.4-triazol-3-yl)-1-methoxypropane-2-sulfonamide. <br> $^1$H NMR (500MHz. DMSO-d$_6$) δ 12.89-12.74 (m, 1H), 9.03-8.85 (m, 2H), 7.53-7.43 (m, 1H). 6.90-6.77 (m, 2H), 5.45-5.36 (m, 1H), 4.82-4.69 (m, 1H), 4.18-4.07 (m, 2H), 3.78-3.74 (m, 3H), 3.74-3.71 (m, 3H), 3.47-3.39 (m, 1H), 3.20-3.11 (m, 3H), 1.21-1.10 (m, 3H), LCMS (pos.) m/z: 499.0 (M + H)$^+$. |

Example 65.0: Preparation of (1R,2S)-1-(5-chloro-2-pyrimidinyl)-N-(5-((difluoromethoxy)methyl)-4-(2,6-dimethoxyphenyl)-4H-1,2,4-triazol-3-yl)-1-methoxy-2-propanesulfonamide

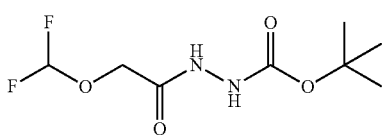

2-(2-(Difluoromethoxy)acetyl)hydrazinecarboxylate, Example 65.1

A flask containing 2-(difluoromethoxy)acetic acid (commercially available from Enamine, 930 mg, 7.38 mmol) in anhydrous DCM (14 mL) was cooled in an ice bath. After 20 min, 1-(3-dimethylaminopropyl)-3-ethylcarbodiimide hydrochloride (1.45 g, 7.57 mmol) and then tert-butyl carbazate (1.05 g, 7.98 mmol) were carefully added in portions to the homogeneous solution. Upon complete addition of tert-butyl carbazate, the homogeneous solution was allowed to warm to RT. After 22 h, the reaction was carefully quenched with water and then extracted three times with DCM. The organic layers were combined and then washed once with brine. The organic layer was dried over anhydrous magnesium sulfate, filtered and concentrated under reduced pressure. The white solid was identified as tert-butyl 2-(2-(difluoromethoxy)acetyl)hydrazinecarboxylate (Example 65.1, 1.77 g, 7.37 mmol, 100% yield) that was used without purification. LCMS (pos.) m/z: 239.2 (M–H)$^-$.

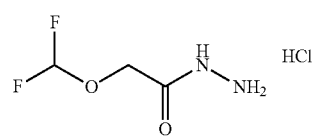

2-(Difluoromethoxy)acetohydrazide hydrochloride, Example 65.2

A flask containing tert-butyl 2-(2-(difluoromethoxy) acetyl)hydrazinecarboxylate (Example 65.1, 1.77 g, 7.37 mmol) in EtOH (7.5 mL) was cooled in an ice water bath. After 20 min, hydrogen chloride, (1.25M in EtOH, 30 mL, 37.5 mmol) was added carefully dropwise. Upon complete addition of acid, the mixture was allowed to warm to RT. After 19 h, the reaction was diluted with EtOAc and then carefully concentrated under reduced pressure. The white solid was suspended in EtOAc. The subsequent white solid was filtered and then identified as 2-(difluoromethoxy)acetohydrazide hydrochloride (Example 65.2) and was used without purification. LCMS (pos.) m/z: 141.0 (M+H)+.

The compounds set forth in the following table were synthesized following the procedure in Example 14.0 using the known starting material as described.

TABLE 8

65.0 (1R,2S)-1-(5-chloropyrimidin-2-yl)-1-methoxypropane-2-sulfonamide (Example 83.3), 2-(difluoromethoxy)acetohydrazide hydrochloride (Example 88.2), and 2-isothiocyanato-1,3-dimethoxybenzene (Example 82.0).

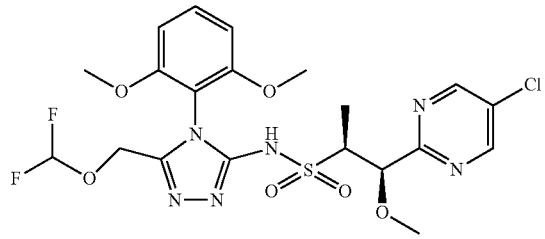 [SMILES: COc1cccc(OC)c1-n1c(COC(F)F)nnc1NS(=O)(=O)[C@@H](C)[C@H](OC)c1ncc(Cl)cn1]

(1R,2S)-1-(5-chloropyrimidin-2-yl)-N-(5-((difluoromethoxy)methyl)-4-(2,6-dimethoxypheyl)-4H-1,2,4-triazol-3-yl)-1-methoxypropane-2-sulfonamide.
$^1$H NMR (500MHz, DMSO-$d_6$) δ 13.14 (s, 1H), 8.93 (s, 2H), 7.50 (t, J = 8.4 Hz, IH), 6.85 (d, J = 8.3 Hz. 2H), 6.72-6.39 (m, 1H), 4.79 (d, J = 4.4 Hz, 1H), 4.62 (s, 2H), 3.75 (s, 3H), 3.74-3.71 (m, 3H), 3.47-3.36 (m, 1H), 3.15 (s, 3H), 1.15 (d, J = 7.0 Hz, 3H). LCMS (pos.) m/z: 549.0 (M + H)+.

66.0 (1R,2S)-1-(5-chloropyrimidin-2-yl)-1-methoxypropane-2-sulfonamide (Example 83.3), propionic acid hydrazide (commercially available from Sigma Aldrich), and 2-isothiocyanato-1,3-dimethoxybenzene (Example 82.0).

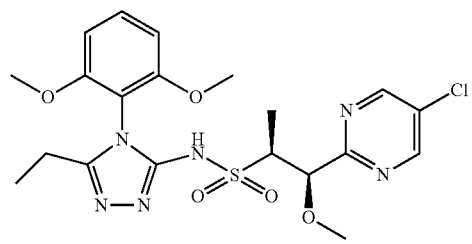 [SMILES: CCc1nnc(NS(=O)(=O)[C@@H](C)[C@H](OC)c2ncc(Cl)cn2)n1-c1c(OC)cccc1OC]

(1R,2S)-1-(5-chloropyrimidin-2-yl)-N-(4-(2,6-dimethoxyphenyl)-5-ethyl-4H-1,2,4-triazol-3-yl)-1-methoxypropane-2-sulfonamide.
$^1$H NMR (500MHz, DMSO-$d_6$) δ 12.69 (s. 1H), 8.93 (s, 2H), 7.51 (t, J = 8.6 Hz, 1H). 6.86 (dd, J = 1.3, 8.6 Hz, 2H), 4.76 (d, J = 4.4 Hz, 1H), 3.76 (s, 3H), 3.76-3.74 (m, 3H), 3.43-3.36 (m. 1H), 3.14 (s, 3H), 2.23 (q, J = 7.4 Hz, 2H), 1.14 (d, J = 6.7 Hz. 3H), 1.02 (t, J = 7.5 Hz, 3H). LCMS (pos.) m/z: 497.2 (M + H)+.

67.0 (1R,2S)-1-(5-chloropyrimidin-2-yl)-1-methoxypropane-2-sulfonamide (Example 83.3), 3,3,3-trifluoropropanehydrazide (commercially available from Enamine), and 5-isothiocyanato-4,6-dimethoxypyrimidine (Example 82.1).

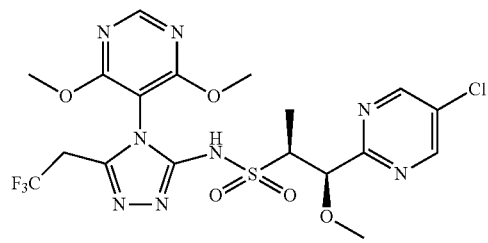 [SMILES: COc1ncnc(OC)c1-n1c(CC(F)(F)F)nnc1NS(=O)(=O)[C@@H](C)[C@H](OC)c1ncc(Cl)cn1]

(1R,2S)-1-(5-chloropyrimidin-2-yl)-N-(4-(4,6-dimethoxypyrimidine-5-yl)-5-(2.2.2-trifluoroethy l)-4H-1.2.4-triazol-3-yl)-1-methoxypropane-2-sulfonamide.
$^1$H NMR (500MHz, CD$_2$Cl$_2$) δ 11.03 (br s, 1H), 8.72 (s, 2H), 8.58-8.51 (m, 1H), 4.90 (d, J = 4.2 Hz, 1H), 4.04-3.99 (m, 6H), 3.60 (dq, J = 4.3, 7.0 Hz, 1H), 3.40-3.30 (m, 2H), 3.28-3.24 (m, 3H), 1.28-1.23 (m, 3H). LCMS (pos.) m/z: 553.0 (M + H)+.

TABLE 8-continued

| | | |
|---|---|---|
| 68.0 | (2S,3R)-3-(5-fluoropyrimidin-2-yl)butane-2-sulfonamide (Example 81.1), methoxyacetic acid hydrazide (commercially available from CombiBlocks Inc.), and 2-isothiocyanato-1,3-dimethoxybenzene (Example 82.0). | 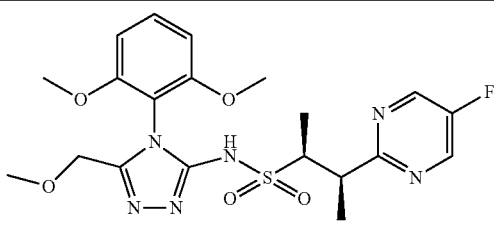<br>(2S,3R)-N-(4-(2,6-dimethoxyphenyl)-5-(methoxymethyl)-4H-1,2,4-triazol-3-yl)-3-(5-fluoropyrimidin-2-yl)butane-2-sulfonamide.<br>$^1$H NMR (500MHz, DMSO-d$_6$) δ 12.98 (s, 1H). 8.81 (s, 2H), 7.47 (t, J = 8.4 Hz, 1H). 6.83 (dd, J = 1.8, 8.6 Hz, 2H), 4.11 (s, 2H), 3.73 (d, J = 1.8 Hz, 7H), 3.54 (dq, J = 4.2, 6.9 Hz, 1H), 3.08 (s, 3H), 1.24 (d, J = 7.3 Hz, 3H), 1.10 (d, J = 7.0 Hz, 3H). LCMS (pos.) m/z: 481.2 (M + H)$^+$. |
| 69.0 | (1R,2S)-1-(5-chloropyrimidin-2-yl)-1-methoxypropane-2-sulfonamide (Example 83.3), 2-isopropoxyacetohydrazide (commercially available from Matrix Scientific), and 2-isothiocyanato-1,3-dimethoxybenzene (Example 82.0). | 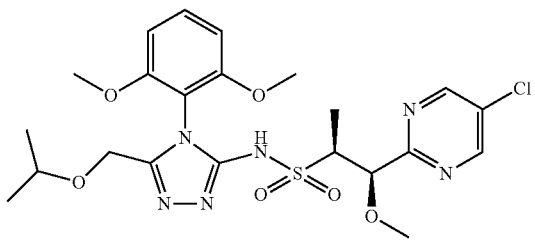 [SMILES: COc1cccc(OC)c1-n1c(COC(C)C)nnc1NS(=O)(=O)[C@@H](C)[C@H](OC)c1ncc(Cl)cn1]<br>(1R,2S)-1-(5-chloropyrimidin-2-yl)-N-(4-(2,6-dimethoxyphenyl)-5-(isopropoxymethyl)-4H-1,2,4-triazol-3-yl)-1-methoxypropane-2-sulfonamide.<br>$^1$H NMR (500MHz, DMSO-d$_6$) δ 12.91 (s, 1H). 8.93 (s, 2H), 7.48 (t, J = 8.4 Hz, 1H). 6.83 (dd, J = 1.6, 8.6 Hz, 2H). 4.78 (d, J = 4.4 Hz, 1H). 4.14 (s, 2H), 3.75 (s, 3H), 3.73 (s, 3H), 3.45-3.38 (m, 1H), 3.35-3.27 (m, 1H), 3.15 (s, 3H), 1.15 (d, J = 7.0 Hz, 3H), 0.85 (s, 3H), 0.84-0.83 (m, 3H). LCMS (pos.) m/z: 541.2 (M + H)$^+$. |
| 70.0 | (1S,2S)-1-(5-chloropyrimidin-2-yl)-1-isopropoxypropane-2-sulfonamide (Example 85.1), methoxyacetic acid hydrazide (commercially available from CombiBlocks Inc.), and 2-isothiocyanato-1,3-dimethoxybenzene (Example 82.0). | 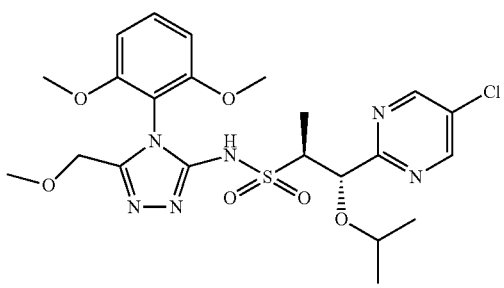 [SMILES: COCc1nnc(NS(=O)(=O)[C@@H](C)[C@@H](OC(C)C)c2ncc(Cl)cn2)n1-c1c(OC)cccc1OC]<br>(1S,2S)-1-(5-chloropyrimidin-2-yl)-N-(4-(2,6-dimethoxyphenyl)-5-(methoxymethyl)-4H-1,2,4-triazol-3-yl)-1-isopropoxy propane-2-sulfonamide.<br>$^1$H NMR (400MHz, DMSO-d$_6$) δ 12.90 (s, 1H), 8.93 (s, 2H), 7.48 (t, J = 8.5 Hz, 1H). 6.84 (d, J = 8.7 Hz, 2H). 4.78 (d, J = 7.0 Hz, 1H), 4.12 (s, 2H), 3.78 (s, 3H), 3.77 (s, 3H), 3.47-3.37 (m, 2H), 3.08 (s, 3H), 0.99 (t, J = 6.9 Hz, 6H), 0.83 (d, J = 6.0 Hz, 3H). LCMS (pos.) m/z: 541.2 (M + H)$^+$. |
| 71.0 | (1R,2S)-1-(5-chloropyrmidin-2-yl)-1-methoxypropane-2-sulfonomide Example 83.3), 2-ethoxyacelohydrazide (commercially available from Matrix Scientific), and 2-isothiocyanato-1,3-dimethoxybenzene (Example 82.0). | 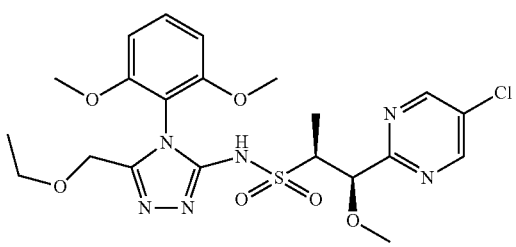 [SMILES: CCOCc1nnc(NS(=O)(=O)[C@@H](C)[C@H](OC)c2ncc(Cl)cn2)n1-c1c(OC)cccc1OC] |

TABLE 8-continued (1R,2S)-1-(5-chloropyrimidin-2-yl)-N-(4-(2,6-dimethoxyphenyl)-5-(ethoxymethyl)-4H-1,2,4-triazol-3-yl)-1-methoxypropane-2-sulfonamide.
$^1$H NMR (500MHz. DMSO-d$_6$) δ 12.96 (s, 1H). 9.00-8.90 (m, 2H), 7.48 (t, J = 8.4 Hz. 1H), 6.90-6.80 (m, 2H), 4.81-4.75 (m, 1H), 4.16 (s, 2H), 3.75 (s, 3H), 3.74-3.71 (m, 3H). 3.44-3.38 (m, 1H), 3.23 (q, J = 7.0 Hz, 2H), 3.18-3.10 (m, 3H), 1.14 (d, J = 7.0 Hz, 3H), 0.90 (t, J = 7.0 Hz, 3H). LCMS (pos.) m/z: 527.2 (M + H)$^+$.

Example 72.0: Preparation of 1-bromo-2-isothiocyanatobenzene

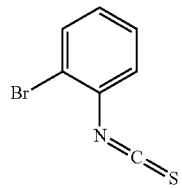

72.1

1-Bromo-2-isothiocyanatobenzene, Example 72.1

To a solution of 1-amino-2bromobenzene (0.63 mL, 5.81 mmol) in DCM (5 ml) was added a solution of 1,1'-thiocarbonyldi-2(1H)-pyridone (1.35 g, 5.81 mmol) in DCM (25 mL) dropwise. The reaction was stirred at RT for 3 d after which complete conversion to product was observed by LCMS. The mixture was concentrated in vacuo and purified by silica gel using 0-50% EtOAc:EtOH (3:1) to yield 1-bromo-2-isothiocyanatobenzene (1.00 g, 4.67 mmol, 80% yield). $^1$H NMR (400 MHz, CDCl$_3$) δ 7.57-7.64 (m, 1H) 7.26-7.34 (m, 2H) 7.12-7.18 (m, 1H).

The compounds set forth in the following table were synthesized following the procedure in Example 14.0 using the known starting material as described.

TABLE 9

| | | |
|---|---|---|
| 72.0 | (1R,2S)-1-methoxy-1-(5-chloropyrimidin-2-yl)propane-2-sulfonamide (Example 83.3), 2-hydroxyacetohydrazide (commercially available from Matrix Scientific), and 1-bromo-2-isothiocyanatobenzene (Example 72.1). | 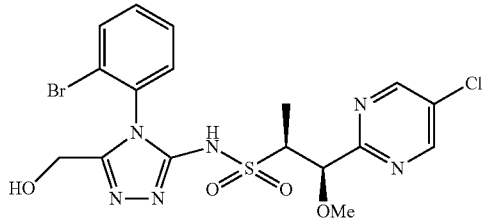 [SMILES: CO[C@H](c1ncc(Cl)cn1)[C@H](C)S(=O)(=O)Nc1nnc(CO)n1-c1ccccc1Br]<br>(1R,2S)-N-(4-(2-bromophenyl)-5-(hydroxymethyl)-4H-1,2,4-triazol-3-yl)-1-(5-chloropyrimidin-2-yl)-1-methoxypropane-2-sulfonamide.<br>$^1$H NMR (500 MHz, DMSO-d$_6$) δ 8.87-8.96 (m, 2H) 7.76-7.86 (m, 1H) 7.53-7.61 (m, 1H) 7.40-7.52 (m, 2H) 4.81-4.89 (m, 1H) 4.23-4.32 (m, 1H) 4.03-4.13 (m, 1H) 3.11-3.21 (m, 4H) 2.47-2.52 (m, 3H). LCMS-ESI (POS.) M/Z: 519.0 (M + H)$^+$ |
| 73.0 | (1R,2S)-1-ethoxy-1-(5-methylpyrimidin-2-yl)propane-2-sulfonamide (Example 95.0), methoxyacetic acid hydrazide (commercially available from CombiBlocks Inc.), and 2-isothiocyanato-1,3-dimethoxybenzene (Example 82.0). | 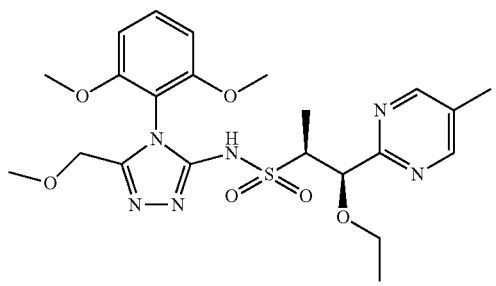<br>(1R,2S)-N-(4-(2,6-dimethoxyphenyl)-5-(methoxymethyl)-4H-1,2,4-triazol-3-yl)-1-ethoxy-1-(5-methylpyrimidin-2-yl)propane-2-sulfonamide<br>$^1$H NMR (500MHz, DMSO-d$_6$) δ 12.94 (s. 1H), 8.63 (s, 2H), 7.47 (t, J = 8.4 Hz. 1H), 6.83 (d, J = 8.6 Hz, 2H), 4.91 (d, J = 3.9 Hz, 1H), 4.12 (s, 2H), 3.76-3.74 (m, 3H), 3.74-3.72 (m, 3H), 3.46-3.38 (m, 2H). 3.32-3.26 (m, 1H), 3.08 (s. 3H), 2.25 (s, 3H). 1.16 (d, J = 7.0 Hz, 3H), 0.99 (t, J = 7.0 Hz, 3H). LCMS (pos.) m/e: 507.2 (M + H)$^+$ |

TABLE 9-continued 74.0 (2S,3R)-3-(5-methoxypyrazin-2-yl)butane-2-sulfonamide (Example 81.5). methoxyacetic acid hydrazide (commercially available from CombiBlocks Inc.), and 2-isothiocyanato-1,3-dimethoxybenzene (Example 82.0).

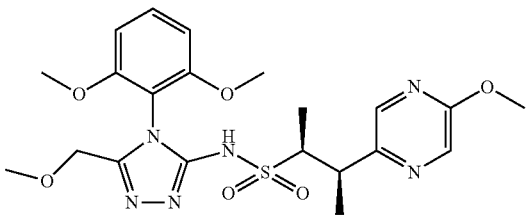

(2S,3R)-N-(4-(2,6-dimethoxyphenyl)-5-(methoxymethyl)-4H-1,2,4-triazol-3-yl)-3-(5-methoxypyrazin-2-yl)butane-2-sulfonamide.
$^1$H NMR (500MHz, DMSO-d$_6$) δ13.00 (s, 1H), 8.24-8.21 (m, 1H), 7.99 (s, 1H), 7.48 (t, J = 8.6 Hz, 1H), 6.83 (dd, J = 2.3, 8.6 Hz, 2H), 4.12 (s, 2H), 3.89-3.86 (m, 3H), 3.77-3.71 (m, 6H), 3.56 (dq, J = 3.9, 7.0 Hz, 1H), 3.30-3.23 (m, 1H), 3.11-3.07 (m, 3H), 1.27-1.17 (m, 3H), 1.15-0.97 (m, 3H). LCMS (pos.) m/e: 493.2 (M + H)$^+$.

75.0 (2S,3R)-3-(5-chloropyridin-2-yl)butane-2-sulfonamide (Example 86.0), methoxyacetic acid hydrazide (commercially available from CombiBlocks Inc.), and 2-isothiocyanato-1,3-dimethoxybenzene (Example 82.0).

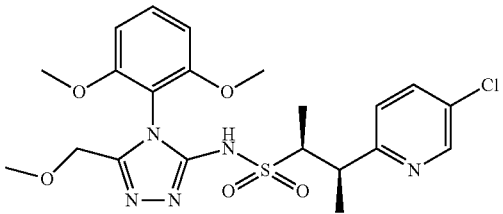 [SMILES: COCc1nnc(NS(=O)(=O)[C@@H](C)[C@H](C)c2ccc(Cl)cn2)n1-c1c(OC)cccc1OC]

(2S,3R)-3-(5-chloropyridin-2-yl)-N-(4-(2,6-dimethoxyphenyl)-5-(methoxymethyl)-4H-1,2,4-triazol-3-yl)butane-2-sulfonamide.
$^1$H NMR (500MHz, DMSO-d$_6$) δ13.02 (s, 1H), 8.53 (d, J = 2.6 Hz, 1H), 7.84 (dd, J = 2.6, 8.3 Hz, 1H), 7.48 (t, J = 8.4 Hz, 1H), 7.25 (d, J = 8.3 Hz, 1H), 6.83 (dd, J = 1.8, 8.6 Hz, 2H), 4.12 (s, 2H), 3.77-3.71 (m, 6H), 3.62-3.56 (m, 1H), 3.38-3.33 (m, 1H), 3.09 (s, 3H), 1.21 (d, J = 7.3 Hz, 3H), 1.08 (d, J = 7.3 Hz, 3H). LCMS (pos.) m/e: 496.2 (M + H)$^+$.

76.0 (1R,2S)-1-(5-chloropyridin-2-yl)-1-methoxypropane-2-sulfonamide (prepared following procedures described in Example 88.4 and 95.1 employing 5-chloropicolinaldehyde (CombiBlocks Inc.), methoxyacetic acid hydrazide (commercially available from CombiBlocks Inc.), and 2-isothiocyanato-1,3-dimethoxybenzene (Example 82.0)

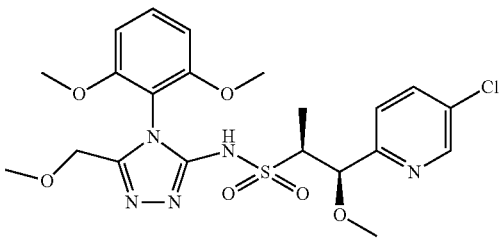 [SMILES: COCc1nnc(NS(=O)(=O)[C@@H](C)[C@H](OC)c2ccc(Cl)cn2)n1-c1c(OC)cccc1OC]

(1R,2S)-1-(5-chloropyridin-2-yl)-N-(4-(2,6-dimethoxyphenyl)-5-(methoxymethyl)-4H-1,2,4-triazol-3-yl)-1-methoxypropane-2-sulfonamide.
$^1$H NMR (500MHz, DMSO-d$_6$) δ13.04 (s, 1H), 8.60 (d, J = 2.3 Hz, 1H), 7.95 (dd, J = 2.3, 8.3 Hz, 1H), 7.47 (t, J = 8.4 Hz, 1H), 7.38 (d, J = 8.3 Hz, 1H), 6.83 (dd, J = 3.1, 8.6 Hz, 2H), 4.87 (d, J = 2.1 Hz, 1H), 4.13 (s, 2H), 3.75-3.73 (m, 3H), 3.72-3.70 (m, 3H), 3.26-3.20 (m, 1H), 3.17 (s, 3H), 3.09 (s, 3H), 0.98 (d, J = 7.0 Hz, 3H). LCMS (pos.) m/e: 512.2 (M + H)$^+$.

TABLE 9-continued

| | | |
|---|---|---|
| 77.0 | (S)-1-(5-fluoropyrimidin-2-yl)piperidine-3-sulfonamide or (R)-1-(5-fluoropyrimidin-2-yl)piperidine-3-sulfonamide (Example 143.2), methoxyacetic acid hydrazide (commercially available from CombiBlocks Inc.), and 2-isothiocyanato-1,3-dimethoxybenzene (Example 82.0). | 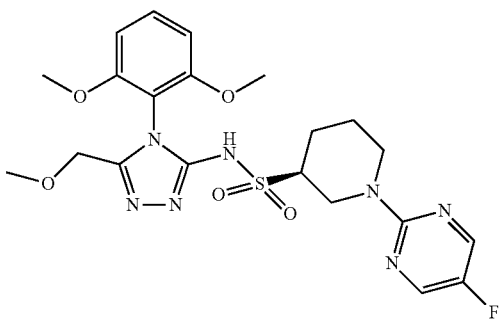<br>OR<br>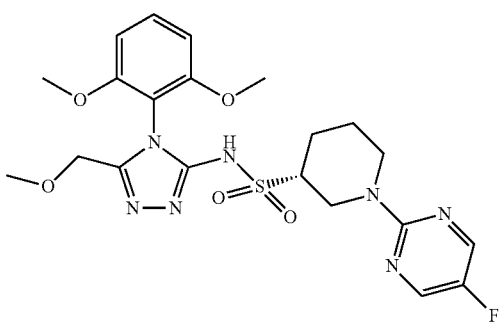<br>(S)-N-(4-(2,6-dimethoxyphenyl)-5-(methoxymethyl)-4H-1,2,4-triazol-3-yl)-1-(5-fluoropyrimidin-2-yl)piperidine-3-sulfonamide or (R)-N-(4-(2,6-dimethoxyphenyl)-5-(methoxymethyl)-4H-1,2,4-triazol-3-yl)-1-(5-fluoropyrimidin-2-yl)piperidine-3-sulfonamide.<br>$^1$H NMR (400MHz, DMSO-$d_6$) δ 13.08 (s, 1H), 8.43 (s, 2H), 7.49 (t, J = 8.5 Hz, 1H), 6.85 (dd, J = 4.4, 8.5 Hz, 2H), 4.91 (d, J = 11.4 Hz, 1H), 4.53 (d, J = 12.6 Hz, 1H), 4.12 (s, 2H), 3.77 (s, 3H), 3.77-3.75 (m, 3H), 3.09 (s, 3H), 2.91-2.66 (m, 3H), 2.08 (d, J = 11.6 Hz, 1H), 1.76 (d, J = 13.1 Hz, 1H), 1.63-1.49 (m, 1H), 1.48-1.33 (m, 1H). LCMS (pos.) m/e: 508.2 (M + H)$^+$. |
| 78.0 | (S)-1-(5-fluoropyrimidin-2-yl)piperidine-3-sulfonamide or (R)-1-(5-fluoropyrimidin-2-yl)piperidine-3-sulfonamide (Example 143.3), methoxyacetic acid hydrazide (commercially available from CombiBlocks Inc.), and 2-isothiocyanato-1,3-dimethoxybenzene (Example 82.0). | 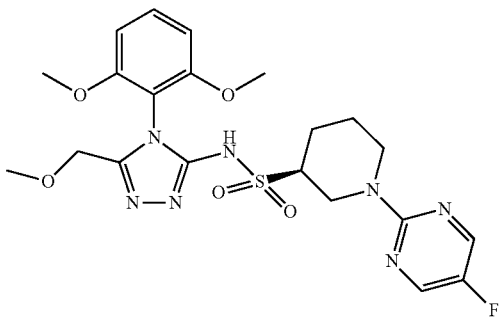<br>OR<br>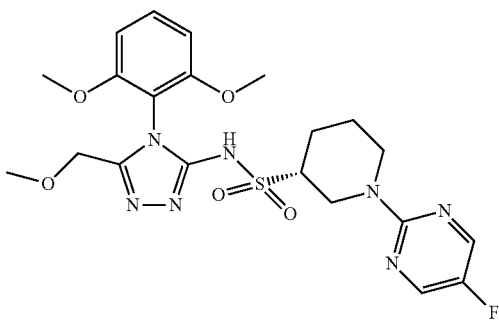<br>(S)-N-(4-(2,6-dimethoxyphenyl)-5-(methoxymethyl)-4H-1,2,4-triazol-3-yl)-1-(5-fluoropyrimidin-2-yl)piperidine-3-sulfonamide or (R)-N-(4-(2,6- | dimethoxyphenyl)-5-(methoxymethyl)-4H-1,2,4-triazol-3-yl)-l-(5-fluoropyrimidin-2-yl)piperidine-3-sulfonamide.
$^1$H NMR (400MHz, DMSO-d$_6$) δ 13.08 (s, 1H), 8.44-8.41 (m, 2H), 7.49 (t, J = 8.5 Hz, 1H), 6.85 (dd, J = 4.4, 8.5 Hz, 2H), 4.91 (d, J = 11.8 Hz, 1H), 4.53 (d, J = 13.1 Hz, 1H), 4.12 (s, 2H), 3.77 (s, 3H), 3.76-3.75 (m, 3H), 3.09 (s, 3H), 2.91-2.66 (m, 3H), 2.08 (d, J = 12.0 Hz, 1H), 1.81-1.72 (m, 1H), 1.56 (dq, J = 3.6, 12.3 Hz, 1H), 1.48-1.33 (m, 1H). LCMS (pos.) m/e: 508.2 (M + H)$^+$.

79.0 (1R,2S)-1-(5-chloropyrimidin-2-yl)-1-methoxypropane-2-sulfonamide (Example 83.3), 2-isopropoxyacetohydrazide (commercially available from Matrix Scientific), and 5-isothiocyanato-4,6-dimethoxypyrimidine (Example 82.1).

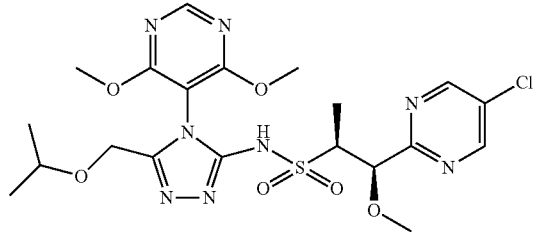 [SMILES: COc1ncnc(OC)c1-n1c(COC(C)C)nnc1NS(=O)(=O)[C@@H](C)[C@H](OC)c1ncc(Cl)cn1]

(1R,2S)-1-(5-chloropyrimidin-2-yl)-N-(4-(4,6-dimethoxypyrimidin-5-yl)-5-(isopropoxymethyl)-4H-1,2,4-triazol-3-yl)-1-methoxypropane-2-sulfonamide.
$^1$H NMR (400MHz, DMSO-d$_6$) δ 13.12 (s, 1H), 8.93 (s, 2H), 8.67 (s, 1H). 4.79 (d. J = 3.9 Hz, 1H), 4.27 (s, 2H). 3.97-3.95 (m, 3H), 3.94-3.92 (m, 3H), 3.46-3.35 (m, 2H), 3.14 (s, 3H), 1.15 (d, J = 7.0 Hz, 3H), 0.88 (s, 3H), 0.87-0.85 (m, 3H). LCMS (pos.) m/e: 543.2 (M + H)$^+$.

80.0 (2S,3R)-3-(5-chloropyrimidin-2-yl)butane-2-sulfonamide (Example 81.4), 2-isopropoxyacetohydrazide (commercially available from Matrix Scientific), and 5-isothiocyanato-4,6-dimethoxypyrimidine (Example 82.1).

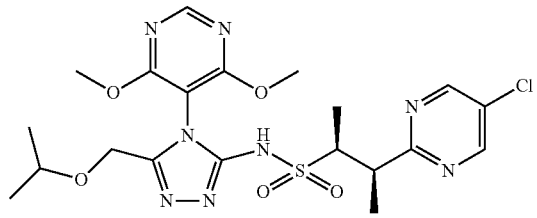 [SMILES: COc1ncnc(OC)c1-n1c(COC(C)C)nnc1NS(=O)(=O)[C@@H](C)[C@H](C)c1ncc(Cl)cn1]

(2S,3R)-3-(5-chloropyrimidin-2-yl)-N-(4-(4,6-dimethoxypyrimidin-5-yl)-5-(isopropoxymethyl)-4H-1,2,4-triazol-3-yl)butane-2-sulfonamide.
$^1$H NMR (400MHz, DMSO-d$_6$) δ 13.11 (br s, 1H), 8.85 (s, 2H), 8.67 (s, 1H), 4.26 (s, 2H), 3.95-3.91 (m, 6H), 3.67-3.62 (m, 1H), 3.61-3.55 (m, 1H), 3.38 (quin, J = 6.1 Hz, 1H), 1.25 (d, J = 7.0 Hz, 3H), 1.13 (d, J = 6.6 Hz, 3H), 0.88-0.87 (m, 3H), 0.86-0.85 (m, 3H). LCMS (pos.) m/e: 527.2 (M + H)$^+$.

Example 81.0: Preparation of (2S,3R)-3-(5-methylpyrimidin-2-yl)butane-2-sulfonamide

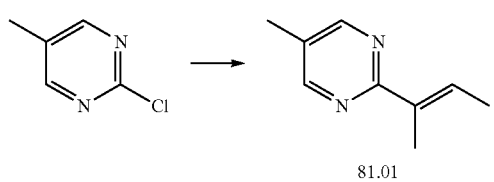

(E)-2-(But-2-en-2-yl)-5-methylpyrimidine, Example 81.01

2-Chloro-5-methyl-pyrimidine (18 mL, 151 mmol), potassium (Z)-but-2-en-2-yltrifluoroborate (Sigma Aldrich, 31 g, 191 mmol), tricyclohexylphosphine (8.5 g, 30.2 mmol), and Pd$_2$(dba)$_3$ (13.82 g, 15.09 mmol) were added to a flask, which was then degassed and backfilled with nitrogen. To the flask was added 1,4-dioxane (252 mL) and aqueous potassium phosphate tribasic (37.5 mL, 453 mmol). The resulting reaction was heated at 100° C. for 16 h. The reaction was then cooled to RT. The residue was filtered through a plug of silica gel, and was then loaded onto silica gel and purified (0-20% EtOAc in heptanes) to afford (E)-2-(but-2-en-2-yl)-5-methylpyrimidine 81.1 (19 g, 125 mmol, 83% yield).

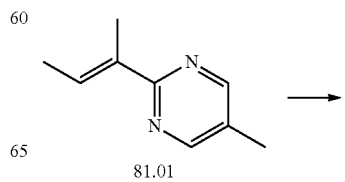

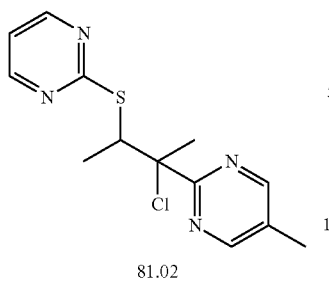

81.02

2-(2-Chloro-3-(pyrimidin-2-ylthio)butan-2-yl)-5-methylpyrimidine, Example 81.02

To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at RT. To the cloudy reaction mixture was added (E)-2-(but-2-en-2-yl)-5-methylpyrimidine 81.01 (20 g, 132 mmol) dropwise and the mixture was further stirred for 2 h. The reaction mixture was then concentrated in vacuo. Aqueous sodium bicarbonate was added to the mixture to neutralize the reaction mixture. The reaction was then extracted with EtOAc and concentrated in vacuo. The residue was purified on silica gel with 0-25% EtOAc in hexanes to give the desired product 2-(2-chloro-3-(pyrimidin-2-ylthio)butan-2-yl)-5-methylpyrimidine 81.02 (30 g, 76% yield).

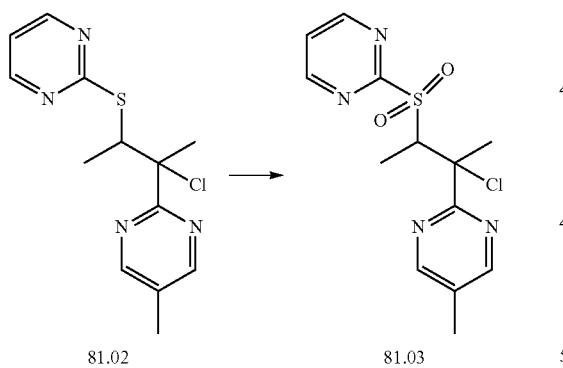

81.02    81.03

2-(2-Chloro-3-(pyrimidin-2-ylsulfonyl)butan-2-yl)-5-methylpyrimidine, Example 81.03

To a solution of 2-(2-chloro-3-(pyrimidin-2-ylthio)butan-2-yl)-5-methylpyrimidine 81.02 (30 g, 100 mmol) in DCM (201 mL) was added meta-chloroperoxybenzoic acid (45.0 g, 201 mmol). The reaction was stirred at RT for 1 d. The reaction was concentrated in vacuo and aqueous sodium bicarbonate and sodium thiosulfate were added. The mixture was extracted with EtOAc and concentrated in vacuo to give the desired product 2-(2-chloro-3-(pyrimidin-2-ylsulfonyl) butan-2-yl)-5-methylpyrimidine 81.03 (33.2 g, 100 mmol, 100% yield).

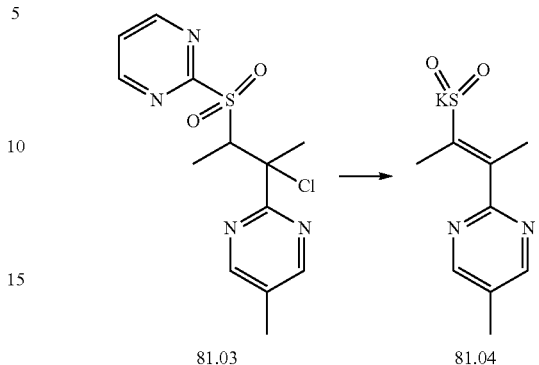

81.03    81.04

Potassium (E)-3-(5-methylpyrimidin-2-yl)but-2-ene-2-sulfinate, Example 81.04

To a solution of 2-(2-chloro-3-(pyrimidin-2-ylsulfonyl) butan-2-yl)-5-methylpyrimidine 81.03 (33 g, 100 mmol) in MeOH (249 mL) was added potassium carbonate (27.6 g, 200 mmol). The reaction was stirred at RT for 16 h. The reaction was then concentrated in vacuo to give the desired product potassium (E)-3-(5-methylpyrimidin-2-yl)but-2-ene-2-sulfinate 81.04 (21.57 g, 100% yield), that was used without further purification.

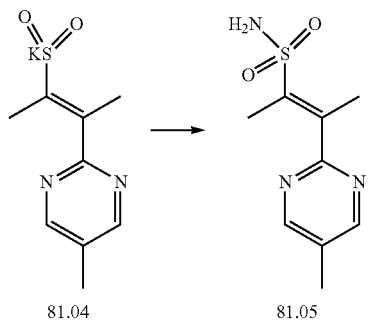

81.04    81.05

(E)-3-(5-Methylpyrimidin-2-yl)but-2-ene-2-sulfonamide, Example 81.05

To a solution of potassium (E)-3-(5-methylpyrimidin-2-yl)but-2-ene-2-sulfinate (Example 81.04, 21.57 g, 85 mmol) in water (424 mL, 85 mmol) was added potassium acetate (5.30 mL, 85 mmol), followed by amidoperoxymonosulfuric acid (19.18 g, 170 mmol). The reaction was stirred at RT for 24 h. The reaction was then extracted with EtOAc and concentrated in vacuo. The product thus obtained was purified on silica gel eluting with 0-50% EtOAc in hexanes to give the desired product (E)-3-(5-methylpyrimidin-2-yl)but-2-ene-2-sulfonamide 81.05 (12 g, 61.2% yield).

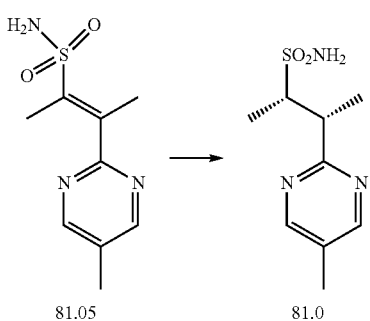

(2S,3R)-3-(5-Methylpyrimidin-2-yl)butane-2-sulfonamide, Example 81.0

A 900 mL pressure reactor was charged under nitrogen flow with (E)-3-(5-methylpyrimidin-2-yl)but-2-ene-2-sulfonamide, Example 81.05 (40.00 g, 0.1760 mol, 1 equiv), zinc trifluoromethane sulfonate (12.79 g, 0.0352 mol, 0.2 equiv, Aldrich), bis(1,5-cyclooctadiene)rhodium(I) tetrafluoroborate (1.43 g, 0.00352 mol, 0.02 equiv, Strem Chemicals, Inc.), and (S)-1-[(R)-2-(di-1-naphtyhlphosphino)ferrocenyl]-ethyl-di-tert.-butylphosphine (2.60 g, 0.00405 mol, 0.023 equiv, Solvias) and MeOH (520 mL). The mixture was purged with nitrogen and then with hydrogen and the media was stirred under 3-4 bars of hydrogen for 20 h. The reaction was monitored by HPLC and showed a complete conversion. The reactor was then purged with nitrogen and the resulting suspension was concentrated at 35° C. under industrial vacuum to give the initial product as an orange solid. The product thus obtained was mixed with EtOH (742 mL), and the resulting suspension was stirred at 20-25° C. for 40 min. The solid was filtered, washed with EtOH (2 7×97 mL) and dried at 40° C. under vacuum to give the title compound as a white powder (85.2% yield, 99% ee). $^1$H NMR (400 MHz, DMSO-$d_6$): δ 8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). LCMS (ESI, positive ion) m/z; 230.1 (M+H)$^+$.

The compounds in the following table were synthesized following the procedure in Example 81.0 using the known starting material as described.

TABLE 10

| Example | Reagents | Structure, Name and Data |
|---|---|---|
| 81.1 | 2-chloro-5-fluoro-pyrimidine | (2S,3R)-3-(5-fluoropyrimidin-2-yl)butane-2-sulfonamide. LCMS ESI (pos.) m/z: 234.2 (M +H )$^+$. |
| 81.2 | 2-bromo-5-methylpyrazine. The title compound was the first isomer to elute under the following SFC conditions: Run on Thar 200 SFC with 250×30 mm AD-H column with 20 mL/min MeOH (+ 20mM NH$_3$) + 80 g/min CO$_2$. 20% co-solvent at 100 g/min. Temperature = 29° C., Outlet pressure = 100 bar. Wavelength = 271 mn. Injected 1.0 mL of 550 mg of the enantiomerically enriched product dissolved in 20 mL MeOH:DCM. 15:5; c = 27.5 mg/mL and 27.5 mg per injection. Cycle time 5.0 min, run time 13 min. | (2S,3R)-3-(5-methylpyrazin-2-yl)butane-2-sulfonamide. $^1$H NMR (400 MHz. DMSO-$d_6$) δ 8.46 (d, J = 6.5 Hz, 2H), 6.84 (s, 2H). 3.63 (qd, J = 7.0, 4.3 Hz, 1H). 3.44 (qd, J = 7.0, 4.3 Hz, 1H), 2.47 (s, 3H), 1.31 (d, J = 7.0 Hz, 3H), 1.23 (d, J = 7.0 Hz, 3H). LCMS (ESI, pos.) m/z; 230.0 (M + H)$^+$. |

TABLE 10-continued

| Example | Reagents | Structure, Name and Data |
|---|---|---|
| 81.3 | 2-bromo-5-methylpyrazine. The title compound is the enantiomer of Example 81.2. Example 81.2 is the second isomer to elute from AD-H column on subjecting the enantiomerically enriched product to the SFC conditions described in Example 81.2. | 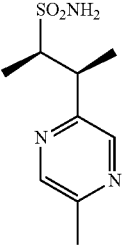<br>(2R,3S)-3-(5-methylpyrazin-2-yl)butane-2-sulfonamide.<br>LCMS-ESI (pos.) m/z: 230.0 (M + H)⁺. |
| 81.4 | 2-chloro-5-chloro-pyrimidine. Recrystallization: Example 81.4 (38 g, 90% ee) was dissolved in IPA (400 mL) at 70° C. | 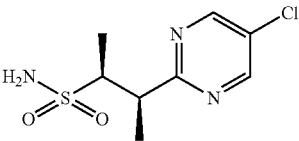<br>(2S,3R)-3-(5-chloropyrimidin-2-yl)butane-2-sulfonamide.<br>¹H NMR (400 MHz, DMSO-d₆) δ 8.93-8.85 (m, 2H), 6.86 (d, J = 4.0 Hz, 2H), 3.73-3.59 (m, 2H). 1.31 (dt, J = 7.3, 2.4 Hz, 3H), 1.25-1.19 (m, 3H). LCMS (ESI pos.) m/z: 250.2 (M + H)⁺. |
| 81.5 | 2-bromo-5-methoxypyrazine | 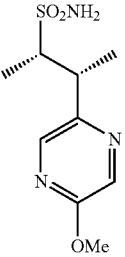<br>(2S,3R)-3-(5-methoxypyrazin-2-yl)butane-2-sulfonamide.<br>¹H NMR (400 MHz. DMSO-d₆) δ 8.26 (d, J = 1.4 Hz, 1H), 8.12 (d, J = 1.4 Hz, 1H), 6.84 (s, 2H), 3.90 (d, J = 1.5 Hz, 3H), 3.62 (dd, J = 7.1, 4.3 Hz, 1H), 3.42-3.38 (m, 1H), 1.32 (d, J = 1.5 Hz, 3H), 1.23-1.21 (m, 3H). LCMS (ESI pos.) m/z: 246.2 (M + H)⁺. |

Example 82.0. Preparation of 2-isothiocyanato-1,3-dimethoxybenzene

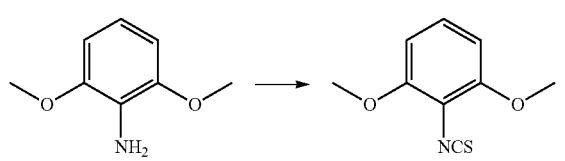

2-Isothiocyanato-1,3-dimethoxybenzene, Example 82.0, Example 82.0

To a solution of 2,6-dimethoxyaniline (500 g, 3.25 mol, 1 eq) in DCM (5.0 L) was added 2,6-lutidine (1.5 L, 13.0 mol, 4 eq). The reaction mixture was cooled to 0° C. (internal temperature) and CSCl₂ (374 mL, 4.88 mol, 1.5 eq) was added dropwise. The reaction mixture was then stirred for 2 h. The solvent was evaporated under reduced pressure and the material thus obtained was purified by SiO₂ column to provide the title compound, 2-isothiocyanato-1,3-dimethoxybenzene, Example 82.0 as a white solid (1.06 g, 2.80 mol, 86%). LCMS (ESI pos. ion) m/z: (M+H)⁺=196. ¹H NMR (400 MHz, CDCl₃) δ 7.16 (t, J=8.48 Hz, 1H), 6.55 (d, J=8.48 Hz, 2H), 3.90 (m, 6H).

The compounds set forth in the following table were synthesized following the procedure in Example 82.0 using the known starting material as described.

TABLE 11

| Example | Reagents | Structure, Name and Data |
|---|---|---|
| 82.1 | 4,6-dimethoxypyrimidin-5-amine (commercially available from D-L Chiral chemicals). | 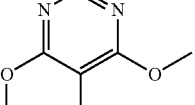 5-isothiocyanato-4,6-dimethoxypyrimidine, LCMS-ESI (pos.) m/z: 198.1 (M + H)+. |
| 82.2 |  |  1-isothiocyanato-2-methoxybenzene. $^1$H NMR (400 MHz. DMSO-$d_6$) δ 3.89 (s, 3H), 6.96 (td, J = 7.68, 1.27 Hz, 1H), 7.16 (dd, J = 8.31, 1.27 Hz, 1H), 7.30 (dd, J = 7.92, 1.66 Hz, 1H). 7.31-7.37 (m, 1H). |
| 82.3 | 3,5-difluoropyridin-4-amine (commercially available from Ark Phann Inc. Libertyville, IL). | 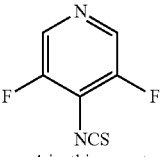 3,5-difluoro-4-isothiocyanatopyridine. LCMS-ESI (pos.) m/z: 173.0 (M + H)+. |

Example 83.0: Preparation of (1R,2S)-1-methoxy-1-(5-methylpyrimidin-2-yl)propane-2-sulfonamide

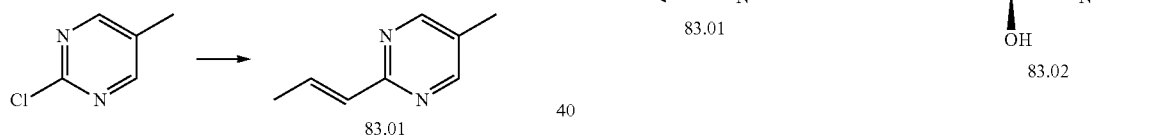

(E)-5-Methyl-2-(prop-1-en-1-yl)pyrimidine, Example 83.01

To a 500 mL round bottomed flask was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with N$_2$ (5×) and then 1,4-dioxane (200 mL) and water (20 mL) were added. The resulting yellow suspension was bubbled with Ar for 15 min and then 1,1-bis[(di-t-butyl-p-methylaminophenyl]palladium(II) chloride (Amphos, commercially available from Strem, 2.64 g, 3.73 mmol) was added, a reflux condenser was attached, and the reaction was warmed to 90° C. in an oil bath and stirred under N$_2$ for 16.5 h. The reaction was then cooled to RT. The reaction was diluted with water (250 mL) and extracted with EtOAc (2×250 mL). The organic layers were combined, dried (MgSO$_4$), and concentrated. The residue was purified by flash chromatography on silica gel eluting with 0-20% EtOAc/hexanes) to afford (E)-5-methyl-2-(prop-1-en-1-yl)pyrimidine 83.01 (12.96 g, 97 mmol, 100% yield) as a yellow/orange oily solid. $^1$H NMR (300 MHz, CDCl$_3$) δ 8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). LCMS (ESI pos.) m/z: 135.2 (M+H)+.

(1R,2R)-1-(5-Methylpyrimidin-2-yl)propane-1,2-diol, Example 83.02

Racemic conditions. To a solution of (E)-5-methyl-2-(prop-1-en-1-yl)pyrimidine, 83.01 (5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.111 mmol). The resulting reaction mixture was stirred at RT under N$_2$ for 21.5 h. LCMS showed complete conversion to a product corresponding to the mass of the desired product (M+H)+=169. The reaction was then passed through a Varian Chem-Elut cartridge to remove water and concentrated in vacuo. Water was still present, the residue was dissolved in DCM, dried (MgSO$_4$), and concentrated. The residue was purified by flash chromatography (120 g SiO$_2$, 0-10% MeOH/DCM) to give the racemic syn-diol (1S,2S)-1-(5-methylpyrimidin-2-yl)propane-1,2-diol and (2R,2R)-1-(5-methylpyrimidin-2-yl)propane-1,2-diol (5.85 g, 34.8 mmol, 81% yield) as a light yellow solid. $^1$H NMR (300 MHz, CDCl$_3$) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). LCMS (ESI pos.) m/z: 169.2 (M+H). Chiral conditions. A batch of AD-mix-beta was prepared from: (26 mg, 0.07 mmol) K$_2$OsO$_2$(OH)$_4$; (16.4 g, 49.9 mmol) K$_3$Fe(CN)$_6$; (6.89 g, 49.9 mmol) K$_2$CO$_3$; (125 mg, 0.16 mmol) (DHQD)

₂PHAL. In a 50 mL round bottom flask was added t-BuOH (5 mL), water (5.00 mL), and 1.4 g of AD-mix-beta (prepared above) and methanesulfonamide (95 mg, 1.00 mmol). The mixture was stirred at RT until clear, and was then cooled to 0° C. (E)-5-methyl-2-(prop-1-en-1-yl)pyrimidine (intermediate 11.1 168 mg, 1 mmol) in t-BuOH (1 mL) was added and the slurry was stirred at 0° C. for 2 h. LCMS (1.5 h) shows ~10% conversion. The reaction was then allowed to warm slowly to RT as the ice bath melted and stirred an additional 22 h. LCMS showed ~90% conversion. The reaction was quenched with saturated aqueous sodium sulfite (10 mL), and extracted with EtOAc (2×20 mL). The combined organic layers were washed with 2 N NaOH (10 mL), dried (MgSO₄), and concentrated. The aqueous layer was extracted with DCM (2×50 mL), EtOAc (2×50 mL), and 10% IPA in CHCl₃ (2×50 mL). The combined organic layers were concentrated and the residue purified by flash column chromatography (12 g SiO₂, 5-100% 3:1 EtOAc:EtOH/heptane) to give (1R,2R)-1-(5-methylpyrimidin-2-yl)propane-1,2-diol (Example 83.02, 88.6 mg, 0.527 mmol, 52.7% yield) as a clear, colorless oil. Chiral Analysis: SFC Chiral Analysis shows the % ee to be 94.8% using an AS-H (100×2.1 mm, 3 um), 10% organic modifier (IPA with 20 mM ammonia), 90% carbon dioxide. F=1.0 mL/min, column temperature=RT, BRP=105 bar.

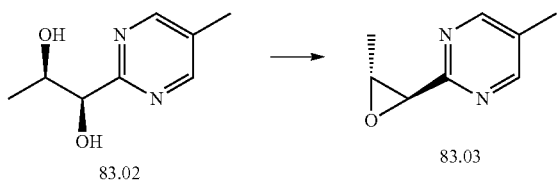

5-Methyl-2-((2R,3R)-3-methyloxiran-2-yl)pyrimidine, Example 83.03

To a solution of syn-diol (1R,2R)-1-(5-methylpyrimidin-2-yl)propane-1,2-diol 11.2 (1.46 g, 8.68 mmol) in DCM (25 mL) (cooled with a RT water bath) was added 1,1,1-trimethoxyethane (2.50 mL, 2.29 mmol). Chlorotrimethylsilane (2.50 mL, 19.7 mmol) was then added in 2 portions 5 min apart. The reaction had a small exotherm on the first portion of addition of TMSCl (23-28° C.). The reaction was stirred at RT under N₂ 23 h. LCMS indicated incomplete conversion. Thus, an additional 1.25 equiv. of 1,1,1-trimethoxyethane (1.25 mL, 9.95 mmol) and chlorotrimethylsilane (1.25 mL, 9.85 mmol) were added and the reaction was stirred for an additional 24 h. LCMS; ((M+H)⁺=229). The reaction was then concentrated in vacuo. The residue was dissolved in MeOH (20 mL) and potassium carbonate (1.50 g, 10.85 mmol) was added, and the reaction was stirred at RT for 4 h. LCMS (4 h) showed complete conversion to product corresponding to the desired epoxide LCMS; ((M+H)⁺=151). The reaction was filtered, the filter cake washed with DCM (5 mL), and the combined filtrates concentrated in vacuo. The residue was purified by flash column chromatography on silica gel eluting with 0-100% EtOAc/hexanes to afford 5-methyl-2-((2R,3R)-3-methyloxiran-2-yl)pyrimidine 83.03 (1.00 g, 6.6 mmol, 77%) as a clear, light yellow oil. ¹H NMR (300 MHz, CDCl₃) δ 8.54 (s, 2H), 3.81 (d, J=1.9 Hz, 1H), 3.32-3.53 (m, 1H), 2.31 (s, 3H), 1.50 (d, J=5.1 Hz, 3H). LCMS (ESI pos.) m/z: 151.2 (M+H)⁺.

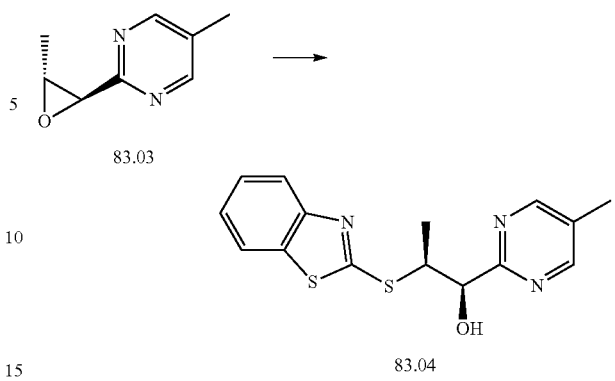

(1R,2S)-2-(Benzo[d]thiazol-2-ylthio)-1-(5-methylpyrimidin-2-yl)propan-1-ol, Example 83.04

To a solution of 5-methyl-2-((2R,3R)-3-methyloxiran-2-yl)pyrimidine 83.03 (250 mg, 1.33 mmol) in DCM (5 mL) was added benzo[d]thiazole-2-thiol (245 mg, 1.465 mmol), followed by tris(((trifluoromethyl)sulfonyl)oxy)ytterbium (83 mg, 0.133 mmol). The suspension was heated in a 35° C. heating block for 17 h and showed 100% conversion to the desired product. The reaction was cooled to RT, loaded on a plug of silica, and purified by flash chromatography (12 g SiO₂, 5-100% 3:1 EtOAc:EtOH/heptane) to afford (1R,2S)-2-(benzo[d]thiazol-2-ylthio)-1-(5-methylpyrimidin-2-yl)propan-1-ol 83.04 (428 mg, 1.35 mmol, 100% yield) as a clear colorless oil. ¹H NMR (300 MHz, CDCl₃) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). LCMS (ESI pos.) m/z: 318.2 (M+H)⁺.

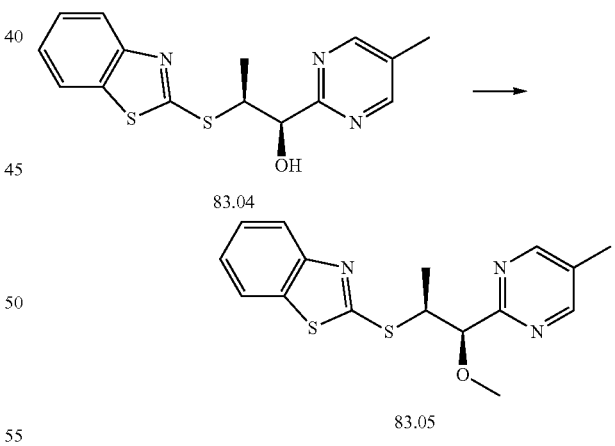

2-(((1R,2S)-1-Methoxy-1-(5-methylpyrimidin-2-yl)propan-2-yl)thio)benzo[d]thiazole, Example 83.05

To a 50 mL flask equipped with a magnetic stirrer was charged (1R,2S)-2-(benzo[d]thiazol-2-ylthio)-1-(5-methylpyrimidin-2-yl)propan-1-ol 83.04 (350 mg, 1.103 mmol) in 2-methyltetrahydrofuran (1.1 mL). The reaction mixture was cooled to −78° C. and potassium bis(trimethylsilyl)amide (1M solution in THF, 1.32 μL, 1.32 mmol)) was added dropwise (total addition time was 2 min). The resulting mixture was stirred for 1 h and then methyl trifluoromethanesulfonate (374 µL, 3.31 mmol) was added dropwise. The reaction mixture was then stirred at −78° C. for 15 min. LCMS showed complete conversion to the product. The reaction mixture was quenched by saturated aqueous NH₄Cl solution (30 mL) at −78° C. The reaction was allowed to warm to RT and the aqueous layer was back extracted with EtOAc (3×75 mL). The combined organic layers were washed with brine, dried (Na₂SO₄), and concentrated. The material thus obtained was purified by chromatography through a Biotage 50 g ultra silica gel column, eluting with a gradient of 0-25% EtOAc in hexanes, to provide 2-(((1R,2S))-1-methoxy-1-(5-methylpyrimidin-2-yl)propan-2-yl)thio)benzo[d]thiazole 83.05 (0.32 g, 75% for two runs) as a light-yellow oil.

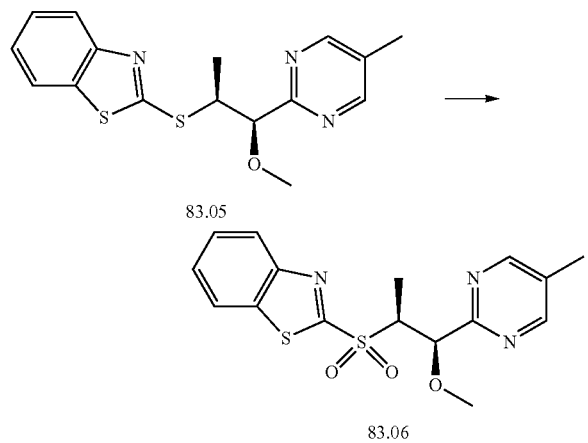

83.05

2-(((1R,2S)-1-Methoxy-1-(5-methylpyrimidin-2-yl) propan-2-yl)sulfonyl)benzo[d]thiazole, Example, Example 83.06

A solution of 2-(((1R,2S)-1-methoxy-1-(5-methylpyrimidin-2-yl)propan-2-yl)thio)benzo[d]thiazole 83.05 (313 mg, 0.94 mmol) in DCM (2.8 mL) at 0° C. was treated with 3-chloroperoxybenzoic acid, 77% max. (476 mg, 2.13 mmol). The reaction was stirred at 0° C. for 1 h before the ice bath was removed. LCMS showed desired product, sulfoxide, and the presumed sulfoxide/sulfone. The mixture was allowed to warm to ambient temperature and stirred for an additional 40 h. The reaction was then quenched with saturated aqueous sodium bisulfite (6 mL) and saturated aqueous sodium bicarbonate (5 mL). The mixture was then stirred for 10 min. The reaction was extracted with EtOAc (2×20 mL) and the organic layers were combined, washed with saturated aqueous NaHCO₃ (10 mL), brine (10 mL), dried (MgSO₄) and filtered. Iodide/starch strip indicator showed no peroxide was present. The filtrates were concentrated to give a clear, colorless oil (360 mg). Purification of the residue by flash chromatography (40 g SiO₂, 0-100% 3:1 EtOAc:EtOH/heptane) gave 2-(((1R,2S)-1-methoxy-1-(5-methylpyrimidin-2-yl)propan-2-yl)sulfonyl)benzo[d]thiazole 11.6 (285 mg, 0.78 mmol, 83% yield, 77% purity) as a white foam. ¹H NMR (300 MHz, CDCl₃) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). LCMS (ESI pos.) m/z: 364.0 (M+H).

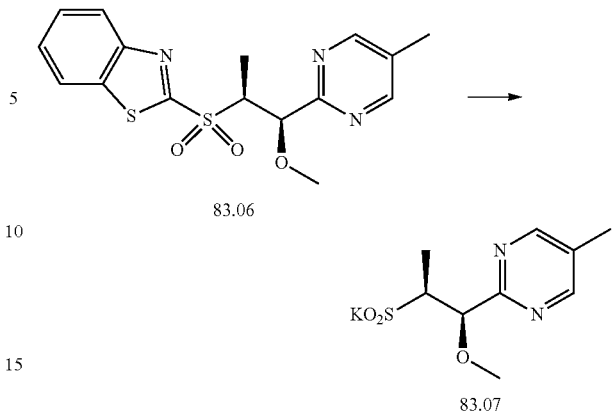

Potassium (1R,2S)-1-methoxy-1-(5-methylpyrimidin-2-yl)propane-2-sulfinate, Example 83.07

To a solution of 2-(((1R,2S)-1-methoxy-1-(5-methylpyrimidin-2-yl)propan-2-yl)sulfonyl)benzo[d]thiazole 83.06 (268 mg, 0.74 mmol) in MeOH (1843 µL) was added potassium carbonate (204 mg, 1.48 mmol). The reaction was stirred at RT for 17 h. LCMS showed desired product formation as the sulfinic acid 83.07. LCMS ((M+H)⁺= 231.1). The reaction was concentrated in vacuo (yellow solid) and used directly in the following step. Note: Epimerization occurred in this reaction (~15%).

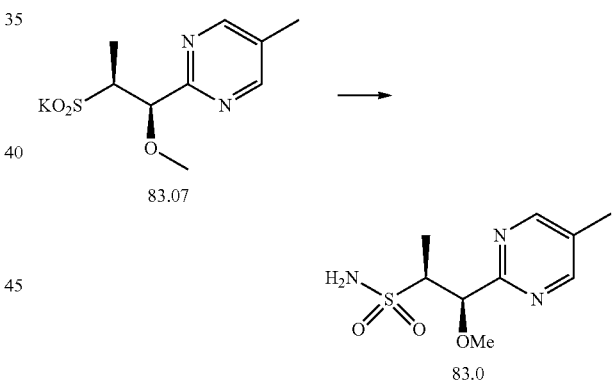

(1R,2S)-1-Methoxy-1-(5-methylpyrimidin-2-yl)propane-2-sulfonamide, Example 83.0

To a suspension of potassium (1R,2S)-1-methoxy-1-(5-methylpyrimidin-2-yl)propane-2-sulfinate (Example 83.07, 198 mg, 0.74 mmol) in water (3.7 mL) was added potassium acetate (72.4 mg, 0.74 mmol), followed by hydroxylamine-o-sulfonic acid, 97% (167 mg, 1.476 mmol). The reaction mixture was stirred at RT for 4.5 h. LCMS showed desired product formation plus a small peak that corresponded to the stereoisomer. The reaction mixture was extracted with EtOAc (2×) and the organic layers were combined, dried (Na₂SO₄), and concentrated in vacuo. The residue was loaded onto a silica gel column eluting with 0-30% (3:1 EtOAc:EtOH)/DCM to afford (1R,2S)-1-methoxy-1-(5- methylpyrimidin-2-yl)propane-2-sulfonamide 83.0 (114 mg, 0.465 mmol, 63.0% yield) as a white solid. (contained ~15% other diastereomer, which could be removed by recrystallization). $^1$H NMR (300 MHz, CDCl$_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). LCMS (ESI pos.) m/z: 246.1 (M+H)$^+$.

The compounds set forth in the following table were synthesized following the procedure in Example 83.0 using the known starting material as described.

TABLE 12

| Example | Reagents | Structure, Name and Data |
|---|---|---|
| 83.1 | 2-bromo-5-methylpyrazine (commercially available from NOWA pharmaceuticals). | 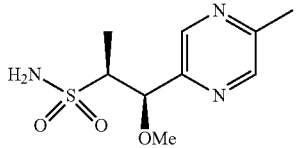 [SMILES: CO[C@H](c1cnc(C)cn1)[C@H](C)S(N)(=O)=O]<br>(1R,2S)-1-methoxy-1-(5-methylpyrazin-2-yl)propane-2-sulfonamide.<br>LCMS-ESI (pos.) m/z: 246.2 (M + H)$^+$. |
| 83.2 | 2-chloro-5-fluoropyrimidine (commercially available from Oakwood). | 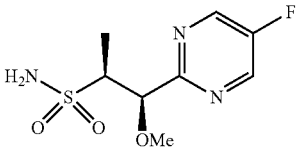 [SMILES: CO[C@H](c1ncc(F)cn1)[C@H](C)S(N)(=O)=O]<br>(1R,2S)-1-(5-chloropyrimidin-2-yl)-1-methoxypropane-2-sulfonamide.<br>LCMS-ESI (pos.) m/z: 250.1 (M + H)$^+$. |
| 83.3 | 2,5-dichloropyrimidine (commercially available from Oakwood). | 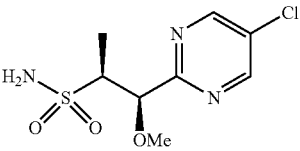 [SMILES: CO[C@H](c1ncc(Cl)cn1)[C@H](C)S(N)(=O)=O]<br>(1R,2S)-1-(5-chloropyrimidin-2-yl)-1-methoxypropane-2-sulfonamide.<br>LCMS-ESI (pos.) m/z: 265.9 (M + H)$^+$. |
| 83.4 | 2-chloropyrimidine (commercially available from Acros Organics). | 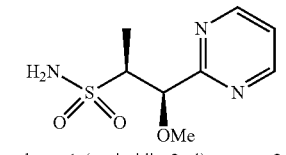<br>(1R,2S)-1-methoxy-1-(pyrimidin-2-yl)propane-2-sulfonamide.<br>LCMS-ESI (pos.) m/z: 232.0 (M + H)$^+$. |
| 83.5 | 2-chloro-5-fluoropyrimidine (commercially available from Oakwood). EtOTf used in place of MeOTf in Example 83.5. | 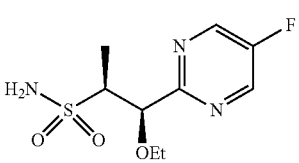 [SMILES: CCO[C@H](c1ncc(F)cn1)[C@H](C)S(N)(=O)=O]<br>(1R,2S)-1-ethoxy-1-(5-fluoropyrimidin-2-yl)propane-2-sulfonamide.<br>LCMS-ESI (pos.) m/z: 264.0 (M + H)$^+$. |
| 83.6 | 2-chloro-5-fluoropyrimidine (commercially available from Oakwood). TBSOTf used in place of MeOTf in Example 83.5. | 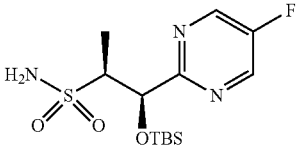 [SMILES: C[C@@H]([C@H](O[Si](C)(C)C(C)(C)C)c1ncc(F)cn1)S(N)(=O)=O]<br>(1R,2S)-1-((tert-butyldimethylsilyl)oxy)-1-(5-fluoropyrimidin-2-yl)propane-2-sulfonamide.<br>LCMS-ESI (pos.) m/z: 350.1 (M + H)$^+$. |

TABLE 12-continued

| Example | Reagents | Structure, Name and Data |
|---|---|---|
| 83.7 | 2,5-dichloropyrimidine (commercially available from Oakwood). EtOTf used in place of MeOTf in Example 83.05. | 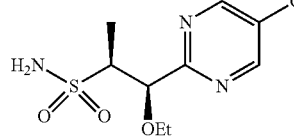<br>(1R,2S)-1-(5-chloropyrimidin-2-yl)-1-ethoxypropane-2-sulfonamide.<br>LCMS-ESI (pos.) m/z: 279.9. |

Example 83.8: Preparation of Example (1R,2S)-1-methoxy-1-(5-methoxypyrimidin-2-yl)propane-2-sulfonamide

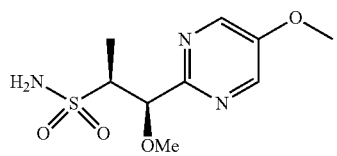

83.8

(1R,2S)-1-Methoxy-1-(5-methoxypyrimidin-2-yl)propane-2-sulfonamide, Example 83.8

This compound was obtained as a by-product of the synthesis of (1R,2S)-1-methoxy-1-(5-fluoropyrimidin-2-yl)propane-2-sulfonamide (Example 83.2) during step 83.07 and isolated in the final step of the synthesis of Example 83.2 to give the title compound 83.8 (240 mg, 10.2% yield) as a white solid. $^1$H NMR (CDCl$_3$) δ: 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (pos.) m/z: 284.1 (M+Na)$^+$.

Example 84.0: Preparation of N,N-bis(4-methoxybenzyl)ethanesulfonamide

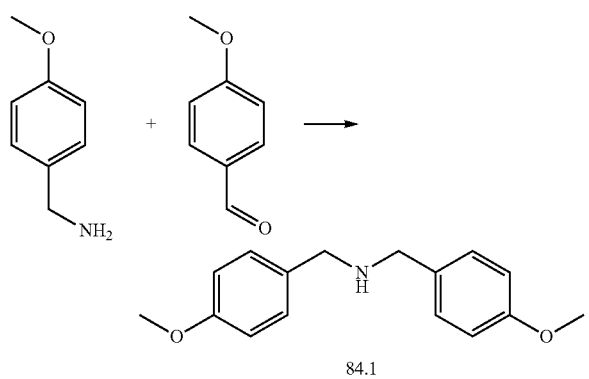

Bis(4-methoxybenzyl)amine, Example 84.1

4-Methoxybenzylamine (neat, 600 g, 4.37 mol, 1 eq) and 4-methoxybenzaldehyde (532 mL, 4.37 mol, 1 eq) were added to a 10 L round bottomed flask at ambient temperature with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portionwise over ~2 h (Note: During the addition of NaBH$_4$, the internal temperature of the reaction rose up to 42° C.). The resulting mixture was then stirred at ambient temperature overnight. The reaction was quenched slowly with water (600 mL). The mixture was then concentrated on a rotary evaporator at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give bis(4-methoxybenzyl)amine 84.1 (1112 g, 99% yield) as a semi-solid. The material was used directly in the next step without further purification. $^1$H-NMR (400 MHz, CDCl$_3$) δ 7.28 (t, J=7.12 Hz, 4H), 6.89 (d, J=8.60 Hz, 4H), 3.83 (m, 6H), 3.76 (s, 4H) (—NH proton not observed). LCMS (ESI pos.) m/z: 258.4 (M+H)$^+$.

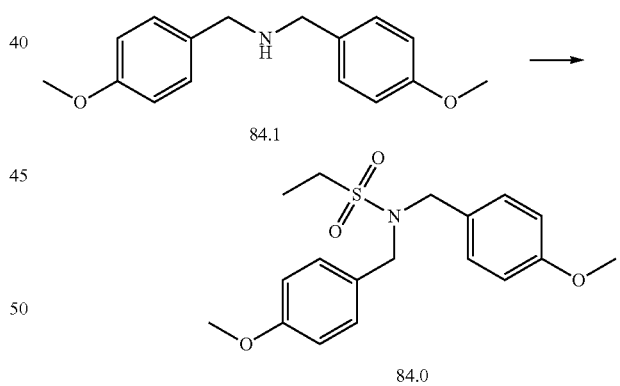

N,N-Bis(4-methoxybenzyl)ethanesulfonamide, Example 84.0

To a solution of bis(4-methoxybenzyl)amine 84.1 (900 g, 3.49 mol, 1 eq) in DCM (9 L) was added TEA (634 mL, 4.55 mol, 1.3 eq) followed by dropwise addition of ethanesulfonyl chloride (399 mL, 4.19 mol, 1.2 eq). The internal temperature was kept between 5-10° C. during the addition of the ethane sulfonyl chloride. Once addition was complete, the cooling bath was removed. After 1.5 h, TLC showed complete loss of starting material. The reaction was quenched by addition of water (4 L) to the reaction mixture.

The layers were separated and the aqueous layer was extracted with DCM (2×2 L). The combined organic layers were washed with brine (2×1 L), dried over $Na_2SO_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound 84.0 (1125 g, 3.22 mol, 92%) as a white solid. $^1$H-NMR (400 MHz, $CDCl_3$) δ 7.23 (dd, J=2.08, 6.62 Hz, 4H), 6.90 (dd, J=2.12, 6.60 Hz, 4H), 4.29 (s, 4H), 3.83 (m, 6H), 2.92 (q, J=7.40 Hz, 2H), 1.33 (t, J=7.40 Hz, 3H). GC-LCMS (ESI pos.) m/z: =372.2 (M+Na)$^+$.

Example 85.0: Preparation of (1S,2S)-1-isopropoxy-1-(5-methylpyrimidin-2-yl)propane-2-sulfonamide

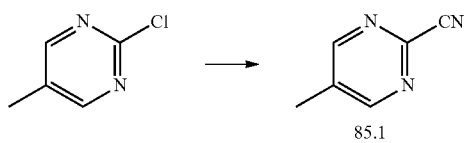

85.1

5-Methylpyrimidine-2-carbonitrile, Example 85.1

A solution of 2-chloro-5-methylpyrimidine (500 g, 3889 mmol, 1.0 equiv) in DMF (5000 mL) was degassed with $N_2$ for 20 min and dppf (108 g, 194 mmol, 0.05 equiv) and $Pd_2(dba)_3$ (178 g, 194 mmol, 0.05 equiv) were added to the reaction mixture. $Zn(CN)_2$ (685 g, 5834 mmol, 1.5 equiv) was then added, and the reaction mixture was heated at 100° C. for 16 h. The reaction was quenched with water (5000 mL) and stirred for 10 min. The reaction mixture was then filtered through Celite® brand filter agent pad. The filtrate was diluted with water (4000 mL) and extracted with EtOAc (2×4000 mL). The combined organic layers were washed with brine (4000 mL), dried over $Na_2SO_4$, filtered and concentrated under reduced pressure to give the initial product which was further purified by column chromatography using silica gel (60-120 mesh) and 0-10% EtOAc in hexane to obtain Example 85.1 (330 g, 71%) as an off white solid. $^1$H NMR (400 MHz, DMSO-$d_6$) δ 8.89 (s, 2H), 2.39 (s, 3H).

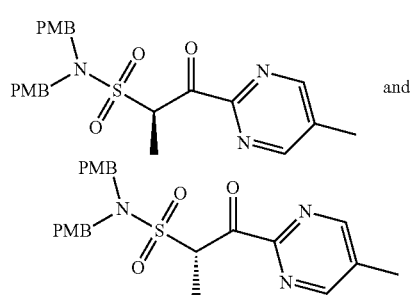

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 85.2

To a solution of Example 84.0 (293 g, 839 mmol, 2.0 equiv) in THF (2000 mL) was added isopropylmagnesium chloride (420 mL, 839 mmol, 2.0 equiv, 2.0 M in diethyl ether) at 0° C. The resulting reaction mixture was stirred at 25° C. for 3 h. To that reaction mixture was added 5-methylpyrimidine-2-carbonitrile (50 g, 420 mmol, 1.0 equiv) in THF (100 mL) at 0° C., and the resulting mixture was stirred at RT for 2 h. The reaction was then quenched with 1.5 N HCl (500 mL) and water (2000 mL) and stirred for 10 min. The mixture was extracted with EtOAc (2×1000 mL) and the combined organic layers were washed with brine (500 mL), dried over $Na_2SO_4$ and filtered. The organic layer was concentrated under reduced pressure to give the initial compound which was purified by column chromatography using silica gel (100-200 mesh) and 0-50% EtOAc in hexanes as eluent to obtain Example 85.2 (60 g, 30% yield) as brown liquid. $^1$H NMR (400 MHz, DMSO-$d_6$) δ 8.90 (s, 2H), 7.15-7.09 (m, 4H), 6.85-6.80 (m, 4H), 4.34-4.18 (m, 5H), 3.71 (m, 6H), 2.39 (s, 3H), 1.50 (d, J=6.9 Hz, 3H). LCMS (ESI pos.) m/z: (M+H)$^+$: 470.0.

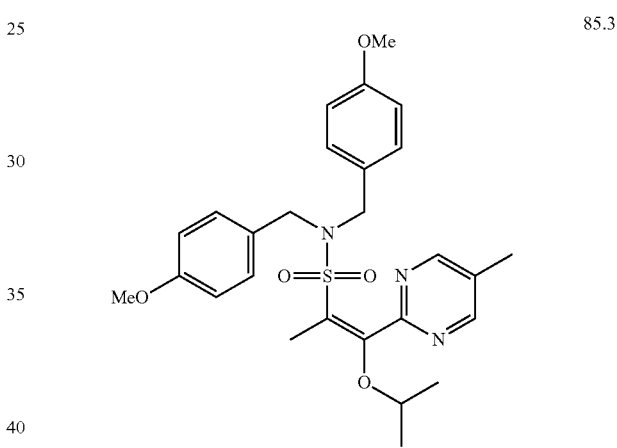

(E)-1-Isopropoxy-N,N-bis(4-methoxybenzyl)-1-(5-methylpyrimidin-2-yl)prop-1-ene-2-sulfonamide, Example 85.3

To a solution of Example 85.2 (120 g, 256 mmol, 1.0 equiv) in DMF (1200 mL) was added 2-iodopropane (129 mL, 1278 mmol, 5.0 equiv) and potassium carbonate (70.6 g, 511 mmol, 2.0 equiv). The reaction mixture was stirred at 60° C. for 14 h. The reaction was then quenched with water (1 L), stirred for 10 min, and extracted with EtOAc (2×1000 mL). The combined organic layers were washed with brine (1000 mL), dried over $Na_2SO_4$, filtered and concentrated under reduced pressure to give the initial material. The product thus obtained was purified by column chromatography using silica gel (100-200 mesh) and 0-50% EtOAc in hexane as eluent to obtain Example 85.3 (75 g, 57.4% yield) as off white solid. $^1$H NMR (400 MHz, DMSO-$d_6$) δ 8.72 (s, 2H), 7.09 (d, J=8.3 Hz, 4H), 6.86 (d, J=8.3 Hz, 4H), 4.16 (s, 4H), 3.73 (s, 3H), 3.73 (s, 3H), 3.71-3.67 (m, 1H), 2.31 (s, 3H), 1.87 (s, 3H), 1.19-1.16 (m, 6H). LCMS (ESI pos.) m/z: (M+H)$^+$: 512.1.

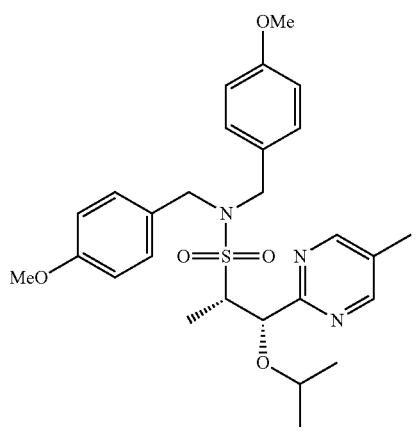

(1S,2S)-1-Isopropoxy-N,N-bis(4-methoxybenzyl)-1-(5-methylpyrimidin-2-yl)propane-2-sulfonamide, Example 85.4

To a solution of Example 85.3 (180 g, 352 mmol, 1.0 equiv) in MeOH (1800 mL) was added zinc triflate (256 g, 704 mmol, 2.0 equiv) and (S)—RuCl[(p-cymene(BINAP)]Cl (6.54 g, 7.04 mmol, 0.02 equiv). The resulting mixture was then heated at 60° C. under $H_2$ pressure (60 psi) for 16 h. The reaction mixture was concentrated under reduced pressure to obtain the initial product which was further purified by column chromatography using silica gel (60-120 mesh) and 0-50% EtOAc in DCM as eluent to obtain Example 85.4 (140 g, 77%, 92% ee) as off white solid. $^1$H NMR (400 MHz, DMSO-$d_6$) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (m, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). LCMS (ESI pos.) m/z: (M+H)$^+$: 514.2.

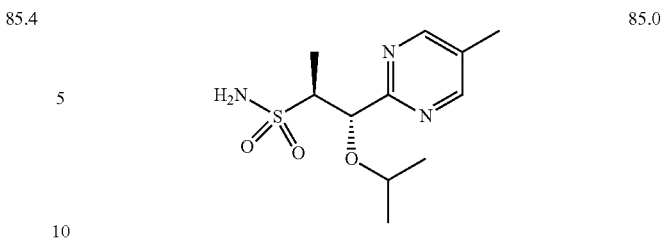

(1S,2S)-1-Isopropoxy-1-(5-methylpyrimidin-2-yl)propane-2-sulfonamide, Example 85.0

To a solution of Example 85.4 (140.0 g, 273 mmol, 1.0 equiv) in DCM (500 mL) was added TFA (250 mL) at 0° C. and the reaction mixture was allowed to stir at RT for 16 h. The reaction mixture was concentrated under reduced pressure to obtain the initial product which was dissolved in DCM (1000 mL) and washed with saturated aqueous NaHCO$_3$ solution (1 L). The organic layer was dried over Na$_2$SO$_4$, filtered and concentrated under reduced pressure to obtain the initial material which was further purified by column chromatography using silica gel (60-120 mesh) and 0-2% MeOH in DCM to obtain Example 85.0 (72 g, 97% yield, 90% ee) as an off white solid. Example 85.0 (72 g, 90% ee) was suspended in IPA (500 mL) and heated to 70° C. until the mixture became homogeneous. Once the solution became homogeneous, the mixture was cooled to RT overnight. The white solid thus obtained was filtered and dried under vacuum to obtain compound-6 (30 g, >99%). The mother liquor was concentrated, and the solid obtained was recrystallized again following the same procedure. $^1$H NMR (400 MHz, DMSO-$d_6$) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). LCMS (ESI pos.) m/z: (M+H)$^+$: 274.1.

The compounds in the following table were synthesized following the procedure in Example 85.0 using the known starting material as described.

TABLE 13

| Example | Reagents | Structure, Name and Data |
|---|---|---|
| 85.1 | 2-chloro-5-chloro-pyrimidine | (1S,2S)-1-(5-chloropyrimidin-2-yl)-1-isopropoxypropane-2-sulfonamide. LMS ESI (pos.) m/z: 234.2 (M + H)$^+$. |

Example 86.0. Preparation of (2S,3R)-3-(5-chloropyridin-2-yl)butane-2-sulfonamide

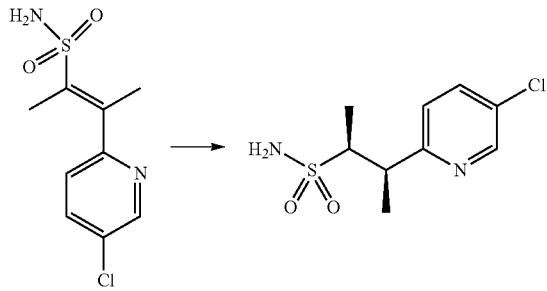

(2S,3R)-3-(5-Chloropyridin-2-yl)butane-2-sulfonamide, Example 86.0

To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1,5-cyclooctadiene)rhodium(I) tetrafluroborate (0.329 g, 0.811 mmol) and (S)-1-[(R)-2-(di-1-naphthylphosphino)ferrocenyl]-ethyl-di-tert-butylphosphine (0.651 g, 1.013 mmol). The reaction mixture was degassed with argon and hydrogen three times and then hydrogen was added (50 Psi). The resulting mixture in a 200 mL Mini-clave, was stirred at RT for 16 h followed by heating at 65° C. for 16 h. TLC indicated completion of reaction, and starting material was completely absent. The reaction mass was concentrated under reduced pressure providing the initial product which was purified by column chromatography (silica gel 60-120 mesh) using 40-45% of EtOAc in petroleum ether as eluent to obtain the desired product (2S,3R)-3-(5-chloropyridin-2-yl)butane-2-sulfonamide (Example 86.0) (9 g, 36.2 mmol, 89%) as a brownish solid in 82% ee. Recrystallization from i-PrOH yielded >97% ee material. 1H NMR (400 MHz, DMSO-d6) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (pos.) m/z: 249.0 (M+H)+.

Example 87.0. Preparation of (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide

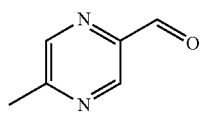

5-Methylpyrazine-2-carbaldehyde, Example 87.1

A solution of LAH (164.0 mL, 0.164 mol, 1.0 M in THF, 0.5 equiv.) was added to a suspension of methyl 5-methylpyrazine-2-carboxylate (50 g, 0.328 mol, 1.0 equiv.) in anhydrous THF (750 mL) at −78° C. (The internal temperature was kept below −72° C. during the addition of LAH). Upon completion of addition, the reaction mixture was left, to stir at −78° C. for further 20 min and then quenched with glacial AcOH (50.0 mL) at the same temperature. The resulting mixture was warmed to RT and the volatiles were removed by evaporation under pressure. The residue was dissolved in 1.5 N hydrochloric acid (500 mL) and extracted with DCM (2×2 L). The extracts were combined, washed with saturated aqueous sodium hydrogen carbonate solution (2×500 mL), (Note: no product observed in HCl or aqueous sodium hydrogen carbonate solution) dried over anhydrous Na2SO4, and concentrated in vacuo, to yield the product as a brown oil. The residue was purified by column chromatography (silica gel 60-120 mesh) eluting with a gradient of 10% EtOAc in petroleum ether to provide the title compound as pale yellow liquid (21.3 g, 53%). TLC Info: (9.0/1.0 Petroleum ether/EtOAc). 1H NMR (400 MHz, CDCl3) δ 10.14 (s, 1H), 9.07 (d, J=1.5 Hz, 1H), 8.63 (d, J=1.4 Hz, 1H), and 2.70 (s, 3H). LCMS (ESI positive ion) m/z: 123 (M+H)+.

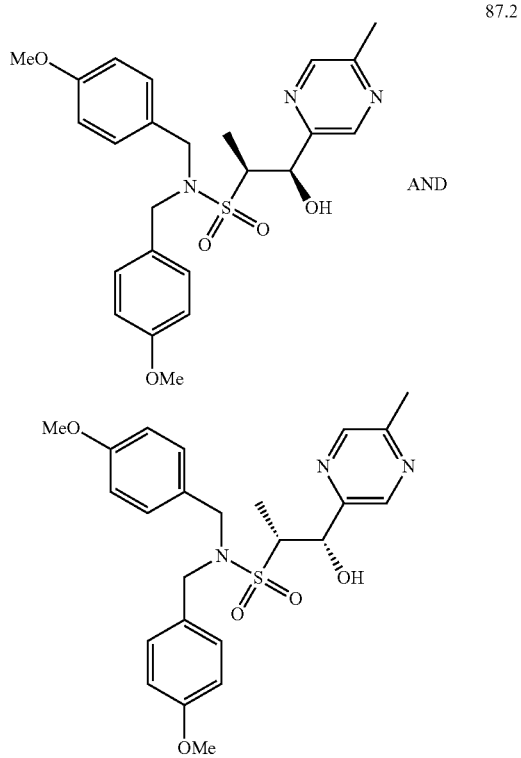

(1R,2S)-1-Hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide, Example 87.2

To a solution of N,N-bis(4-methoxybenzyl)ethanesulfonamide (Example 84.0, 73.13 g, 0.209 mol, 1.2 equiv.) in anhydrous THF (600 mL) at −78° C. was slowly added n-butyl lithium (83.71 mL, 0.209 mol, 2.5 M solution in hexanes, 1.2 equiv.) via additional funnel. The resulting mixture was then stirred for 10 min. Next, a solution of 5-methylpyrazine-2-carbaldehyde (Example 87.1, 21.3 g, 0.174 mol, 1.0 equiv.) in anhydrous THF (150 mL) was added, and the resulting mixture was stirred at same temperature for 45 min and then allowed to warm to RT for 2 h. The reaction mixture was quenched by addition of aqueous ammonium chloride (200 mL) and extracted with EtOAc (2×2 L). The combined organic layers were washed with brine (2×500 mL) (Note: no product was observed in the ammonium chloride or brine layer). After drying over anhydrous Na$_2$SO$_4$, the filtrate was concentrated in vacuo affording the initial product as an oil. The oil was purified by flash column chromatography (silica gel, 230-400 mesh) to afford the two isomers. The faster moving isomer (32 g as a white solid) was obtained from the column with a gradient of 10% to 30% EtOAc in petroleum ether. $^1$H NMR (400 MHz, DMSO-d$_6$) δ 8.61 (d, J=1.5 Hz, 1H), 8.51 (d, J=1.5 Hz, 1H), 7.22-7.11 (m, 4H), 6.90-6.80 (m, 4H), 6.10 (d, J=5.9 Hz, 1H), 5.29 (dd, J=5.9, 2.2 Hz, 1H), 4.36-4.16 (m, 4H), 3.73 (m, 6H), 3.70-3.66 (m, 1H) 2.50 (merged with solvent peak, 3H) and 1.10 (d, J=7.0 Hz, 3H). LCMS (ESI positive ion) m/z: 472.4 (M+H)$^+$.

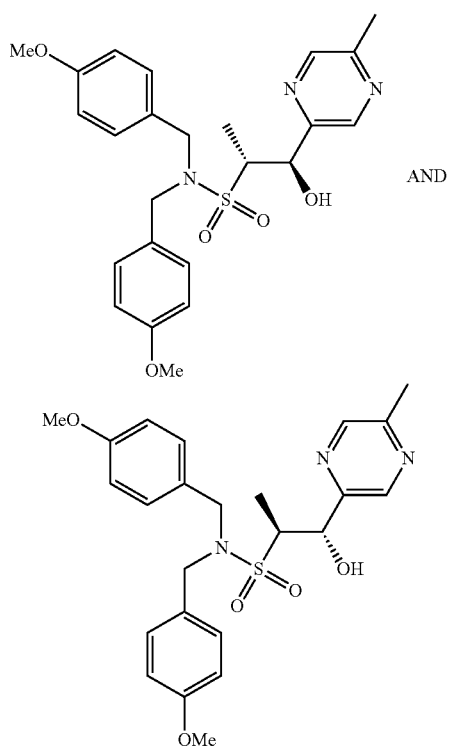

(1S,2S)-1-Hydroxy-N,N-bis(4-methoxybenzyl)-1-(5-methyl-pyrazin-2-yl)propane-2-sulfonamide and (1R,2R)-1-hydroxy-N,N-bis(4-methoxybenzyl)-1-(5-methyl-pyrazin-2-yl)propane-2-sulfonamide, Example 28.3

Further elution of the mixture with a gradient of 30% to 35% EtOAc in petroleum ether yielded Example 87.3 (16 g, pale yellow gummy liquid). $^1$H NMR (400 MHz, CDCl$_3$) δ 8.62 (d, J=1.6 Hz, 1H), 8.44 (d, J=1.5 Hz, 1H), 7.25-7.12 (m, 4H), 6.93-6.82 (m, 4H), 5.17 (d, J=7.1 Hz, 1H), 4.47 (d, J=15.2 Hz, 3H), 4.14 (d, J=15.4 Hz, 2H), 3.82 (s, 3H), 3.82 (s, 3H), 3.66-3.61 (m, 1H), 2.60 (d, J=2.0 Hz, 3H), and 1.08 (dd, J=7.2, 2.1 Hz, 3H). LCMS (ESI pos.) m/z: 472.4 (M+H)$^+$.

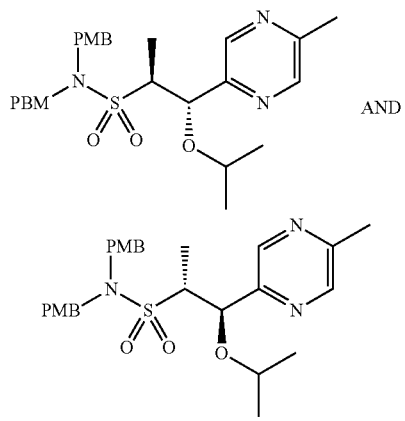

(1S,2S)-1-Isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide, Example 87.4

To a flask containing (1S,2S)-1-hydroxy-N,N-bis(4-methoxybenzyl)-1-(5-methylpyrazin-2-yl)propane-2-sulfonamide and (1R,2R)-1-hydroxy-N,N-bis(4-methoxybenzyl)-1-(5-methylpyrazin-2-yl)propane-2-sulfonamide (Example 87.3, 4.16 g, 8.81 mmol) and isopropyl iodide (12.3 mL, 123 mmol) in anhydrous toluene (35 mL) was added silver(I) oxide (4.17 g, 18.0 mmol) carefully in portions. Upon complete addition of silver oxide, the reaction was protected from light and heated to an internal temperature of 72° C. After 60 h, the mixture was cooled to RT and then filtered through a Chemglass disposable filter that was rinsed with EtOAc. The filtrate was concentrated under reduced pressure. The resulting dark brown residue was loaded onto a silica gel column (10-55% EtOAc in heptanes). Fractions containing the product were combined and then concentrated under reduced pressure to afford a dark brown oil as (1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide (Example 87.4, 1.52 g, 2.97 mmol, 34% yield) which was used without further purification. $^1$H NMR (400 MHz, DMSO-d$_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). LCMS (ESI pos.) m/z: 514.0 (M+H)$^+$.

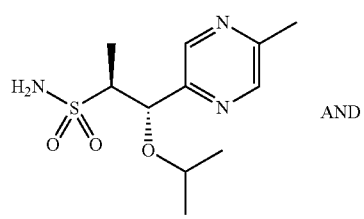

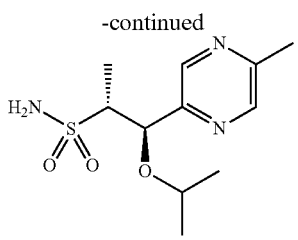

(1R,2R)-1-Isopropoxy-1-(5-methylpyrazin-2-yl)propane-2-sulfonamide and (1S,2S)-1-isopropoxy-1-(5-methylpyrazin-2-yl)propane-2-sulfonamide (Example 87.0), Example 87.5

Anisole (1.3 mL, 11.9 mmol) was added to a flask containing (1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide (Example 87.4, 1.5 g, 3 mmol) and DCM (7.5 mL). The homogeneous solution was cooled in an ice-water bath. After 15 min, TFA (7.6 mL, 99 mmol) was added dropwise to the reaction solution. Upon complete addition of TFA, the reaction was allowed to warm to RT. After 20 h, the brownish reaction solution was concentrated under reduced pressure. The residue was loaded onto a silica gel column (15-85% EtOAc in heptanes). Fractions containing the product were concentrated under reduced pressure to afford off white solid as (1R,2R)-1-isopropoxy-1-(5-methylpyrazin-2-yl)propane-2-sulfonamide and (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 87.5, 714 mg, 2.6 mmol, 88% yield). LCMS (ESI pos.) m/z: 274.0 (M+H)+.

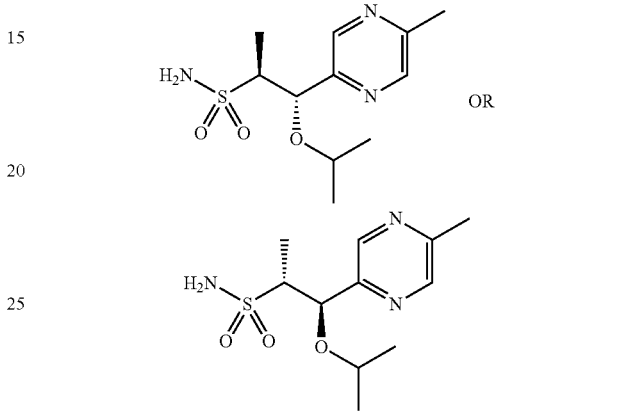

(1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide, Example 87.6

(1R,2R)-1-Isopropoxy-1-(5-methylpyrazin-2-yl)propane-2-sulfonamide and (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 87.5, 714 mg, 2.6 mmol) was purified by preparative SFC method: Column: IC (2×25 cm) Mobile Phase: 70:30 (A:B) A: Liquid $CO_2$, B: IPA to afford peak 1 as (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 87.6, 293 mg, 1.07 mmol, 36% yield). $^1$H NMR (400 MHz, DMSO-$d_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured $CH_3$ in DMSO peak). LCMS (ESI pos.) m/z: 274.2 (M+H)+.

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide Example 87.0

Further elution under the conditions described in Example 87.5 delivered Second eluting peak as (1R,2R)-1-isopropoxy-1-(5-methylpyrazin-2-yl)propane-2-sulfonamide or (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 87.0, 303 mg, 1.11 mmol, 37% yield). $^1$H NMR (400 MHz, DMSO-$d_6$) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured $CH_3$ in DMSO peak). LCMS (ESI pos.) m/z: 274.2 (M+H)+.

Example 88.0: Preparation of (1R,2S)-1-((tert-butyldimethylsilyl)oxy)-N,N-bis(4-methoxybenzyl)-1-(5-methylpyrimidin-2-yl)propane-2-sulfonamide

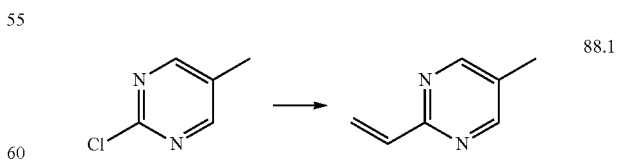

5-Methyl-2-vinylpyrimidine, Example 88.1

A 3 L 3-neck round bottomed flask was fitted with a reflux condenser, a temperature controller and a septum and charged with 2-chloro-5-methylpyrimidine (81 mL, 778 mmol), potassium vinyltrifluoroborate (156 g, 1167 mmol), triphenylphosphine (18.02 mL, 78 mmol), cesium carbonate (156 mL, 1945 mmol) and a large stir bar. Water (1565 mL) was added, and the mixture was stirred for several min before THF (244 mL) was added. Argon was bubbled through the mixture for 5 min and then palladium (II) chloride (1.72 g, 38.9 mmol) was added. The reaction was further sparged with argon for 5 mins. The temperature was raised to 62° C. and stirring was continued to completion. The reaction was then cooled to RT and filtered through two Whatman GF/F filter cups, rinsing with ether. The mixture was transferred to a separatory funnel, and the layers were separated. The aqueous layer was further extracted with diethyl ether (4×200 mL). The organic layers were combined and dried over anhydrous MgSO$_4$ and then filtered. The mixture was partially concentrated on the rotary evaporator at 20° C. and 115 torr for an extended period of time to give an orange liquid. The material was further purified by Kugelrohr distillation to isolate the title compound (65.4 g, 70%) as a light yellow oil. $^1$H NMR (400 MHz, CDCl$_3$) δ 2.31 (s, 3H), 5.68 (d, J=10.56 Hz, 1H), 6.55 (d, J=17.22 Hz, 1H), 6.86 (dd, J=17.41, 10.56 Hz, 1H), 8.54 (s, 2H). LCMS-ESI (pos.) m/z: 121.1 (M+H)$^+$.

(0.204 mL, 3.93 mmol), 1,4-dioxane (537 mL, 537 mmol), 4-methylmorpholine-n-oxide, 50% wt. in water (40 mL, 341 mmol) and 4-methylmorpholine-4-oxide (94 g, 805 mmol). The reaction mixture was stirred over 2 d. LCMS showed that the reaction was complete and the solvent was removed in vacuo. The compound was purified by silica gel chromatogrtaphy. The gradient was 100% heptane for 3CV's, then 0-100% EtOAc-EtOH(3:1) in heptane for 6 CV's, then 100% EtOAc:EtOH (3:1) for 5 CV's. The desired compound was collected and concentrated in vacuo. The material was triturated with 40% EtOAc in hexanes to give a solid, which was filtered. The solid was washed with 20% EtOAc in hexanes several times and then dried to give the title compound (67.3 g). $^1$H NMR (400 MHz, CDCl$_3$) δ 8.59 (s, 2H), 4.81-4.98 (m, 1H), 3.88-4.19 (m, 2H), 2.36 (s, 3H).

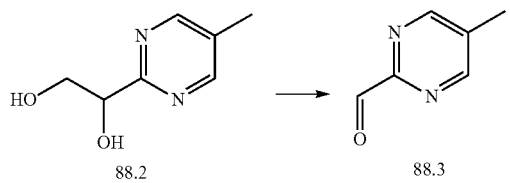

5-Methylpyrimidine-2-carbaldehyde, Example 88.3

A 5 L flask equipped with a mechanical stirrer was charged with 1-(5-methylpyrimidin-2-yl)ethane-1,2-diol (64.3 g, 417 mmol) and 1,4-dioxane (1043 mL) and water (261 mL). The reaction was cooled in an ice-water bath. Sodium periodate (223 g, 1043 mmol) was added and the internal temperature was monitored until it returned to RT. The reaction was further stirred at RT for 2 hr and 20 min. DCM (2 L) was then added. The resulting solution was filtered through a plug of dried MgSO$_4$ (700 g). The plug was washed with DCM (7 L). The solvent was concentrated in vacuo, and the aldehyde was azeotroped with toluene to deliver the title compound (44g) as a white solid. LCMS-ESI (pos.) m/z: 122.8 (M+H)$^+$.

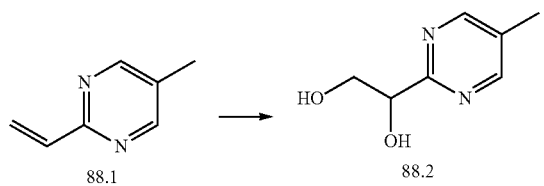

1-(5-Methylpyrimidin-2-yl)ethane-1,2-diol, Example 88.2

To a 2 L round-bottomed flask was added 5-methyl-2-vinylpyrimidine (64.5 g, 537 mmol), osmium tetroxide

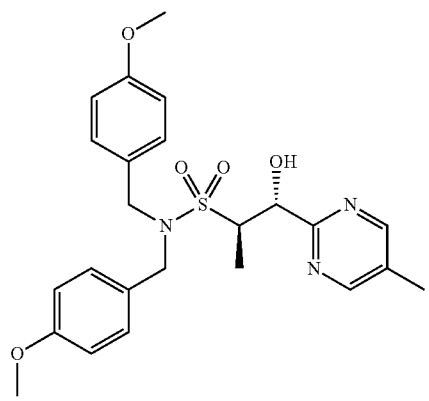

and

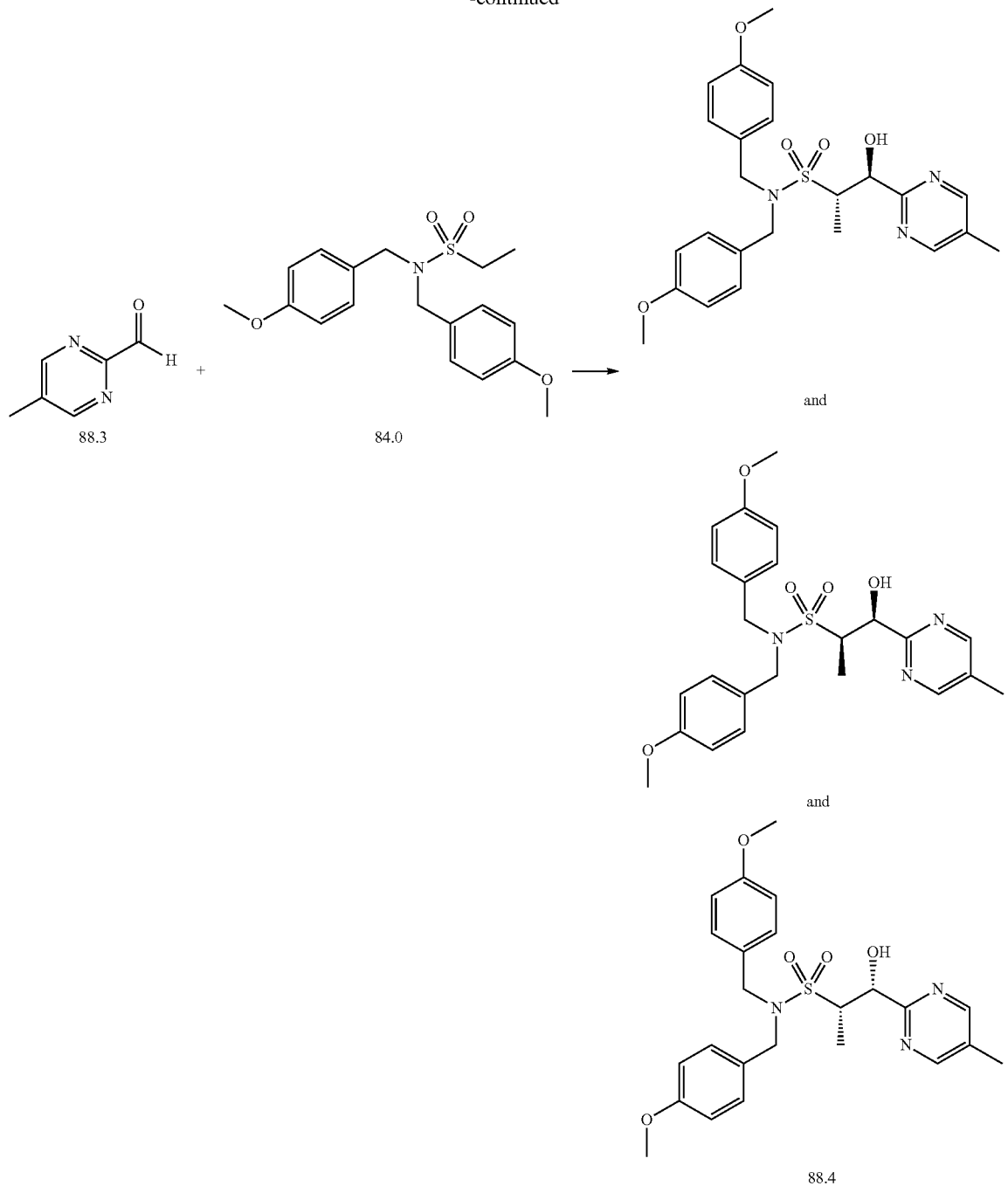

(1R,2S)-1-Hydroxy-N,N-bis(4-methoxybenzyl)-1-(5-methylpyrimidin-2-yl)propane-2-sulfonamide and 1 (1S,2S)-1-hydroxy-N,N-bis(4-methoxybenzyl)-1-(5-methylpyrimidin-2-yl)propane-2-sulfonamide and 1 (1R,2R)-1-hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide Example 88.4

A 3 L flask was charged with N,N-bis(4-methoxybenzyl) ethanesulfonamide (Example 84.0, 151 g, 432 mmol) and anhydrous THF (1200 mL) under nitrogen and then equipped with a pre-dried addition funnel under nitrogen. The flask was cooled in a dry ice-acetone bath. n-Butyllithium (1.6 M, 270 mL, 432 mmol) was first cannulated into the additional funnel and was then added slowly into the reaction flask which was stirred for 10 min. 5-Methylpyrimidine-2-carbaldehyde (88.3, 44 g, 360 mmol) in THF (300 mL) was next cannulated into the reaction. The reaction was stirred at −78° C. for 45 min and then was warmed to RT and stirred for 2 h and 10 min. A saturated solution of ammonium chloride was added to quench the reaction, and the mixture was extracted with EtOAc and concentrated in vacuo to give the product.

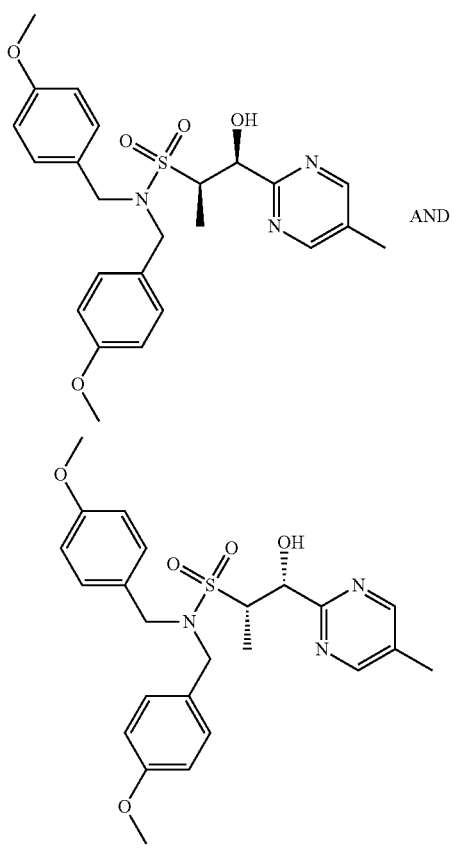

(1R,2S)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide, Example 88.5

The mixture of diastereomers of Example 85.4 was separated and purified on silica gel eluting with 0-50% EtOAc gradient in DCM to give the title compound (56.4 g). LCMS-ESI (pos.) m/z: 472.1 (M+H)⁺.

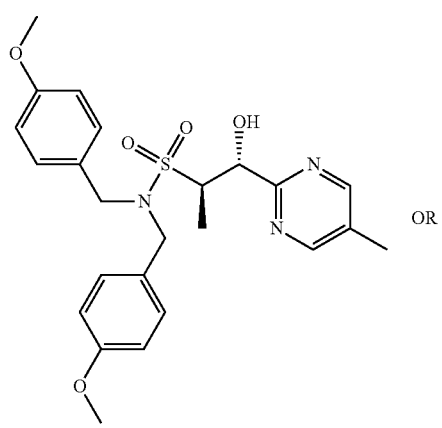

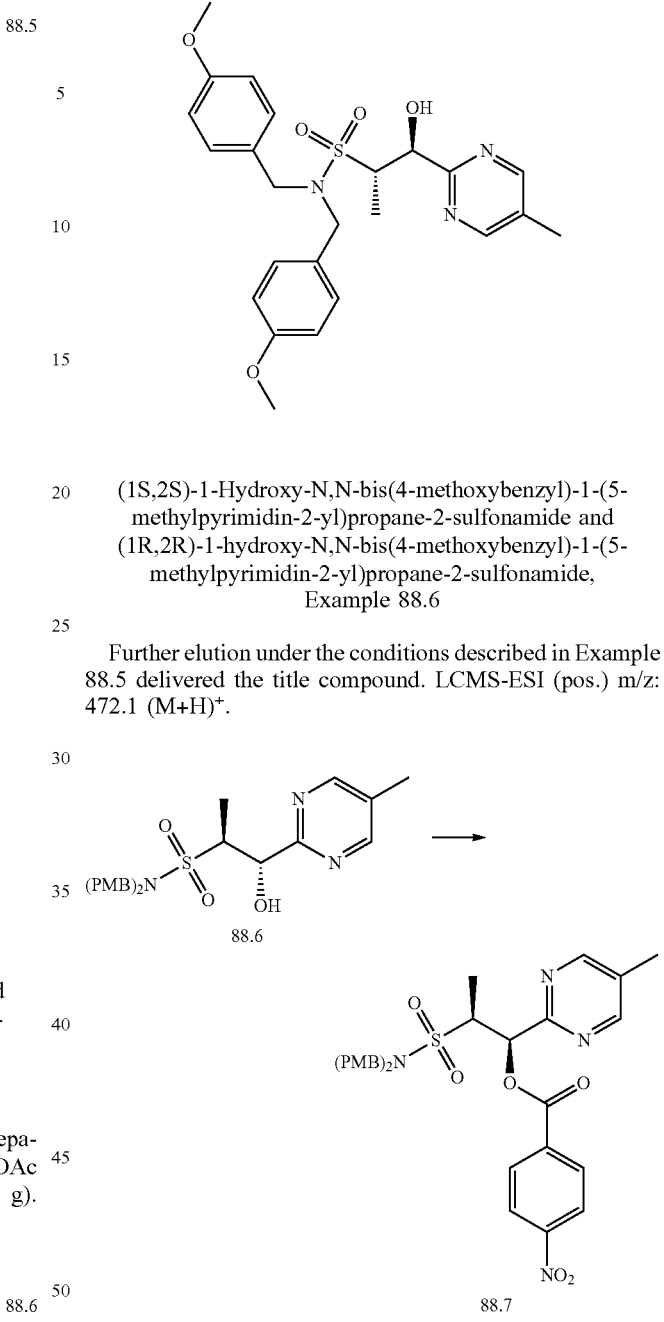

(1S,2S)-1-Hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide, Example 88.6

Further elution under the conditions described in Example 88.5 delivered the title compound. LCMS-ESI (pos.) m/z: 472.1 (M+H)⁺.

(1R,2S)-2-(N,N-Bis(4-methoxybenzyl)sulfamoyl)-1-(5-methylpyrimidin-2-yl)propyl 4-nitrobenzoate, Example 88.7

To a stirred solution of (1S,2S)-1-hydroxy-N,N-bis(4-methoxybenzyl)-1-(5-methylpyrimidin-2-yl)propane-2-sulfonamide (22.7 g, 48.1 mmol) in toluene (241 mL) was added 4-nitrobenzoic acid (12.07 g, 72.2 mmol) and triphenylphosphine (18.94 g, 72.2 mmol) followed by dropwise addition of (E)-diisopropyl diazene-1,2-dicarboxylate (14.22 mL, 72.2 mmol). The mixture was stirred at RT overnight. The reaction was then concentrated in vacuo and purified on silica gel eluting with 0-50% EtOAc/hexanes to give the desired compound (1R,2S)-2-(N,N-bis(4-methoxybenzyl)sulfamoyl)-1-(5-methylpyrimidin-2-yl)propyl 4-nitrobenzoate, Example 88.7 (29.9 g, 48.1 mmol, 100% yield). LCMS-ESI (pos.) m/z: 621.3 (M+H)+.

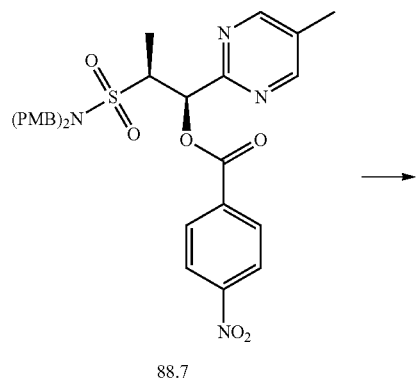

88.7

(1R,2S)-2-(N,N-Bis(4-methoxybenzyl)sulfamoyl)-1-(5-methylpyrimidin-2-yl)propyl 4-nitrobenzoate, Example 88.9

To a stirred solution of 88.8 (76 g, 122 mmol) in MeOH (612 mL) at 0° C. was added potassium carbonate (16.92 g, 122 mmol). The mixture was allowed to warm to RT over 1 h and showed the desired product by LCMS. The reaction was then concentrated in vacuo and purified on silica gel eluting with 0-40% EtOAc in hexanes to give (1R,2S)-1-hydroxy-N,N-bis(4-methoxybenzyl)-1-(5-methylpyrimidin-2-yl)propane-2-sulfonamide. LCMS-ESI (pos.) m/z: 472.0 (M+H)+.

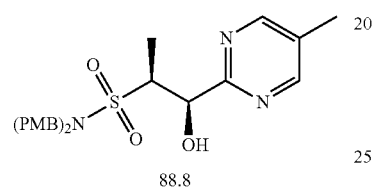

88.8

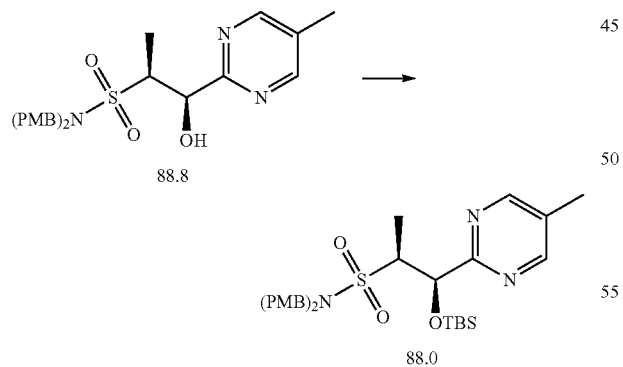

88.0

(1R,2S)-1-((tert-Butyldimethylsilyl)oxy)-N,N-bis(4-methoxybenzyl)-1-(5-methylpyrimidin-2-yl)propane-2-sulfonamide, Example 88.0

To a stirred solution of (1R,2S)-1-hydroxy-N,N-bis(4-methoxybenzyl)-1-(5-methylpyrimidin-2-yl)propane-2-sulfonamide (88.8, 28 g, 59.4 mmol) in DCM (297 mL, 59.4 mmol) at 0° C. was added tert-butyldimethylsilyl trifluoromethanesulfonate (15.00 mL, 65.3 mmol), followed by TEA (9.12 mL, 65.3 mmol). The mixture was allowed to warm to RT over 1 h. The reaction mixture was then concentrated in vacuo and purified on silica gel eluting with 0-30% EtOAc in hexane to give the desired compound (1R,2S)-1-((tert-butyldimethylsilyl)oxy)-N,N-bis(4-methoxybenzyl)-1-(5-methylpyrimidin-2-yl)propane-2-sulfonamide (15 g, 25.6 mmol, 43.1% yield). LCMS-ESI (pos.) m/z: 586.0 (M+H)+.

Example 89.0. Preparation of (2R,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide

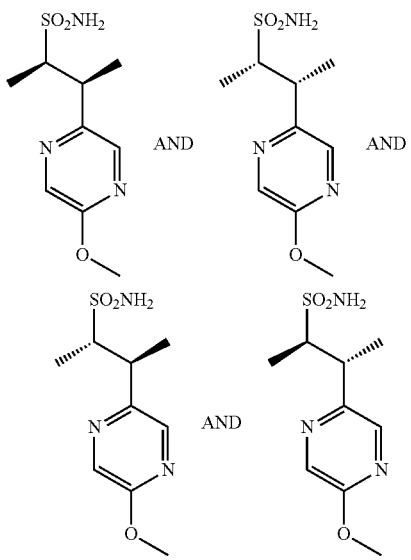

(2R,3R)-3-(5-Methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 89.0

Example 89.0 was synthesized following the procedure in Example 86.0 using 2-bromo-5-methoxypyrazine (commercially available from Ark Pharm, Inc.). LCMS-ESI (pos.) m/z: 246.2 (M+H)+.

Example 90.0. Preparation of (2S,3R)-3-(5-methoxypyrimidin-2-yl)butane-2-sulfonamide

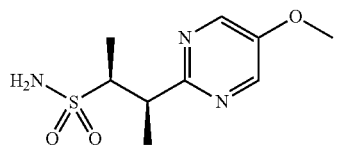

(2S,3R)-3-(5-methoxypyrimidin-2-yl)butane-2-sulfonamide, Example 90.0

A round bottom flask was charged with (2S,3R)-3-(5-fluoropyrimidin-2-yl)butane-2-sulfonamide (575 mg, 2.47 mmol, Example 81.1), MeOH (7 mL), and potassium carbonate (679 mg, 4.91 mmol). The reaction was stirred at RT. After 48 h, the reaction was heated to 50° C. and stirred for 24 h and then the temperature was raised to 65° C. and the reaction was stirred for 48 h. LCMS-ESI showed the reaction was 75% complete. The reaction was allowed to cool to RT and filtered. The solids were rinsed with MeOH (2×5 mL). The filtrate was concentrated in vacuo and adsorbed onto a plug of silica gel and chromatographed through a RediSep® pre-packed silica gel column, eluting with 0-40% EtOAc:EtOH (3:1) in heptanes. The organic layers from several fractions were concentrated in vacuo to give a mixture of starting material and the title compound (56 mg, 0.23 mmol, 9% yield) as an off-white solid. Water was found to be present in the chromatography solvents and some fractions contained water. The fractions containing water were combined and the aqueous layer was saturated with NaCl and extracted with CHCl$_3$:IPA (9:1, 3×15 mL). The combined organic layers were dried over MgSO$_4$ and concentrated in vacuo to give more title compound (114 mg). The material was carried forward as is. LCMS-ESI (pos.) m/z: 246.1 (M+H)$^+$.

Example 91.4. Preparation of (3R,5R)-1-(5-fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide

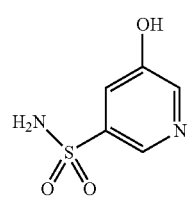

5-Hydroxypyridine-3-sulfonamide, Example 91.1

To a 100-mL round-bottomed flask was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-1-isopropyl-biphenyl (commercially available from Strem Chemicals, Inc., MA, USA, 0.079 g, 0.16 mmol) and Pd$_2$(dba)$_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was allowed to cool to RT. The reaction mixture was then diluted with 1 N HCl and washed with Et$_2$O. The aqueous phase was concentrated in vacuo to afford the title compound 91.1 (0.387 g, 2.22 mmol, 100% yield) as a white solid, which was directly used in the next step without further purification. LCMS-ESI (pos.), m/z: 175.1 (M+H)$^+$.

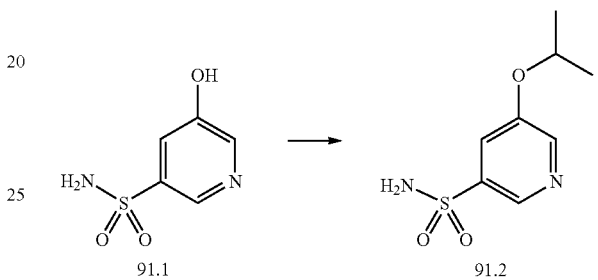

5-Isopropoxypyridine-3-sulfonamide, Example 91.2

To a suspension of 5-hydroxypyridine-3-sulfonamide, Example 91.1 (1.1 g, 6.32 mmol) in THF (16 mL) and IPA (16 mL) was added triphenylphosphine (1.99 g, 7.58 mmol). The mixture was bubbled with argon for 3 min before diisopropyl azodicarboxylate (1.49 mL, 7.58 mmol) was added dropwise at 0° C. under a N$_2$ stream. The reaction was then stirred at 0° C. to RT for 15 h. The reaction mixture was next concentrated in vacuo. The material thus obtained was absorbed onto a plug of silica gel and purified by chromatography through a RediSep pre-packed silica gel column (40 g), eluting with a gradient of 0% to 100% EtOAc in heptane, to provide the enriched product fractions, which were combined and extracted with 1N HCl. The desired product was enriched in acidic aqueous solution, which was then modified by saturated aqueous NaHCO$_3$ to pH>8. The basic aqueous solution was then extracted with DCM. The organic extract was washed with brine and dried over Na$_2$SO$_4$. The solution was filtered and concentrated in vacuo to give 5-isopropoxypyridine-3-sulfonamide, Example 91.2, (0.95 g, 70% yield) as a white solid. LCMS-ESI (pos.), m/z: 217.2 (M+H)$^+$.

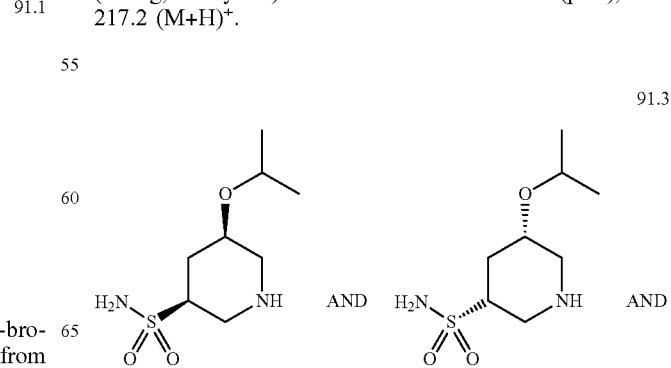

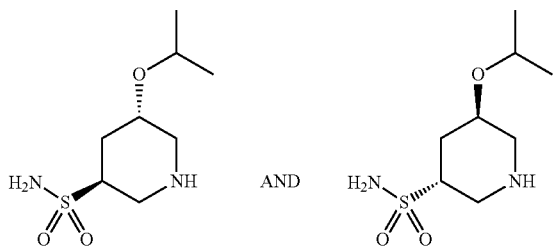

(3S,5R)-5-Isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide, Example 91.3

A solution of Example 91.2, 5-isopropoxypyridine-3-sulfonamide (1.8 g, 8.32 mmol) in AcOH (41.6 mL) was bubbled with argon gas for 2 min before platinum (IV) oxide (1.89 g, 8.32 mmol) was added under argon stream. The above reaction mixture was stirred at RT under 45 psi of hydrogen gas for 2 d. Next, Celite® brand filter agent (5 g) was added to the reaction mixture, and the mixture was stirred at RT for 10 min. The mixture was then filtered and the solution was concentrated in vacuo to give the initial product mixture as a light yellow oil, which was used as such in the next step. LCMS-ESI (pos.), m/z: 223.3 (M+H)+.

(3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 91.4

To a 40 mL vial (with pressure release septa) was added Example 91.3 (3S,5R)-5-isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide (2.0 g, 4.96 mmol) and 2-chloro-5-fluoropyrimidine (3.29 g, 24.79 mmol). The reaction mixture was stirred at 90° C. for 21 h. LCMS indicated the reaction was complete. Next, the reaction mixture was concentrated in vacuo. The material thus obtained was absorbed onto a plug of silica gel and purified by chromatography through RediSep pre-packed silica gel column (40 g), eluting with a gradient of 0% to 100% EtOAc in heptane, to provide Example 91.4, as a mixture of diastereomers (0.5 g, 1.6 mmol, 32% yield) as an off-white solid. LCMS-ESI (pos.), m/z: 319.2 (M+H)+.

91.4

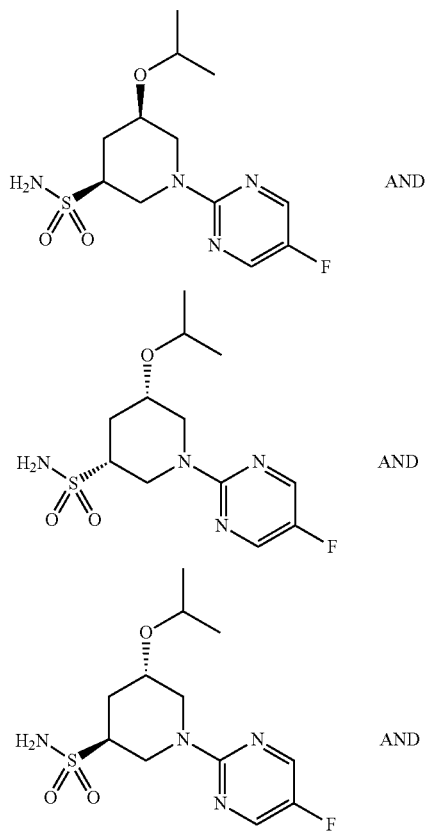

91.5

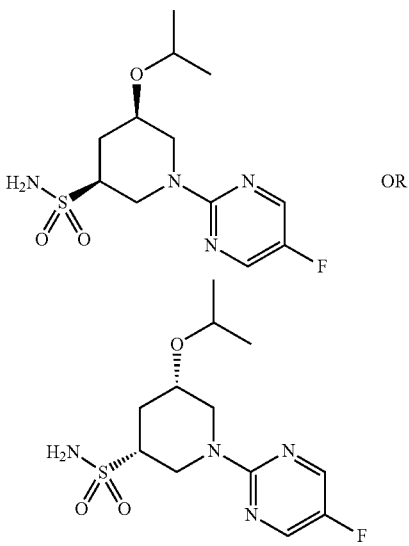

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 91.5

Example 91.4 was separated by SFC on a Chiralpak AS-H column using 15% MeOH/CO$_2$. Example 91.5 and Example 91.6 are a pair of enantiomers, Example 91.5 was the second peak among 4 isomers (earlier peak vs. its opposite enantiomer) on AS-H column. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)⁺.

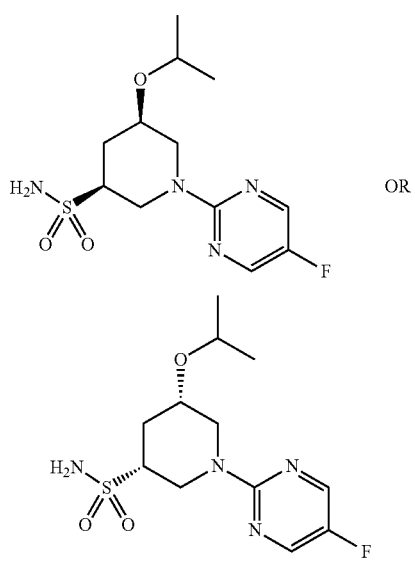

91.6

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 91.6

Further elution under the conditions described in Example 91.5 gave Example 91.6 as the third peak. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)⁺.

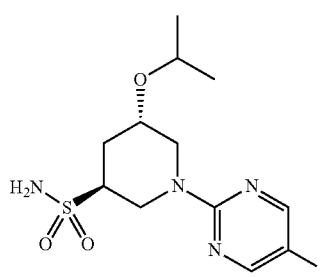

91.7

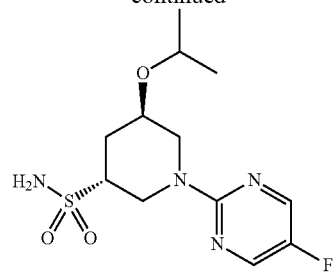

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 91.7

91.7 and 91.8 are a pair of enantiomers, (3S,5S)-1-(5-fluoropyrimidin-2-yl)-5-isopropoxypiperidine-3-sulfonamide or (3R,5R)-1-(5-fluoropyrimidin-2-yl)-5-isopropoxypiperidine-3-sulfonamide 91.7 was the first peak among 4 isomers (earlier peak vs. its opposite enantiomer) on AS-H column under conditions described in Example 91.5. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)⁺.

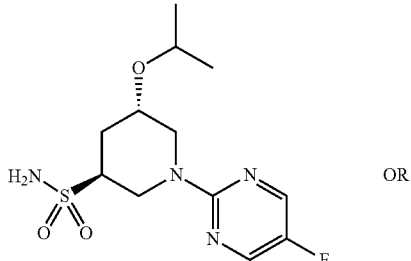

91.8

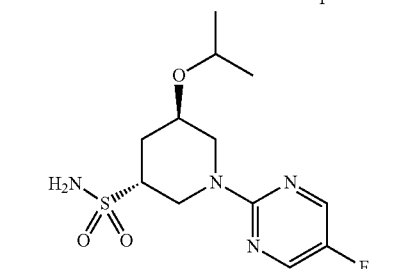

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 91.8

Further elution under the conditions described in Example 91.5 gave Example 91.8 as the fourth peak. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)⁺.

Example 92.0. Preparation of (S)-tert-butyl 3-sulfamoylpiperidine-1-carboxylate and (R)-tert-butyl 3-sulfamoylpiperidine-1-carboxylate

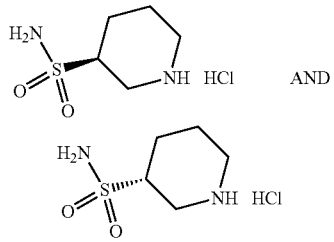

(S)-Piperidine-3-sulfonamide hydrochloride and (R)-piperidine-3-sulfonamide hydrochloride, Example 92.1

A solution of 4-chloropyridine-3-sulfonamide (5.0 g, 25.9 mmol) in AcOH (150 mL) was placed in a parr bottle. The mixture was bubbled with nitrogen gas for 5 min. To this solution was added a suspension of platinum (IV) oxide (5.9 g, 25.9 mmol) in AcOH (30 mL). The reaction was stirred under an atmosphere of hydrogen (50 psi) for 72 h. The reaction mixture was filtered through Celite® brand filter agent pad and the pad was washed with MeOH (2×50 mL). The combined filtrate was concentrated under reduced pressure to provide Example 92.1 (6.0 g) as an oil which was used in the next step without further purification. LCMS-ESI (pos.) m/z: 165.2 (M+H)⁺.

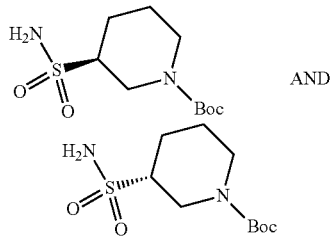

(S)-tert-Butyl 3-sulfamoylpiperidine-1-carboxylate and (R)-tert-butyl 3-sulfamoylpiperidine-1-carboxylate, Example 92.0

To a mixture of 92.1 (12.0 g, 59.8 mmol) and TEA (41.6 mL, 299 mmol) in DCM (215 mL) was added a solution of boc anhydride (15.7 mL, 71.8 mmol) in DCM (70 mL) at RT. The reaction mixture was stirred for 16 h at RT. The reaction mixture was washed with water (2×200 mL). The combined organic layers were washed with brine (100 mL), dried over sodium sulfate and evaporated under reduced pressure to obtain the initial product which was purified by column chromatography (silica: 100-200 mesh; elution: 0-30% EtOAc in DCM) to provide 92.0 (4.6 g, 34%, over two steps) as a white solid. ¹H NMR (400 MHz, CD₃CN) δ 5.30 (s, 2H), 4.36 (d, J=11.8 Hz, 1H), 3.94 (d, J=13.3 Hz, 1H), 3.01-2.84 (m, 2H), 2.64-2.58 (s, 1H), 2.20 (d, J=13.3 Hz, 1H), 1.78 (d, J=13.5 Hz, 1H), 1.74-1.57 (m, 2H), 1.43 (s, 9H). LCMS-ESI (pos.) m/z: 263 (M–H)⁺.

Example 93.0: Preparation of (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide

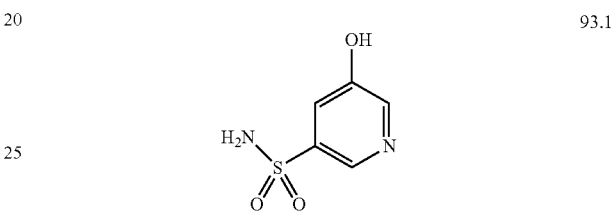

5-Hydroxypyridine-3-sulfonamide, Example 93.1

To a 100-mL round-bottomed flask was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-1-isopropyl-biphenyl (commercially available from Strem Chemicals, Inc., MA, USA, 0.079 g, 0.16 mmol) and Pd₂(dba)₃ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was stirred at 100° C. under N₂ for 17 h. LCMS analysis indicated the reaction was complete. The reaction mixture was allowed to cool to RT. The reaction mixture was diluted with 1 N HCl and washed with Et₂O. The aqueous phase was concentrated in vacuo to afford the title compound 93.1 (0.387 g, 2.22 mmol, 100% yield) as a white solid, which was directly used in the next step without further purification. LCMS-ESI (pos.), m/z: 175.1 (M+H)⁺.

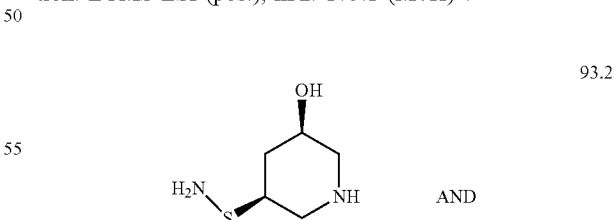

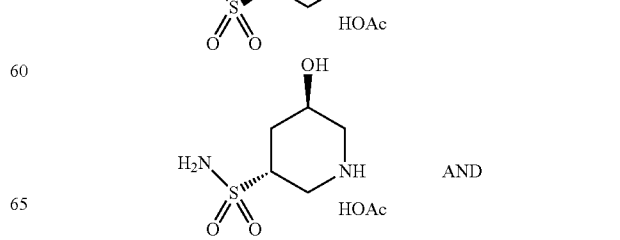

-continued

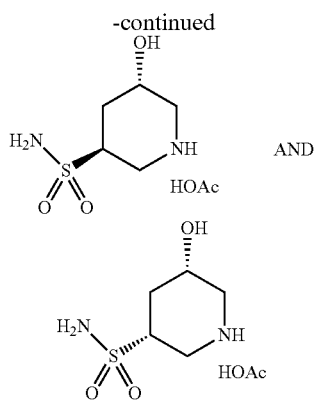

(3R,5R)-5-Hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 93.2

To a 1-L hydrogenation flask was added 93.1 (6.46 g, 37.1 mmol) and AcOH (250 mL, 4330 mmol). Water (20 mL) was added as co-solvent. The mixture was bubbled with $N_2$ for 2 min before platinum (IV) oxide hydrate (8.42 g, 37.1 mmol) was added under $N_2$ flow. The flask was set up on a Parr shaker, vacuumed and back-filled with $N_2$ two times, and then placed under vacuum and back-filled with hydrogen gas (tank). The reaction mixture was stirred at RT under 50 psi of hydrogen gas for 24 h. LCMS analysis indicated that the reaction was complete. Celite® brand filter agent (20 g) was then added to the mixture with stirring. The solid was removed by filtration after 10 min of stirring. The filter cake was rinsed with MeOH. The combined organic layers were concentrated in vacuo to afford 93.2 (8.91 g, 100% yield) as a light-yellow oil, which was directly used in the next step without purification. LCMS-ESI (pos.), m/z: 181.1 (M+H)$^+$.

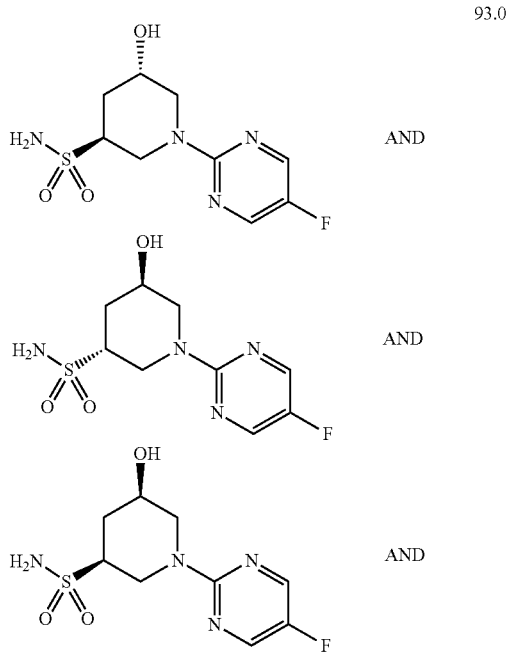

93.0

-continued

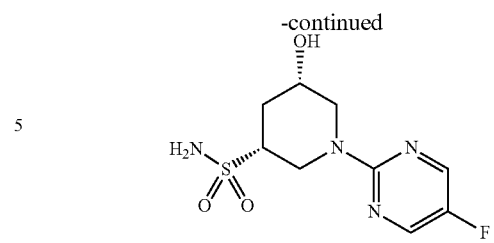

(3S,5S)-1-(5-Fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 93.0

To a 500-mL round-bottomed flask was added 93.2 (8.91 g, 37.1 mmol) and Hunig's base (32.3 mL, 185 mmol) in DMF (80 mL). 2-Chloro-5-fluoro-pyrimidine (18.32 mL, 148 mmol) was then added with stirring. The reaction mixture was stirred at 120° C. for 18 h. LCMS analysis indicated the reaction was complete. The reaction mixture was allowed to cool to RT and then was diluted with water and extracted with DCM. The organic layers were washed with brine and dried over $Na_2SO_4$. The solution was filtered and concentrated in vacuo to give the initial material as an orange oil. The material thus obtained was purified by silica gel chromatography (a gradient of 0-100% EtOAc in DCM), to provide 93.0 (3.7 g, 10.93 mmol, 36% yield) as a light-yellow solid. LCMS-ESI (pos.), m/z: 277.0 (M+H)$^+$.

Example 94.3. Preparation of (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide

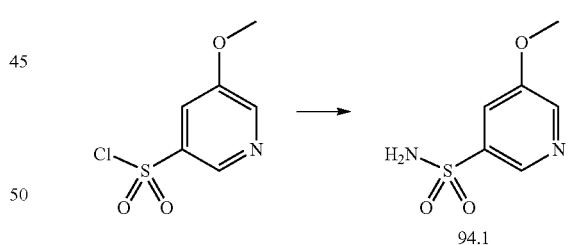

94.1

5-Methoxypyridine-3-sulfonamide, Example 94.1

A reaction mixture of 5-methoxypyridine-3-sulfonyl chloride (commercially available from Enamine, KIEV, Ukraine) (1.0 g, 4.82 mmol) and ammonia, (0.5 M solution in 1,4-dioxane. 96 mL, 48.2 mmol) was stirred at 0 to RT for 30 min. LCMS indicated the reaction was complete. The reaction was then filtered and the filter cake was rinsed with dioxane. The combined solution was concentrated in vacuo to give the title compound (0.91 g, 100% yield) as light yellow foam which was used as such in the next step without purification. LCMS-ESI (pos.) m/z: 189.2 (M+H)$^+$.

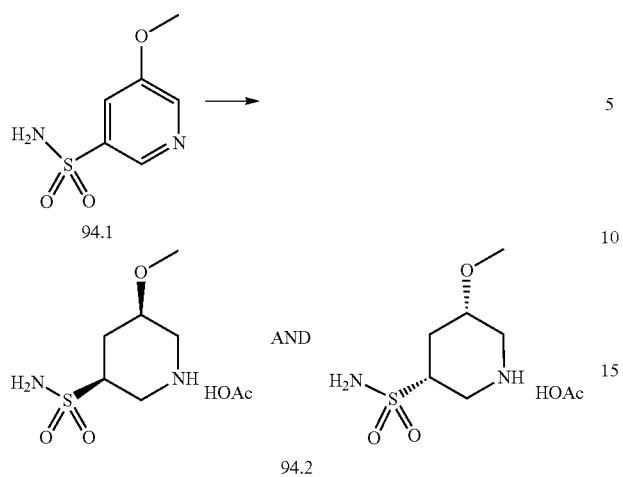

94.1

94.2

(3S,5R)-5-Methoxypiperidine-3-sulfonamide acetate and (3R,5S)-5-methoxypiperidine-3-sulfonamide acetate, Example 94.2

A solution of 5-methoxypyridine-3-sulfonamide (0.9 g, 4.78 mmol) in AcOH (31.9 mL) was bubbled with argon gas for 2 min before platinum (IV) oxide ((1.09 g, 4.78 mmol) was added under an argon stream. The reaction mixture was stirred at RT under 45 psi of hydrogen gas for 38 h. The mixture was filtered and the filtrate was concentrated in vacuo to give the title compound (1.22 g, 100% yield) as light yellow foam which was used as such for the next step. LCMS-ESI (pos.) m/z: 195.2 (M+H)$^+$.

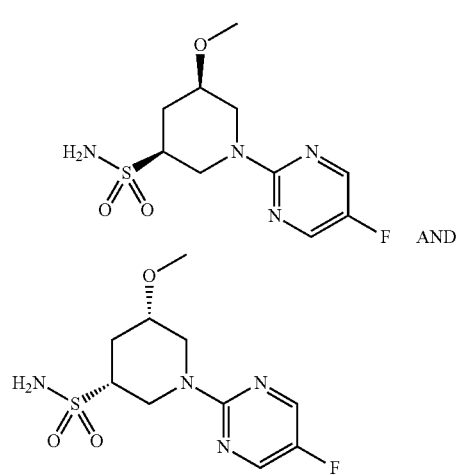

94.3

(3S,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide, Example 94.3

To a 40 mL vial (w/ pressure release septa) was added 5-methoxypiperidine-3-sulfonamide acetate (94.2, 2.45 g, 9.62 mmol), N-ethyl-N-isopropylpropan-2-amine (16.75 mL, 96 mmol) and 2-chloro-5-fluoropyrimidine (6.37 g, 48.1 mmol) in dimethyl sulfoxide (48 mL). The reaction mixture was stirred at 100° C. for 23 h. LCMS indicated formation of the desired product. The reaction mixture was diluted with water and extracted with DCM. The organic extract was washed with saturated aqueous NaCl, brine and dried over Na$_2$SO$_4$. The resulting solution was filtered and concentrated in vacuo to give the initial product as an orange oil. The material thus obtained was absorbed onto a plug of silica gel and purified by chromatography through RediSeppre-packed silica gel column (40 g), eluting with a gradient of 0% to 100% 1/3 EtOH/EtOAc in heptanes to provide the title compound, 94.3 (0.51 g, 18% yield) as a white solid, LCMS-ESI (pos.) m/z: 291.0 (M+H)$^+$.

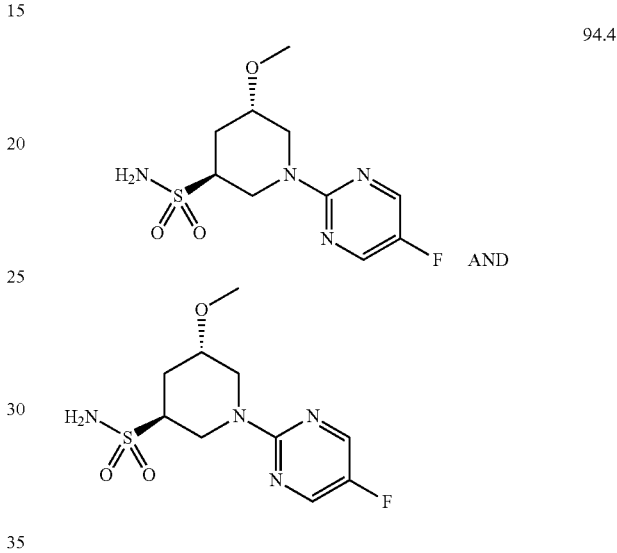

94.4

(3S,5S)-1-(5-Fluoropyrimidin-2-yl)-5-methoxypiperidine-3-sulfonamide and (3R,5R)-1-(5-fluoropyrimidin-2-yl)-5-methoxypiperidine-3-sulfonamide. Example 94.4

Further elution under the conditions described in Example 94.3 delivered 94.4 (0.24 g, 0.832 mmol, 8.65% yield) as light yellow solid. LCMS-ESI (pos.) m/z: 291.0 (M+H)$^+$.

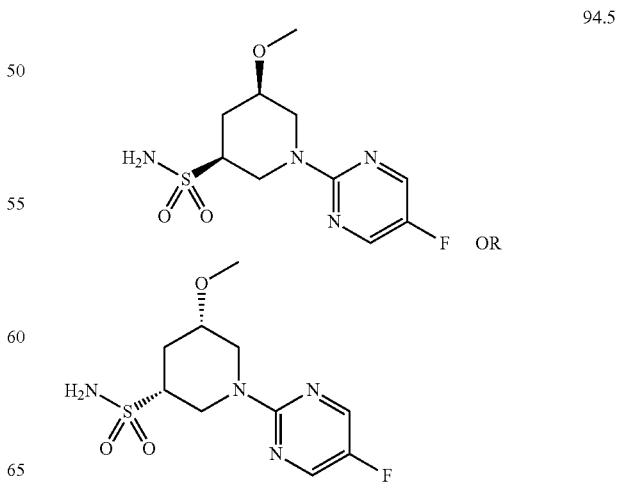

94.5

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 94.5

Example 94.5 was obtained by chiral separation of 94.3 on SFC: Chiralpak AD-H, 30% MeOH/CO$_2$, with 0.2% DEA. Example 94.5 was the earlier peak to elute on Chiralpak AD-H column. $^1$H NMR (400 MHz, CD$_3$OD) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (pos.) m/z: 291.0 (M+H)$^+$.

94.6

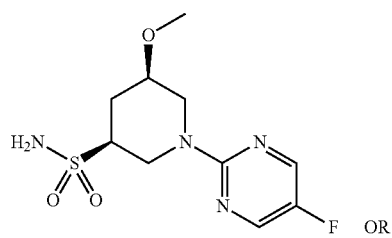 OR

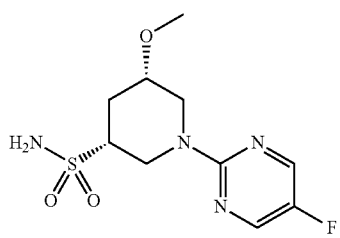

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 94.6

Further elution under the conditions described in Example 94.5 delivered Example 94.6. $^1$H NMR (400 MHz, CD$_3$OD) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45 (s, 3H) 4.97 (ddt, 1H) 5.17 (ddt, 1H) 8.32 (s, 2H). LCMS-ESI (pos.) m/z: 291.0 (M+H)$^+$.

94.7

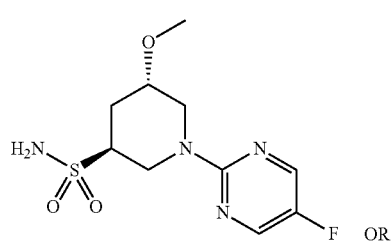 OR

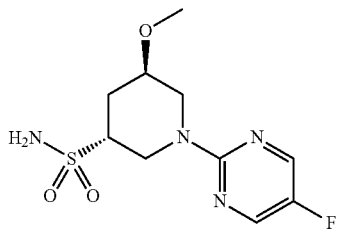

(3S,5S)-1-(5-Fluoropyrimidin-2-yl)-5-methoxypiperidine-3-sulfonamide or (3R,5R)-1-(5-fluoropyrimidin-2-yl)-5-methoxypiperidine-3-sulfonamide, Example 94.7

Example 94.7 was obtained by chiral separation of 94.3 on SFC: Chiralpak AD-H, 25% MeOH/CO$_2$, with 0.2% DEA. 94.7 was the earlier peak to elute on the Chiralpak AD-H column. $^1$H NMR (400 MHz, CD$_3$OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H) LCMS-ESI (pos.) m/z: 291.0 (M+H)$^+$.

94.8

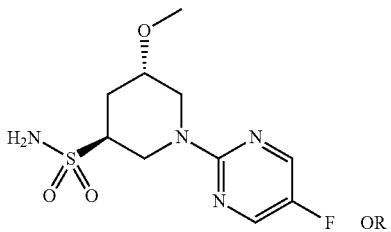

(3R,5R)-1-(5-Fluoropyrimidin-2-yl)-5-methoxypiperidine-3-sulfonamide or (3S,5S)-1-(5-fluoropyrimidin-2-yl)-5-methoxypiperidine-3-sulfonamide, Example 94.8

Further elution under the conditions described in Example 94.7 delivered Example 94.8. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 291.0 (M+H)$^+$.

Example 95.0: Preparation of (1R,2S)-1-ethoxy-1-(5-methylpyrimidin-2-yl)propane-2-sulfonamide or (1S,2R)-1-ethoxy-1-(5-methylpyrimidin-2-yl)propane-2-sulfonamide

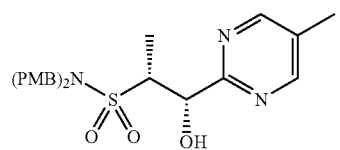

AND

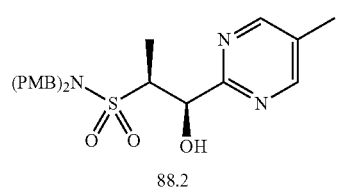

88.2

(1R,2S)-1-Ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 95.1

To a −78° C. solution of 88.2 (1.62 g, 3.4 mmol) in THF (70 mL) was added potassium bis(trimethylsilyl)amide (1 M solution in THF, 10.6 mL, 10.6 mmol) slowly via syringe. After 1.25 h, ethyl trifluoromethanesulfonate (1.4 mL, 10.6 mmol) was added slowly via syringe. The resulting orange solution was stirred at −78° C. for 45 min and was then quenched with a 2:1 mixture of saturated aqueous ammonium chloride and water (75 mL). The resulting mixture was extracted with EtOAc (4×). The combined organic layers were dried over anhydrous sodium sulfate and concentrated in vacuo. The residue was purified by silica gel chromatography (eluent: 10-65% EtOAc in hexanes over a 40 min period) to provide 95.1 (1.02 g, 60% yield) as a light yellow oil. LCMS-ESI (pos.) m/z: 500.1 (M+H)$^+$.

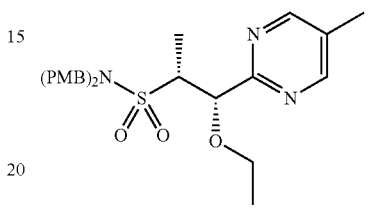

AND

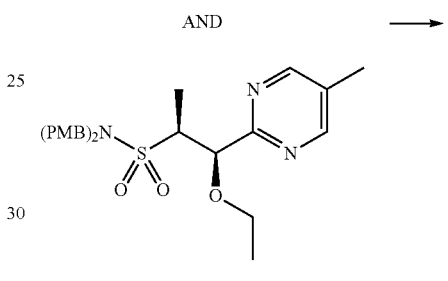

95.1

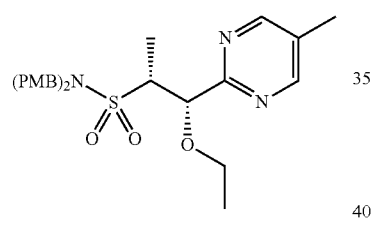

AND

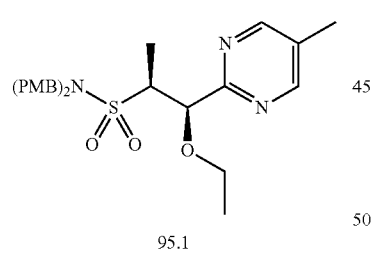

95.1

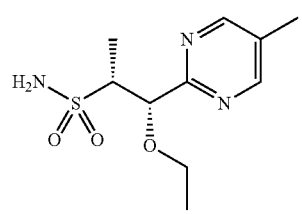

AND

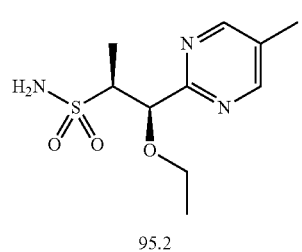

95.2

(1R,2S)-1-Ethoxy-1-(5-methylpyrimidin-2-yl)propane-2-sulfonamide and (1S,2R)-1-ethoxy-1-(5-methylpyrimidin-2-yl)propane-2-sulfonamide, Example 95.2

Example 95.1 (1.02 g, 2.0 mmol) was dissolved in TFA (14 mL). Anisole (466 µL, 4.3 mmol) was then added via syringe. The resulting orange solution was stirred at RT for 16.5 h and then concentrated in vacuo. The residue was purified by silica gel chromatography (eluent: pure DCM grading to 4.5% MeOH in DCM over a 45 min period) to provide the title compound 95.2 (495 mg, 93% yield) as a white solid. LCMS-ESI (pos.) m/z: 260.0 (M+H)$^+$.

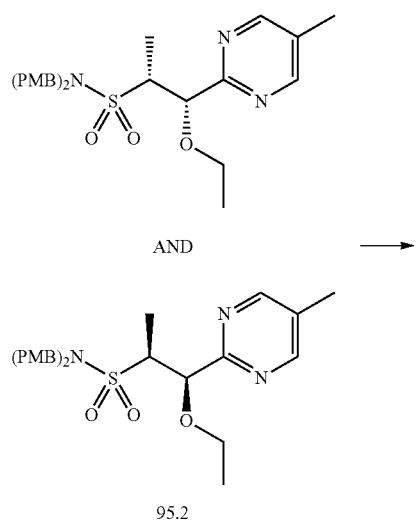

95.2

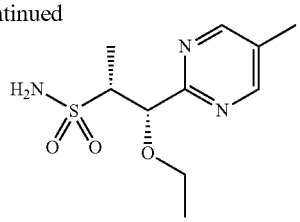

OR

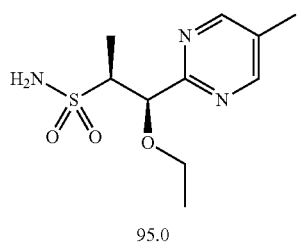

95.0

(1R,2S)-1-Ethoxy-1-(5-methylpyrimidin-2-yl)propane-2-sulfonamide or (1S,2R)-1-ethoxy-1-(5-methylpyrimidin-2-yl)propane-2-sulfonamide, Example 95.0

Example 95.2 was purified by preparative SFC method: Column: AD-H (2×25 cm) Mobile Phase: 88:12 (A:B) A: Liquid CO$_2$, B: Ethanol, Flow Rate: 70 mL/min, 220 nm, 165-172 bar inlet pressure to deliver Peak 2 as, Example 95.0. LCMS-ESI (pos.) m/z: 260.0 (M+H)$^+$ The compounds set forth in the following table were synthesized following the procedure in Example 95.0 using the known starting material as described.

TABLE 14

| Example | Reagents | Structure, Name and Data |
|---|---|---|
| 95.2 | (PMB)₂N-SO₂-...-pyrimidine-OH AND (PMB)₂N-SO₂-...-pyrimidine-OH. Material prepared in an analogous manner to that of Example 88.2 employing the cis olefin. | H₂N-SO₂-...-pyrimidine-OEt AND H₂N-SO₂-...-pyrimidine-OEt. (1R,2R)-1-ethoxy-1-(5-methylpyrimidin-2-yl)propane-2-sulfonamide and (1S,2S)-1-ethoxy-1-(5-methylpyrimidin-2-yl)propane-2-sulfonamide. LCMS-ESI (pos.) m/z: 260.0 (M + H)$^+$. |

Following the procedures in Example 14.0 and Example 129.0, the following compounds may be synthesized using the intermediates and conditions described in the following table.

TABLE 15

| Example | Reagents | Structure, Name and Data |
|---|---|---|
| 96.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 2-chlorophenyl isothiocyanate (commercially available from Acros). | 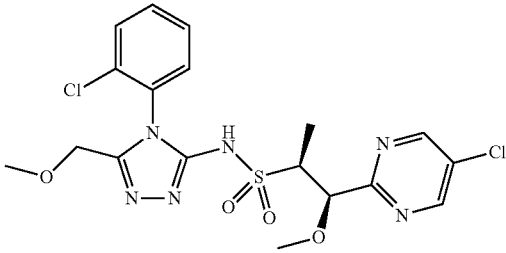 [SMILES: COCc1nnc(NS(=O)(=O)[C@@H](C)[C@H](OC)c2ncc(Cl)cn2)n1-c1ccccc1Cl]<br>(1R,2S)-N-(4-(2-chlorophenyl)-5-(methoxymethyl)-4H-1,2,4-triazol-3-yl)-1-(5-chloropyrimidin-2-yl)-1-methoxypropane-2-sulfonamide. |
| 97.0 | (1R,2S)-1-(5-chloropyrimidin-2-yl)-1-methoxypropane-2-sulfonamide (Example 83.3), glycolic-2,2-d$_2$ acid (commercially available from C D N Isotopes Inc.), and 2-isothiocyanato-1,3-dimethoxybenzene (Example 82.0). | 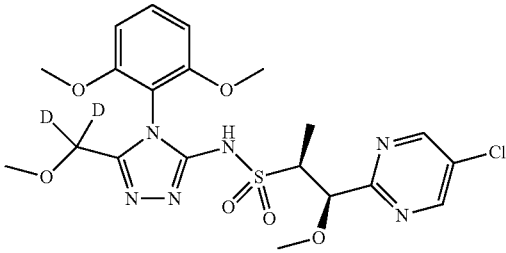 [SMILES: [2H]C([2H])(OC)c1nnc(NS(=O)(=O)[C@@H](C)[C@H](OC)c2ncc(Cl)cn2)n1-c1c(OC)cccc1OC] |
| 98.0 | (1R,2S)-1-(5-chloropyrimidin-2-yl)-1-methoxypropane-2-sulfonamide (Example 83.3), glycolic-2,2-d$_2$ acid (commercially available from C D N Isotopes Inc.), iodomethane-d$_3$ (commercially available from Acros), and 2-isothiocyanato-1,3-dimethoxybenzene (Example 82.0). | 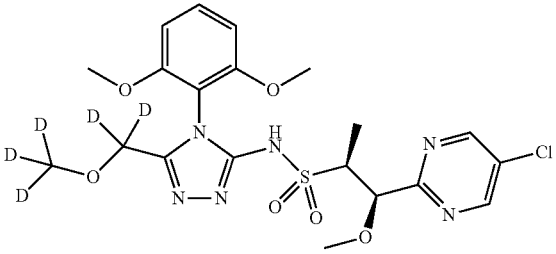 [SMILES: [2H]C([2H])([2H])OC([2H])([2H])c1nnc(NS(=O)(=O)[C@@H](C)[C@H](OC)c2ncc(Cl)cn2)n1-c1c(OC)cccc1OC] |
| 99.0 | (1R,2S)-1-(5-chloropyrimidin-2-yl)-1-methoxypropane-2-sulfonamide (Example 83.3), 2-ethoxyacetohydrazide (commercially available from Enamine), and 5-isothiocyanato-4,6-dimethoxypyrimidine (Example 82.1). | 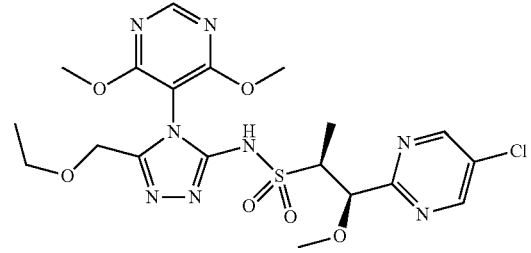 [SMILES: CCOCc1nnc(NS(=O)(=O)[C@@H](C)[C@H](OC)c2ncc(Cl)cn2)n1-c1c(OC)ncnc1OC]<br>(1R,2S)-1-(5-chloropyrimidin-2-yl)-N-(4-(4,6-dimethoxypyrimidin-5-yl)-5-(ethoxymethyl)-4H-1,2,4-triazol-3-yl)-1-methoxypropane-2-sulfonamide. |
| 100.0 | (2S,3R)-3-(5-chloropyrimidin-2-yl)butane-2-sulfonamide (Example 81.4), 2-ethoxyacetohydrazide (commercially available from Enamine), and 5-isothiocyanato-4,6-dimethoxypyrimidine (Example 82.1). | 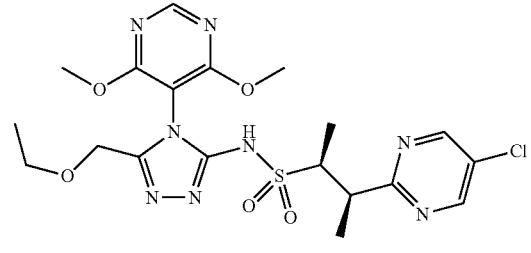 [SMILES: CCOCc1nnc(NS(=O)(=O)[C@@H](C)[C@H](C)c2ncc(Cl)cn2)n1-c1c(OC)ncnc1OC]<br>(2S,3R)-3-(5-chloropyrimidin-2-yl)-N-(4-(4,6-dimethoxypyrimidin-5-yl)-5-(ethoxymethyl)-4H-1,2,4-triazol-3-yl)butane-2-sulfonamide. |

TABLE 15-continued

| Example | Reagents | Structure, Name and Data |
|---|---|---|
| 101.0 | (1S,2S)-1-isopropoxy-1-(5-methylpyrimidin-2-yl)propane-2-sulfonamide (Example 85.0), 2-ethoxyacetohydrazide (commercially available from Enamine), and 2-isothiocyanato-1,3-dimethoxybenzene (Example 82.0). | 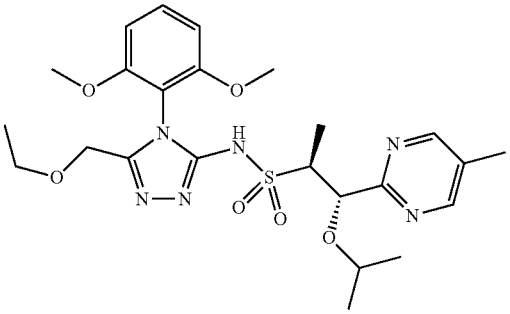 [SMILES: CCOCc1nnc(NS(=O)(=O)[C@@H](C)[C@@H](OC(C)C)c2ncc(C)cn2)n1-c1c(OC)cccc1OC]<br>(1S,2S)-N-(4-(2,6-dimethoxyphenyl)-5-(ethoxymethyl)-4H-1,2,4-triazol-3-yl)-1-isopropoxy-1-(5-methylpyrimidin-2-yl)propane-2-sulfonamide. |
| 102.0 | (1S,2S)-1-(5-chloropyrimidin-2-yl)-1-isopropoxypropane-2-sulfonamide (Example 85.1), 2-ethoxyacetohydrazide (commercially available from Enamine), and 5-isothiocyanato-4,6-dimethoxypyrimidine (Example 82.1). | 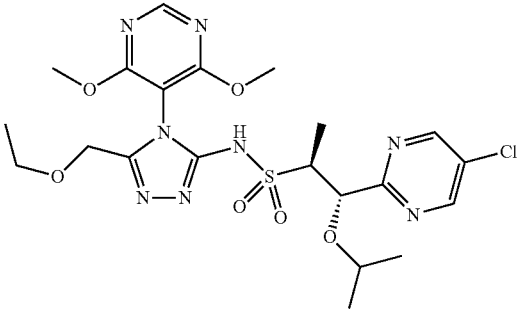 [SMILES: CCOCc1nnc(NS(=O)(=O)[C@@H](C)[C@@H](OC(C)C)c2ncc(Cl)cn2)n1-c1c(OC)ncnc1OC]<br>(1S,2S)-1-(5-chloropyrimidin-2-yl)-N-(4-(4,6-dimethoxypyrimidin-5-yl)-5-(ethoxymethyl)-4H-1,2,4-triazol-3-yl)-1-isopropoxypropane-2-sulfonamide. |
| 103.0 | (1R,2S)-1-(5-chloropyrimidin-2-yl)-1-methoxypropane-2-sulfonamide (Example 83.3), 2-propoxyacetohydrazide (commercially available from Aurora Fine Chemicals LLC), and 2-isothiocyanato-1,3-dimethoxybenzene (Example 82.0). | 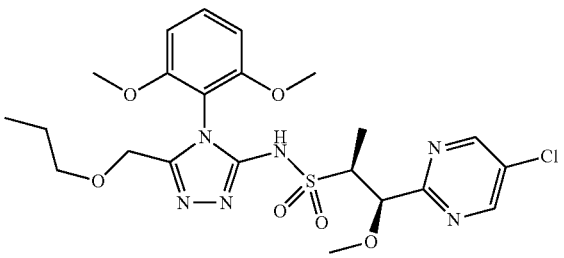 [SMILES: CCCOCc1nnc(NS(=O)(=O)[C@@H](C)[C@H](OC)c2ncc(Cl)cn2)n1-c1c(OC)cccc1OC]<br>(1R,2S)-1-(5-chloropyrimidin-2-yl)-N-(4-(2,6-dimethoxyphenyl)-5-(propoxymethyl)-4H-1,2,4-triazol-3-yl)-1-methoxypropane-2-sulfonamide. |
| 104.0 | (2S,3R)-3-(5-chloropyrimidin-2-yl)butane-2-sulfonamide (Example 81.4), 2-propoxyacetohydrazide (commercially available from Aurora Fine Chemicals LLC), and 2-isothiocyanato-1,3-dimethoxybenzene (Example 82.0). | 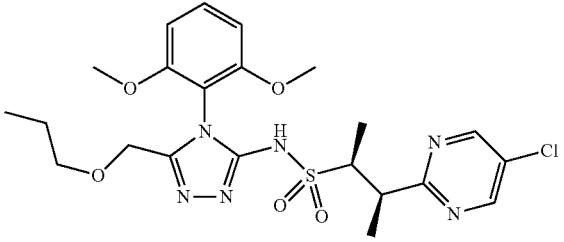 [SMILES: CCCOCc1nnc(NS(=O)(=O)[C@@H](C)[C@H](C)c2ncc(Cl)cn2)n1-c1c(OC)cccc1OC]<br>(2S,3R)-3-(5-chloropyrimidin-2-yl)-N-(4-(2,6-dimethoxyphenyl)-5-(propoxymethyl)-4H-1,2,4-triazol-3-yl)butane-2-sulfonamide. |

TABLE 15-continued

| Example | Reagents | Structure, Name and Data |
|---|---|---|
| 105.0 | (2S,3R)-3-(5-chloropyrimidin-2-yl)butane-2-sulfonamide (Example 81.4), 2-propoxyacetohydrazide (commercially available from Aurora Fine Chemicals LLC), and 5-isothiocyanato-4,6-dimethoxypyrimidine (Example 82.1). | 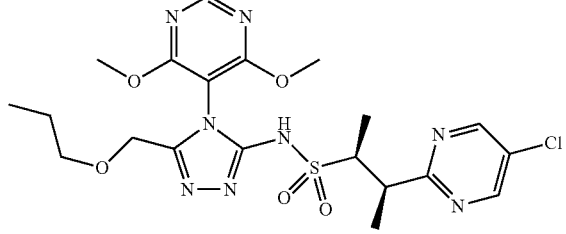<br>(2S,3R)-3-(5-chloropyrimidin-2-yl)-N-(4-(4,6-dimethoxypyrimidin-5-yl)-5-(propoxymethyl)-4H-1,2,4-triazol-3-yl)butane-2-sulfonamide |
| 106.0 | (1R,2S)-1-(5-chloropyrimidin-2-yl)-1-methoxypropane-2-sulfonamide (Example 83.3), 2-(butan-2-yloxy)acetohydrazide (commercially available from Aurora Fine Chemicals LLC), and 2-isothiocyanato-1,3-dimethoxybenzene (Example 82.0). | 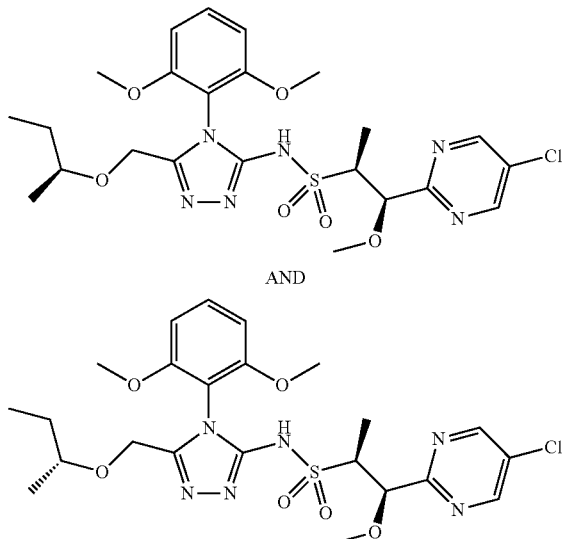 [SMILES: CC[C@H](C)OCc1nnc(NS(=O)(=O)[C@@H](C)[C@H](OC)c2ncc(Cl)cn2)n1-c1c(OC)cccc1OC ; CC[C@@H](C)OCc1nnc(NS(=O)(=O)[C@@H](C)[C@H](OC)c2ncc(Cl)cn2)n1-c1c(OC)cccc1OC]<br>AND<br>(1R,2S)-N-(5-((S)-sec-butoxymethyl)-4-(2,6-dimethoxyphenyl)-4H-1,2,4-triazol-3-yl)-1-(5-chloropyrimidin-2-yl)-1-methoxypropane-2-sulfonamide and (1R,2S)-N-(5-((R)-sec-butoxymethyl)-4-(2,6-dimethoxyphenyl)-4H-1,2,4-triazol-3-yl)-1-(5-chloropyrimidin-2-yl)-1-methoxypropane-2-sulfonamide. |
| 107.0 | (1R,2S)-1-(5-chloropyrimidin-2-yl)-1-methoxypropane-2-sulfonamide (Example 83.3), 2-(2-methylpropoxy)acetohydrazide (commercially available from Aurora Fine Chemicals LLC), and 2-isothiocyanato-1,3-dimethoxybenzene (Example 82.0). | 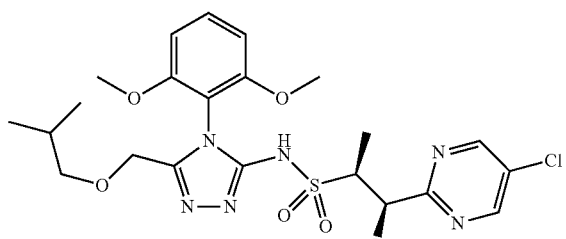<br>(1R,2S)-1-(5-chloropyrimidin-2-yl)-N-(4-(2,6-dimethoxyphenyl)-5-(isobutoxymethyl)-4H-1,2,4-triazol-3-yl)-1-methoxypropane-2-sulfonamide. |

TABLE 15-continued

| Example | Reagents | Structure, Name and Data |
|---|---|---|
| 108.0 | (1R,2S)-1-(5-chloropyrimidin-2-yl)-1-methoxypropane-2-sulfonamide (Example 83.3), 2-(cyclopropylmethoxy)acetohydrazide (commercially available from Aurora Fine Chemicals LLC), and 2-isothiocyanato-1,3-dimethoxybenzene (Example 82.0). | 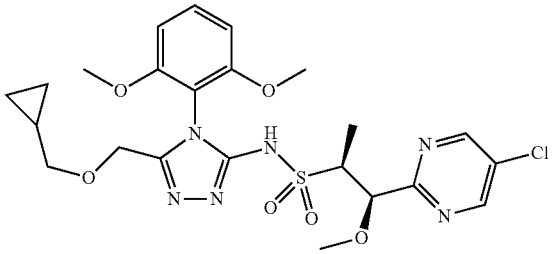 [SMILES: COc1cccc(OC)c1-n1c(COCC2CC2)nnc1NS(=O)(=O)[C@@H](C)[C@H](OC)c1ncc(Cl)cn1]<br>(1R,2S)-1-(5-chloropyrimidin-2-yl)-N-(5-((cyclopropylmethoxy)methyl)-4-(2,6-dimethoxyphenyl)-4H-1,2,4-triazol-3-yl)-1-methoxypropane-2-sulfonamide. |
| 109.0 | (1R,2S)-1-(5-chloropyrimidin-2-yl)-1-methoxypropane-2-sulfonamide (Example 83.3), 2-cyclopropoxyacetic acid (commercially available from Aurora Fine Chemicals LLC), and 2-isothiocyanato-1,3-dimethoxybenzene (Example 82.0). | 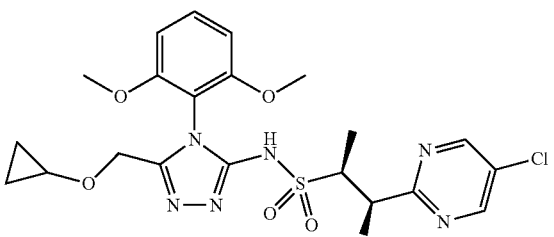<br>(1R,2S)-1-(5-chloropyrimidin-2-yl)-N-(5-(cyclopropoxymethyl)-4-(2,6-dimethoxyphenyl)-4H-1,2,4-triazol-3-yl)-1-methoxypropane-2-sulfonamide. |
| 110.0 | (1R,2S)-1-(5-chloropyrimidin-2-yl)-1-methoxypropane-2-sulfonamide (Example 83.3), 2-cyclobutoxyacetohydrazide (commercially available from Aurora Fine Chemicals LLC), and 2-isothiocyanato-1,3-dimethoxybenzene (Example 82.0). | 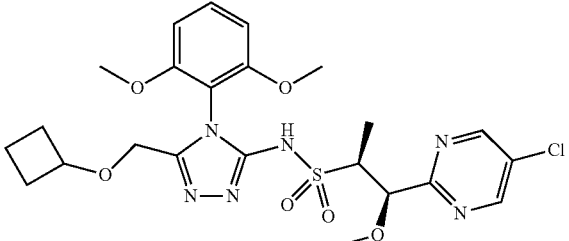<br>(1R,2S)-1-(5-chloropyrimidin-2-yl)-N-(5-(cyclobutoxymethyl)-4-(2,6-dimethoxyphenyl)-4H-1,2,4-triazol-3-yl)-1-methoxypropane-2-sulfonamide. |
| 111.0 | (1R,2S)-1-(5-chloropyrimidin-2-yl)-1-methoxypropane-2-sulfonamide (Example 83.3), 2-hydroxyacetohydrazide (commercially available from Enamine), tert-butyl 2-hydroxyazetidine-1-carboxylate (commercially available from Apichemical (Shanghai) Co., Ltd.), and 2-isothiocyanato-1,3-dimethoxybenzene (Example 82.0). | 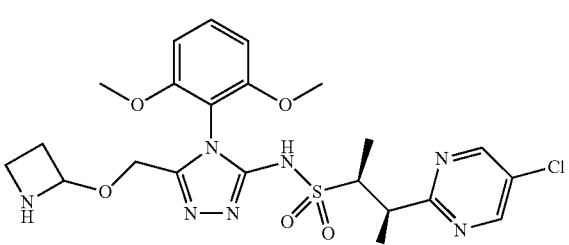<br>(1R,2S)-N-(5-((azetidin-2-yloxy)methyl)-4-(2,6-dimethoxyphenyl)-4H-1,2,4-triazol-3-yl)-1-(5-chloropyrimidin-2-yl)-1-methoxypropane-2-sulfonamide. |

TABLE 15-continued

| Example | Reagents | Structure, Name and Data |
|---|---|---|
| 112.0 | (1R,2S)-1-(5-chloropyrimidin-2-yl)-1-methoxypropane-2-sulfonamide (Example 83.3), (commercially available from Aldrich), tert-butyl 2-hydroxyazetidine-1-carboxylate (commercially available from Apichemical (Shanghai) Co., Ltd.), and 2-isothiocyanato-1,3-dimethoxybenzene (Example 82.0). | 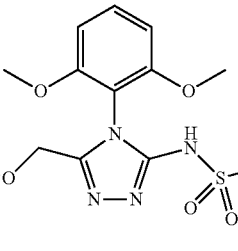<br>(1R,2S)-1-(5-chloropyrimidin-2-yl)-N-(4-(2,6-dimethoxyphenyl)-5-(((4-oxoazetidin-2-yl)oxy)methyl)-4H-1,2,4-triazol-3-yl)-1-methoxypropane-2-sulfonamide. |
| 113.0 | (1R,2S)-1-(5-chloropyrimidin-2-yl)-1-methoxypropane-2-sulfonamide (Example 83.3), 2-hydroxyacetohydrazide, (Enamine), 3-hydroxycyclobutanone (commercially available from PharmaBlock (USA), Inc.), and 2-isothiocyanato-1,3-dimethoxybenzene (Example 82.0). | 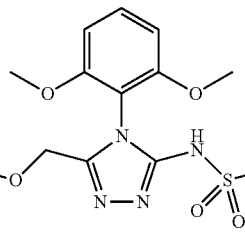<br>(1R,2S)-1-(5-chloropyrimidin-2-yl)-N-(4-(2,6-dimethoxyphenyl)-5-((3-hydroxycyclobutoxy)methyl)-4H-1,2,4-triazol-3-yl)-1-methoxypropane-2-sulfonamide. |
| 114.0 | (1R,2S)-1-(5-chloropyrimidin-2-yl)-1-methoxypropane-2-sulfonamide (Example 83.3), 2-(cyclopentyloxy) acetic acid (commercially available from Enamine), and 2-isothiocyanato-1,3-dimethoxybenzene (Example 82.0). | 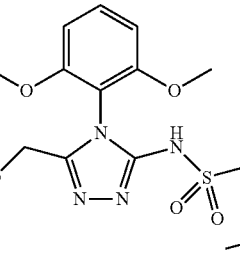<br>(1R,2S)-1-(5-chloropyrimidin-2-yl)-N-(5-((cyclopentyloxy)methyl)-4-(2,6-dimethoxyphenyl)-4H-1,2,4-triazol-3-yl)-1-methoxypropane-2-sulfonamide. |
| 115.0 | (1R,2S)-1-(5-chloropyrimidin-2-yl)-1-methoxypropane-2-sulfonamide (Example 83.3), 2-(oxolan-3-yloxy) acetic acid commercially available from (Enamine), and 2-isothiocyanato-1,3-dimethoxybenzene (Example 82.0). | 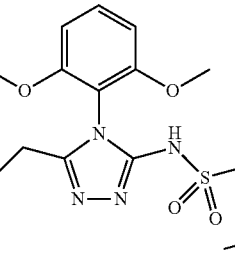<br>(1R,2S)-1-(5-chloropyrimidin-2-yl)-N-(4-(2,6-dimethoxyphenyl)-5-(((tetrahydrofuran-3-yl)oxy)methyl)-4H-1,2,4-triazol-3-yl)-1-methoxypropane-2-sulfonamide. |

TABLE 15-continued

| Example | Reagents | Structure, Name and Data |
|---|---|---|
| 116.0 | (2S,3R)-3-(5-chloropyrimidin-2-yl)butane-2-sulfonamide (Example 81.4), 2-(2-methoxyethoxy) acetohydrazide (commercially available from Aurora Fine Chemicals LLC), and 2-isothiocyanato-1,3-dimethoxybenzene (Example 82.0). | 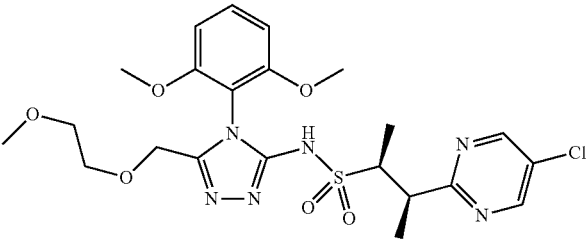 [SMILES: COCCOCc1nnc(NS(=O)(=O)[C@@H](C)[C@H](C)c2ncc(Cl)cn2)n1-c1c(OC)cccc1OC]<br>(2S,3R)-3-(5-chloropyrimidin-2-yl)-N-(4-(2,6-dimethoxyphenyl)-5-((2-methoxyethoxy)methyl)-4H-1,2,4-triazol-3-yl)butane-2-sulfonamide. |
| 117.0 | (2S,3R)-3-(5-chloropyrimidin-2-yl)butane-2-sulfonamide (Example 81.4), propanoic acid, 3-(difluoromethoxy)- (commercially available from Aurora Fine Chemicals LLC), and 2-isothiocyanato-1,3-dimethoxybenzene (Example 82.0). | 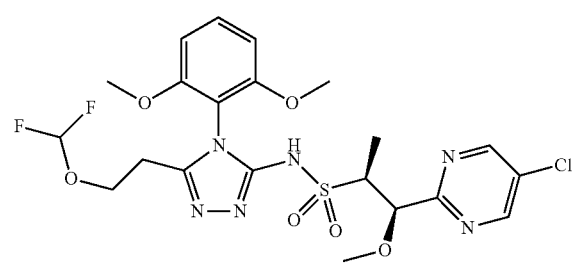 [SMILES: COc1cccc(OC)c1-n1c(CCOC(F)F)nnc1NS(=O)(=O)[C@@H](C)[C@H](OC)c1ncc(Cl)cn1]<br>(1R,2S)-1-(5-chloropyrimidin-2-yl)-N-(5-(2-(difluoromethoxy)ethyl)-4-(2,6-dimethoxyphenyl)-4H-1,2,4-tiazol-3-yl)-1-methoxypropane-2-sulfonamide. |
| 118.0 | (2S,3R)-3-(5-chloropyrimidin-2-yl)butane-2-sulfonamide (Example 81.4), 3-(propan-2-yloxy) propanehydrazide (commercially available from Aurora Fine Chemicals LLC), and 2-isothiocyanato-1,3-dimethoxybenzene (Example 82.0). | 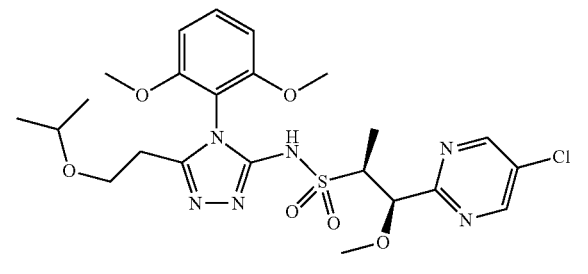 [SMILES: COc1cccc(OC)c1-n1c(CCOC(C)C)nnc1NS(=O)(=O)[C@@H](C)[C@H](OC)c1ncc(Cl)cn1]<br>(1R,2S)-1-(5-chloropyrimidin-2-yl)-N-(4-(2,6-dimethoxyphenyl)-5-(2-isopropoxyethyl)-4H-1,2,4-triazol-3-yl)-1-methoxypropane-2-sulfonamide. |
| 119.0 | (2S,3R)-3-(5-chloropyrimidin-2-yl)butane-2-sulfonamide (Example 81.4), 3-cyanopropanoic acid (commercially available from Matrix Scientific), and 2-isothiocyanato-1,3-dimethoxybenzene (Example 82.0). | 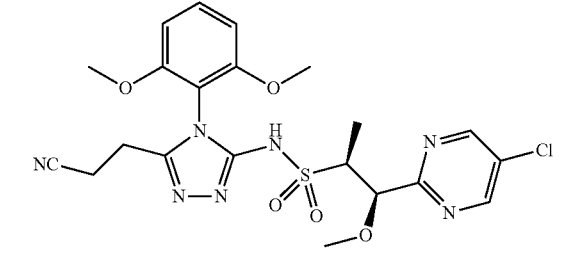 [SMILES: COc1cccc(OC)c1-n1c(CCC#N)nnc1NS(=O)(=O)[C@@H](C)[C@H](OC)c1ncc(Cl)cn1]<br>(1R,2S)-1-(5-chloropyrimidin-2-yl)-N-(5-(2-cyanoethyl)-4-(2,6-dimethoxyphenyl)-4H-1,2,4-triazol-3-yl)-1-methoxypropane-2-sulfonamide. |

TABLE 15-continued

| Example | Reagents | Structure, Name and Data |
|---|---|---|
| 120.0 | (2S,3R)-3-(5-chloropyrimidin-2-yl)butane-2-sulfonamide (Example 81.4), 3-cyanopropanoic acid (commercially available from Matrix Scientific), and 2-isothiocyanato-1,3-dimethoxybenzene (Example 82.0). | 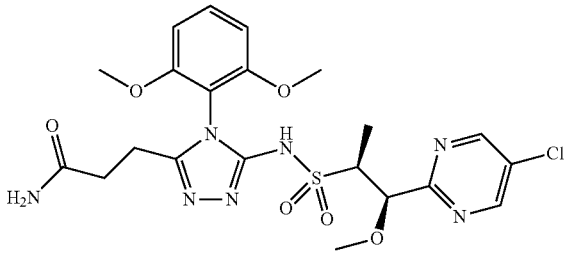 [SMILES: COc1cccc(OC)c1-n1c(CCC(N)=O)nnc1NS(=O)(=O)[C@@H](C)[C@H](OC)c1ncc(Cl)cn1]<br>3-(5-((1S,2R)-2-(5-chloropyrimidin-2-yl)-2-methoxy-1-methylethylsulfonamido)-4-(2,6-dimethoxyphenyl)-4H-1,2,4-triazol-3-yl)propanamide |
| 121.0 | (2S,3R)-3-(5-chloropyrimidin-2-yl)butane-2-sulfonamide (Example 81.4) 3-methylbutanohydrazide (commercially available from Matrix Scientific), and 2-isothiocyanato-1,3-dimethoxybenzene (Example 82.0). | 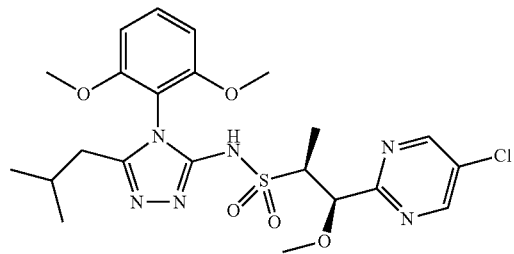 [SMILES: COc1cccc(OC)c1-n1c(CC(C)C)nnc1NS(=O)(=O)[C@@H](C)[C@H](OC)c1ncc(Cl)cn1]<br>(1R,2S)-1-(5-chloropyrimidin-2-yl)-N-(4-(2,6-dimethoxyphenyl)-5-isobutyl-4H-1,2,4-triazol-3-yl)-1-methoxypropane-2-sulfonamide. |
| 122.0 | (2S,3R)-3-(5-chloropyrimidin-2-yl)butane-2-sulfonamide (Example 81.4), 4,4-difluorobutanehydrazide (commercially available from DSK Biopharma, Inc.), and 2-isothiocyanato-1,3-dimethoxybenzene (Example 82.0). | 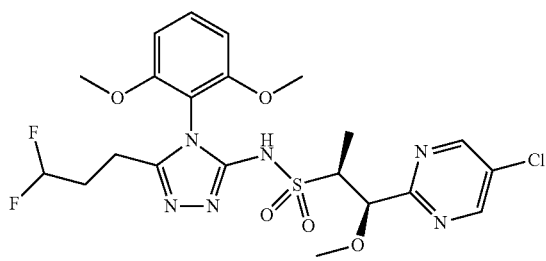 [SMILES: COc1cccc(OC)c1-n1c(CCC(F)F)nnc1NS(=O)(=O)[C@@H](C)[C@H](OC)c1ncc(Cl)cn1]<br>(1R,2S)-1-(5-chloropyrimidin-2-yl)-N-(5-(3,3-difluoropropyl)-4-(2,6-dimethoxyphenyl)-4H-1,2,4-triazol-3-yl)-1-methoxypropane-2-sulfonamide. |
| 123.0 | (2S,3R)-3-(5-chloropyrimidin-2-yl)butane-2-sulfonamide (Example 81.4), 3-hydroxypropanohydrazide, (commercially available from Enamine), and 2-isothiocyanato-1,3-dimethoxybenzene (Example 82.0). | 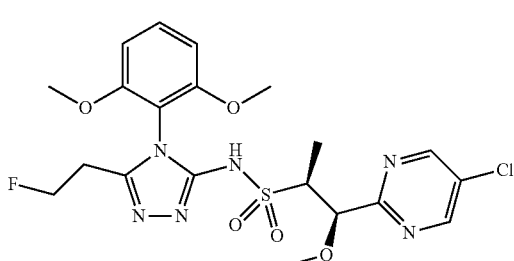<br>(1R,2S)-1-(5-chloropyrimidin-2-yl)-N-(4-(2,6-dimethoxyphenyl)-5-(2-fluoroethyl)-4H-1,2,4-triazol-3-yl)-1-methoxypropane-2-sulfonamide. |

Example 124.0. Preparation of (1R,2S)-1-(5-chloro-2-pyrimidinyl)-N-(4-(1,3-dimethoxy-2-propanyl)-5-(methoxymethyl)-4H-1,2,4-triazol-3-yl)-1-methoxy-2-propanesulfonamide

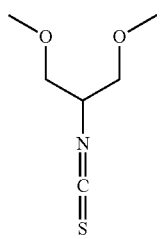

124.1

2-Isothiocyanato-1,3-dimethoxypropane, Example 124.1

To a dry 200 round-bottomed flask was added di(2-pyridyl) thionocarbonate (5.34 g, 23.00 mmol) in DCM (73.0 ml). 2-Amino-1,3-dimethoxypropane (commericially available from Combi-Blocks Inc., 2.61 g, 21.90 mmol) in DCM (15 mL) was then added dropwise via an addition funnel over 5 min at RT with stirring. The reaction mixture was stirred at RT for 3.5 h. The reaction mixture was then concentrated in vacuo. The product was absorbed onto a plug of silica gel and purified by chromatography through a Redi-Sep pre-packed silica gel column (40 g), eluting with a gradient of 0% to 50% EtOAc in heptane, to provide the title compound Example 124.1 (3.28 g, 20.34 mmol, 93% yield) as colorless oil. $^1$H NMR (400 MHz, CDCl$_3$) δ 3.95 (quin, J=5.49 Hz, 1H) 3.50-3.60 (m, 4H) 3.41 (s, 6H). LCMS (pos.) m/z: 162.2 (M+H)$^+$.

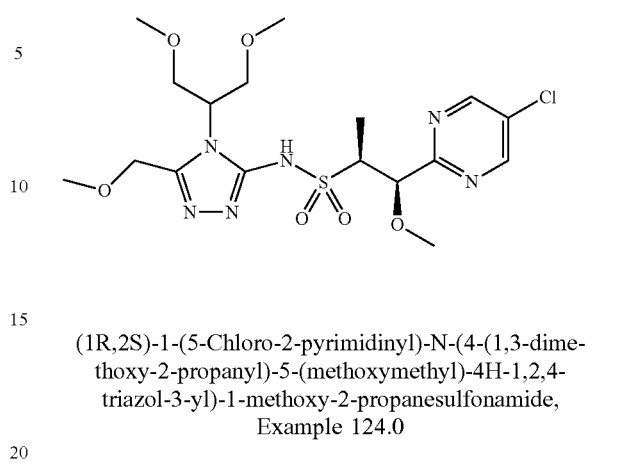

124.0

(1R,2S)-1-(5-Chloro-2-pyrimidinyl)-N-(4-(1,3-dimethoxy-2-propanyl)-5-(methoxymethyl)-4H-1,2,4-triazol-3-yl)-1-methoxy-2-propanesulfonamide, Example 124.0

The title compound was prepared from 2-isothiocyanato-1,3-dimethoxypropane, Example 124.1, methoxyacetic acid hydrazide (commercially available from CombiBlocks Inc.) and (1R,2S)-1-(5-chloropyrimidin-2-yl)-1-methoxypropane-2-sulfonamide, Example 83.3 following the procedure described in Example 14.0. $^1$H NMR (500 MHz, DMSO-d$_6$) δ 12.88 (br s, 1H) 8.94 (s, 2H) 4.92 (br d, J=3.89 Hz, 1H) 4.57 (br s, 1H) 4.35-4.52 (m, 2H) 3.87-4.02 (m, 2H) 3.61 (br dd, J=10.12, 5.19 Hz, 2H) 3.46 (br dd, J=6.88, 4.02 Hz, 1H) 3.31 (s, 3H) 3.23-3.29 (m, 6H) 3.07-3.18 (m, 3H) 2.50 (br s, 1H) 1.25 (br d, J=7.01 Hz, 3H). LCMS (pos.) m/z: 479.1 (M+H)$^+$.

Following the procedure in Example 14.0 the following compounds may be or were synthesized using the intermediates and conditions described in the following table.

TABLE 16

| | | |
|---|---|---|
| 125.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 2-methoxyethyl isothiocyanate (commercially available from Sigma Aldrich). | 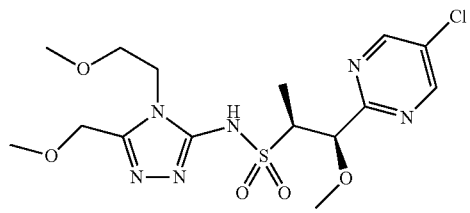 [SMILES: COCCn1c(COC)nnc1NS(=O)(=O)[C@@H](C)[C@H](OC)c1ncc(Cl)cn1]<br>(1R,2S)-1-(5-chloropyrimidin-2-yl)-1-methoxy-N-(4-(2-methoxyethyl)-5-(methoxymethyl)-4H-1,2,4-triazol-3-yl)propane-2-sulfonamide. |
| 126.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 1-isothiocyanato-1-(methoxymethyl)cyclopropane (Example 124.1) | 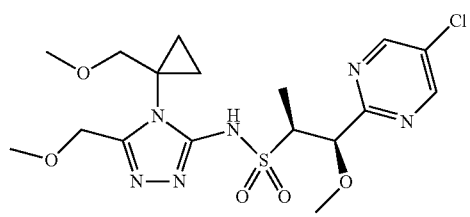 [SMILES: COCc1nnc(NS(=O)(=O)[C@@H](C)[C@H](OC)c2ncc(Cl)cn2)n1C1(COC)CC1]<br>(1R,2S)-1-(5-chloropyrimidin-2-yl)-1-methoxy-N-(5-(methoxymethyl)-4-(1-(methoxymethyl)cyclopropyl)-4H-1,2,4-triazol-3-yl)propane-2-sulfonamide. |

TABLE 16-continued

| 127.0 | (2S,3R)-3-(5-chloropyrimidin-2-yl)butane-2-sulfonamide (Example 81.4), 2-(difluoromethoxy)acetohydrazide hydrochloride (Example 65.2), and 5-isothiocyanato-4,6-dimethoxypyrimidine (Example 82.1). | 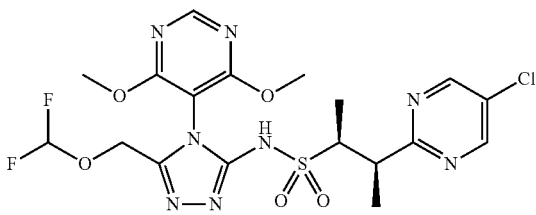 [SMILES: COc1ncnc(OC)c1-n1c(COC(F)F)nnc1NS(=O)(=O)[C@@H](C)[C@H](C)c1ncc(Cl)cn1]<br>(2S,3R)-3-(5-chloropyrimidin-2-yl)-N-(5-((difluoromethoxy)methyl)-4-(4,6-dimethoxypyrimidin-5-yl)-4H-1,2,4-triazol-3-yl)butane-2-sulfonamide.<br>$^1$H NMR (400 MHz, DMSO-$d_6$) δ 13.34 (s, 1H), 8.86 (s, 2H), 8.68 (s, 1H), 6.83-6.43 (m, 1H), 4.78 (s, 2H), 3.95-3.93 (m, 3H), 3.93-3.89 (m, 3H), 3.67-3.51 (m, 2H), 1.25 (d, J = 6.8 Hz, 3H), 1.12 (d, J = 6.8 Hz, 3H). LCMS (pos.) m/e: 535.1 (M + H)$^+$. |
|---|---|---|
| 128.0 | (1R,2S)-1-(5-chloropyrimidin-2-yl)-1-methoxypropane-2-sulfonamide (Example 83.3), 2-(difluoromethoxy)acetohydrazide hydrochloride (Example 65.2), and 5-isothiocyanato-4,6-dimethoxypyrimidine (Example 82.1). | 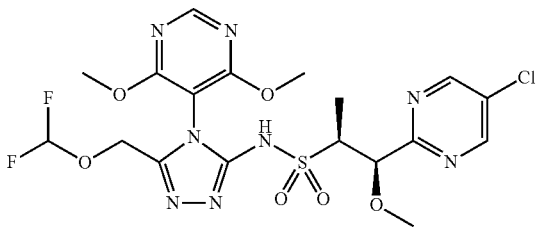 [SMILES: COc1ncnc(OC)c1-n1c(COC(F)F)nnc1NS(=O)(=O)[C@@H](C)[C@H](OC)c1ncc(Cl)cn1]<br>(1R,2S)-1-(5-chloropyrimidin-2-yl)-N-(5-((difluoromethoxy)methyl)-4-(4,6-dimethoxypyrimidin-5-yl)-4H-1,2,4-triazol-3-yl)-1-methoxypropane-2-sulfonamide.<br>$^1$H NMR (400 MHz, DMSO-$d_6$) δ 13.34 (s, 1H), 8.93 (s, 2H), 8.68 (s, 1H), 6.84-6.42 (m, 1H), 4.82-4.75 (m, 3H), 3.99-3.94 (m, 3H), 3.94-3.91 (m, 3H), 3.43 (dd, J = 3.9, 6.6 Hz, 1H), 3.16-3.11 (m, 3H), 1.17-1.12 (m, 3H). LCMS (pos.) m/e: 551.0 (M + H)$^+$. |

Example 129.0: Preparation of (1R,2S)-1-(5-chloro-2-pyrimidinyl)-N-(4-(2,6-dimethoxyphenyl)-5-(((~2-H_3_)methyloxy)methyl)-4H-1,2,4-triazol-3-yl)-1-methoxy-2-propanesulfonamide

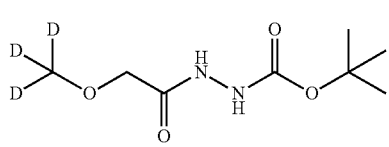

Example 129.1

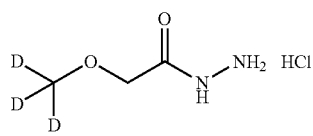

Example 129.2

A flask containing 2-methoxy-$D_3$-acetic acid (0.82 mL, 10.3 mmol) (CDN Isotopes) in anhydrous DCM (21 mL) was cooled in an ice bath. After 20 min, 1-(3-dimethylaminopropyl)-3-ethylcarbodiimide hydrochloride (2.03 g, 10.6 mmol) and then tert-butyl carbazate (1.42 g, 10.8 mmol) were carefully added in portions to the homogeneous solution. Upon complete addition of tert-butyl carbazate, the homogeneous solution was allowed to warm to RT and was monitored with LC-MS. After 22 h, the reaction was carefully quenched with water and then extracted three times with DCM. The organic layers were pooled and then washed once with brine. The organic layer was dried over anhydrous magnesium sulfate, filtered, and concentrated under reduced pressure. The colorless residue was identified as Example 129.1 and was used without further purification. LCMS (pos.) m/z: 206.4 (M–H)$^-$.

A flask containing Example 129.1 (2.1 g, 10.13 mmol) in EtOH (10 mL) was cooled in an ice water bath. After 20 min, hydrogen chloride, 1.25 M in EtOH (41 mL, 51.2 mmol) was added carefully dropwise. Upon complete addition of acid, the mixture was allowed to warm to RT and monitored with LCMS. After 19 h, the reaction was diluted with EtOAc and then carefully concentrated under reduced pressure. The white solid was suspended in EtOAc. The subsequent white solid was filtered, identified as Example 129.2 (856 mg, 6.0 mmol, 59% yield) and used without purification. LCMS (pos.) m/e: 108.2 (M+H)*.

Following the procedure in Example 14.0 the following compounds were synthesized using the intermediates and conditions described in the following table.

TABLE 17

| | | |
|---|---|---|
| 129.0 | (1R,2S)-1-(5-chloropyrimidin-2-yl)-1-methoxypropane-2-sulfonamide (Example 83.3) Example 129.2, and 2-isothiocyanato-1,3-dimethoxybenzene (Example 82.0) | 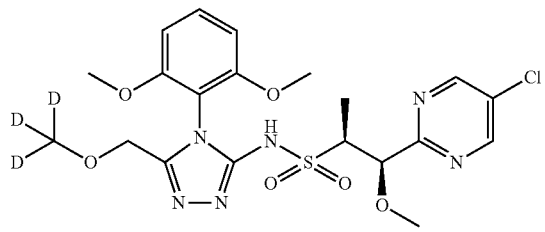<br>1R,2S)-1-(5-chloro-2-pyrimidinyl)-N-(4-(2,6-dimethoxyphenyl)-5-(((~2~H_3_)methyloxy)methyl)-4H-1,2,4-triazol-3-yl)-1-methoxy-2-propanesulfonamide.<br>$^1$H NMR (400 MHz, DMSO-$d_6$) δ 12.97 (s, 1H), 8.93 (s, 2H), 7.48 (t, J = 8.5 Hz, 1H), 6.84 (dd, J = 0.7, 8.6 Hz, 2H), 4.79 (d, J = 4.4 Hz, 1H), 4.12 (s, 2H), 3.76-3.74 (m, 3H), 3.74-3.72 (m, 3H), 3.41 (dq, J = 4.5, 6.9 Hz, 1H), 3.16-3.13 (m, 3H), 1.14 (d, J = 7.0 Hz, 3H). LCMS (pos.) m/e: 516.0 (M + H)$^+$. |
| 130.0 | (2S,3R)-3-(5-methoxypyrimidin-2-yl)butane-2-sulfonamide (Example 90.0), methoxyacetic acid hydrazide (commercially available from Combi-Blocks, Inc.), and 2-isothiocyanato-1,3-dimethoxybenzene (Example 82.0). | 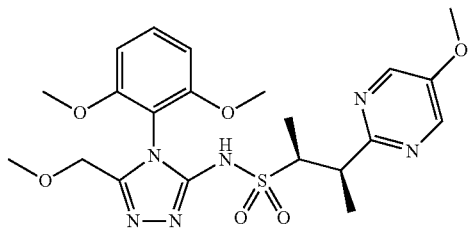<br>(2S,3R)-N-(4-(2,6-dimethoxyphenyl)-5-(methoxymethyl)-4H-1,2,4-triazol-3-yl)-3-(5-methoxypyrimidin-2-yl)butane-2-sulfonamide.<br>$^1$H NMR (400 MHz, DMSO-$d_6$) δ 12.98 (br s, 1H), 8.48 (s, 2H), 7.47 (t, J = 8.5 Hz, 1H), 6.82 (dd, J = 0.9, 8.6 Hz, 2H), 4.11 (s, 2H), 3.87 (s, 3H), 3.74-3.72 (m, 3H), 3.72 (s, 3H), 3.69-3.64 (m, 1H), 3.54 (dq, J = 3.3, 6.9 Hz, 1H), 3.08 (s, 3H), 1.23 (d, J = 7.0 Hz, 3H), 1.07 (d, J = 7.0 Hz, 3H). LCMS (pos.) m/e: 493.2 (M + H)$^+$. |
| 131.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 2 2,6-difluorophenyl isothiocyanate (commercially available from Sigma-Aldrich). | 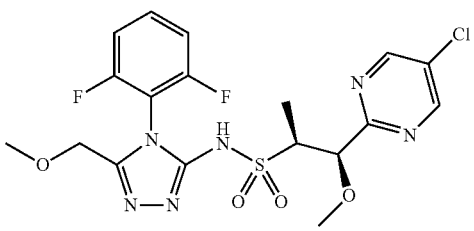<br>(1R,2S)-1-(5-chloropyrimidin-2-yl)-N-(4-(2,6-difluorophenyl)-5-(methoxymethyl)-4H-1,2,4-triazol-3-yl)-1-methoxypropane-2-sulfonamide.<br>$^1$H NMR (400 MHz, DMSO-$d_6$) δ 13.38 (s, 1H), 8.92 (s, 2H), 7.78-7.68 (m, 1H), 7.43 (t, J = 8.6 Hz, 2H), 4.82 (d, J = 3.9 Hz, 1H), 4.33 (s, 2H), 3.51-3.38 (m, 1H), 3.15-3.07 (m, 6H), 1.13 (d, J = 7.0 Hz, 3H). LCMS (pos.) m/e: 489.0 (M + H)$^+$. |

TABLE 17-continued

| 132.0 | (1R,2S)-1-(5-chloropyrimidin-2-yl)-1-methoxypropane-2-sulfonamide (Example 83.3), methoxyacetic acid hydrazide (commercially available from Combi-Blocks, Inc.), and 2-methoxyphenyl isothiocyanate (commercially available from Sigma Aldrich) | 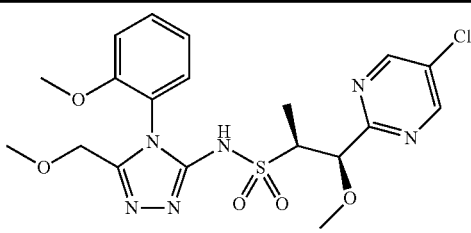 (1R,2S)-1-(5-chloropyrimidin-2-yl)-1-methoxy-N-(5-(methoxymethyl)-4-(2-methoxyphenyl)-4H-1,2,4-triazol-3-yl)propane-2-sulfonamide. <br> $^1$H NMR (400 MHz, DMSO-d$_6$) δ 13.17-12.91 (m, 1H), 9.00-8.85 (m, 2H), 7.57-7.49 (m, 1H), 7.41-7.33 (m, 1H), 7.29-7.21 (m, 1H), 7.16-7.06 (m, 1H), 4.88-4.77 (m, 1H), 4.29-4.19 (m, 1H), 4.18-4.10 (m, 1H), 3.81-3.72 (m, 3H), 3.49-3.34 (m, 1H), 3.18-3.04 (m, 6H), 1.20-1.09 (m, 3H). LCMS (pos.) m/e: 483.0 (M + H)$^+$. |
|---|---|---|
| 134.0 | (1S,2S)-1-(5-chloropyrimidin-2-yl)-1-isopropoxypropane-2-sulfonamide (Example 85.1), methoxyacetic acid hydrazide (commercially available from CombiBlocks Inc.), and 5-isothiocyanato-4,6-dimethoxypyrimidine (Example 82.1). | 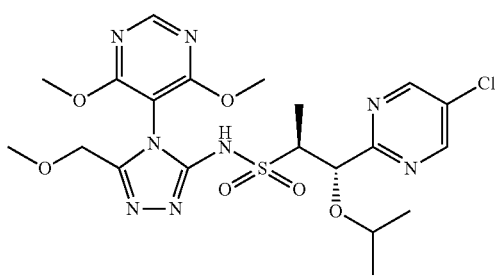 (1S,2S)-1-(5-chloropyrimidin-2-yl)-N-(4-(4,6-dimethoxypyrimidin-5-yl)-5-(methoxymethyl)-4H-1,2,4-triazol-3-yl)-1-isopropoxypropane-2-sulfonamide. <br> $^1$H NMR (400 MHz, DMSO-d$_6$) δ 13.07 (br s, 1H), 8.93 (s, 2H), 8.66 (s, 1H), 4.76 (d, J = 7.0 Hz, 1H), 4.25 (s, 2H), 3.99-3.97 (m, 3H), 3.97 (s, 3H), 3.49-3.37 (m, 2H), 3.12 (s, 3H), 0.99 (d, J = 2.5 Hz, 3H), 0.98-0.95 (m, 3H), 0.82 (d, J = 6.2 Hz, 3H). LCMS (pos.) m/e: 543.0 (M + H)$^+$. |

Example 135.0: Preparation of (1R,2S)-1-(5-chloro-2-pyrimidinyl)-N-(4-(4,6-dimethoxy-5-pyrimidinyl)-5-((2,2,2-trifluoroethoxy)methyl)-4H-1,2,4-triazol-3-yl)-1-methoxy-2-propanesulfonamide

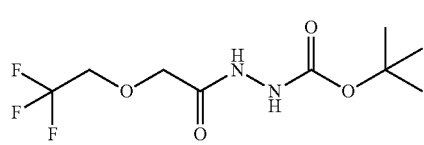

tert-Butyl 2-(2-(2,2,2-trifluoroethoxy)acetyl)hydrazinecarboxylate, Example 135.1

A flask containing potassium 2-(2,2,2-trifluoroethoxy)acetate (Enamine) (1.24 g, 6.3 mmol) in anhydrous DCM (12.5 mL) was cooled in an ice bath. After 20 min, N-(3-dimethylaminopropyl)-N'-ethylcarbodiimide hydrochloride (1.23 g, 6.4 mmol) and then tert-butyl carbazate (849 mg, 6.4 mmol) were carefully added in portions to the heterogeneous solution. Upon complete addition of tert-butyl carbazate, the heterogeneous solution was allowed to warm to RT and monitored with LC-MS. After 22 h, the reaction was carefully quenched with water and then extracted three times with DCM. The organic layers were pooled and then washed once with brine. The organic layer was dried over anhydrous magnesium sulfate and then filtered and concentrated under reduced pressure. The colorless residue was identified as tert-butyl 2-(2-(2,2,2-trifluoroethoxy)acetyl) hydrazinecarboxylate, Example 135.1 (1.7 g, 6.2 mmol, 99% yield) and was used without further purification. LCMS (pos.) m/e: 271.2 (M−H)$^-$.

213

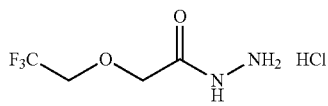

135.2

2-(2,2,2-Trifluoroethoxy)acetohydrazide hydrochloride, Example 135.2

A flask containing tert-butyl 2-(2-(2,2,2-trifluoroethoxy)acetyl)hydrazinecarboxylate, Example 135.1 (1.7 g, 6.24 mmol) in EtOH (6.3 mL) was cooled in an ice water bath. After 20 min, hydrogen chloride, 1.25M in EtOH (26 mL, 32.5 mmol) was added carefully dropwise. Upon complete addition of acid, the mixture was allowed to warm to RT and monitored with LCMS. After 19 h, the reaction was diluted with EtOAc and then carefully concentrated under reduced pressure. The sticky gum was identified as 2-(2,2,2-trifluoroethoxy)acetohydrazide hydrochloride, Example 135.2 (1 g, 4.79 mmol, 77% yield) which was used without purification. LCMS (pos.) m/e: 174.2 (M+H)$^+$.

Following the procedure in Example 48.0 the following compounds may be synthesized using the intermediates and conditions described in the following table.

214

Example 136.0: Preparation of 2,2-difluoro-2-(pyridin-2-yl)acetohydrazide

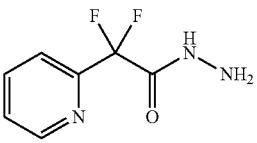

136.1

2,2-Difluoro-2-(pyridin-2-yl)acetohydrazide, Example 136.1

To a solution of difluoro(pyridin-2-yl)acetic acid (1 g, 5.78 mmol) in MeOH (11.55 ml) was added sulfuric acid (0.031 mL, 0.578 mmol). The reaction mixture was then heated to reflux for 4 hrs. The mixture was cooled to RT, concentrated in vacuo and dissolved in DCM. The organic layers were washed with NaHCO$_3$, extracted with DCM, dried over Na$_2$SO$_4$ and concentrated in vacuo to yield methyl 2,2-difluoro-2-(pyridin-2-yl)acetate that was carried forward directly. The methyl 2,2-difluoro-2-(pyridin-2-yl)acetate thus obtained was dissolved in MeOH (7.77 mL) and

TABLE 18

| | | |
|---|---|---|
| 135.0 (1R,2S)-1-(5-chloropyrimidin-2-yl)-1-methoxypropane-2-sulfonamide (Example 83.3), 2-(2,2,2-trifluoroethoxy)acetohydrazide hydrochloride (Example 135.2), and 5-isothiocyanato-4,6-dimethoxypyrimidine (Example 82.1). | 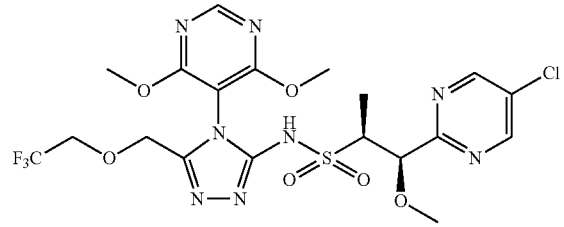 | (1R,2S)-1-(5-chloropyrimidin-2-yl)-N-(4-(4,6-dimethoxypyrimidin-5-yl)-5-((2,2,2-trifluoroethoxy)methyl)-4H-1,2,4-triazol-3-yl)-1-methoxypropane-2-sulfonamide.<br>$^1$H NMR (400 MHz, DMSO-d$_6$) δ 13.28 (s, 1H), 8.94 (s, 2H), 8.67 (s, 1H), 4.79 (d, J = 3.9 Hz, 1H), 4.53 (s, 2H), 4.04-3.96 (m, 2H), 3.96-3.93 (m, 3H), 3.93-3.91 (m, 3H), 3.43 dd, J = 3.9, 6.6 Hz, 1H), 3.14 (s, 3H), 1.15 (d, J = 6.8 Hz, 3H). LCMS (pos.) m/e: 583.0 (M + H)$^+$. |
| 139.0 (1R,2S)-1-(5-chloropyrimidin-2-yl)-1-methoxypropane-2-sulfonamide (Example 83.3), 3,3,3-trifluoropropanehydrazide (commercially available from Enamine), and 4-isothiocyanato-oxane (commercially available from Oakwood Products, Inc.). | 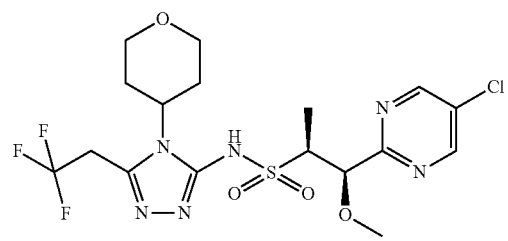 | (1R,2S)-1-(5-chloropyrimidin-2-yl)-1-methoxy-N-(4-(tetrahydro-2H-pyran-4-yl)-5-(2,2,2-trifluoroethyl)-4H-1,2,4-triazol-3-yl)propane-2-sulfonamide.<br>$^1$H NMR (500 MHz, CD$_2$Cl$_2$) δ 11.10 (br s, 1H), 8.73 (s, 2H), 5.03 (d, J = 3.4 Hz, 1H), 4.16-4.07 (m, 3H), 3.70-3.63 (m, 2H), 3.62-3.56 (m, 1H), 3.44 (dt, J = 1.6, 12.1 Hz, 2H), 3.26 (s, 3H), 2.81 (dq, J = 4.7, 12.6 Hz, 2H), 2.56 (s, 1H), 1.72-1.67 (m, 1H), 1.34 (d, J = 7.0 Hz, 3H). LCMS (pos.) m/e: 499.0 (M + H)$^+$. | hydrazine, monohydrate (0.499 ml, 10.26 mmol), and the reaction was heated to reflux. After 1 hr, the reaction showed complete conversion to product by LCMS. The reaction was cooled to RT and EtOAc was added. The resulting mixture was stirred for 30 min. The mixture was then concentrated in vacuo to yield 2,2-difluoro-2-(pyridin-2-yl)acetohydrazide (0.93 g, 4.97 mmol, 86%). LCMS-ESI (POS.) m/z: 188.2 (M+H)$^+$. The material was carried forward without purification.

The compounds set forth in the following table were synthesized following the procedure in Example 48.0 using the known starting material as described.

TABLE 19

| | | |
|---|---|---|
| 136.0 | (2S,3R)-3-(5-chloropyrimidin-2-yl)butane-2-sulfonamide (Example 81.4), 2,2-difluoro-2-(pyridin-2-yl)acetohydrazide (Example 136.1), and isothiocyanato-1,3-dimethoxybenzene (Example 82.0). | 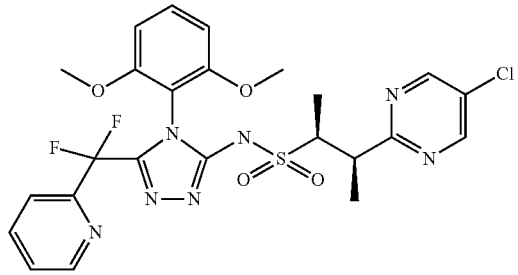<br>(2S,3R)-3-(5-chloropyrimidin-2-yl)-N-(5-(difluoro(pyridin-2-yl)methyl)-4-(2,6-dimethoxyphenyl)-4H-1,2,4-triazol-3-yl)butane-2-sulfonamide.<br>$^1$H NMR (500 MHz, CDCl$_3$) δ 11.06-11.18 (m, 1H) 8.67-8.73 (m, 1H) 8.57-8.63 (m, 2H) 7.68-7.76 (m, 1H) 7.37-7.43 (m, 1H) 7.31-7.37 (m, 2H) 6.43-6.54 (m, 2H) 3.79-3.85 (m, 1H) 3.71-3.76 (m, 1H) 3.59-3.67 (m, 6 H) 1.31-1.35 (m, 4H) 1.23-1.28 (m, 3H). LCMS-ESI (pos.) m/z: 580.2 (M + H)$^+$. |
| 137.0 | (2S,3R)-3-(5-methylpyrimidin-2-yl)butane-2-sulfonamide (Example 81.0), 2-2,2-difluoro-2-(pyridin-2-yl)acetohydrazide (Example 136.1), and isothiocyanato-1,3-dimethoxybenzene (Example 82.0). | 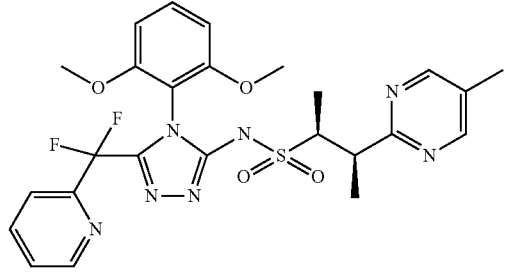<br>(2S,3R)-N-(5-(difluoro(pyridin-2-yl)methyl)-4-(2,6-dimethoxyphenyl)-4H-1,2,4-triazol-3-yl)-3-(5-methylpyrimidin-2-yl)butane-2-sulfonamide<br>$^1$H NMR (500 MHz, CDCl$_3$) δ 11.42-11.63 (m, 1H) 8.62-8.72 (m, 1H) 8.45-8.53 (m, 2H) 7.62-7.74 (m, 1H) 7.36-7.41 (m, 1H) 7.29-7.35 (m, 2H) 6.42-6.50 (m, 2H) 3.80-3.86 (m, 1H) 3.71-3.74 (m, 1H) 3.56-3.65 (m, 6H) 2.23-2.29 (m, 3H) 1.31-1.36 (m, 3H) 1.26-1.30 (m, 3H). LCMS-ESI (pos.) m/z: 560.2 (M + H)$^+$. |

The compounds set forth in the following table were synthesized following the procedure in Example 14.0 using the known starting material as described.

TABLE 20

| 138.0 | ((2S,3R)-3-(5-methylpyrimidin-2-yl)butane-2-sulfonamide (Example 81.0), 2-methyl-2-phenylpropanehydrazide (commercially avilable from Frontier Scientific Services Inc.), and isothiocyanato-1,3-dimethoxybenzene (Example 82.0). | 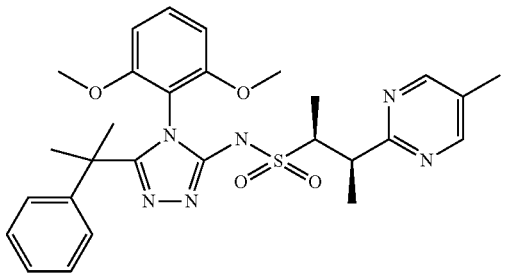 |
| --- | --- | --- |
| | | (2S,3R)-N-(4-(2,6-dimethoxyphenyl)-5-(2-phenylpropan-2-yl)-4H-1,2,4-triazol-3-yl)-3-(5-methylpyrimidin-2-yl)butane-2-sulfonamide. $^1$H NMR (500 MHz, DMSO-d6) δ 12.83 (br s, 1H) 8.53-8.59 (m, 1H) 8.57 (s, 1H) 7.26-7.33 (m, 1H) 7.12-7.19 (m, 3H) 6.92-6.98 (m, 2H) 6.48 (br t, J = 7.6 Hz, 2H) 3.57-3.64 (m, 1H) 3.44-3.51 (m, 1H) 3.32-3.37 (m, 6H) 2.19-2.25 (m, 3H) 1.13-1.18 (m, 3H) 0.96-1.02 (m, 3H). LCMS-ESI (pos.) m/z: 551.2 (M + H)$^+$. |

Example 140.0. Preparation of (1R,2S)-1-(5-chloropyrimidin-2-yl)-1-methoxy-N-(5-(methoxymethyl)-4-(1-(pyridin-3-yl)cyclopropyl)-4H-1,2,4-triazol-3-yl)propane-2-sulfonamide 140.1

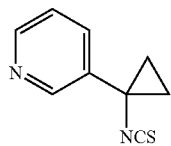

3-(1-isothiocyanatocyclopropyl)pyridine, Example 140.1

To a flask containing 1-pyridin-3-yl-cyclopropylamine bis(4-nitrobenzoate) (commercially available from Chem-Ipex International, Inc.) (2.09 g, 4.46 mmol) in anhydrous DCM (17 mL) was added N,N-diisopropylethylamine (1.7 mL, 9.7 mmol) dropwise at RT. After 15 min, 1,1"-thiocarbonyldi-2(1H)-pyridone (1.04 g, 4.5 mmol) was added carefully in portions to the reaction mixture which was then monitored by LC-MS. After 1 h, the reaction mixture was concentrated under reduced pressure to a volume 1 mL and then loaded onto a silica gel column (15-65% EtOAc in heptane). Fractions containing desired product were combined and then concentrated under reduced pressure to afford 3-(1-isothiocyanatocyclopropyl)pyridine (Example 140.1) (464 mg, 2.6 mmol, 59%) as a colorless liquid as that was used without further purification. LCMS (pos.) m/z: 177.0 (M+H)$^+$.

The compounds set forth in the following table were synthesized following the procedure in Example 14.0 using the known starting material as described.

TABLE 21

| 140.0 | (1R,2S)-1-(5-chloropyrimidin-2-yl)-1-methoxypropane-2-sulfonamide (Example 83.3), methoxyacetic acid hydrazide (commercially available from CombiBlocks Inc.), and 3-(1-isothiocyanatocyclopropyl)pyridine (Example 140.1). | 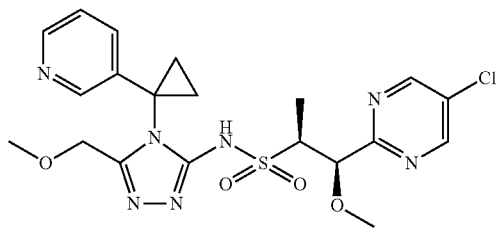 |
| --- | --- | --- |
| | | (1R,2S)-1-(5-chloropyrimidin-2-yl)-1-methoxy-N-(5-(methoxymethyl)-4-(1-(pyridin-3-yl)cyclopropyl)-4H-1,2,4-triazol-3-yl)propane-2-sulfonamide. $^1$H NMR (400 MHz, DMSO-d$_6$) δ 12.98 (br s, 1H), 8.93 (s, 2H), 8.43 (dd, J = 1.6, 4.7 Hz, 1H), 8.29 (d, J = 2.3 Hz, 1H), 7.49 (td, J = 1.8, 8.3 Hz, 1H), 7.32 (dd, J = 4.8, 8.1 Hz, 1H), 4.89 (d, J = 3.7 Hz, 1H), 4.47 (br s, 1H), 3.47-3.38 (m, 1H), 3.14 (s, 3H), 3.13-3.02 (m, 3H), 1.88-1.75 (m, 2H), 1.65 (br s, 2H), 1.19 (d, J = 7.0 Hz, 3H). LCMS (pos.) m/e: 494.0 (M + H)$^+$. |

Example 141.0: Preparation of (2S,3R)-3-(5-chloro-2-pyrimidinyl)-N-(4-(2,6-dimethoxyphenyl)-5-(4-pyridinylmethyl)-4H-1,2,4-triazol-3-yl)-2-butanesulfonamide

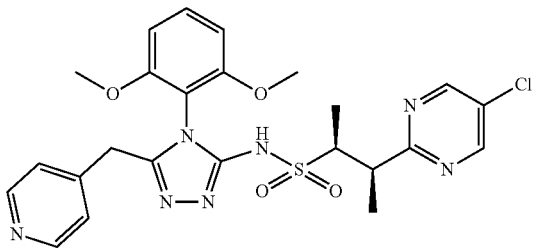

(2S,3R)-3-(5-Chloro-2-pyrimidinyl)-N-(4-(2,6-dimethoxyphenyl)-5-(4-pyridinylmethyl)-4H-1,2,4-triazol-3-yl)-2-butanesulfonamide, Example 141.0

The title compound was prepared from (2S,3R)-3-(5-chloropyrimidin-2-yl)butane-2-sulfonamide, Example 81.4, 2-isothiocyanato-1,3-dimethoxybenzene, Example 82.0 and 2-(pyridin-4-yl)acetohydrazide (commercially available from FSSI) following the precedure as described in Example 14.0. $^1$H NMR (500 MHz, CD$_3$OD) δ 8.72 (s, 2H) 8.60-8.66 (m, 2H) 7.58 (d, J=6.63 Hz, 2H) 7.44-7.54 (m, 1H) 6.73 (dd, J=8.60, 3.63 Hz, 2H) 4.08 (s, 2H) 3.63-3.78 (m, 8H) 1.32 (d, J=6.84 Hz, 3H) 1.27 (d, J=6.84 Hz, 3H). LCMS (pos.) m/z: 544.1 (M+H)$^+$.

Example 88.8: Preparation of (1R,2R)-1-hydroxy-N,N-bis(4-methoxybenzyl)-1-(5-methylpyrimidin-2-yl)propane-2-sulfonamide

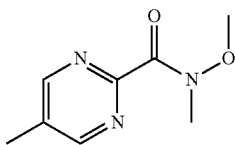

N-Methoxy-N,5-dimethylpyrimidine-2-carboxamide, Example 142.1

To a solution of 5-methylpyrimidine-2-carboxylic acid (1 g, 7.24 mmol) in DMF (72.4 ml) was added 5-methylpyrimidine-2-carboxylic acid (1 g, 7.24 mmol), and N,O-dimethylhydroxylamine hydrochloride (0.777 g, 7.96 mmol). The mixture was cooled to 0° C. and 1-propanephosphonic acid cyclic anhydride, 50 wt. % solution in EtOAc (9.21 ml, 14.48 mmol) was added droppwise. The mixture was allowed to warm to RT overnight. LCMS indicated complete conversion to product. The mixture was diluted with water, extracted with CHCl$_3$:IPA (3:1) and washed with brine and NaHCO$_3$. The mixture was dried over Na$_2$SO$_4$, concentrated in vacuo and purified by silica gel chromatography (0-100% heptanes:EtOAc) to yield N-methoxy-N,5-dimethylpyrimidine-2-carboxamide (0.7 g, 3.86 mmol, 53.4% yield). $^1$H NMR (500 MHz, CDCl$_3$) δ 8.61-8.69 (m, 2H) 3.61-3.79 (m, 3H) 3.27-3.47 (m, 3H) 2.34-2.45 (m, 3H). LCMS-ESI (pos.) m/z: 182.2 (M+H)$^+$.

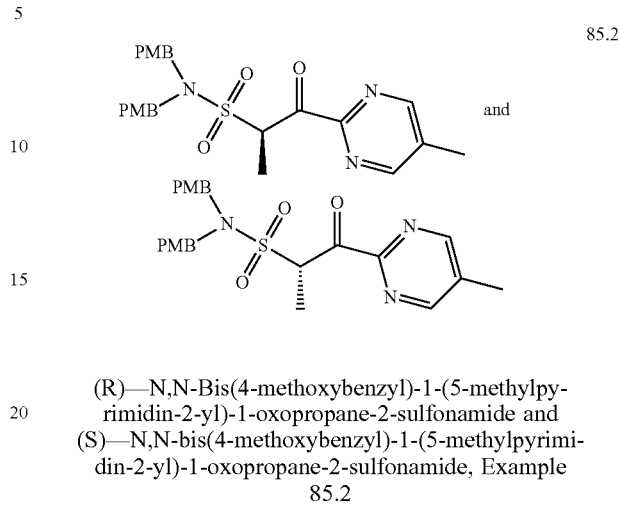

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 85.2

A solution of N,N-bis(4-methoxybenzyl)ethanesulfonamide (azeotroped three times with toluene before use) (Example 84.0, 0.771 g, 2.21 mmol) was dissolved in THF (3.68 ml) and then cooled to −78° C. using a dry ice acetone bath (internal reaction temperature/bath temperature not monitiored). To this was added a solution of n-butyllithium (0.883 ml, 2.21 mmol, 2.5 M in hexanes). The reaction turned pink immediately and then slowly faded to yellow upon stirring at ~78° C. for 30 mins. This solution was then added quickly to a solution of N-methoxy-N,5-dimethylpyrimidine-2-carboxamide (Example 142.1, 0.2 g, 1.104 mmol) in THF (0.5 mL) at RT. The reaction was stirred at RT for ~20 mins after which LCMS indicated complete consumption of Weinreb amide and conversion to product. The reaction was quenched by addition to separation funnel that contained 1M HCl (~15 mL). The mixture was extracted with DCM, (aqueous layer was checked for product by LCMS) dried over Na$_2$SO$_4$ and concentrated in vacuo. The mixture was purified by silica gel chromatography 0-100% EtOAc:heptanes to yield N,N-bis(4-methoxybenzyl)-1-(5-methylpyrimidin-2-yl)-1-oxopropane-2-sulfonamide (0.36 g, 0.767 mmol, 69.5% yield) $^1$H NMR (500 MHz, DMSO-d$_6$) δ 8.86-8.93 (m, 2H) 7.06-7.15 (m, 4H) 6.79-6.87 (m, 4H) 5.87-5.95 (m, 1H) 4.20-4.34 (m, 4H) 3.67-3.73 (m, 6H) 2.38-2.42 (m, 3H) 1.46-1.55 (m, 3H). LCMS-ESI (pos.) m/z: 470.0 (M+H)$^+$.

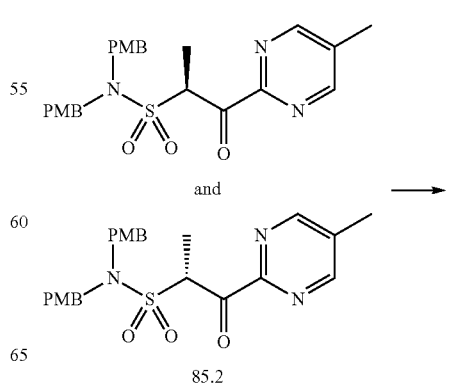

-continued

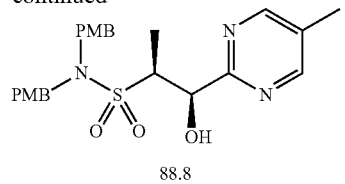

88.8

(1R,2R)-1-hydroxy-N,N-bis(4-methoxybenzyl)-1-(5-methylpyrimidin-2-yl)propane-2-sulfonamide, Example 88.8

To a solution of Example 85.2 (1.0 g, 2.130 mmol) in N,N-dimethylformamide (22.18 ml) was added (N-((1S,2S)-1,2-diphenyl-2-((3-phenylpropyl)amino)ethyl)-4-methylphenylsulfonamido)ruthenium(II) chloride (9.91 mg, 0.016 mmol). The mixture was then degassed by placing under vacuum and backfilling with $N_2$ three times. To this was added a solution of $HCOOH:Et_3N$ (5:2 v/v) (0.55 mL) and the reaction stirred at RT for 12 hrs after which LCMS indicated complete conversion to product and 7:1 d.r. (syn: anti). The mixture was then washed with 5% LiCl (aq), extracted with DCM then $CHCl_3$:IPA (3:1). The aqueous layer was checked for product by LCMS. The organics where dried over $Na_2SO_4$ and concentrated in vacuo. The mixture was loaded directly on to a silica gel column and purified using a gradient of 0-100% Heptanes:EtOAc. DMF caused both syn and anti to co-elute. The factions were combined and concentrated. The mixture was repurified using the same gradient to yield (1R,2R)-1-hydroxy-N,N-bis(4-methoxybenzyl)-1-(5-methylpyrimidin-2-yl)propane-2-sulfonamide (0.77 g, 1.63 mmol, 77% yield) as an off white solid. $^1$H NMR (500 MHz, DMSO-$d_6$) δ 8.85-8.93 (m, 2H) 7.08-7.15 (m, 4H) 6.78-6.86 (m, 4H) 5.86-5.96 (m, 1H) 4.20-4.35 (m, 4H) 3.68-3.75 (m, 6H) 3.28-3.34 (m, 2H) 2.37-2.42 (m, 3H) 1.47-1.54 (m, 3H). LCMS-ESI (pos.) m/z: 572.2 (M+H)$^+$

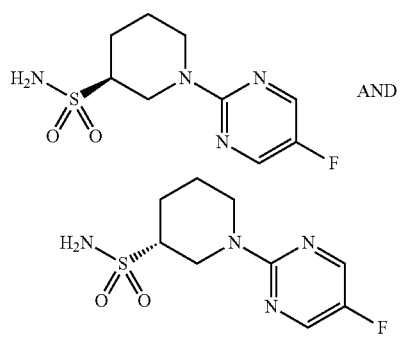

143.1

(R)-1-(5-fluoropyrimidin-2-yl)piperidine-3-sulfonamide and (S)-1-(5-fluoropyrimidin-2-yl)piperidine-3-sulfonamide, Example 143.1

To a 50-mL vial was added Example 92.1 (200 mg, 1.0 mmol) and 2-chloro-5-fluoro-pyrimidine (Matrix Scientific, SC, USA, 0.66 mL, 4.98 mmol) in DMSO (5 mL). Hunig's base (0.87 mL, 4.98 mmol) was added and the reaction mixture was stirred at 100° C. for 2 h. LCMS analysis indicated the reaction was complete. The reaction mixture was allowed to cool to RT. The reaction mixture was diluted with water and extracted with DCM. The organic extract was washed with brine and dried over $Na_2SO_4$. The solution was filtered and concentrated in vacuo to give a light-yellow glass, which was triturated with i-PrOH to afford Example 143.1 (240 mg, 93% yield) as an off-white solid. $^1$H NMR (500 MHz, CDCl$_3$) δ 8.21 (s, 2H) 4.98-5.07 (m, 1H) 4.76 (s, 2H) 4.49-4.59 (m, 1H) 3.31 (dd, J=12.96, 10.27 Hz, 1H) 3.15 (tt, J=10.51, 3.91 Hz, 1H) 3.04 (ddd, J=13.69, 11.49, 2.69 Hz, 1H) 2.32-2.43 (m, 1H) 1.87-2.02 (m, 2H) 1.51-1.63 (m, 1H). LCMS-ESI (pos.), m/z: 261.2 (M+H)$^+$.

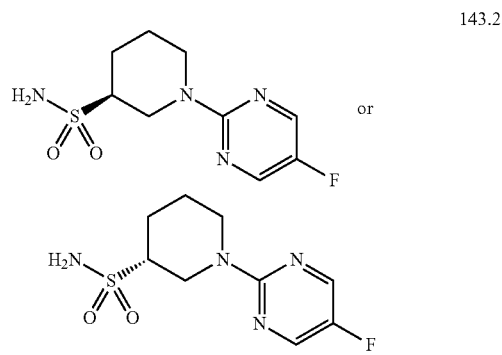

143.2

(R)-1-(5-fluoropyrimidin-2-yl)piperidine-3-sulfonamide or (S)-1-(5-fluoropyrimidin-2-yl)piperidine-3-sulfonamide, Example 143.2

The title compound Example 143.2 was prepared by chiral separation of Example 143.1 and was the first peak to elute from AD column under the condition described below: 250×30 mm AD column with 42 mL/min MeOH +(20 mM Ammonia)+78 g/min $CO_2$ on Thar 200 SFC. Outlet pressure=100 bar; Temp.=23° C.; Wavelength=242 nm. Using 2.0 mL injections of 240 mg/10 mL (24 mg/mL) sample solution in MeOH, i.e. 48 mg/injection. Runtime=9 min, Cycle time=6 min. [α]=+58.19° (CDCl$_3$, 23.1° C.). LCMS-ESI (pos.), m/z: 261.2 (M+H)$^+$.

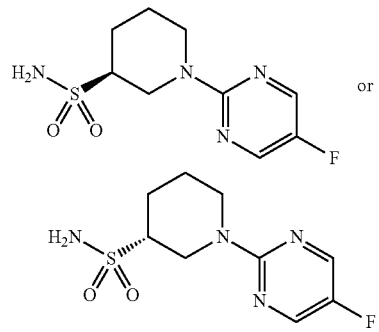

143.3

(R)-1-(5-fluoropyrimidin-2-yl)piperidine-3-sulfonamide or (S)-1-(5-fluoropyrimidin-2-yl)piperidine-3-sulfonamide, Example 143.3

The title compound Example 143.3 was prepared by chiral separation of Example 143.1 and was the second peak to elute from AD column under the condition described in Example 143.2. [α]=−58.34° (CDCl₃, 23.1° C.). LCMS-ESI (pos.), m/z: 261.2 (M+H)⁺.

The compounds in the following table were synthesized following the procedure in Example 21.0 using the known starting material as described.

TABLE 22

| Example | Reagents | Structure, Name and Data |
|---|---|---|
| 144.0 | 1R,2S)-1-(5-chloropyrimidin-2-yl)-1-methoxypropane-2-sulfonamide (Example 83.3), methoxyacetic acid hydrazide (commercially available from Combi-Blocks, Inc.), and 2-isothiocyanatopropane (commercially available from Sigma-Aldrich Inc.). | 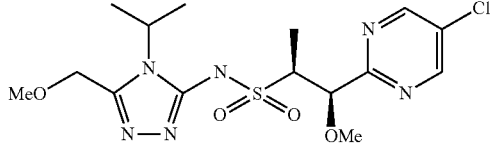<br>(1R,2S)-1-(5-chloropyrimidin-2-yl)-N-(4-isopropyl-5-(methoxymethyl)-4H-1,2,4-triazol-3-yl)-1-methoxypropane-2-sulfonamide.<br>¹H NMR (600 MHz, DMSO-d₆) δ 12.57-12.98 (m, 1H) 4.83-4.94 (m, 1H) 4.45-4.52 (m, 2H) 4.39-4.44 (m, 1H) 3.45-3.53 (m, 1H) 3.26-3.32 (m, 3H) 3.09-3.15 (m, 3H) 2.53-2.58 (m, 3H) 1.43-1.48 (m, 6H) 1.23-1.29 (m, 3H). LCMS-ESI (pos.) m/z: 419.2 (M + H)⁺. |
| 145.0 | 1R,2S)-1-(5-chloropyrimidin-2-yl)-1-methoxypropane-2-sulfonamide (Example 83.3), methoxyacetic acid hydrazide (commercially available from Combi-Blocks, Inc.), and 1-isothiocyanato-1-(methoxymethyl)cyclopropane) (prepared following Example 72.0 using 1-(methoxymethyl)cyclopropanamine (commercially available from J & W Pharm Lab)). | 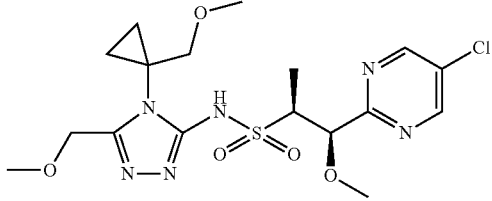<br>(1R,2S)-1-(5-chloropyrimidin-2-yl)-1-methoxy-N-(5-(methoxymethyl)-4-(1-(methoxymethyl)cyclopropyl)-4H-1,2,4-triazol-3-yl)propane-2-sulfonamide.<br>¹H NMR (500 MHz, CDCl₃) δ 1.05-1.17 (m, 2H) 1.22-1.33 (m, 2H) 1.42 (s, 5H) 3.29 (s, 6H) 3.41 (s, 3H) 3.69 (dd, J = 7.07, 3.70 Hz, 1H) 4.32-4.81 (m, 2H) 5.09 (d, J = 3.76 Hz, 1H) 8.73 (s, 2H) 10.83 (br s, 1H). LCMS-ESI (pos.) m/z: 461.0 (M + H)⁺. |
| 146.0 | (1R,2S)-1-(5-chloropyrimidin-2-yl)-1-methoxypropane-2-sulfonamide (Example 83.3), 3-methoxypropane-hydrazide (commercially available from FSSI), and 2-isothiocyanato-1,3-dimethoxy-propane (Example 124.1). | 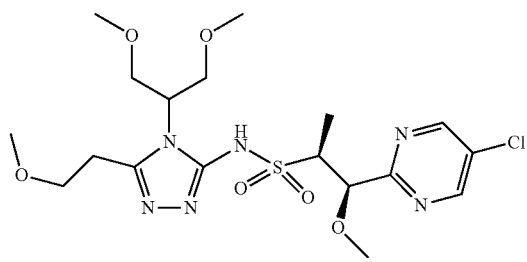<br>(1R,2S)-1-(5-chloro-2-pyrimidinyl)-N-(4-(1,3-dimethoxy-2-propanyl)-5-(2-methoxyethyl)-4H-1,2,4-triazol-3-yl)-1-methoxy-2-propanesulfonamide.<br>¹H NMR (600 MHz, DMSO-d₆) δ 8.95 (s, 2H) 4.91 (d, J = 3.89 Hz, 1H) 4.46 (br s, 1H) 3.86-4.05 (m, 2H) 3.56-3.66 (m, 4H) 3.42-3.52 (m, 1H) 3.25 (s, 3H) 3.24 (s, 3H) 3.24 (s, 3H) 3.13 (s, 3H) 2.85 (br t, J = 6.31 Hz, 2H) 1.23 (d, J = 7.01 Hz, 3H). LCMS-ESI (pos.) m/z: 493.2 (M + H)⁺. |

TABLE 22-continued

| Example | Reagents | Structure, Name and Data |
|---|---|---|
| 147.0 | (1R,2S)-1-(5-chloropyrimidin-2-yl)-1-methoxypropane-2-sulfonamide (Example 83.3), 2-methoxyacetohydrazide (commercially available from CombiBlocks Inc.), and 3-isothiocyanatopentane (commercially available from Oakwood Products, Inc.). | 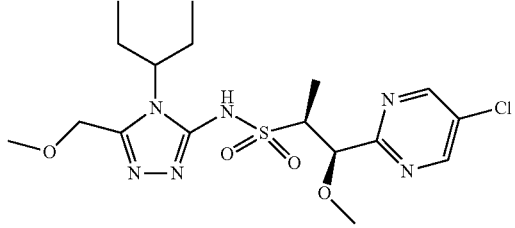(1R,2S)-1-(5-chloro-2-pyrimidinyl)-1-methoxy-N-(5-(methoxymethyl)-4-(3-pentanyl)-4H-1,2,4-triazol-3-yl)-2-propanesulfonamide. $^1$H NMR (500 MHz, CDCl$_3$) δ 11.02 (br s, 1H) 8.72 (s, 2 H) 5.04 (d, J = 4.28 Hz, 1H) 4.43 (s, 2H) 4.01 (br s, 1H) 3.70 (qd, J = 6.96, 4.41 Hz, 1H) 3.36 (s, 3H) 3.37 (s, 3H) 2.26 (br d, J = 4.28 Hz, 2H) 1.73-1.89 (m, 2H) 1.40 (d, J = 7.01 Hz, 3H) 0.87 (dt, J = 13.23, 7.40 Hz, 6H). LCMS-ESI (pos.) m/z: 447.0 (M + H)$^+$. |
| 151.0 | (2S,3R)-3-(5-chloropyrimidin-2-yl)butane-2-sulfonamide (Example 81.4), 2-(2-methoxyethoxy)acetohydrazide (commercially available from ChemShuttle), and 2-isothiocyanato-1,3-dimethoxybenzene (Example 82.0). | 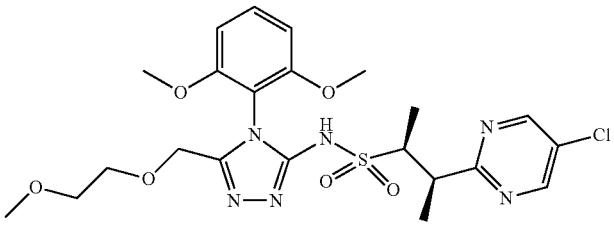(2S,3R)-3-(5-chloro-2-pyrimidinyl)-N-(4-(2,6-dimethoxyphenyl)-5-((2-methoxyethoxy)methyl)-4H-1,2,4-triazol-3-yl)-2-butanesulfonamide. $^1$H NMR (500 MHz, CDCl$_3$) δ 10.90 (br s, 1H) 8.63 (s, 2H) 7.40 (t, J = 8.56 Hz, 1H) 6.64 (dd, J = 8.50, 4.61 Hz, 2H) 4.34 (s, 2H) 3.76-3.86 (m, 8H) 3.50 (dd, J = 5.45, 3.63 Hz, 2H) 3.36-3.42 (m, 2H) 3.30 (s, 3H) 1.37 (d, J = 7.01 Hz, 3H) 1.33 (d, J = 6.88 Hz, 3H). LCMS-ESI (pos.) m/z: 541.0 (M + H)$^+$. |

The compounds in the following table were synthesized following the procedure in Example 85.0 using the known starting material as described.

TABLE 23

| Example | Reagents | Structure, Name and Data |
|---|---|---|
| 154.1 | 2-chloro-5-fluoro-pyrimidine | 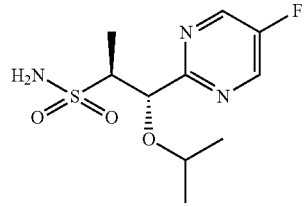(1S,2S)-1-(5-fluoropyrimidin-2-yl)-1-isopropoxypropane-2-sulfonamide. LCMS ESI (pos.) m/z: 278.2 (M + H)$^+$. |
| 155.1 | 2-chloro-5-methyl-pyridine | 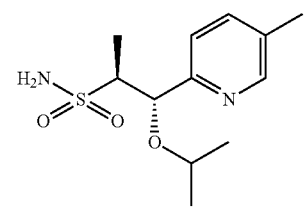(1S,2S)-1-isopropoxy-1-(5-methyl-pyridin-2-yl)propane-2-sulfonamide. LCMS ESI (pos.) m/z: 273.2 (M + H)$^+$. |

The compounds in the following table were synthesized following the procedure in Example 21.0 using the known starting material as described.

TABLE 24

| Example | Reagents | Structure, Name and Data |
|---|---|---|
| 152.0 | (1S,2S)-1-isopropoxy-1-(5-methylpyrimidin-2-yl)propane-2-sulfonamide (Example 85.0), Example 129.2), and 2-isothiocyanato-1,3-dimethoxybenzene (Example 82.0). | 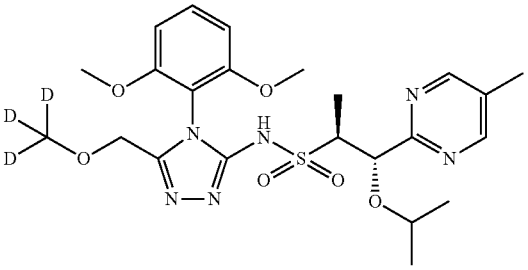<br>(1S,2S)-N-(4-(2,6-dimethoxyphenyl)-5-((trideuteromethyloxy)methyl)-4H-1,2,4-triazol-3-yl)-2-(5-methyl-2-pyrimidinyl)-1-(2-propanyloxy)-2-propanesulfonamide.<br>$^1$H NMR (400 MHz, DMSO-d$_6$) δ 12.97 (s, 1H), 8.65 (s, 2H), 7.47 (t, J = 8.5 Hz, 1H), 6.84 (d, J = 8.5 Hz, 2H), 4.70 (d, J = 7.3 Hz, 1H), 4.12 (s, 2H), 3.79 (s, 3H), 3.78-3.74 (m, 3H), 3.45-3.36 (m, 2H), 2.27 (s, 3H), 0.98 (d, J = 6.0 Hz, 3H), 0.92 (d, J = 7.0 Hz, 3H), 0.79 (d, J = 6.2 Hz, 3H). LCMS-ESI (pos): 524.3 (M + H)$^+$. |
| 153.0 | (1S,2S)-1-(5-chloro-pyrimidin-2-yl)-1-isopropoxypropane-2-sulfonamide (Example 85.1), Example 129.2, and 2-isothiocyanato-1,3-dimethoxybenzene (Example 82.0). | 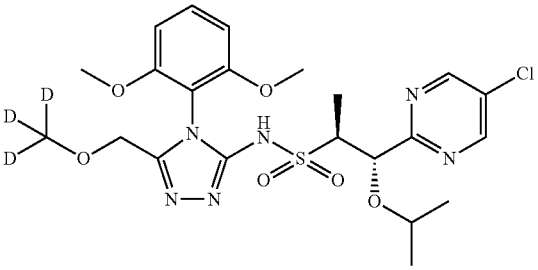<br>(1S,2S)-1-(5-chloro-2-pyrimidinyl)-N-(4-(2,6-dimethoxyphenyl)-5-((trideuteromethyloxy)methyl)-4H-1,2,4-triazol-3-yl)-1-(2-propanyloxy)-2-propanesulfonamide.<br>$^1$H NMR (400 MHz, DMSO-d$_6$) δ 12.88 (s, 1H), 8.92 (s, 2H), 7.48 (t, J = 8.5 Hz, 1H), 6.84 (d, J = 8.5 Hz, 2H), 4.78 (d, J = 6.8 Hz, 1H), 4.12 (s, 2H), 3.78 (s, 3H), 3.77-3.75 (m, 3H), 3.47-3.37 (m, 2H), 1.06-0.95 (m, 6H), 0.83 (d, J = 6.2 Hz, 3H). LCMS-ESI (pos): 544.2 (M + H)$^+$. |
| 154.0 | (1S,2S)-1-(5-fluoro-pyrimidin-2-yl)-1-isopropoxypropane-2-sulfonamide (Example 154.1), methoxyacetic acid hydrazide (commercially available from CombiBlocks Inc.), and 2-isothiocyanato-1,3-dimethoxybenzene (Example 82.0). | 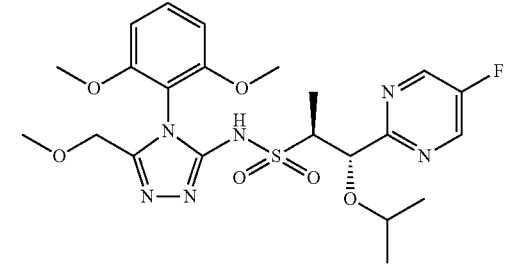<br>(1S,2S)-N-(4-(2,6-dimethoxyphenyl)-5-(methoxymethyl)-4H-1,2,4-triazol-3-yl)-1-(5-fluoro-2-pyrimidinyl)-1-(2-propanyloxy)-2-propanesulfonamide.<br>$^1$H NMR (400 MHz, DMSO-d$_6$) δ 12.89 (s, 1H), 8.87 (s, 2H), 7.47 (t, J = 8.5 Hz, 1H), 6.84 (d, J = 8.7 Hz, 2H), 4.81 (d, J = 7.0 Hz, 1H), 4.12 (s, 2H), 3.84-3.78 (m, 3H), 3.78-3.75 (m, 3H), 3.45-3.37 (m, 2H), 3.08 (s, 3H), 0.99 (d, J = 6.0 Hz, 3H), 0.97-0.92 (m, 3H), 0.81 (d, J = 6.2 Hz, 3H). LCMS-ESI (pos): 525.2 (M + H)$^+$. |

TABLE 24-continued

| Example | Reagents | Structure, Name and Data |
|---|---|---|
| 155.0 | (1S,2S)-1-isopropoxy-1-(5-methylpyridin-2-yl)propane-2-sulfonamide (Example 155.1), methoxyacetic acid hydrazide (commercially available from CombiBlocks Inc.), and 2-isothiocyanato-1,3-dimethoxybenzene (Example 82.0). | 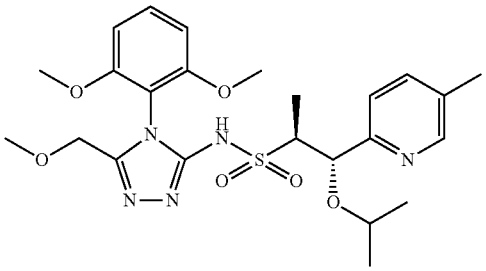<br>(1S,2S)-N-(4-(2,6-dimethoxyphenyl)-5-(methoxymethyl)-4H-1,2,4-triazol-3-yl)-1-(5-methyl-2-pyridinyl)-1-(2-propanyloxy)-2-propanesulfonamide.<br>$^1$H NMR (400 MHz, DMSO-d$_6$) δ 13.04 (br s, 1H), 8.35-8.31 (m, 1H), 7.58 (dd, J = 1.8, 8.0 Hz, 1H), 7.47 (t, J = 8.5 Hz, 1H), 7.26 (d, J = 8.1 Hz, 1H), 6.84 (d, J = 8.5 Hz, 2H), 4.63 (d, J = 7.0 Hz, 1H), 4.12 (s, 2H), 3.80-3.77 (m, 3H), 3.77-3.74 (m, 3H), 3.40-3.34 (m, 1H), 3.30-3.25 (m, 1H), 3.08 (s, 3H), 2.28 (s, 3H), 0.99 (d, J = 6.0 Hz, 3H), 0.86 (d, J = 7.3 Hz, 3H), 0.84-0.81 (m, 3H). LCMS-ESI (pos): 520.2 (M + H)$^+$. |
| 156.0 | (1R,2S)-1-(5-chloro-pyrimidin-2-yl)-1-methoxypropane-2-sulfonamide (Example 83.3), methoxyacetic acid hydrazide (commercially available from CombiBlocks Inc.), and 2-methoxyethyl isothiocyanate (commercially available from Sigma Aldrich). | 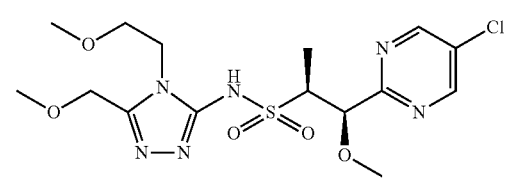<br>(1R,2S)-1-(5-chloro-2-pyrimidinyl)-1-methoxy-N-(4-(2-methoxyethyl)-5-(methoxymethyl)-4H-1,2,4-triazol-3-yl)-2-propanesulfonamide.<br>$^1$H NMR (400 MHz, DMSO-d$_6$) δ 12.92 (s, 1H), 8.91 (s, 2H), 4.85 (d, J = 4.6 Hz, 1H), 4.46 (s, 2H), 3.90-3.76 (m, 2H), 3.59-3.47 (m, 3H), 3.30-3.28 (m, 3H), 3.25 (s, 3H), 3.09 (s, 3H), 1.27 (d, J = 6.8 Hz, 3H). LCMS-ESI (pos): 435.2 (M + H)$^+$. |
| 157.0 | (1R,2S)-1-(5-chloro-pyrimidin-2-yl)-1-methoxypropane-2-sulfonamide (Example 83.3), methoxyacetic acid hydrazide (commercially available from CombiBlocks Inc.), and 1,3-dichloro-2-isothiocyanatobenzene (commercially available from Sigma Aldrich). | 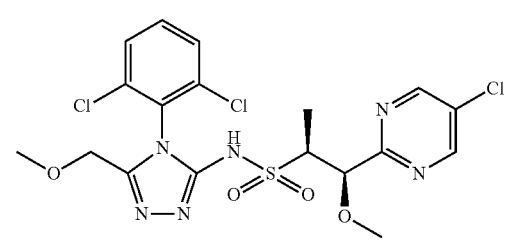<br>(1R,2S)-1-(5-chloro-2-pyrimidinyl)-N-(4-(2,6-dichlorophenyl)-5-(methoxymethyl)-4H-1,2,4-triazol-3-yl)-1-methoxy-2-propanesulfonamide.<br>$^1$H NMR (400 MHz, DMSO-d$_6$) δ 13.34 (s, 1H), 8.93 (s, 2H), 7.80-7.73 (m, 2H), 7.69-7.61 (m, 1H), 4.87 (d, J = 3.9 Hz, 1H), 4.24 (s, 2H), 3.55-3.37 (m, 1H), 3.17-3.14 (m, 3H), 3.13 (s, 3H), 1.16 (d, J = 6.8 Hz, 3H). LCMS-ESI (pos): 521.0 (M + H)$^+$. |

TABLE 24-continued

| Example | Reagents | Structure, Name and Data |
|---|---|---|
| 158.0 | (1R,2S)-1-(5-chloro-pyrimidin-2-yl)-1-methoxypropane-2-sulfonamide (Example 83.3), methoxyacetic acid hydrazide (commercially available from CombiBlocks Inc.), and 1-chloro-2-isothiocyanato-4-methoxybenzene (commercially available from Enamine). | 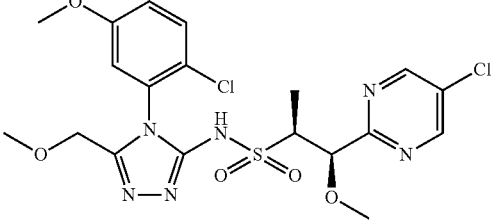<br>(1R,2S)-N-(4-(2-chloro-5-methoxyphenyl)-5-(methoxymethyl)-4H-1,2,4-triazol-3-yl)-1-(5-chloro-2-pyrimidinyl)-1-methoxy-2-propanesulfonamide.<br>$^1$H NMR (400 MHz, DMSO-d$_6$) δ 13.32-13.04 (m, 1H), 8.92 (s, 2H), 7.61 (dd, J = 8.9, 12.0 Hz, 1H), 7.37-7.23 (m, 1H), 7.22-7.14 (m, 1H), 4.91-4.83 (m, 1H), 4.38-4.29 (m, 1H), 4.22-4.15 (m, 1H), 3.84-3.78 (m, 3H), 3.52-3.42 (m, 1H), 3.18-3.12 (m, 6H), 1.22-1.14 (m, 3H). LCMS-ESI (pos): 516.9 (M + H). |
| 159.0 | (1R,2S)-1-(5-chloro-pyrimidin-2-yl)-1-methoxypropane-2-sulfonamide (Example 83.3), (Example 129.2), and 1-chloro-2-isothiocyanato-4-methoxybenzene (commercially available from Enamine). | 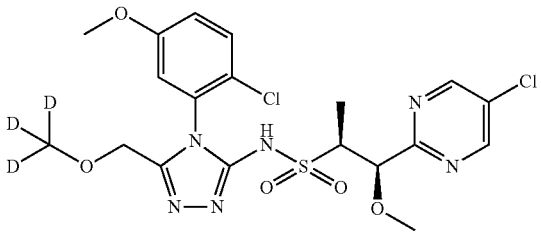<br>(1R,2S)-N-(4-(2-chloro-5-methoxyphenyl)-5-((trideuteromethyloxy)methyl)-4H-1,2,4-triazol-3-yl)-1-(5-chloro-2-pyrimidinyl)-1-methoxy-2-propanesulfonamide.<br>$^1$H NMR (400 MHz, DMSO-d$_6$) δ 13.32-13.03 (m, 1H), 8.93 (s, 2H), 7.61 (dd, J = 8.9, 12.0 Hz, 1H), 7.36-7.24 (m, 1H), 7.22-7.14 (m, 1H), 4.91-4.83 (m, 1H), 4.39-4.29 (m, 1H), 4.24-4.15 (m, 1H), 3.84-3.79 (m, 3H), 3.49-3.39 (m, 1H), 3.20-3.11 (m, 3H), 1.21-1.14 (m, 3H). LCMS-ESI (pos): 520.0 (M + H)$^+$. |
| 160.0 | (1R,2S)-1-(5-chloro-pyrimidin-2-yl)-1-methoxypropane-2-sulfonamide (Example 83.3), 2-(difluoromethoxy)acetohydrazide hydrochloride (Example 65.2), and 1-chloro-2-isothiocyanato-4-methoxybenzene (commercially available from Enamine). | 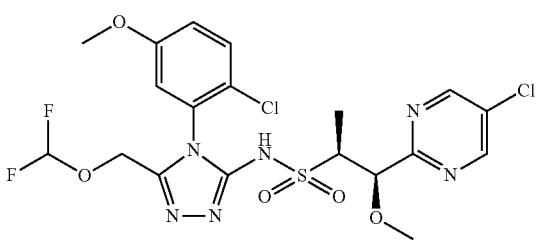<br>(1R,2S)-N-(4-(2-chloro-5-methoxyphenyl)-5-((difluoromethoxy)methyl)-4H-1,2,4-triazol-3-yl)-1-(5-chloro-2-pyrimidinyl)-1-methoxy-2-propanesulfonamide.<br>$^1$H NMR (400 MHz, DMSO-d$_6$) δ 13.44-13.11 (m, 1H), 8.97-8.90 (m, 2H), 7.62 (dd, J = 8.9, 11.2 Hz, 1H), 7.39-7.25 (m, 1H), 7.24-7.16 (m, 1H), 6.82-6.41 (m, 1H), 4.94-4.72 (m, 3H), 3.83-3.78 (m, 3H), 3.52-3.41 (m, 1H), 3.19-3.09 (m, 3H), 1.22-1.12 (m, 3H). LCMS-ESI (pos): 552.8 (M + H)$^+$. |

TABLE 24-continued

| Example | Reagents | Structure, Name and Data |
|---|---|---|
| 161.0 | (2S,3R)-3-(5-chloro-pyrimidin-2-yl)butane-2-sulfonamide, (Example 81.4), 2-isopropoxyaceto-hydrazide hydrochloride (commercially available from Matrix Scientific), and 2-isothiocyanato-1,3-dimethoxybenzene (Example 82.0). | 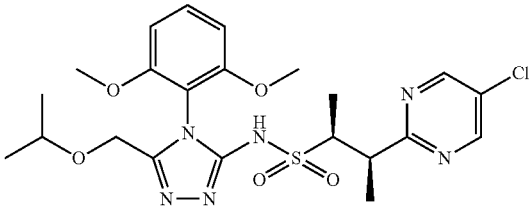<br>(2S,3R)-3-(5-chloro-2-pyrimidinyl)-N-(4-(2,6-dimethoxyphenyl)-5-((2-propanyloxy)methyl)-4H-1,2,4-triazol-3-yl)-2-butanesulfonamide.<br>$^1$H NMR (500 MHz, DMSO-$d_6$) δ 13.01-12.79 (m, 1H), 8.86 (s, 2H), 7.47 (t, J = 8.6 Hz, 1H), 6.82 (dd, J = 2.1, 8.6 Hz, 2H), 4.16-4.10 (m, 2H), 3.74-3.71 (m, 6H), 3.68-3.63 (m, 1H), 3.60-3.53 (m, 1H), 3.32-3.26 (m, 1H), 1.24 (d, J = 7.3 Hz, 3H), 1.11 (d, J = 7.0 Hz, 3H), 0.87-0.84 (m, 3H), 0.84-0.83 (m, 3H). LCMS-ESI (pos): 525.2 (M + H)$^+$. |
| 162.0 | (2S,3R)-3-(5-chloro-pyrimidin-2-yl)butane-2-sulfonamide, (Example 81.4), methoxyacetic acid hydrazide (commercially available from CombiBlocks Inc.), and 1-chloro-2-isothiocyanato-4-methoxybenzene (commercially available from Enamine). | 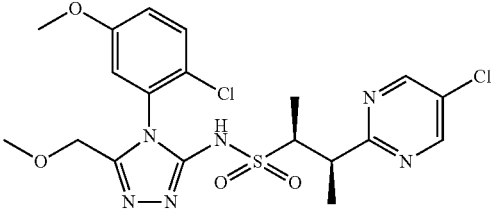<br>(2S,3R)-N-(4-(2-chloro-5-methoxyphenyl)-5-(methoxymethyl)-4H-1,2,4-triazol-3-yl)-3-(5-chloro-2-pyrimidinyl)-2-butanesulfonamide.<br>$^1$H NMR (500 MHz, DMSO-$d_6$) δ 13.11 (br s, 1H), 8.84 (d, J = 3.6 Hz, 2H), 7.59 (t, J = 8.4 Hz, 1H), 7.33 (dd, J = 2.9, 19.5 Hz, 1H), 7.17 (td, J = 2.7, 9.0 Hz, 1H), 4.32 (dd, J = 3.5, 13.6 Hz, 1H), 4.18 (d, J = 13.5 Hz, 1H), 3.79 (s, 3H), 3.68 (ddd, J = 4.3, 7.1, 14.3 Hz, 1H), 3.60 (ddd, J = 4.7, 7.0, 14.8 Hz, 1H), 3.12 (d, J = 2.3 Hz, 3H), 1.25 (dd, J = 7.1, 12.1 Hz, 3H), 1.16 (dd, J = 3.4, 6.7 Hz, 3H). LCMS-ESI (pos): 501.0 (M + H)$^+$. |
| 163.0 | (1S,2S)-1-isopropoxy-1-(5-methylpyrimidin-2-yl)propane-2-sulfonamide (Example 85.0), methoxyacetic acid hydrazide (commercially available from CombiBlocks Inc.), and 1-chloro-2-isothiocyanato-4-methoxybenzene (commercially available from Enamine). | 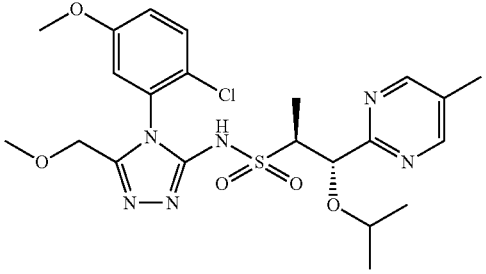<br>(1S,2S)-N-(4-(2-chloro-5-methoxyphenyl)-5-(methoxymethyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 13.18-13.02 (m, 1H), 8.66-8.62 (m, 2H), 7.64-7.59 (m, 1H), 7.32-7.23 (m, 1H), 7.21-7.16 (m, 1H), 4.78-4.73 (m, 1H), 4.37-4.32 (m, 1H), 4.23-4.17 (m, 1H), 3.85-3.80 (m, 3H), 3.53-3.33 (m, 2H), 3.15-3.12 (m, 3H), 2.29-2.25 (m, 3H), 1.04-0.94 (m, 6H), 0.80 (dd, J = 6.2, 8.6 Hz, 3H). LCMS-ESI (pos): 525.2 (M + H)$^+$. |

TABLE 24-continued

| Example | Reagents | Structure, Name and Data |
|---|---|---|
| 164.0 | (2S,3R)-3-(5-chloro-pyrimidin-2-yl)butane-2-sulfonamide (Example 81.4), pentanehydrazide (commercially available from Ark Pharm, Inc.), and 2-isothiocyanato-1,3-dimethoxybenzene (Example 82.0). | 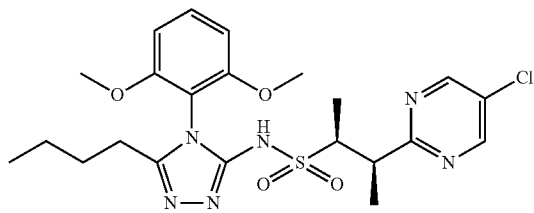<br>(2S,3R)-N-(5-butyl-4-(2,6-dimethoxyphenyl)-4H-1,2,4-triazol-3-yl)-3-(5-chloro-2-pyrimidinyl)-2-butanesulfonamide.<br>$^1$H NMR (400 MHz, DMSO-$d_6$) δ 12.68 (s, 1H), 8.85 (s, 2H), 7.50 (t, J = 8.5 Hz, 1H), 6.85 (dd, J = 1.1, 8.6 Hz, 2H), 3.75-3.72 (m, 6H), 3.64 (dq, J = 4.3, 7.0 Hz, 1H), 3.52 (dq, J = 4.5, 6.9 Hz, 1H), 2.23 (t, J = 7.4 Hz, 2H), 1.39 (quin, J = 7.4 Hz, 2H), 1.24-1.18 (m, 5H), 1.09 (d, J = 7.0 Hz, 3H), 0.76 (t, J = 7.4 Hz, 3H). LCMS-ESI (pos): 509.2 (M + H)$^+$. |
| 174.0 | (1R,2S)-1-(5-chloro-pyrimidin-2-yl)-1-methoxypropane-2-sulfonamide (Example 83.3), pentanehydrazide (commercially available from Ark Pharm, Inc.), and 2-isothiocyanato-1,3-dimethoxybenzene (Example 82.0). | 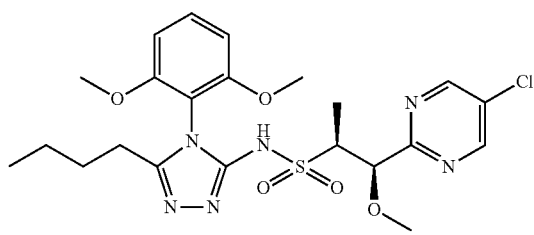<br>(1R,2S)-N-(5-butyl-4-(2,6-dimethoxyphenyl)-4H-1,2,4-triazol-3-yl)-1-(5-chloropyrimidin-2-yl)-1-methoxypropane-2-sulfonamide.<br>$^1$H NMR (500 MHz, DMSO-$d_6$) δ 12.66 (br s, 1H), 8.92 (s, 2H), 7.52-7.47 (m, 1H), 6.86 (dd, J = 1.3, 8.6 Hz, 2H), 4.78 (d, J = 4.4 Hz, 1H), 3.78-3.72 (m, 6H), 3.44-3.38 (m, 1H), 3.15 (s, 3H), 2.26-2.19 (m, 2H), 1.42-1.34 (m, 2H), 1.24-1.17 (m, 2H), 1.14 (br d, J = 7.0 Hz, 3H), 0.76 (t, J = 7.4 Hz, 3H). LCMS-ESI (pos.) m/z: 525.2 (M + H)$^+$. |

TABLE 24-continued

| Example | Reagents | Structure, Name and Data |
|---|---|---|
| 175.0 | (1R,2S)-1-methoxy-1-(5-methylpyrimidin-2-yl)propane-2-sulfonamide, Example 83.0, pentanehydrazide (commercially available from Ark Pharm, Inc.), and 2-isothiocyanato-1,3-dimethoxybenzene (Example 82.0). | 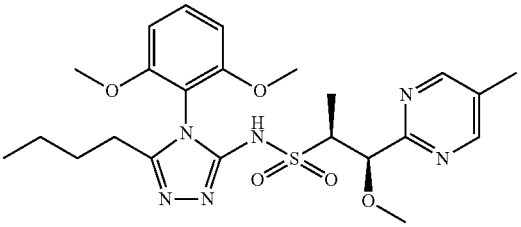<br>(1R,2S)-N-(5-butyl-4-(2,6-dimethoxyphenyl)-4H-1,2,4-triazol-3-yl)-1-methoxy-1-(5-methylpyrimidin-2-yl)propane-2-sulfonamide.<br>$^1$H NMR (500 MHz, DMSO-$d_6$) δ 12.66 (s, 1H), 8.64 (s, 2H), 7.52-7.46 (m, 1H), 6.85 (dd, J = 1.8, 8.6 Hz, 2H), 4.80 (d, J = 3.6 Hz, 1H), 3.77-3.71 (m, 6H), 3.41-3.34 (m, 1H), 3.14 (s, 3H), 2.28-2.20 (m, 5H), 1.42-1.33 (m, 2H), 1.21 (sxt, J = 7.3 Hz, 2H), 1.17-1.08 (m, 3H), 0.76 (br t, J = 7.3 Hz, 3H). LCMS-ESI (pos.) m/z: 505.3 (M + H)$^+$. |
| 176.0 | (2S,3R)-3-(5-methylpyrimidin-2-yl)butane-2-sulfonamide (Example 81.0,) pentanehydrazide (commercially available from Ark Pharm, Inc.), and 2-isothiocyanato-1,3-dimethoxybenzene (Example 82.0). | 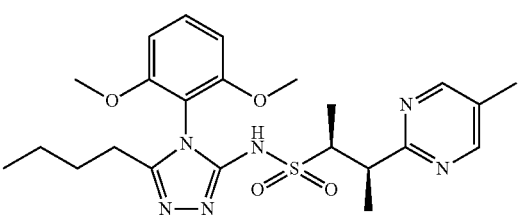<br>(2S,3R)-N-(5-butyl-4-(2,6-dimethoxyphenyl)-4H-1,2,4-triazol-3-yl)-3-(5-methylpyrimidin-2-yl)butane-2-sulfonamide.<br>$^1$H NMR (500 MHz, DMSO-$d_6$) δ 12.64 (br s, 1H), 8.58 (s, 2H), 7.52-7.47 (m, 1H), 6.84 (br d, J = 8.6 Hz, 2H), 3.77-3.71 (m, 6H), 3.69-3.64 (m, 1H), 3.56 (br dd, J = 3.1, 6.7 Hz, 1H), 2.26-2.20 (m, 5H), 1.39 (quin, J = 7.3 Hz, 2H), 1.26-1.18 (m, 5H), 1.07 (br d, J = 6.7 Hz, 3H), 0.79-0.73 (m, 3H). LCMS-ESI (pos.) m/z: 489.2 (M + H)$^+$. |

The compounds set forth in the following table were synthesized following the procedure in Example 72.0 using the known starting material as described.

TABLE 25

| Example | Reagents | Structure, Name and Data |
|---|---|---|
| 168.1 | 2-bromo-6-methoxyaniline (commercially available from Combi-blocks Inc.). | <br>1-bromo-2-isothiocyanato-3-methoxybenzene.<br>$^1$H NMR (500 MHz, CDCl$_3$) δ 7.02-7.09 (m, 2H) 6.94-7.00 (m, 1H) 3.92 (s, 3H). |

Example 167.0. Preparation of (1R,2S)-1-(5-chloro-2-pyrimidinyl)-N-(5-((1R)-1-cyclopropylethyl)-4-(4,6-dimethoxy-5-pyrimidinyl)-4H-1,2,4-triazol-3-yl)-1-methoxy-2-propanesulfonamide and (1R,2S)-1-(5-chloro-2-pyrimidinyl)-N-(5-((1S)-1-cyclopropylethyl)-4-(4,6-dimethoxy-5-pyrimidinyl)-4H-1,2,4-triazol-3-yl)-1-methoxy-2-propanesulfonamide

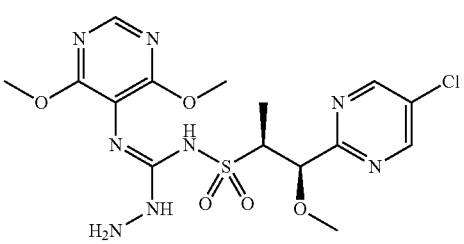

167.1

(Z)—N-(((1R,2S)-1-(5-chloropyrimidin-2-yl)-1-methoxypropan-2-yl)sulfonyl)-N'-(4,6-dimethoxypyrimidin-5-yl)hydrazinecarboximidamide, Example 167.1

To a solution of (1R,2S)-1-(5-chloropyrimidin-2-yl)-1-methoxypropane-2-sulfonamide (Example 83.3, 1.00 g, 3.76 mmol) in ACN (36 mL) was added cesium carbonate (1.47 g, 4.52 mmol) followed by 5-isothiocyanato-4,6-dimethoxypyrimidine (Example 82.1, 0.742 g, 3.76 mmol). The mixture was stirred at rt under an atmosphere of nitrogen for 16 h. Upon stirring, a white precipitate formed. The mixture was then cooled in an ice-water bath for 20 min. To the reaction mixture was added hydrazine hydrate (0.34 mL, 4.52 mmol) followed by slow addition of silver nitrate (1.28 g, 7.53 mmol), and the mixture was stirred in an ice-bath for 30 min. Analysis by LCMS showed formation of the desired product. The resulting mixture was filtered to remove the solids and was washed with ACN (5 mL) and DCM (1 mL). The material thus obtained was absorbed onto a plug of silica gel and purified by chromatography through a Redi-Sep pre-packed silica gel column (120 g) 25% to 75% EtOAc:EtOH (3:1) in heptanes, to provide Example 167.1 (824 mg, 1.79 mmol, 47.5% yield). Mass Spectrum (pos.) m/z: 461.0 (M+H)$^+$.

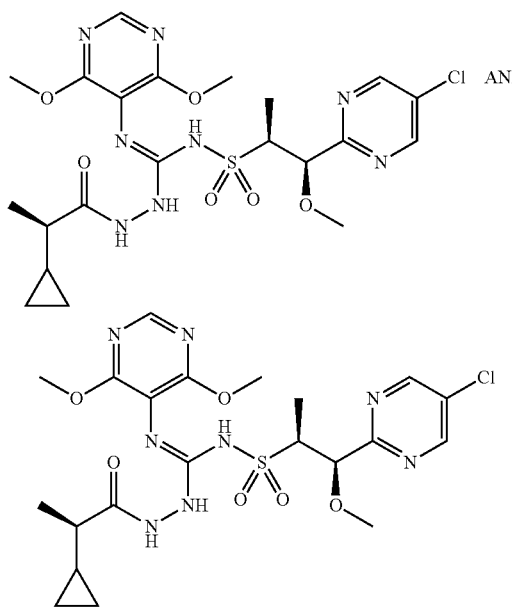

167.2

Preparation of (Z)—N-(((1R,2S)-1-(5-chloropyrimidin-2-yl)-1-methoxypropan-2-yl)sulfonyl)-2-((R)-2-cyclopropylpropanoyl)-N'-(4,6-dimethoxypyrimidin-5-yl)hydrazinecarboximidamide and (Z)—N-(((1R,2S)-1-(5-chloropyrimidin-2-yl)-1-methoxypropan-2-yl)sulfonyl)-2-((S)-2-cyclopropylpropanoyl)-N'-(4,6-dimethoxypyrimidin-5-yl)hydrazinecarboximidamide, Example 167.2

To a screw cap vial was added Example 167.1 (300 mg, 0.651 mmol) followed by EtOAc (3.3 mL) and diisopropylethylamine (0.4 mL, 2.3 mmol). The mixture was stirred at rt and then 2-cyclopropylpropanoic acid (commercially available from Enamine, 74.3 mg, 0.65 mmol) was added followed by 1-propanephosphonic acid cyclic anhydride, (50 wt. % solution in EtOAc, 0.78 mL, 1.30 mmol). The mixture was stirred at rt for 16 h. The mixture was then concentrated in vacuo and the residue was purified by silica gel chromatography (eluting 25-75% EtOAc:EtOH (3:1) in heptane). The desired fractions were collected and concentrated in vacuo to give the product, Example 167.2 (310 mg, 0.557 mmol, 86%), as a white solid. Mass Spectrum (pos.) m/z: 557.0 (M+H)$^+$.

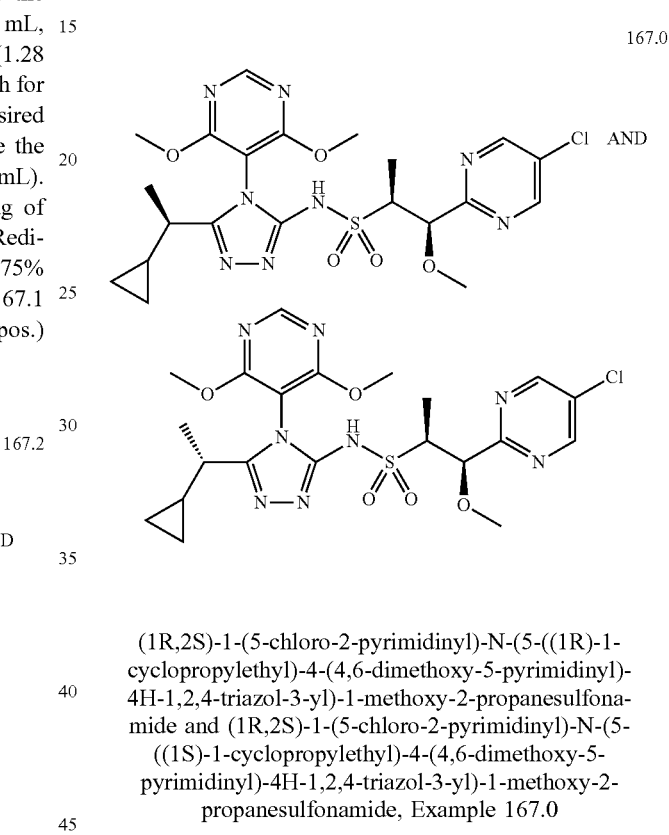

167.0

(1R,2S)-1-(5-chloro-2-pyrimidinyl)-N-(5-((1R)-1-cyclopropylethyl)-4-(4,6-dimethoxy-5-pyrimidinyl)-4H-1,2,4-triazol-3-yl)-1-methoxy-2-propanesulfonamide and (1R,2S)-1-(5-chloro-2-pyrimidinyl)-N-(5-((1S)-1-cyclopropylethyl)-4-(4,6-dimethoxy-5-pyrimidinyl)-4H-1,2,4-triazol-3-yl)-1-methoxy-2-propanesulfonamide, Example 167.0

To a solution of Example 167.2 (310 mg, 0.557 mmol) in IPA (1.85 mL)/water (0.9 mL)/was added sodium hydroxide (1.0 N, 0.7 mL, 0.7 mmol), and the reaction was heated to 80° C. for 16 h. The mixture was neutralized to pH 7 with HCl, extracted with DCM, dried over MgSO$_4$, filtered, and concentrated in vacuo. The material was absorbed onto a plug of silica gel and purified by chromatography through a Redi-Sep pre-packed silica gel column (40 g) eluting with a gradient of 25% to 70% EtOAc:EtOH (3:1) in heptanes to provide Example 167.0 (127 mg, 0.24 mmol, 42.3% yield). $^1$H NMR (400 MHz, DMSO-d$_6$) δ 12.97 (s, 1H), 8.94 (s, 2H), 8.69 (s, 1H), 4.85-4.72 (m, 1H), 3.96 (s, 3H), 3.95 (d, J=1.7 Hz, 3H) 3.48-3.34 (m, 1H), 3.13 (s, 3H), 1.81 (br d, J=6.8 Hz, 1H), 1.17 (dd, J=1.6, 6.9 Hz, 3H), 1.13 (d, J=7.0 Hz, 3H), 0.96-0.78 (m, 1H), 0.50-0.26 (m, 2H), 0.13 (br d, J=4.8 Hz, 1H), −0.15--0.22 (m, 1H). LCMS-ESI (pos.) m/z: 539.0 (M+H)$^+$.

The compounds in the following table were synthesized following the procedure in Example 167.0 using the known starting material as described.

TABLE 26

| Example | Reagents | Structure, Name and Data |
|---|---|---|
| 168.0 | (1S,2S)-1-isopropoxy-1-(5-methylpyrimidin-2-yl)propane-2-sulfonamide (Example 85.0), pent-4-enoic acid (commercially available from Sigma Aldrich), and 1-bromo-2-isothiocyanato-3-methoxybenzene (Example 168.1). | 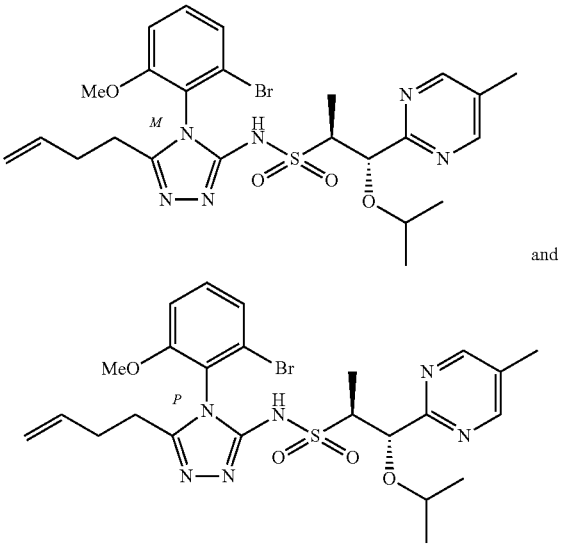 1:1 mixture of (P) (1S,2S)-N-(4-(2-bromo-6-methoxyphenyl)-5-(but-3-en-1-yl)-4H-1,2,4-triazol-3-yl)-1-isopropoxy-1-(5-methylpyrimidin-2-yl)propane-2-sulfonamide and (M) (1S,2S)-N-(4-(2-bromo-6-methoxyphenyl)-5-(but-3-en-1-yl)-4H-1,2,4-triazol-3-yl)-1-isopropoxy-1-(5-methylpyrimidin-2-yl)propane-2-sulfonamide. $^1$H NMR (500 MHz, CD$_3$OD) δ 8.68 (s, 1H) 8.66 (s, 1H) 7.26-7.48 (m, 3H) 5.69-5.85 (m, 1H) 4.78-5.07 (m, 5H) 3.90 (d, J = 4.15 Hz, 3H) 3.55-3.67 (m, 1H) 3.40-3.53 (m, 1H) 2.43-2.59 (m, 2H) 2.27-2.39 (m, 5H) 1.06-1.17 (m, 6H) 0.88-0.92 (m, 3H). Mass Spectrum (pos.) m/z: 579.2 (M + H)$^+$. |

Biological Activity

[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in 9 µL assay buffer [20 mM HEPES, pH 7.5, 5 mM MgCl$_2$, 100 mM NaCl and 0.1% (w/v) BSA], 1 µL of diluted test compound (starting with 0.75 mM, 2-fold serial dilution with DMSO, total 22 points), 10 µL of 18 M GDP (final concentration of 3 µM GDP), 20 µL of 0.25 µg/mL membrane protein expressing human APJ receptor captured with WGA PS beads (final concentration of 5 µg per well), and 20 µL of 0.3 nM [$^{35}$S]GTPγS (final concentration is 0.1 nM [$^{35}$S]GTPγS)(Perkin Elmer Life and Analytical Sciences, Waltham USA). One column of the plate was 1 µL of DMSO as background and another column of the plate was 1 µL of 180 M Pyr-Apelin-13 which was used as control at a final concentration of 3 M. Incubation was at RT for 90 min and the microplate was read using a ViewLux™ ultra HTS Microplate Imager (PerkinElmer, Inc.). All the results presented are means of several independent experiments and analyzed by non-linear regression methods using the commercially available program Prism (GraphPad, San Diego, Calif.) providing the EC$_{50}$ values detailed in Table 27.

The following table includes biological activity data obtained using the procedures and assays set forth above for the Example compounds described herein.

TABLE 27

Biological Activity Information for Example Compounds.

| Example | Activity hAPJ SPA EC$_{50}$ IP (µM) |
|---|---|
| 1.0 | 0.24 |
| 2.0 | 0.17 |
| 3.0 | 0.32 |
| 4.0 | 0.27 |
| 5.0 | 0.31 |
| 6.0 | 0.74 |
| 7.0 | 0.36 |
| 8.0 | 0.26 |
| 9.0 | 0.63 |
| 10.0 | 0.015 |
| 11.0 | 0.088 |
| 12.0 | 0.0048 |
| 13.0 | 0.11 |
| 14.0 | 0.0046 |
| 15.0 | 0.18 |
| 16.0 | 0.12 |
| 17.0 | 0.35 |
| 18.0 | 0.24 |
| 19.0 | 0.20 |
| 20.0 | >4.2 |
| 21.0 | 0.12 |
| 22.0 | 0.12 |
| 23.0 | 0.40 |
| 24.0 | 0.0015 |
| 25.0 | 0.37 |
| 26.0 | 0.12 |
| 27.0 | 0.0076 |
| 28.0 | 0.0045 |
| 29.0 | 0.021 |
| 30.0 | 0.24 |
| 31.0 | 0.0076 |

TABLE 27-continued

Biological Activity Information for Example Compounds.

| Example | Activity hAPJ SPA EC$_{50}$ IP (µM) |
|---|---|
| 32.0 | 0.010 |
| 33.0 | 0.21 |
| 34.0 | 0.016 |
| 35.0 | 0.032 |
| 36.0 | 0.0029 |
| 37.0 | 0.34 |
| 38.0 | 0.0060 |
| 39.0 | 0.0058 |
| 40.0 | 0.11 |
| 41.0 | 0.32 |
| 42.0 | 0.33 |
| 43.0 | 0.0027 |
| 44.0 | 0.036 |
| 45.0 | 0.0017 |
| 46.0 | 0.33 |
| 47.0 | 0.070 |
| 48.0 | 0.44 |
| 49.0 | 0.17 |
| 50.0 | 0.94 |
| 51.0 | 0.52 |
| 52.0 | 0.65 |
| 53.0 | 0.054 |
| 54.0 | 0.30 |
| 55.0 | 0.54 |
| 56.0 | 0.42 |
| 57.0 | 0.042 |
| 58.0 | 0.33 |
| 59.0 | 0.033 |
| 60.0 | 0.022 |
| 61.0 | 0.0067 |
| 62.0 | 1.0 |
| 63.0 | 0.010 |
| 64.0 | 0.02 |
| 65.0 | 0.0057 |
| 66.0 | 0.0023 |
| 67.0 | 0.23 |
| 68.0 | 0.033 |
| 69.0 | 0.0012 |
| 70.0 | 0.002 |
| 71.0 | 0.0052 |
| 72.0 | n/a |
| 73.0 | 0.0375 |
| 74.0 | 0.016 |
| 75.0 | 0.0031 |
| 76.0 | 0.0048 |
| 77.0 | 0.176 |
| 78.0 | 0.615 |
| 79.0 | 0.0029 |
| 80.0 | 0.0024 |
| 96.0 | — |
| 97.0 | — |
| 98.0 | — |
| 99.0 | — |
| 100.0 | — |
| 101.0 | — |
| 102.0 | — |
| 103.0 | — |
| 104.0 | — |
| 105.0 | — |
| 106.0 | — |
| 107.0 | — |
| 108.0 | — |
| 109.0 | — |
| 110.0 | — |
| 111.0 | — |
| 112.0 | — |
| 113.0 | — |
| 114.0 | — |
| 115.0 | — |
| 116.0 | — |
| 117.0 | — |
| 118.0 | — |
| 119.0 | — |
| 120.0 | — |
| 121.0 | — |
| 122.0 | — |
| 123.0 | — |
| 124.0 | 0.085 |
| 125.0 | — |
| 126.0 | — |
| 127.0 | 0.038 |
| 128.0 | 0.060 |
| 129.0 | 0.0043 |
| 130.0 | 0.012 |
| 131.0 | 0.020 |
| 132.0 | 0.011 |
| 133.0 | 0.022 |
| 134.0 | 0.012 |
| 135.0 | 0.040 |
| 136.0 | 0.035 |
| 137.0 | 0.23 |
| 138.0 | 0.86 |
| 139.0 | >4.2 |
| 140.0 | 0.029 |
| 141.0 | 0.10 |
| 144.0 | 1.2 |
| 145.0 | 0.24 |
| 146.0 | 0.25 |
| 147.0 | 0.17 |
| 151.0 | 0.024 |
| 152.0 | 0.0061 |
| 153.0 | 0.00031 |
| 154.0 | 0.0066 |
| 155.0 | 0.012 |
| 156.0 | 0.52 |
| 157.0 | >12.5 |
| 158.0 | 0.014 |
| 159.0 | 0.031 |
| 160.0 | 0.021 |
| 161.0 | 0.0022 |
| 162.0 | 0.024 |
| 163.0 | 0.040 |
| 164.0 | 0.00084 |
| 167.0 | 0.11 |
| 168.0 | 0.12 |
| 174.0 | 0.0003 |
| 175.0 | 0.0017 |
| 176.0 | 0.0019 |

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several hours. A balloon was inserted into the left ventricle (LV) to measure dP/dt$_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects at varying degrees (Table 28). APJ agonists of the present invention showed improvement in cardiac contractility and relaxation when perfused into the heart as described above.

Evidence for Improvement in Cardiac Contractility In Vivo in Heart Failure Rat Model Based on the ex vivo findings in isolated heart assay, APJ agonists may be dosed in vivo to investigate the translation of cardiac contractility in in vivo settings. Male Lewis rats (Charles River, USA) at 2-3 months of age are used for the study. Heart failure is induced by permanent ligation of the left descending coronary artery which results in injury to the heart with an ejection fraction of <35%. APJ agonists are administered dose dependently acutely for a period of 30 min. Administration of example compounds will be found to lead to an increase in cardiac contractility as measured by $dP/dt_{max}$ (derivative of left ventricular pressure).

The following table includes data obtained using the procedures and assays set forth above for the Example compounds described herein.

TABLE 28

Contractile Effects of Examples Observed in ex vivo (Isolated Heart Assay) and in vivo (MI Rat Model).

| Example(s) | Isolated Heart Assay | | MI Rat Model |
| --- | --- | --- | --- |
| | $dP/dt_{max}$ (%) | $dP/dt_{min}$ (%) | $dP/dt_{max}$ (%) |
| 12 | 16.4 | 16.8 | nd* |
| 27 | No effect | No effect | nd* |
| 69 | 4.68 | 1.48 | nd* |
| 134 | 4.13 | 4.16 | nd* |
| 129 | 2.5 | 4.4 | nd* |

*nd is not determined.

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun., 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15 k/well in a 96 well plate overnight. The next day, the culture medium was replaced with medium containing no serum for 4 h. The compound AngII at a range of concentrations (1 pM-10 µM) with or without different concentrations of APJ agonists were diluted in stimulation buffer and added to the cell plate. The plate was sealed and incubated for 1 h. This was followed by addition of IP-d2 conjugate followed by europium cryptate antibody conjugate into the wells. The plate was sealed, followed with incubation for 2 h at RT. Time-resolved fluorescence resonance energy (TR-FRET) at 620 nm and 665 nm was measured after 2 h with an Envision reader. The signal ratios and delta F were calculated and the amount of IP1 produced was inversely proportional to the TR-FRET ratio, 665/620 nm.

Results

Figure 2:
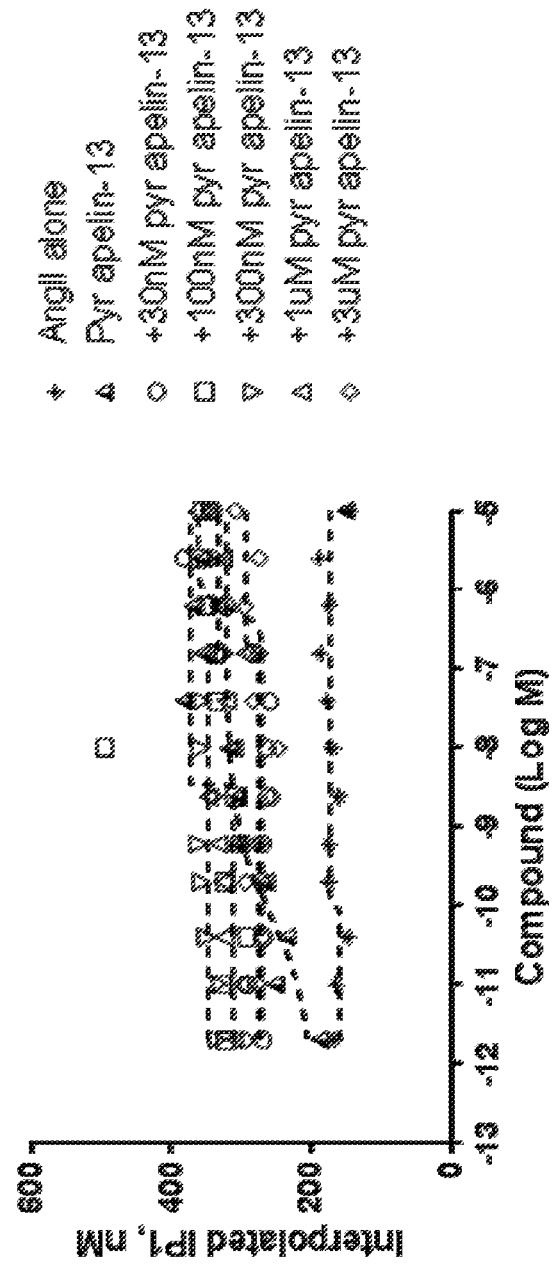
FIG. 2 is a graph plotting different concentrations of angiotensin (AngII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.
Figure 3:
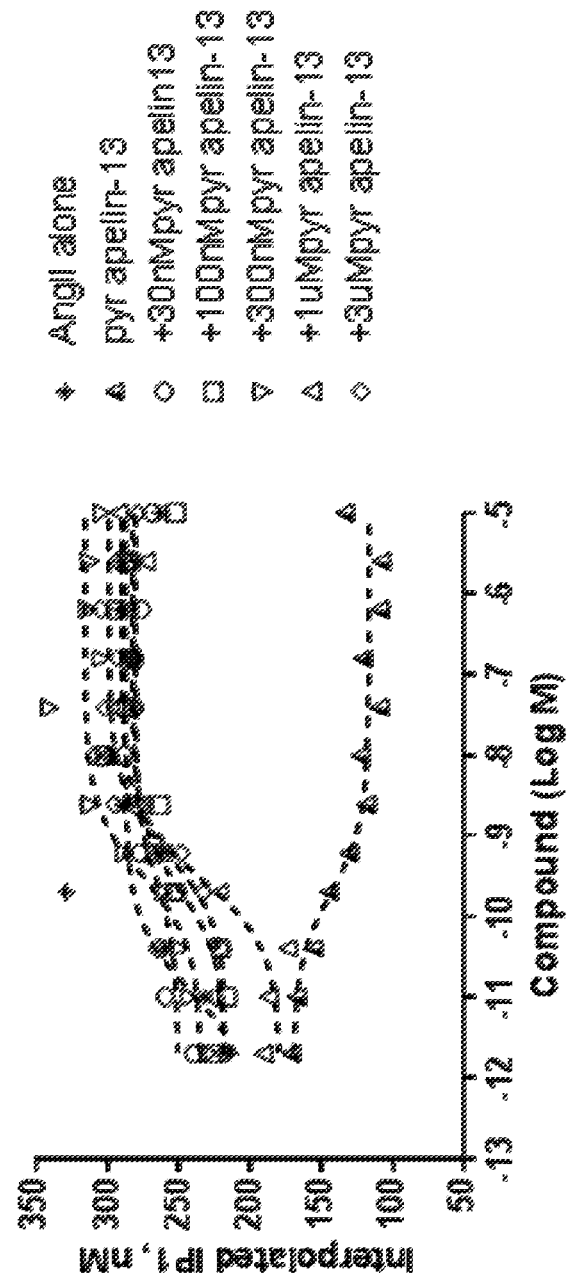
FIG. 3 is a graph plotting different concentrations of angiotensin (AngII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 1). However, this effect of cooperativity was not observed in either APJ or AT1R recombinant stable cell lines indicating that there is functional cross-talk between the two receptors through physical interaction or with downstream effectors (FIG. 2 and FIG. 3). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound of Formula I or Formula II:

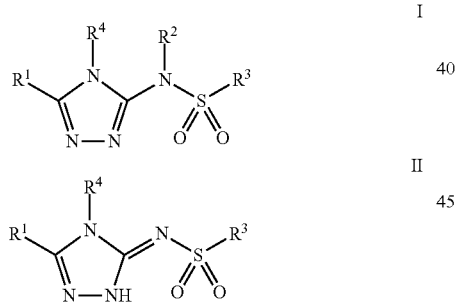

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted $C_1$-$C_8$ straight or branched chain alkyl or $R^1$ is a $C_1$-$C_8$ straight or branched chain alkyl substituted with 1, 2, or 3 $R^{1a}$ substituents;

$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —NHS(=O)$_2$—($C_1$-$C_6$ alkyl), —S(=O)$_2$—($C_1$-$C_6$ alkyl), a monocyclic or bicyclic $C_6$-$C_{10}$ aryl group, —O-(monocyclic or bicyclic $C_6$-$C_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), $C_3$-$C_8$ cycloalkyl, —O—($C_3$-$C_8$ cycloalkyl), —O—($C_1$-$C_6$ alkyl)-($C_3$-$C_8$ cycloalkyl), —O—($C_1$-$C_6$ alkyl)-(monocyclic or bicyclic $C_6$-$C_{10}$ aryl group), O—($C_1$-$C_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—($C_1$-$C_6$ alkyl)-(heterocyclyl group containing 3 to 8 ring members and 1, 2, or 3 heteroatoms independently selected from N, O, or S), wherein the $C_6$-$C_{10}$ aryl of any of the $R^{1a}$ groups that include a $C_6$-$C_{10}$ aryl group, the heteroaryl of any of the $R^{1a}$ groups that include a heteroaryl group, the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group are unsubstituted or are substituted with 1, 2, or 3 $R^{1a'}$ substituents; and further wherein the $C_3$-$C_8$ cycloalkyl of any of the $R^{1a}$ groups that include a —$C_3$-$C_8$ cycloalkyl group, and the heterocyclyl of any of the $R^{1a}$ groups that include a heterocyclyl group may additionally be substituted with 1 or 2 oxo substituents, and the S atom of the heterocyclyl of any of the $R^{1a}$ groups that include a heterocyclyl group may contain one or two oxo substituents, and still further wherein, the heteroaryl of any of the $R^{1a}$ groups that include a heteroaryl group may include an N-oxide if the heteroaryl includes a N heteroatom;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, a group of formula -($C_3$-$C_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^{3h}$ —C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), —($C_1$-$C_6$ alkyl)-NH$_2$, —($C_1$-$C_6$ alkyl)-NH—($C_1$-$C_6$ alkyl), —($C_1$-$C_6$ alkyl)-N—($C_1$-$C_6$ alkyl)$_2$, phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 3 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NH($C_1$-$C_6$alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, a monocyclic heteroaryl group with 5 or 6 ring members containing 1, 2, or 3 N atoms, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{4c}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

wherein if R⁴ is a cyclopropyl group then R³ is a group of formula —(CR³ᵈR³ᵉ)—(CR³ᶠR³ᵍ)-Q or R³ is a group of formula -(heterocyclyl)-Q.

2. The compound of claim 1 or the pharmaceutically acceptable salt thereof, the tautomer thereof, the pharmaceutically acceptable salt of the tautomer, the stereoisomer of any of the foregoing, or the mixture thereof, wherein R³ is selected from a group of formula —(CR³ᵈR³ᵉ)—(CR³ᶠR³ᵍ)-Q, or a group of formula -(heterocyclyl)-Q.

3. The compound of claim 2 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)—(CR³ᶠR³ᵍ)-Q.

4. The compound of claim 3 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)—(CR³ᶠR³ᵍ)-Q and further wherein, R³ᵈ and R³ᵉ are independently selected from —H, —C₁-C₆ alkyl, —(C₁-C₆ alkyl)-OH, or —(C₁-C₆ alkyl)-O—(C₁-C₆ alkyl); and R³ᶠ and R³ᵍ are independently selected from —H, —F, —C₁-C₆ alkyl, —C₁-C₆ haloalkyl, —C₁-C₆ perhaloalkyl, —OH, —O—(C₁-C₆ alkyl), —O—(C₁-C₆ haloalkyl), —O—(C₁-C₆ perhaloalkyl), or —O—(C₂-C₆ alkenyl).

5. The compound of claim 1 or the pharmaceutically acceptable salt thereof, the tautomer thereof, the pharmaceutically acceptable salt of the tautomer, the stereoisomer of any of the foregoing, or the mixture thereof, wherein R³ is selected from

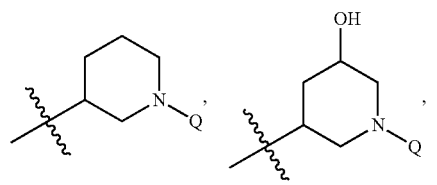
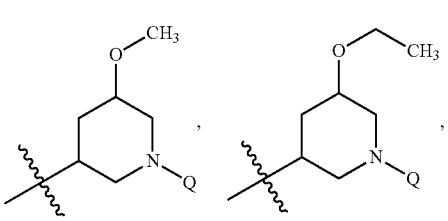
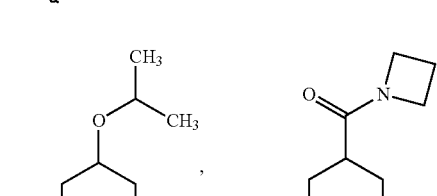
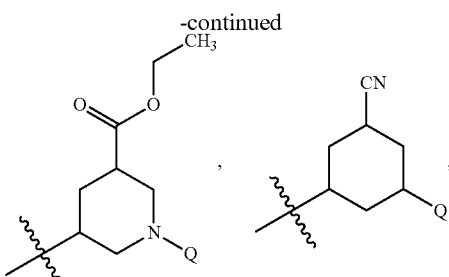
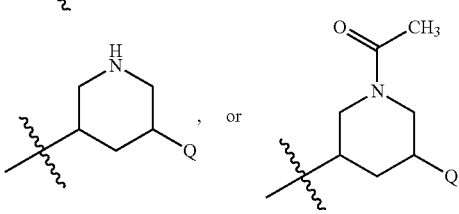

wherein the symbol ⌇, when drawn across a bond, indicates the point of attachment to the rest of the molecule.

6. The compound of claim 1 or the pharmaceutically acceptable salt thereof, the tautomer thereof, the pharmaceutically acceptable salt of the tautomer, the stereoisomer of any of the foregoing, or the mixture thereof, wherein R³ is selected from

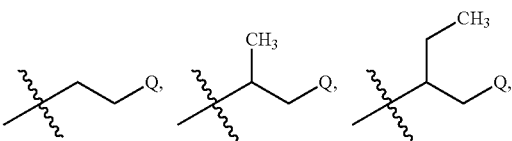
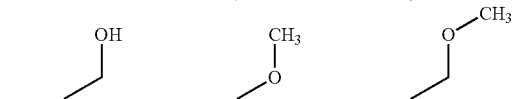
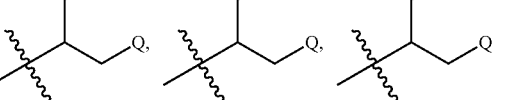
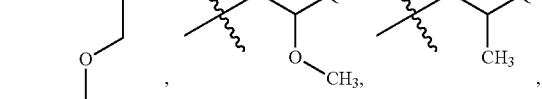
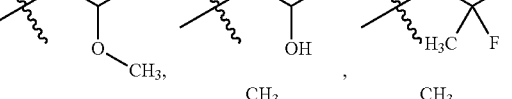
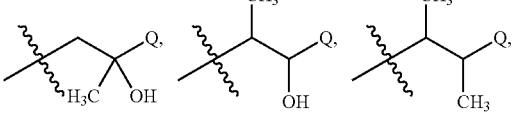

-continued

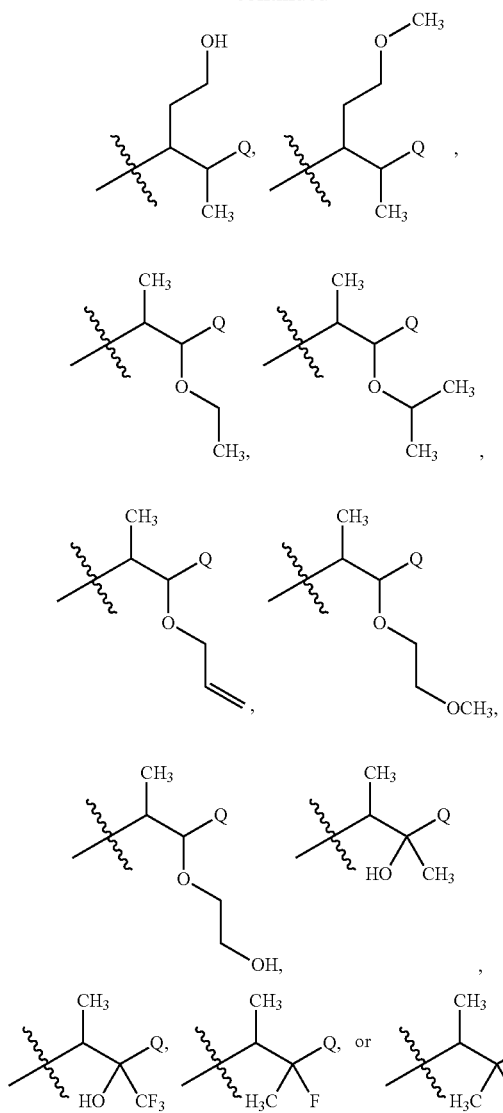

wherein the symbol ⁓, when drawn across a bond, indicates the point of attachment to the rest of the molecule.

7. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from

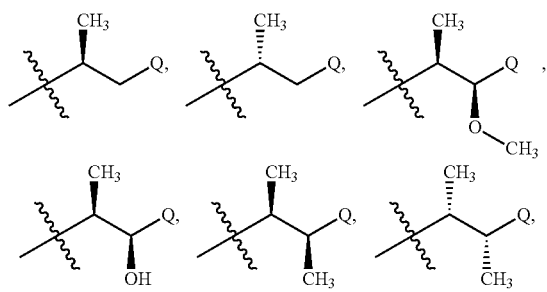

-continued

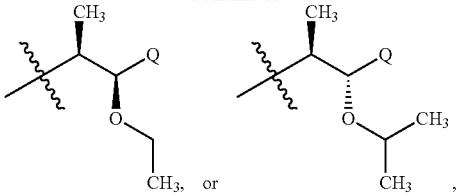

wherein the symbol ⁓, when drawn across a bond, indicates the point of attachment to the rest of the molecule.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyridinyl, or phenyl, any of which may be unsubstituted or substituted with 1, 2, or 3 $R^Q$ substituents.

9. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 3 or 6 ring members containing 1 or 2 heteroatoms selected from N, O, or S and Q is unsubstituted or is substituted with 1 or 2 $R^Q$ substituents.

10. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), or —O—($C_1$-$C_6$ perhaloalkyl).

11. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

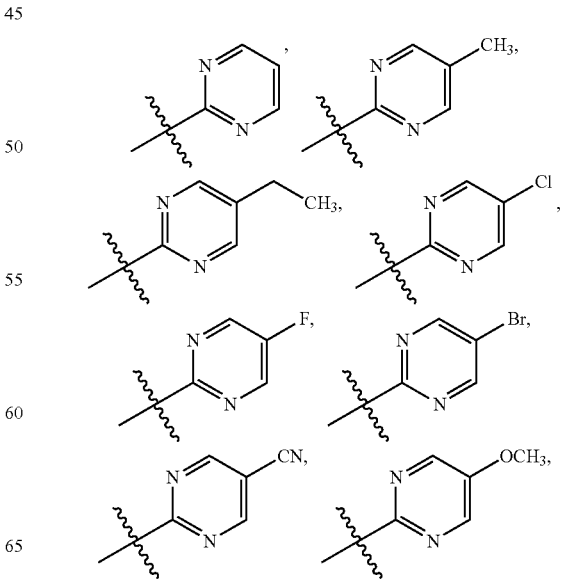

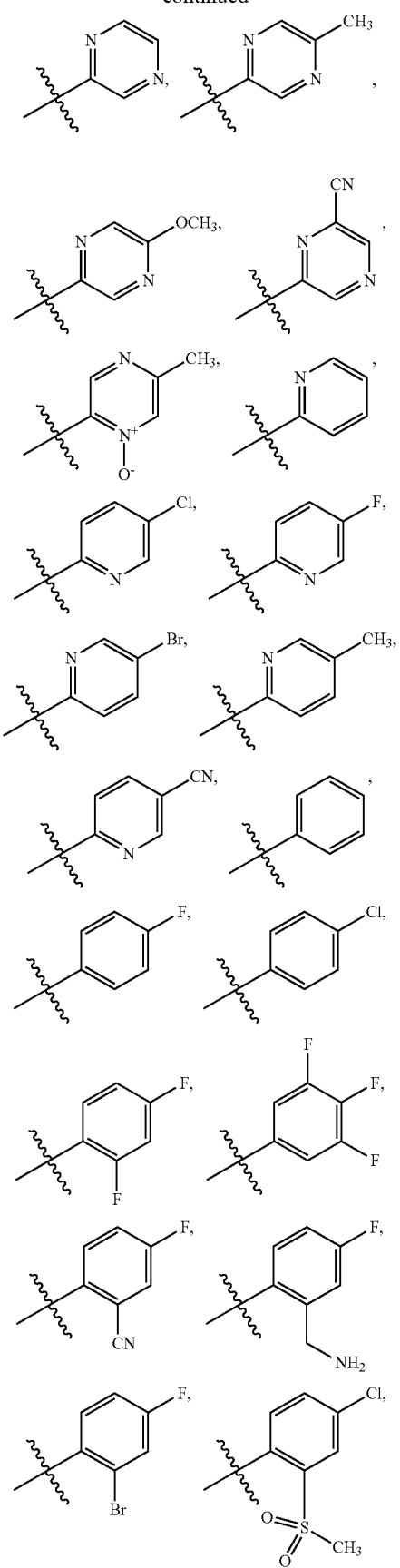
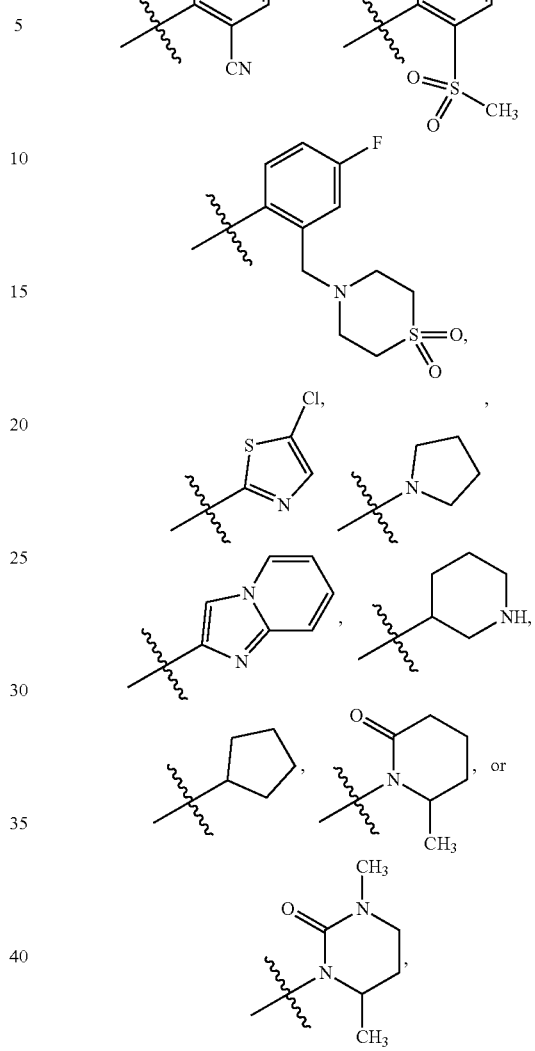

wherein the symbol ⁓, when drawn across a bond, indicates the point of attachment to the rest of the molecule.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, or 3 $R^{4a}$ substituents.

14. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—(C$_1$-C$_6$ alkyl), —NH$_2$, —NH(C$_1$-C$_6$ alkyl), —N(C$_1$-C$_6$ alkyl)$_2$, NH(C$_1$-C$_6$ alkyl-OH), —C(=O)NH$_2$, —C(=O)NH(C$_1$-C$_6$ alkyl), or —C(=O)N(C$_1$-C$_6$ alkyl)$_2$.
15. The compound of claim 1 or the pharmaceutically acceptable salt thereof, the stereoisomer of any of the foregoing, or the mixture thereof, wherein R$^4$ is selected from
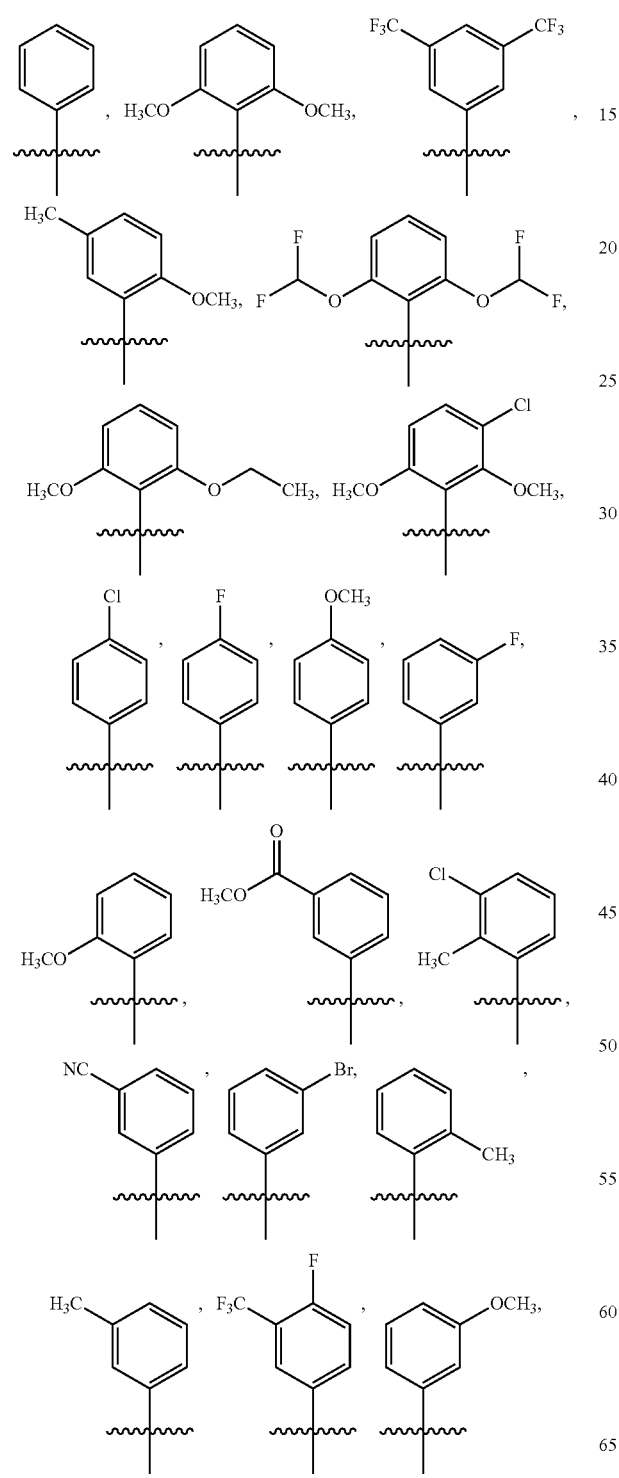
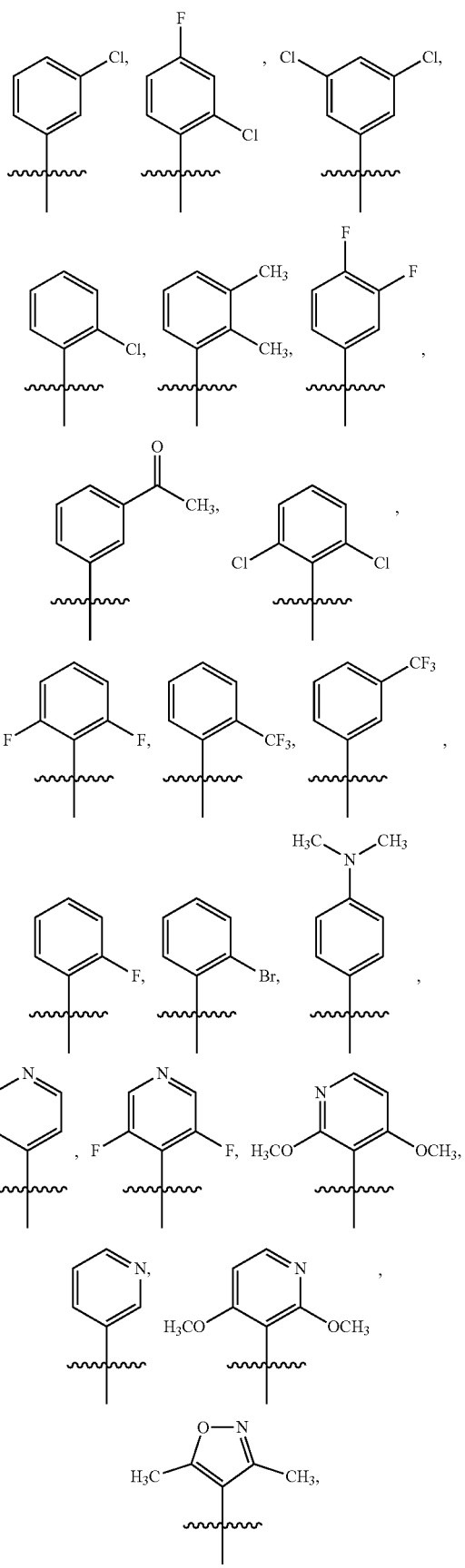

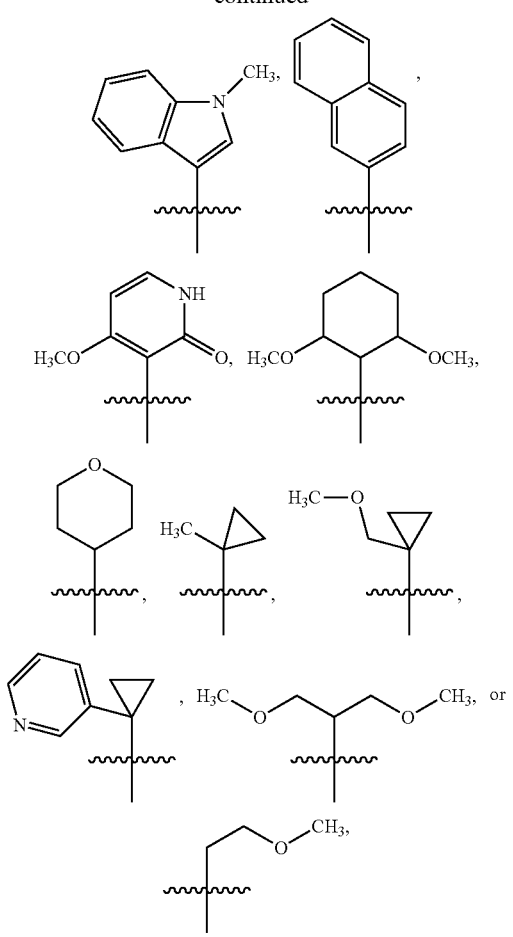
wherein the symbol ⌇, when drawn across a bond, indicates the point of attachment to the rest of the molecule.
16. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from
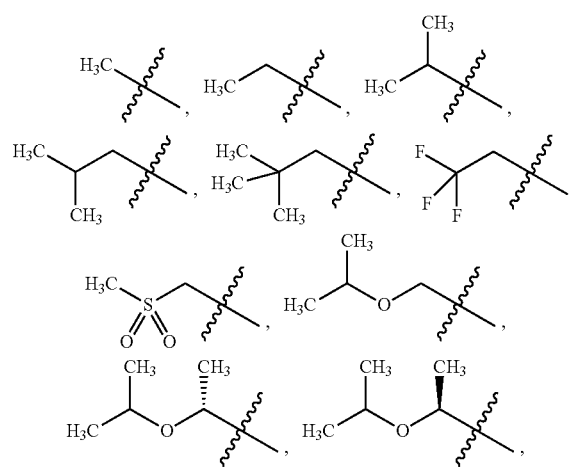
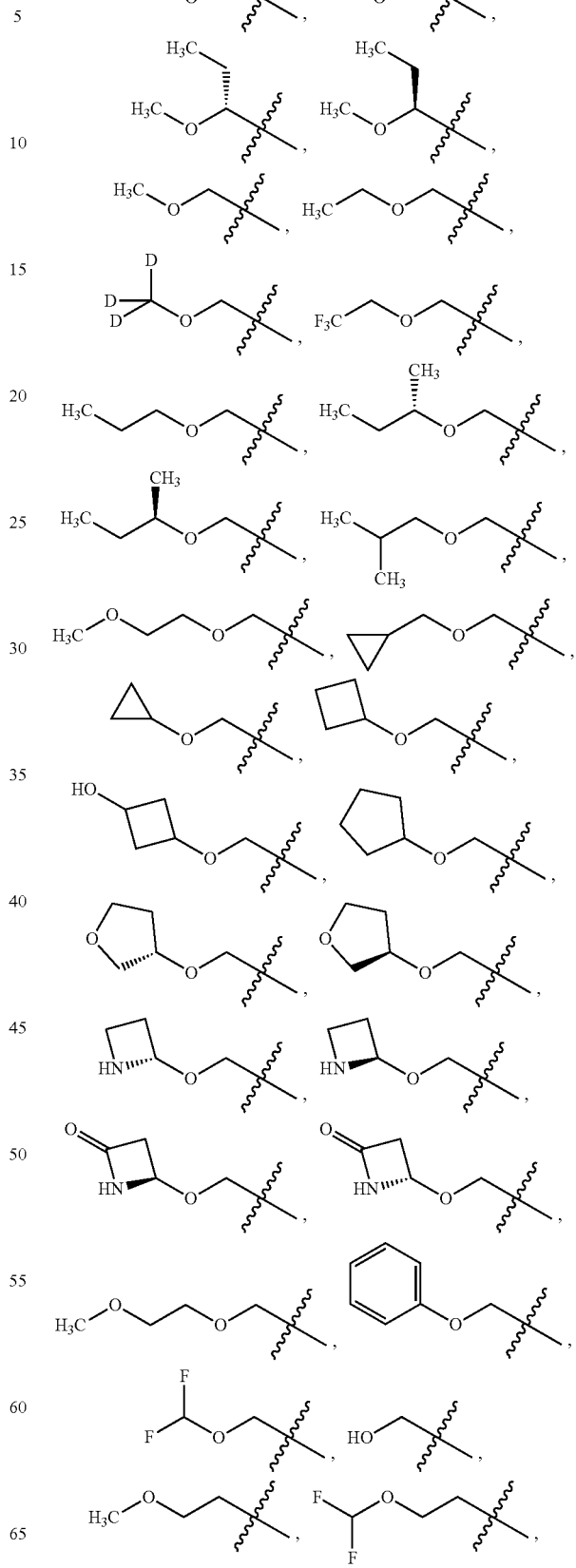

-continued

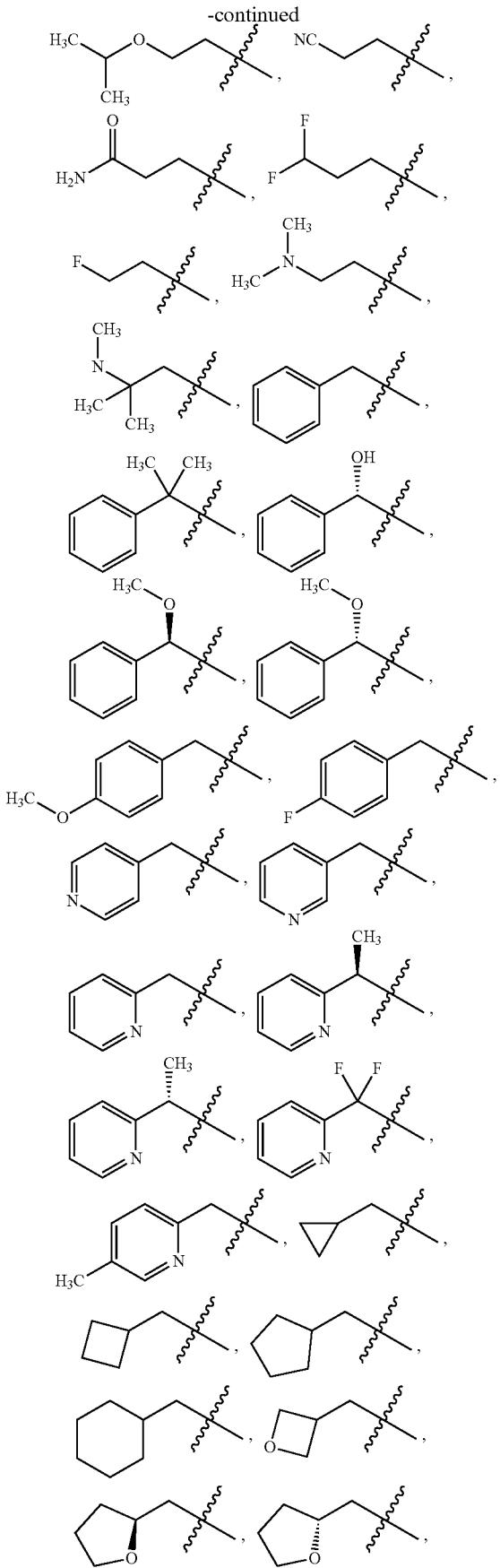

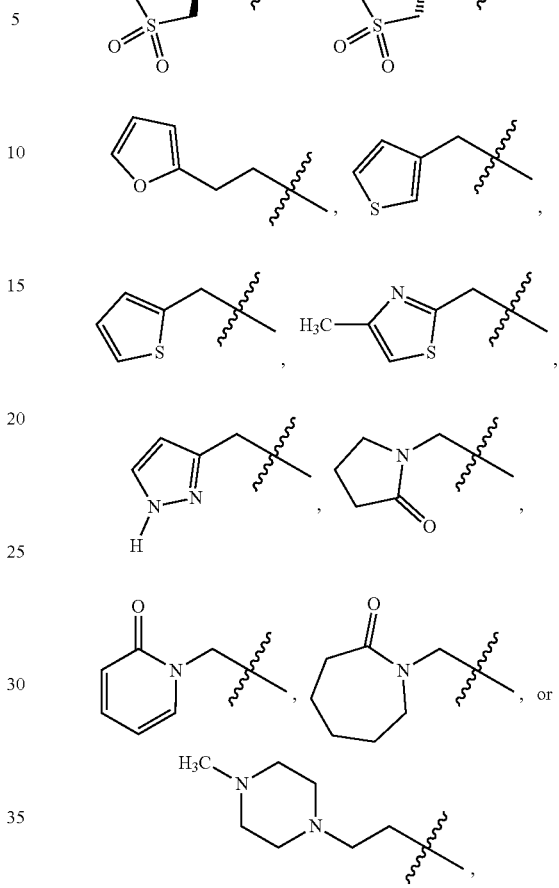

wherein the symbol ⌇, when drawn across a bond, indicates the point of attachment to the rest of the molecule.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a $C_1$-$C_8$ straight or branched chain alkyl substituted with 1, 2, or 3 $R^{1a}$ substituents, wherein at least one of the $R^{1a}$ substituents is selected from a $C_3$-$C_8$ cycloalkyl group, a monocyclic or bicyclic $C_6$-$C_{10}$ aryl group, a monocyclic or bicyclic heteroaryl group with 3 to 10 ring members containing 1, 2, or 3 heteroatoms independently selected from N, O, or S, or a 3 to 8 membered heterocyclyl group containing 1, 2, or 3 heteroatoms independently selected from N, O, or S, wherein the $C_3$-$C_8$ cycloalkyl, the $C_6$-$C_{10}$ aryl, the heteroaryl, and the heterocyclyl $R^{1a}$ groups are unsubstituted or are substituted with 1, 2, or 3 $R^{1a'}$ substituents; and further wherein the $R^{1a}$ $C_3$-$C_8$ cycloalkyl and heterocyclyl group may additionally be substituted with 1 or 2 oxo substituents, and the S atom of a heterocyclyl group may contain one or two oxo substituents, and still further wherein, the $R^{1a}$ heteroaryl group may include an N-oxide if the heteroaryl includes a N heteroatom.

18. The compound of claim 1, wherein the compound has the Formula IA

IA or is the pharmaceutically acceptable salt thereof, the tautomer thereof, the pharmaceutically acceptable salt of the tautomer, the stereoisomer of any of the foregoing, or the mixture thereof,
wherein:
$R^1$ is as defined in claim 1;
X is selected from CH or N;
Z is selected from CH or N;
$R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and
$R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl),
Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and
$R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —S(=O)$_2$—($C_1$-$C_6$ alkyl).

19. The compound of claim 1, wherein the compound has the Formula IB

IB or is the pharmaceutically acceptable salt thereof, the tautomer thereof, the pharmaceutically acceptable salt of the tautomer, the stereoisomer of any of the foregoing, or the mixture thereof,
wherein:
$R^1$ is as defined in claim 1;
X is selected from CH or N;
Z is selected from CH or N;
$R^{3h}$ is independently selected from —OH, or —O—($C_1$-$C_6$ alkyl);
The subscript p is selected from 0, 1, 2, or 3;
Q is a phenyl group or a monocyclic heteroaryl group with 6 ring members containing 1 or 2 N heteroatoms, wherein the phenyl and the monocyclic heteroaryl Q groups are unsubstituted or are substituted with 1, 2, or 3 $R^Q$ substituent; and
$R^Q$ is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), —($C_1$-$C_6$ alkyl)-$NH_2$ or —S(=O)$_2$—($C_1$-$C_6$ alkyl).

20. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

21. A pharmaceutical composition, comprising the compound of claim 1 or the pharmaceutically acceptable salt thereof and at least one pharmaceutically acceptable excipient.

22. The pharmaceutical composition of claim 21, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

23. A method of treating a cardiovascular condition, the method comprising: administering to a subject an effective amount of the compound of claim 1 or the pharmaceutically acceptable salt thereof, the stereoisomer of any of the foregoing, or the mixture thereof.

24. The method of claim 23, wherein the cardiovascular condition is heart failure.

25. The method of claim 23, wherein the cardiovascular condition is heart failure with reduced ejection fraction.

26. The method of claim 23, wherein the cardiovascular condition is heart failure with preserved ejection fraction.

27. The method of claim 23, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

28. A compound of Formula V, a salt thereof, a tautomer thereof, or a salt of the tautomer:

V wherein:
$R^1$ is an unsubstituted $C_1$-$C_8$ straight or branched chain alkyl or $R^1$ is a $C_1$-$C_8$ straight or branched chain alkyl substituted with 1, 2, or 3 $R^{1a}$ substituents;
$R^{1a}$ in each instance is independently selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$C_2$-$C_4$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —NHS(=O)$_2$—(C$_1$-C$_6$ alkyl), —S(=O)$_2$—(C$_1$-C$_6$ alkyl), a monocyclic or bicyclic C$_6$-C$_{10}$ aryl group, —O-(monocyclic or bicyclic C$_6$-C$_{10}$ aryl group), a monocyclic or bicyclic heteroaryl group with 5 to 10 ring members containing 1, 2, or 3 heteroatoms independently selected from N, O, or S, —O-(monocyclic or bicyclic heteroaryl group with 5 to 10 ring members containing 1, 2, or 3 heteroatoms independently selected from N, O, or S), C$_3$-C$_8$ cycloalkyl, —O—(C$_3$-C$_8$ cycloalkyl), —O—(C$_1$-C$_6$ alkyl)-(C$_3$-C$_8$ cycloalkyl), —O—(C$_1$-C$_6$ alkyl)-(monocyclic or bicyclic C$_6$-C$_{10}$ aryl group), O—(C$_1$-C$_6$ alkyl)-(monocyclic or bicyclic heteroaryl group with 5 to 10 ring members containing 1, 2, or 3 heteroatoms independently selected from N, O, or S), a 3 to 8 membered heterocyclyl group containing 1, 2, or 3 heteroatoms independently selected from N, O, or S, —O-(heterocyclyl group containing 3 to 8 ring members and 1, 2, or 3 heteroatoms independently selected from N, O, or S), or an —O—(C$_1$-C$_6$ alkyl)-(heterocyclyl group containing 3 to 8 ring members and 1, 2, or 3 heteroatoms independently selected from N, O, or S), wherein the C$_6$-C$_{10}$ aryl of any of the R$^{1a}$ groups that include a C$_6$-C$_{10}$ aryl group, the heteroaryl of any of the R$^{1a}$ groups that include a heteroaryl group, the C$_3$-C$_8$ cycloalkyl of any of the R$^{1a}$ groups that include a —C$_3$-C$_8$ cycloalkyl group, and the heterocyclyl of any of the R$^{1a}$ groups that include a heterocyclyl group are unsubstituted or are substituted with 1, 2, or 3 R$^{1a'}$ substituents; and further wherein the C$_3$-C$_8$ cycloalkyl of any of the R$^{1a}$ groups that include a —C$_3$-C$_8$ cycloalkyl group, and the heterocyclyl of any of the R$^{1a}$ groups that include a heterocyclyl group may additionally be substituted with 1 or 2 oxo substituents, and the S atom of the heterocyclyl of any of the R$^{1a}$ groups that include a heterocyclyl group may contain one or two oxo substituents, and still further wherein, the heteroaryl of any of the R$^{1a}$ groups that include a heteroaryl group may include an N-oxide if the heteroaryl includes a N heteroatom;

R$^{1a'}$ is in each instance independently selected from —F, —Cl, —Br, —I, —C$_1$-C$_6$ alkyl, —C$_1$-C$_6$ haloalkyl, —C$_1$-C$_6$ perhaloalkyl, —(C$_1$-C$_6$ alkyl)-O—(C$_1$-C$_6$ alkyl), —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —O—(C$_1$-C$_6$ haloalkyl)-OH, —O—(C$_1$-C$_6$ haloalkyl)-O—(C$_1$-C$_6$ alkyl), —O—(C$_1$-C$_6$ perhaloalkyl)-OH, —O—(C$_1$-C$_6$ perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH(C$_1$-C$_6$ alkyl), —C(=O)N(C$_1$-C$_6$ alkyl)$_2$, or —S(=O)$_2$—(C$_1$-C$_6$ alkyl);

R$^3$ is selected from a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, a group of formula —(C$_3$-C$_8$ cycloalkyl)-Q, or a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 R$^{3h}$ substituents, and further wherein the C$_3$-C$_8$ cycloalkyl of the —(C$_3$-C$_8$ cycloalkyl)-Q group is unsubstituted or is substituted with 1 or 2 R$^{3h}$ substituents;

R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —(C$_1$-C$_6$ alkyl)-O—(C$_1$-C$_6$ alkyl)-phenyl, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3f}$ and R$^{3g}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —O—(C$_1$-C$_6$ alkyl), —O—(C$_1$-C$_6$ haloalkyl), —O—(C$_1$-C$_6$ perhaloalkyl), —O—(C$_2$C$_6$ alkenyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3h}$ in each instance is independently selected from —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)—(C$_3$-C$_6$ cycloalkyl), —C(=O)—O—(C$_1$-C$_6$ alkyl), oxo, or —C(=O)-(heterocyclyl), wherein the heterocyclyl group of the R$^{3h}$—C(=O)-(heterocyclyl) has 5 or 6 ring members of which 1 or 2 are heteroatoms independently from N, or S or has 3 or 4 ring members of which 1 is a heteroatom selected from N, O, or S;

Q is a monocyclic or bicyclic C$_6$-C$_{10}$ aryl group, a monocyclic or bicyclic heteroaryl group with 3 to 10 ring members containing 1, 2, or 3 heteroatoms independently selected from N, O, or S, a C$_3$-C$_8$ cycloalkyl group, a 3 to 10 membered heterocyclyl group containing 1, 2, or 3 heteroatoms independently selected from N, O, or S, wherein the C$_6$-C$_{10}$ aryl, the heteroaryl, the cycloalkyl, and the heterocyclyl Q groups are unsubstituted or are substituted with 1, 2, 3, or 4 R$^Q$ substituents; and further wherein the Q heterocyclyl group may additionally be substituted with 1 or 2 oxo substituents, and the Q heteroaryl group may include an N-oxide if the heteroaryl includes a N heteroatom;

R$^Q$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —C$_2$-C$_6$ alkenyl, —C$_2$-C$_6$ alkynyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —NHC(=O)(C$_1$-C$_6$ alkyl), —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), —(C$_1$-C$_6$ alkyl)-OH, —(C$_1$-C$_6$ alkyl)-O—(C$_1$-C$_6$ alkyl), —(C$_1$-C$_6$ alkyl)-NH$_2$, —(C$_1$-C$_6$ alkyl)-NH—(C$_1$-C$_6$ alkyl), —(C$_1$-C$_6$ alkyl)-N—(C$_1$-C$_6$ alkyl)$_2$, phenyl, a heterocyclyl group, a —(C$_1$-C$_6$ alkyl)heterocyclyl group, or a heteroaryl group with 5 or 6 ring members and 1, 2, or 3, heteroatoms independently selected from N, O, or S, wherein the heterocyclyl groups of the R$^Q$ heterocyclyl and —(C$_1$-C$_6$ alkyl)heterocyclyl groups have 3 to 6 ring members of which 1 or 2 are heteroatoms independently selected from N, O, or S, and further wherein the heterocyclyl and the heterocyclyl of the —(C$_1$-C$_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 3 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, a monocyclic heteroaryl group with 3 or 6 ring members containing 1, 2, or 3 N atoms, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents, and further wherein the heterocyclyl of the $R^4$ group may be further substituted with 1 oxo substituent; and further wherein the phenyl and monocyclic heteroaryl $R^{4a}$ groups are unsubstituted or are substituted with 1, 2, or 3 $R^{40}$ substituents;

$R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl); and $R^{4c}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl).

\* \* \* \* \*

UNITED STATES PATENT AND TRADEMARK OFFICE
CERTIFICATE OF CORRECTION

PATENT NO. : 11,191,762 B2
APPLICATION NO. : 16/347924
DATED : December 7, 2021
INVENTOR(S) : Chen et al.

Page 1 of 1

It is certified that error appears in the above-identified patent and that said Letters Patent is hereby corrected as shown below:

In the Claims

In Column 248, in Claim 1, Line 14, delete "O–" and insert -- –O– --, therefor.

In Column 250, in Claim 1, Line 12, delete "3 to 10" and insert -- 5 to 10 --, therefor.

In Column 250, in Claim 1, Line 49, delete "$R^{40}$" and insert -- $R^{4c}$ --, therefor.

In Column 254, in Claim 9, Line 27, delete "3 or 6" and insert -- 5 or 6 --, therefor.

In Column 262, in Claim 17, Line 52, delete "3 to 10" and insert -- 5 to 10 --, therefor.

In Column 265, in Claim 28, Line 16, delete "O–" and insert -- –O– --, therefor.

In Column 265, in Claim 28, Line 56, delete "–C(=O)NH($C_1$-$C_6$ alkyl)," and insert -- –C(=O)$NH_2$, –C(=O)NH($C_1$-$C_6$ alkyl), --, therefor.

In Column 266, in Claim 28, Line 35, delete "3 to 10" and insert -- 5 to 10 --, therefor.

In Column 267, in Claim 28, Line 7, delete "3 to 10" and insert -- 5 to 10 --, therefor.

In Column 267, in Claim 28, Line 29, delete "3 or 6" and insert -- 5 or 6 --, therefor.

In Column 268, in Claim 28, Line 12, delete "$R^{40}$" and insert -- $R^{4c}$ --, therefor.

In Column 268, in Claim 28, Line 21, delete "$R^{4C}$" and insert -- $R^{4c}$ --, therefor.

Signed and Sealed this
First Day of April, 2025

Coke Morgan Stewart
*Acting Director of the United States Patent and Trademark Office*